(12) United States Patent
Parrish et al.

(10) Patent No.: US 7,368,237 B2
(45) Date of Patent: May 6, 2008

(54) CELL DEATH-RELATED NUCLEASES AND THEIR USES

(76) Inventors: Jay Parrish, 1410 Willard St., San Francisco, CA (US) 94117; Ding Xue, 978 Arapahoe Cir., Louisville, CO (US) 80024-1094

( * ) Notice: Subject to any disclaimer, the term of this patent is extended or adjusted under 35 U.S.C. 154(b) by 460 days.

(21) Appl. No.: 10/830,828

(22) Filed: Apr. 23, 2004

(65) Prior Publication Data

US 2005/0142568 A1 Jun. 30, 2005

Related U.S. Application Data

(60) Provisional application No. 60/498,065, filed on Aug. 26, 2003, provisional application No. 60/465,086, filed on Apr. 23, 2003.

(51) Int. Cl.
- *C12Q 1/68* (2006.01)
- *C12P 21/06* (2006.01)
- *C12N 15/70* (2006.01)
- *C07K 16/00* (2006.01)
- *C07K 1/00* (2006.01)
- *C07H 21/04* (2006.01)

(52) U.S. Cl. .............. 435/6; 435/69.1; 435/320.1; 435/19; 530/350; 530/388.26; 536/23.2; 536/23.5

(58) Field of Classification Search .............. 435/6, 435/69.1, 7.6; 530/350, 388.26; 536/23.2
See application file for complete search history.

(56) References Cited

U.S. PATENT DOCUMENTS

2003/0165863 A1* 9/2003 Chiang .................... 435/6

OTHER PUBLICATIONS

Xia et al. Modulation of apoptosis induced by tricyclic antidepressants in human peripheral lymphocytes. J Biochem Mol Toxicol. 1998;12(2):115-23.*

* cited by examiner

*Primary Examiner*—Rebecca E. Prouty
*Assistant Examiner*—Iqbal Chowdhury
(74) *Attorney, Agent, or Firm*—Lathrop & Gage LC

(57) ABSTRACT

An assay uses apoptotic nucleases to screen for apoptosis modulators, in a method of modulating apoptosis, and in a method of aiding in a diagnosis of a disease, among other methods. materials for use in the assay include isolated or recombinant polypeptides and polynucleotides, compositions comprising those isolated or recombinant polypeptides and polynucleotides, vectors, transgenic organisms, and integrated systems among other aspects.

4 Claims, 23 Drawing Sheets

CELL DEATH-RELATED NUCLEASES AND THEIR USES

RELATED APPLICATIONS

The present application claims benefit of priority to U.S. Provisional Patent Application Ser. No. 60/465,086 filed Apr. 23, 2003 and 60/498,065 filed Aug. 26, 2003, both of which applications are hereby incorporated by reference to the same extent as though fully replicated herein.

GOVERNMENT INTERESTS

This invention was made with government support under Grant Nos. GM59083-04 and DAMD17-01-1-0214 awarded by the National Institutes of Health and the U.S. Army Research Office, respectively. The government has certain rights in the invention.

SEQUENCE LISTING

This application is accompanied by a Sequence Listing in printed and computer readable forms that are identical to one another, which are hereby incorporated by reference to the same extent as though fully replicated herein.

BACKGROUND

1. Field of the Invention

The invention pertains to materials and methods that may be used in investigating the mechanisms of apoptosis and, more particularly, nucleases that are implicated in apoptotic DNA degradation. The invention also further relates to materials and methods that may be useful for identifying therapeutic agents that target the apoptotic pathways.

2. Description of the Related Art

As used in the discussion below, references by author name and publication year are more particularly cited in the References section. Programmed cell death or apoptosis is needed for the development and tissue homeostasis of metazoans, for example, as discussed in Steller (1995); and Vaux and Korsmeyer (1999). Despite its significant role in many biological processes; apoptosis and its associated biochemical pathways are poorly understood. There is a need to improve understanding about apoptosis pathways for the development of useful pharmacological agents.

One step in apoptosis is the fragmentation of chromosomal DNA at internucleosomal regions. This fragmentation generates DNA ladders approximately 180 base pairs (bp) in length, as described by Wyllie (1980); and Zhang and Xu (2002). Several nucleases have been implicated in mediating this chromosome fragmentation processes, including DFF40/CAD, a 40 kD DNA fragmentation factor (DFF)/Caspase-Activated Deoxyribonuclease (CAD) (see Enari et al., (1998); Liu et al. (1997); and Liu et al. (1998)) and mitochondrial endonuclease G (Endo G) (see Li et al., 2001; and Parrish et al. (2001). Parrish et al. (2001) is incorporated by reference to the same extent as though fully replicated herein.

DFF40/CAD normally associates tightly with its cognate inhibitor, DFF45/ICAD, but is activated during apoptosis when it is released from DFF45/ICAD as a result of caspase cleavage of DFF45/ICAD. In contrast, Endo G is released from mitochondria and translocates to nuclei during apoptosis to induce DNA fragmentation in a manner that is independent of caspase and DFF40, as reported by Li et al. (2001). These different mechanisms show that multiple DNA degradation pathways exist. In addition, several other mammalian proteins, including apoptosis-inducing factor (AIF), DNaseII, Topoisomerase II, and cyclophilins have been implicated in mediating apoptotic DNA degradation, mostly based on in vitro studies, as described in Zhang and Xu (2002).

In the nematode C. elegans, at least two nucleases have been shown to mediate apoptotic DNA degradation: NUC-1, a worm type-II DNase discussed in Wu et al. (2000), and CPS-6, which is the C. elegans ortholog of Endo G described in Parrish et al. (2001). Loss-of-function mutations in either cps-6 or nuc-1 genes result in accumulation of TUNEL (for "'TdT-mediated dUTP nick end labeling'")-positive nuclei in mutant embryos. Thus, both CPS-6 and NUC-1 proteins appear to function to play a role in resolving 3'OH DNA breaks labeled by TUNEL, that are generated during apoptosis, as described in Parrish et al. (2001; and Wu et al. (2000). In addition, cell deaths in the cps-6 mutant are delayed, and sometimes blocked in sensitized genetic backgrounds, suggesting that the DNA degradation process is implicated in apoptosis, as reported by Parrish et al. (2001).

Unlike cps-6, nuc-1 appears to be dispensable for apoptosis. NUC-1 likely acts in a different DNA degradation pathway because cps-6, nuc-1 double mutants have higher numbers of TUNEL-positive cells than those of either mutant alone, as reported by Parrish et al. (2001). Recently, WAH-1, a C. elegans homolog of human apoptosis-inducing factor (AIF), was found to associate with and cooperate with cps-6 to promote DNA degradation in C. elegans, as reported in Wang et al. (2002). These results indicate that other unidentified proteins may be involved in the regulation of apoptotic DNA degradation in C. elegans. It is problematic that neither nuc-1 or cps-6 mutants nor wah-1 RNA-mediated interference animals display easily detectable phenotypes which would encourage additional genetic screens for mutants with similar cell death defects. Thus, there is a need to develop a more powerful and systematic method to identify molecular components that are involved in apoptotic DNA degradation. There is also a need to identify proteins that are involved in the execution of apoptosis and to gain knowledge on their mechanisms of action, because knowledge about these proteins may prove valuable for the diagnosis as well as treatment of diseases.

SUMMARY

The instrumentalities described herein overcome the problems outlined above and advance the art by providing an assay together with related materials and methods that may be used to investigate the molecular components of apoptotic DNA degradation. The nucleases are particularly described herein in context of the nematode C. elegans and in mammalian systems; however, the nucleases have homologs or orthologs across many species of plants and animals.

In one aspect, the molecular components relate to the molecular genetic and biochemical characterization of proteins implicated in DNA fragmentation, which are exemplified by seven nucleases isolated from C. elegans and are referred to herein as cell death-related nucleases (CRN). Members of the CRN family of nucleases may be identified and/or characterized by genetic screening or biochemical methods, such as RNAi (RNA-mediated interference)-based screens or co-IP (immunoprecipitation) techniques. The CRN nucleases may act alone or form protein complexes with other nucleases and non-nuclease factors. The CRN nucleases and related materials may be provided in an assay kit that may be used for a variety of purposes including but not limited to, the screening of candidate apoptosis modulators to develop pharmacological agents, characterization of functional domains by use of the wild-type or mutated CRN nucleases, development and assessment of transgenic hosts capable of overexpressing or underexpressing the CRN nucleases, and development and assessment of host organisms or host cells in which the expression levels of the CRN nucleases are altered, or genes encoding the CRN nucleases are mutated, or disrupted.

As illustrated herein by way of example, genetic screening may be performed in *C. elegans* and other organisms, to isolate mutations that enhance or suppress CRN-mediated apoptosis. For example, this type of screening may be used to identify genes having protein expression products that cooperate with the CRN nucleases in *C. elegans* and other organisms to promote apoptosis.

In one example, a method of screening for an apoptosis modulator includes contacting at least one candidate apoptosis modulator with at least one CRN polypeptide including a sequence selected from SEQ ID NOS: 1-51, and/or at least one crn polynucleotide that encodes the CRN polypeptide. The method may also include detecting a modulated activity of the CRN polypeptide, thereby screening to confirm the apoptosis modulator. Alternatively, screening may be performed to modulate expression of a crn polynucleotide, for example, by imposing environmental conditions that activate or inactivate a promoter. Detection may be accomplished, for example, by antibody techniques such as ELISA to detect polypeptides or nucleic acids, or in the case of nucleic acids by amplification with polymerase chain reaction and/or micro array techniques.

In another aspect, the apoptosis modulator may be used in a method of modulating apoptosis. The method includes administering an effective amount of at least one apoptosis modulator to a test subject or host, where the apoptosis modulator modulates the activity of at least one CRN polypeptide including, for example, a sequence selected from SEQ ID NOS: 1-51. Alternatively, the method may entail administering an apoptosis modulator that modulates the expression of a crn gene. In certain embodiments, apoptosis modulators may be administered to tumor cells to increase the activity of one or more of these CRN polypeptides and kill the tumor cells. In other exemplary embodiments, apoptosis modulators are administered to subjects afflicted with autoimmune diseases, for example, systemic lupus erythematosus (SLE) among many other such autoimmune diseases, to modulate defects in apoptosis and clearance of apoptotic cellular debris. In some embodiments, nuclease activity is beneficially increased, for example, to degrade extracellular DNA such as in the kidneys of lupus patients. In other embodiments, inhibitors of the nucleases described herein are administered to inhibit apoptosis, which has the effect of decreasing certain autoimmune disease responses, e.g., by sustaining white blood cells in diseases that produce low white blood cell counts.

In yet another aspect, a method of diagnosing a disease, such as cancer or autoimmune diseases among many others, may include detecting the expression at either the mRNA or protein levels of at least one crn gene at either the mRNA or protein levels, for example, including crn polynucleotide that encodes the CRN polypeptide selected from SEQ ID NOS: 1-51, in one or more samples from a subject to produce expression data. The method may further include detecting in an organism, including but not limited to human, mutations in at least one crn gene, including crn polynucleotide that encodes the CRN polypeptide selected from SEQ ID NOS: 1-51. The method may further include correlating the expression data or the mutation data with a probable diagnosis of the disease or a negative diagnosis.

A kit may be provided for identifying apoptosis modulators. The kit may contain at least one CRN polypeptide or a fragment thereof, including, for example, a polypeptide sequence selected from SEQ ID NOS: 1-51, and/or at least one crn polynucleotide that encodes the CRN polypeptide or a fragment thereof. The kit may further contain instructions describing the use of the kit. Such kits may be used to screen for compounds or drugs that interact with the CRN polypeptides of SEQ ID NOS: 1-51 and/or at least one crn polynucleotide that encodes the CRN polypeptide to modulate apoptosis.

A kit may be used to diagnose a disease, where the kit may contain an antibody that specifically binds to a CRN polypeptide having a sequence selected from SEQ ID NOS: 1-51, wherein the antibody may form part of an antisera. Other diagnostic tools may include an antigen or antibody bound to a substrate, for example, to facilitate optical detection of an antibody/antigen interaction. Additional diagnostic tools may be included, for example, PCR primers targeting a crn polynucleotide for use in polymerase chain reaction amplification and/or microarrays capable of detecting the amplified polynucleotide. The kit may further include directions describing the use of the kit.

Various organisms, such as mammals including rodents, etc., may be genetically altered to disrupt one or more of the crn genes. crn gene-deficient organisms such as these are useful, for example, in examining potential pathological phenotypes or the like, which provide additional information on the pathological and physiological roles of CRN homologs or orthologs in other organisms, such as humans. In other contexts, expression of proteins encoded by the crn genes may be blocked, for example, using RNAi to modulate mammalian crn gene expression.

In a further aspect, an isolated CRN polypeptide may have a sequence selected or derived from SEQ ID NOS: 1-51. An isolated or recombinant crn polynucleotide may encode the CRN polypeptide or a variant thereof. The crn polynucleotide, either full-length or in its truncated version, may be inserted into a vector, and the resultant vector may be used to transform a host, such as a cell that is transduced by the vector. Moreover, chimeric higher organisms may contain the crn polynucleotide, variants of the crn polynucleotide and/or the vector.

The crn polynucleotide may be used to produce a CRN polypeptide. This can be achieved by introducing into a cell a crn polynucleotide that encodes a CRN polypeptide including, for example, a sequence selected from SEQ ID NOS: 1-51. The crn polynucleotide can be operatively linked to a regulatory sequence that controls the production of the encoded CRN polypeptide in the cells. The method may also include growing the cells in a culture medium to produce the polypeptide, and isolating the polypeptide from the cells or from the culture medium. Alternatively, the CRN polypeptide can be obtained using a crn polynucleotide as a template in an in vitro expression system.

BRIEF DESCRIPTION OF THE FIGURES

FIGS. 2A through 2F show a comparison of bioinformatic data relating sequence identities between the crn nucleases and human homologues of the CRN nucleases;

FIG. 6A shows sequence alignment of CRN-1 and human FEN-I where black shaded residues are identical and gray shaded residues are similar in two proteins;

DETAILED DESCRIPTION

Figure 1:
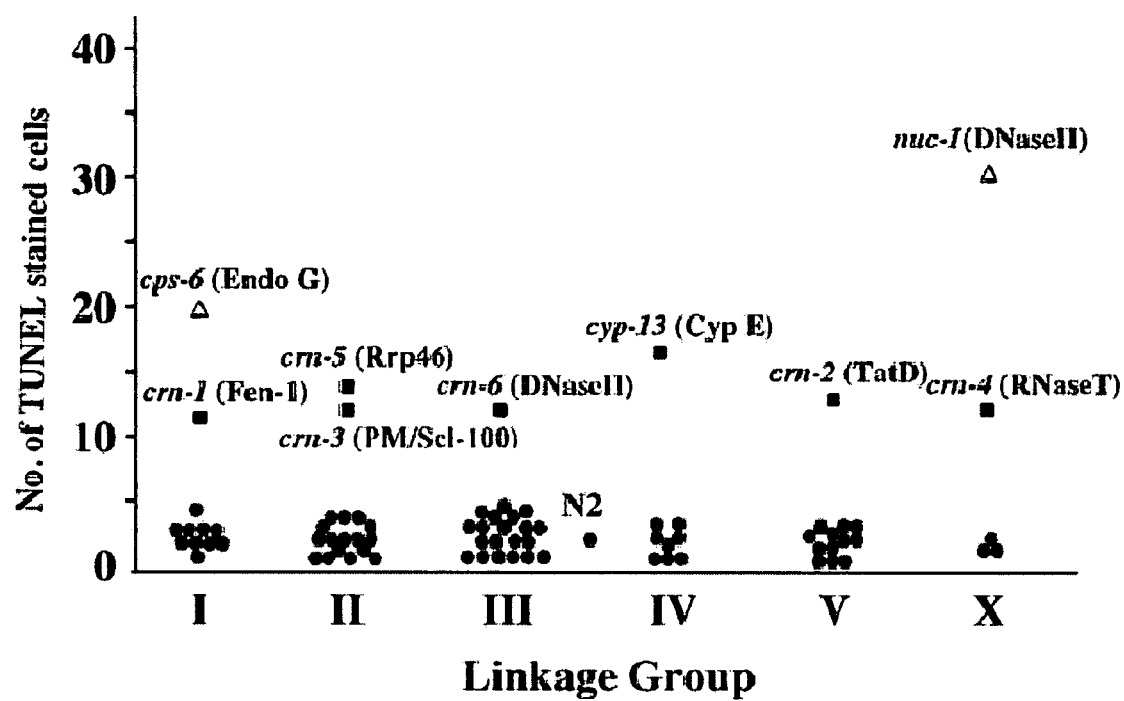
FIG. 1 illustrates CRN nucleases grouped according to apoptosis activity level, as confirmed by TUNEL assay in screening data from the *C. elegans* genome.

The methods and materials described herein relate to cell-death related or CRN nucleases, together with vectors and host cells that contain the nucleic acids encoding the CRN nucleases, homologs and orthologs of the CRN nucleases, methods for producing the CRN nucleases and methods for identifying compounds which bind to and/or modulate the activity of the CRN nucleases.

It is to be understood that the following text teaches by way of example, and not by limitation. the instrumentalities described herein are broader than the particular methods and materials, which may vary within the skill of the art. It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the related art. The following terminology and grammatical variants are used in accordance with the definitions set out below.

A "host cell," as used herein, refers to a prokaryotic or eukaryotic cell that contains heterologous DNA which has been introduced into the cell by any means, e.g., electroporation, calcium phosphate precipitation, microinjection, transformation, viral infection, and/or the like.

A "vector" is a composition for facilitating introduction, replication and/or expression of a selected nucleic acid in a cell. Vectors include, for example, plasmids, cosmids, viruses, yeast artificial chromosomes (YACs), etc. A "vector nucleic acid" is a nucleic acid vector into which heterologous nucleic acid is optionally inserted and which can then be introduced into an appropriate host cell. Vectors preferably have one or more origins of replication, and one or more sites into which the recombinant DNA can be inserted. Vectors often have convenient markers by which cells with vectors can be selected from those without. By way of example, a vector may encode a drug resistance gene to facilitate selection of cells that are transformed with the vector. Common vectors include plasmids, phages and other viruses, and "artificial chromosomes." "Expression vectors" are vectors that comprise elements that provide for or facilitate transcription of nucleic acids which are cloned into the vectors. Such elements can include, for example, promoters and/or enhancers operably coupled to a nucleic acid of interest.

A "CRN material" includes crn polynucleotides, CRN polypeptides, mutated forms of crn polynucleotides, mutated forms of CRN polypeptides, and fragments thereof. Unless otherwise indicated, this definition does not require the CRM material to be designated with a crn or CRN prefix in the discussion below, for example, in that CYP-13 is included as a CRN material unless otherwise indicated. The fragments may be of sufficient length to cover a region of interest in the polynucleotide or polypeptide, for example, in the case of a polypeptide the fragment may include 10 residues, 15 residues, 25 residues, 50 residues, 100 residues, 250 residues 500 residues, or more. A polynucleotide may be of sufficient length to encode the fragment. The fragments may be spliced, for example, as a fusion protein or synthetic gene. A mutated form may contain a single site mutation or a plurality of such mutations in a region compared to the native form of the crn polynucleotide or CRN polypeptide, but also retains high sequence identify over that region, such as at least 99%, 98% or 95% sequence identify. CRN materials at least include those shown in SEQ ID NOS. 1-51. Where the CRN material is a polynucleotide and an open reading frame is shown in any one of SEQ ID NOs. 1-51, the CRN material is hereby defined as the open reading frame exclusive of other nucleotides that are not in the open reading frame as shown.

"Plasmids" generally are designated herein by a lower case "p" preceded and/or followed by capital letters and/or numbers, in accordance with standard nomenclatures that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors are well known and readily available to those of skill in the art. Moreover, those of skill readily may construct any number of other plasmids suitable for use as described below. The properties, construction and use of such plasmids, as well as other vectors, is readily apparent to those of ordinary skill upon reading the present disclosure.

The term "isolated" means that the material is removed from its original environment, such as the native or natural environment if the material is naturally occurring. For example, a naturally-occurring nucleic acid, polypeptide, or cell present in a living animal is not isolated, but the same polynucleotide, polypeptide, or cell separated from some or all of the coexisting materials in the natural system, is isolated, even if subsequently reintroduced into the natural system. Such nucleic acids can be part of a vector and/or such nucleic acids or polypeptides could be part of a composition, and still be isolated in that such vector or composition is not part of its natural environment.

A "recombinant nucleic acid" is one that is made by recombining nucleic acids, e.g., during cloning, DNA evolution or other procedures. A "recombinant polypeptide" is a polypeptide which is produced by expression of a recombinant nucleic acid. An "amino acid sequence" is a polymer of amino acid residues (a protein, polypeptide, etc.) or a character string representing an amino acid polymer, depending on context. Either the given nucleic acid or the complementary nucleic acid can be determined from any specified polynucleotide sequence.

The terms "nucleic acid," or "polynucleotide" refer to a deoxyribonucleotide, in the case of DNA, or ribonucleotide in the case of RNA polymer in either single- or double-stranded form, and unless otherwise specified, encompasses known analogues of natural nucleotides that can be incorporated into nucleic acids in a manner similar to naturally occurring nucleotides. A "polynucleotide sequence" is a nucleic acid which is a polymer of nucleotides (A,C,T,U,G, etc. or naturally occurring or artificial nucleotide analogues) or a character string representing a nucleic acid, depending on context. Either the given nucleic acid or the complementary nucleic acid can be determined from any specified polynucleotide sequence.

A "subsequence" or "fragment" is any portion of an entire sequence of a DNA, RNA or polypeptide molecule, up to and including the complete sequence. Typically a subsequence or fragment comprises less than the full-length sequence, and is sometimes referred to as the "truncated version."

A "polynucleotide construct" is a polynucleotide, a fragment of a polynucleotide or a vector comprising a polynucleotide or fragment thereof. Polynucleotide constructs may be used prophylactically or therapeutically to modulate gene expression when administered in vivo or ex vivo to a cell or cell population of a subject.

Nucleic acids and/or nucleic acid sequences are "homologous" when they are derived, naturally or artificially, from a common ancestral nucleic acid or nucleic acid sequence. Proteins and/or protein sequences are homologous when their encoding DNAs are derived, naturally or artificially, from a common ancestral nucleic acid or nucleic acid sequence. Similarly, nucleic acids and/or nucleic acid sequences are homologous when they are derived, naturally or artificially, from a common ancestral nucleic acid or nucleic acid sequence. For example, any naturally occurring nuclease-encoding nucleic acid, as described herein, can be modified by any available mutagenesis method. When expressed, this mutagenized nucleic acid encodes a polypeptide that is homologous to the protein encoded by the original nuclease-encoding nucleic acid. Homology is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95% or 99% or more can also be used to establish homology. Methods for determining sequence identity percentages (e.g., BLASTP and BLASTN using default parameters) are described herein and are generally available.

The terms "identical", "sequence identical" or "sequence identity" in the context of two nucleic acid sequences or amino acid sequences refers to the residues in the two sequences which are the same when aligned for maximum correspondence over a specified comparison window. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are aligned optimally. Methods of alignment of sequences for comparison are well-known in the art. Optimal alignment of sequences for comparison may be conducted by the local homology algorithm of Smith and Waterman (1981) *Adv. Appl. Math.* 2:482; by the alignment algorithm of Needleman and Wunsch (1970) *J. Mol. Biol.* 48:443; by the search for similarity method of Pearson and Lipman (1988) *Proc. Nat. Acad. Sci U.S.A.* 85:2444; by computerized implementations of these algorithms (including, but not limited to CLUSTAL in the PC/Gene program by Intelligentics, Mountain View Calif., GAP, BESTFIT, BLAST, FASTA, and TFASTA in the Wisconsin Genetics Software Package, Genetics Computer Group (GCG), 575 Science Dr., Madison, Wis., U.S.A.); the CLUSTAL program is well described by Higgins and Sharp (1988) *Gene* 73:237-244 and Higgins and Sharp (1989) *CABIOS* 5:151-153; Corpet et al. (1988) *Nucleic Acids Res.* 16:10881-10890; Huang et al (1992) *Computer Applications in the Biosciences* 8:155-165; and Pearson et al. (1994) *Methods in Molecular Biology* 24:307-331. Alignment is also often performed by inspection and manual alignment. In one class of embodiments, the polypeptides herein are at least 70%, generally at least 75%, optionally at least 80%, 85%, 90%, 95% or 99% or more identical to a reference polypeptide, e.g., as set forth at any one of SEQ ID NO: 1-51 or a fragment thereof, e.g., as measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 95%, 99% or more identical to a reference nucleic acid, e.g., a polynucleotide that encodes a polypeptide as set forth at any one of SEQ ID NO: 1-51 or a fragment thereof, e.g., as measured by BLASTN (or CLUSTAL, or any other available alignment software) using default parameters.

The term "substantially identical" as applied to nucleic acid or amino acid sequences means that a nucleic acid or amino acid sequence comprises a sequence that has at least 90% sequence identity or more, preferably at least 95%, more preferably at least 98% and most preferably at least 99%, compared to a reference sequence using the programs described above (preferably BLAST) using standard parameters. For example, the BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, *Proc. Natl. Acad. Sci. USA* 89:10915 (1989)). Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

"Stringent hybridization" conditions or "stringent conditions" in the context of nucleic acid hybridization assay formats highly stringent conditions are generally selected to be about 5° C. lower than the thermal melting point ($T_m$) for the specific sequence at a defined ionic strength and pH. The $T_m$ is the temperature, under defined other conditions of ionic strength and pH, at which 50% of the target sequence hybridizes to a perfectly matched probe. Very stringent conditions are selected to be equal to the $T_m$ point for a particular nucleic acid, This occurs, for example, when a copy of a nucleic acid is created using the maximum codon degeneracy permitted by the genetic code.

The term "polypeptide" is used interchangeably herein with the terms "polypeptides" and "protein(s)", and refers to a polymer of amino acid residues, e.g., as typically found in proteins in nature. A 'mature protein' is a protein which is full-length and which, optionally, includes glycosylation or other modifications typical for the protein in a given cellular environment.

The term "modulate" with respect to a nuclease as described herein refers to a change in the activity of the nuclease or fragment thereof. For example, modulation may cause an increase or a decrease in catalytic activity, binding characteristics, membrane permeability, phosphorylation status, posttranslational modifications such as phosphorylation, or any other biological, functional, or immunological properties of such proteins. Modulation may result from protein degradation, a chemical change or mutation in the protein itself, the association between the protein and other cofactors, and a chemical change in a receptor or binding site on a substrate for the nuclease. For example, a molecule that binds to a receptor can cause an increase or decrease in the biological activity of the receptor. As applied to polynucleotides, the term modulate means a change in the level of expression from the polynucleotide. The change in expression level can arise from, for example, an increase or decrease in the transcription of the genes that encode the protein, the stability of the mRNA that encodes the protein, translation efficiency.

The term "variant" or "mutant" with respect to a polypeptide refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variation can also include amino acid deletion or insertion, or both. Guidance in determining which amino acid residues can be substituted, inserted, or deleted without eliminating biological or immunological activity can be found using computer programs well known in the art, for example, DNASTAR software.

As used herein, an "antibody" is a protein comprising one or more polypeptides substantially or partially encoded by immunoglobulin genes or fragments of immunoglobulin genes. A typical immunoglobulin (antibody) structural unit comprises a tetramer. Each tetramer is composed of two identical pairs of polypeptide chains. The N-terminus of each chain defines a variable region of about 100 to 110 or more amino acids primarily responsible for antigen recognition. Antibodies exist as intact immunoglobulins or as a number of well characterized fragments produced by digestion with various peptidases. While various antibody fragments are defined in terms of the digestion of an intact antibody, one of skill will appreciate that such fragments may be synthesized de novo either chemically or by utilizing recombinant DNA methodology. Thus, the term antibody, as used herein, includes antibodies or fragments either produced by the modification of whole antibodies or synthesized de novo using recombinant DNA methodologies. Antibodies include multiple or single chain antibodies.

A variety of additional terms are defined or otherwise characterized herein.

In practicing the instrumentalities described herein, many conventional techniques in molecular biology, microbiology, and recombinant DNA are optionally used. These techniques are well known to those of ordinary skill in the art. For example, one skilled in the art would be familiar with techniques for in vitro amplification methods, including the polymerase chain reaction (PCR), Qβ-replicase amplification and other RNA polymerase mediated techniques such as NASBA, e.g., for the production of the homologous nucleic acids described herein.

In addition, commercially available kits may facilitate the purification of plasmids or other relevant nucleic acids from cells. See, for example, EasyPrep™ and FlexiPrep™ kits, both from Pharmacia Biotech; StrataClean™ from Stratagene; and, QIAprep™ from Qiagen. Any isolated and/or purified nucleic acid can be further manipulated to produce other nucleic acids, used to transfect cells, incorporated into related vectors to infect organisms, or the like. Typical cloning vectors contain transcription terminators, transcription initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both.

Various types of mutagenesis are optionally used to modify nucleases, nucleic acids and encoded polypeptides, as described herein, to produce conservative or non-conservative variants. Any available mutagenesis procedure can be used. Such mutagenesis procedures optionally include selection of mutant nucleic acids and polypeptides for one or more activity of interest. Procedures that can be used include, but are not limited to: site-directed point mutagenesis, random point mutagenesis, in vitro or in vivo homologous recombination (DNA shuffling), mutagenesis using uracil-containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, double-strand break repair, mutagenesis by chimeric constructs, and many others known to persons of skill in the art.

In one embodiment, mutagenesis can be guided by known information about the naturally occurring molecule or altered or mutated naturally occurring molecule. By way of example, this known information may include sequence, sequence comparisons, physical properties, crystal structure and the like. In another class of mutagenesis, modification is essentially random, e.g., as in classical DNA shuffling.

Polypeptides include isolated polypeptides, e.g., variants, in which the amino acid sequence has at least 75% identity, preferably at least 80% identity, typically 90% identity, preferably at least 95% identity, more preferably at least 98% identity and most preferably at least 99% identity, to the amino acid sequences as set forth in any one of SEQ ID NO: 1-51.

The aforementioned polypeptides can be obtained by any of a variety of methods. Smaller peptides (less than 50 amino acids long) are conveniently synthesized by standard chemical techniques and can be chemically or enzymatically ligated to form larger polypeptides. Polypeptides can be purified from biological sources by methods well known in the art, for example, as described in *Protein Purification, Principles and Practice, Second Edition* Scopes, Springer Verlag, N.Y. (1987) Polypeptides are optionally but preferably produced in their naturally occurring, truncated, or fusion protein forms by recombinant DNA technology using techniques well known in the art. These methods include, for example, in vitro recombinant DNA techniques, synthetic techniques and in vivo genetic recombination. See, for example, the techniques described in Sambrook et al. (2001) *Molecular Cloning, A Laboratory Manual*, Third Edition, Cold Spring Harbor Press, N.Y.; and Ausubel et al., eds. (1997) *Current Protocols in Molecular Biology*, Green Publishing Associates, Inc., and John Wiley & Sons, Inc., N.Y (supplemented through 2002). RNA encoding the proteins may also be chemically synthesized. See, for example, the techniques described in *Oligonucleotide Synthesis*, (1984) Gait ed., IRL Press, Oxford, which is incorporated by reference herein in its entirety.

The nucleic acid molecules described herein can be expressed in a suitable host cell or animal to produce active nucleases described herein. Expression occurs by placing a nucleotide sequence encoding these proteins into an appropriate expression vector and introducing the expression vector into a suitable host cell, culturing the transformed host cell under conditions suitable for expression of the proteins described or variants thereof, or a polypeptide that comprises one or more domains of such proteins, and purifying the recombinant proteins from the host cell to obtain purified and, preferably, active protein. Appropriate expression vectors are known in the art, and may be purchased or applied for use according to the manufacturer's instructions to incorporate suitable genetic modifications. For example, pET-14b, pcDNA1Amp, and pVL1392 are available from Novagen and Invitrogen, and are suitable vectors for expression in *E. coli*, mammalian cells and insect cells, respectively. These vectors are illustrative of those that are known in the art, and many other vectors can be used for the same purposes. Suitable host cells can be any cell capable of growth in a suitable media and allowing purification of the expressed protein. Examples of suitable host cells include bacterial cells, such as *E. coli, Streptococci, Staphylococci, Streptomyces* and *Bacillus subtilis* cells; fungal cells such as *Saccharomyces* and *Aspergillus* cells; insect cells such as *Drosophila* S2 and *Spodoptera* Sf9 cells, mammalian cells such as CHO, COS, HeLa, 293 cells; and plant cells.

Culturing and growth of the transformed host cells can occur under conditions that are known in the art. The conditions will generally depend upon the host cell and the type of vector used. Suitable culturing conditions may be used such as temperature and chemicals and will depend on the type of promoter utilized.

Purification of the proteins described herein, or domains of such proteins, can be accomplished using known techniques without performing undue experimentation. Generally, the transformed cells expressing one of these proteins are broken, crude purification occurs to remove debris and some contaminating proteins, followed by chromatography to further purify the protein to the desired level of purity. Cells can be broken by known techniques such as homogenization, sonication, detergent lysis and freeze-thaw techniques. Crude purification can occur using ammonium sulfate precipitation, centrifugation or other known techniques. Suitable chromatography includes anion exchange, cation exchange, high performance liquid chromatography (HPLC), gel filtration, affinity chromatography, hydrophobic interaction chromatography, etc. Well known techniques for refolding proteins can be used to obtain the active conformation of the protein when the protein is denatured during intracellular synthesis, isolation or purification.

In general, proteins that include nuclease sequences or domains, or antibodies to such proteins can be purified, either partially (e.g., achieving a 5×, 10×, 100×, 500×, or 1000× or greater purification), or even substantially to homogeneity (e.g., where the protein is the main component of a solution, typically excluding the solvent (e.g., water or DMSO) and buffer components (e.g., salts and stabilizers) that the protein is suspended in, e.g., if the protein is in a liquid phase), according to standard procedures known to and used by those of skill in the art. Accordingly, the polypeptides can be recovered and purified by any of a number of methods well known in the art, including, e.g., ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against the proteins described herein are used as purification reagents, e.g., for affinity-based purification of proteins comprising one or more nuclease domains or antibodies thereto. Once purified, partially or to homogeneity, as desired, the polypeptides are optionally used e.g., as assay components, therapeutic reagents or as immunogens for antibody production.

In addition to other references noted herein, a variety of purification methods are well known in the art, including, for example, those set forth in R. Scopes, *Protein Purification*, Springer-Verlag, N.Y. (1982); Deutscher, Methods in Enzymology Vol. 182: *Guide to Protein Purification*, Academic Press, Inc. N.Y. (1990); Sandana, *Bioseparation of Proteins*, Academic Press, Inc. (1997); Bollag et al., *Protein Methods*, 2nd Edition Wiley-Liss, NY; Walker (1996) *The Protein Protocols Handbook* Humana Press, NJ; Harris and Angal *Protein Purification Applications: A Practical Approach* IRL Press at Oxford, Oxford, England (1990); Scopes, *Protein Purification: Principles and Practice* 3rd Edition Springer Verlag, NY (1993); Janson and Ryden, *Protein Purification: Principles, High Resolution Methods and Applications, Second Edition* Wiley-VCH, NY (1998); and Walker, *Protein Protocols on CD-ROM* Humana Press, NJ (1998); and the references cited therein.

After synthesis, expression and/or purification, proteins can possess a conformation different from the desired conformations of the relevant polypeptides. For example, polypeptides produced by prokaryotic systems often are optimized by exposure to chaotropic agents to achieve proper folding. During purification from, e.g., lysates derived from *E. coli*, the expressed protein is optionally denatured and then renatured. This is accomplished, e.g., by solubilizing the proteins in a chaotropic agent such as guanidine HCl. In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are well known to those of skill in the art. Debinski, et al., for example, describe the denaturation and reduction of inclusion body proteins in guanidine-DTE. The proteins can be refolded in a redox buffer containing, e.g., oxidized glutathione and L-arginine. Refolding reagents can be flowed or otherwise moved into contact with the one or more polypeptide or other expression product, or vice-versa.

In another aspect, antibodies to CRN nucleases or fragments thereof can be generated using methods that are well known in the art. The antibodies can be utilized for detecting and/or purifying the CRN nucleases, optionally discriminating the proteins from various homologues, and/or in biosensor nuclease activity detection applications. As used herein, the term "antibody" includes, but is not limited to, polyclonal antibodies, monoclonal antibodies, humanized or chimeric antibodies and biologically functional antibody fragments, which are those fragments sufficient for binding of the antibody fragment to the protein.

General protocols that may be adapted for detecting and measuring the expression of the described CRN nucleases using the above mentioned antibodies are known. Such methods include, but are not limited to, dot blotting, western blotting, competitive and noncompetitive protein binding assays, enzyme-linked immunosorbant assays (ELISA), immunohistochemistry, fluorescence-activated cell sorting (FACS), and other protocols that are commonly used and widely described in scientific and patent literature.

The roles of the CRN proteins in apoptosis suggest that mutations in the crn genes may be the cause of some diseases. Sequence of the crn polynucleotides may be used in genetic mapping of diseases. For example, DNA fragment derived from the full-length crn genes may be used in Southern blot analysis to detect the existence or deletion of the crn genes. This method can be applied to the mapping of disease locus, as well as to the generation of crn transgenic or knock-out animals.

The crn polynucleotides also provide information and materials for detecting naturally occurring or artificially introduced mutations in a cell or an organism. For example, cells may be removed from human bodies and tested for the existence of certain mutations in the crn genes. More particularly, oligonucleotides can be synthesized based on the DNA sequences of the crn genes disclosed in this invention. These oligonucleotides may be used as primers in a PCR to amplify crn genes from genomic DNA prepared from the organisms, for example, from human biopsies.

Sequence of the crn polynucleotides may also be used in genetic mapping of diseases. Polynucleotides derived from the crn gene sequences can be used in in situ hybridization to determine the chromosomal locus of the crn genes on the chromosomes. Given the significance of apoptosis in development, high resolution map of the crn genes on the arms of human chromosomes may be used in prenatal screening to detect deletion or other mutations in the crn genes.

Sequence information of the crn genes can be used to design oligonucleotides for detecting crn mRNA levels in the cells. For example, the oligonucleotides can be used in a Northern blot analysis to quantify the levels of crn mRNA. Moreover, full-length or fragment of the crn genes can also be used in microarray experiments. High-throughput screening can be conducted to measure expression levels of the crn genes in different cells or tissues. More importantly, large number of chemical compounds can be screened for their effects on apoptosis, more particularly, on the induction of crn gene expression.

Sequences of the crn genes and proteins also provide a tool for identification of other proteins that may be involved in DNA fragmentation during apoptosis. For example, chimeric CRN proteins can be used as a "bait" to identify other proteins that interact with CRN proteins in a yeast two-hybrid screening. Recombinant CRN proteins can also be used in pull-down experiment to identify their interacting proteins. These other proteins may be cofactors that possess no nuclease activity but are required for CRN proteins to effectively cleave DNAs, or they may be nucleases themselves and may cooperate with CRN proteins in DNA fragmentation.

The CRN polypeptides also provide structural features which can be recognized, for example, by using immunological assays. The generation of antisera which specifically bind the CRN polypeptides, as well as the polypeptides which are bound by such antisera, are a feature of the disclosed embodiments.

In order to produce antisera for use in an immunoassay, one or more of the immunogenic CRN polypeptides or fragments thereof are produced and purified as described herein. For example, recombinant protein can be produced in a host cell such as a bacterial or insect cell. The resultant proteins can be used to immunize a host organism in combination with a standard adjuvant, such as Freund's adjuvant. Commonly used host organisms include rabbits, mice, rats, donkeys, chickens, goats, horses, etc. An inbred strain of mice may also be used to obtain more reproducible results due to the virtual genetic identity of the mice. The mice are immunized with the immunogenic CRN polypeptides in combination with a standard adjuvant, such as Freund's adjuvant, and a standard mouse immunization protocol. See, for example, Harlow and Lane, *Antibodies, A Laboratory Manual*, Cold Spring Harbor Publications, New York (1988), which provides comprehensive descriptions of antibody generation, immunoassay formats and conditions that can be used to determine specific immunoreactivity. Alternatively, one or more synthetic or recombinant CRN polypeptides or fragments thereof derived from the sequences disclosed herein is conjugated to a carrier protein and used as an immunogen.

Antisera that specifically bind the CRN proteins can be used in a range of applications, including but not limited to immunofluorescence staining of cells for the expression level and localization of the CRN nucleases, cytological staining for the expression of CRN nucleases in tissues, FACS analysis for determining CRN protein expression and for cell sorting.

Another aspect includes screening for potential or candidate modulators of CRN nuclease activity. For example, potential modulators may include small molecules, organic molecules, inorganic molecules, proteins, hormones, transcription factors, or the like, which can be contacted to a cell to assess the effects, if any, of the candidate modulator upon CRN nuclease activity.

Alternatively, candidate modulators may be screened to modulate expression of CRN nucleases. For example, potential modulators may include small molecules, organic molecules, inorganic molecules, proteins, hormones, transcription factors, or the like, which can be contacted to a cell to assess the effects, if any, of the candidate modulator upon CRN nuclease expression. Expression of a crn gene described herein can be detected, for example, via Northern blot analysis or quantitative (optionally real time) RT-PCR, before and after application of potential expression modulators. Alternatively, promoter regions of the various genes are generally sequences in the region of the start site of transcription, such as within 5 Kb of the start site, within 1 Kb or less of the start site, within 500 bp, 250 bp or 100 bp of the start site. These promoter regions can be coupled to reporter constructs including, without limitation, CAT, beta-galactosidase, luciferase or any other available reporter, and can similarly be tested for expression activity modulation by the candidate modulator.

In either case, whether the assay is to detect modulated activity or expression, a plurality of assays can be performed in a high-throughput fashion, for example, using automated fluid handling and/or detection systems in serial or parallel fashion. Similarly, candidate modulators can be tested by contacting a potential modulator to an appropriate cell using any of the activity detection methods herein, regardless of whether the activity that is detected is the result of activity modulation, expression modulation or both.

A method of therapeutically or prophylactically treating a disease or disorder may include administering to a subject one or more or the CRN polypeptides or apoptosis modulators described above. Treatment compositions may also contain a pharmaceutically acceptable excipient and one or more such nucleic acids or polypeptides. The subject may include a mammal, for example, a human, primate, rodent, mouse, pig, cow, goat, rabbit, rat, guinea pig, hamster, horse, or sheep. The subject may also include a non-mammalian vertebrate, such as a bird, a fish, or even an invertebrate.

Ex vivo methods of administration to a subject include genetic modification of cells followed by introducing the cells to the subject. For example, this may entail using genetically modified stem cells to perform gene therapy that introduces expression products including those from overexpression or underexpression of the CRN nucleases or use of an apoptosis modulator as an expression product. Other cells that may be used for this purpose include, for example, cells of interest taken from the subject, such as tumor cells, tumor tissue samples, organ cells, blood cells, cells of the skin, lung, heart, muscle, brain, mucosa, liver, intestine, spleen, stomach, lymphatic system, cervix, vagina, prostate, mouth, tongue, etc. These cells are obtained or removed from the subject and may be transformed using a vector to introduce a synthetic gene that is effective in prophylactically or therapeutically treating the disease, disorder, or other condition. The transformed cells may then be returned or delivered to the subject to the site from which they were obtained or to another site of interest in the subject to be treated, such as another site specified above other than the native site from which the cells were obtained. If desired, the contacted cells may be grafted onto a tissue, organ, or system site of interest in the subject using standard and well-known grafting techniques or, for example, delivered to the blood or lymph system using standard delivery or transfusion techniques.

In vivo methods of administration include those in which one or more cells or a population of cells of interest of the subject are contacted directly or indirectly with an amount of a material of interest, such as a modulator that is effective in prophylactically or therapeutically treating the disease, disorder, or other condition. In direct contact/administration formats, the modulator is typically administered or transferred directly to the cells to be treated or to the tissue site of interest. Cells or tissue that may be subject to this type of administration include, for example, tumor cells, tumor tissue sample, organ cells, blood cells, cells of the skin, lung, heart, muscle, brain, mucosa, liver, intestine, spleen, stomach, kidney, lymphatic system, cervix, vagina, prostate, mouth, tongue, etc. Contacting may occur by any of a variety of formats, including topical administration, injection by use of a needle or syringe, vaccine or gene gun delivery, pushing the modulator, nuclease or polypeptide into a tissue, organ, or skin site. The modulator can be delivered, for example, intramuscularly, intradermally, subdermally, subcutaneously, orally, intraperitoneally, intrathecally, intravenously, or placed within a cavity of the body including a surgical cavity, by inhalation, oral, vaginal or rectal administration.

In the in vivo indirect contact/administration formats, the modulator is typically administered or transferred indirectly to the cells to be treated or to the tissue site of interest, including those described above, such as skin cells, organ systems, lymphatic system, or blood cell system, etc. Administration is by contacting the modulator directly to one or more cells or population of cells from which treatment can be facilitated. For example, tumor cells within the body of the subject can be treated by contacting cells of the blood or lymphatic system, skin, or an organ with a sufficient amount of the modulator such that delivery of the modulator to the site of interest occurs to provide effective prophylactic or therapeutic treatment results. Such contact, administration, or transfer is typically made by using one or more of the routes or modes of administration described above.

In vivo methods may also include those in which one or more cells of interest or a population of cells of the subject are transformed in the body of the subject by contacting with, administering, or transferring to the cells a polynucleotide construct comprising a nucleic acid sequence that encodes a biologically active polypeptide of interest. The polypeptide may be effective in prophylactically or therapeutically treating the disease, disorder, or other condition.

Ex vivo methods may similarly include those in which one or more cells of interest or a population of cells of interest of the subject are obtained or removed from the subject. The cells may be transformed by contact with a polynucleotide construct including a nucleic acid sequence that encodes a biologically active polypeptide of interest. The polypeptide is effective in prophylactically or therapeutically treating the disease, disorder, or other condition. The polynucleotide construct also includes a promoter controlling expression of said nucleic acid sequence such that uptake of the polynucleotide construct into the cell(s) occurs. Sufficient expression of the target nucleic acid sequence results to produce an effective amount of the biologically active polypeptide to prophylactically or therapeutically treat the disease, disorder, or condition. The polynucleotide construct may include a promoter sequence that controls expression of the nucleic acid sequence and/or, if desired, one or more additional nucleotide sequences encoding at least one or more of, e.g., a cytokine, an adjuvant, or a co-stimulatory molecule, or other polypeptide of interest.

Following transfection, the transformed cells are returned, delivered, or transferred to the subject to the tissue site or system from which they were obtained or to another site that is to be treated in the subject. If desired, the cells may be grafted onto a tissue, skin, organ, or body system of interest in the subject using standard and well-known grafting techniques or delivered to the blood or lymphatic system using standard delivery or transfusion techniques. Such delivery, administration, or transfer of transformed cells is typically made by using one or more of the routes or modes of administration described above. Expression of the target nucleic acid occurs naturally or can be induced, as described in greater detail below. An amount of the encoded polypeptide is expressed and is sufficient and effective to treat the disease or condition at the site or tissue.

In each of the in vivo and ex vivo treatment methods as described above, a composition comprising an excipient and the modulator, polypeptide, nucleic acid, etc. of the invention can be administered or delivered. In one aspect, a composition comprising a pharmaceutically acceptable excipient and a polypeptide or nucleic acid of the invention is administered or delivered to the subject as described above in an amount effective to treat the disease or disorder.

In another aspect, in each in vivo and ex vivo treatment method described above, the amount of polynucleotide administered to the cell(s) or subject can be an amount sufficient that uptake of the polynucleotide into one or more cells of the subject occurs and sufficient expression of said nucleic acid sequence results to produce an amount of a biologically active polypeptide effective to enhance an immune response in the subject, including an immune response induced by an immunogen (e.g., antigen). In another aspect, for each such method, the amount of polypeptide administered to cell(s) or subject can be an amount sufficient to enhance an immune response in the subject, including that induced by an immunogen (e.g., antigen).

In yet another aspect, in an in vivo or ex vivo treatment method in which a polynucleotide construct is used to deliver a physiologically active polypeptide to a subject, the expression of the polynucleotide construct can be induced by using an inducible on- and off-gene expression system. Examples of such on- and off-gene expression systems include the Tet-On™ Gene Expression System and Tet-Off™ Gene Expression System (see, e.g., Clontech Catalog 2000, pg. 110-111 for a detailed description of each such systems), respectively. Other controllable or inducible on- and off-gene expression systems are known to those of ordinary skill in the art. With such system, expression of the target nucleic acid of the polynucleotide construct can be regulated in a precise, reversible, and quantitative manner. Gene expression of the target nucleic acid can be induced, for example, after the stable transfected cells containing the polynucleotide construct comprising the target nucleic acid are delivered or transferred to or made to contact the tissue site, organ or system of interest. Such systems are of particular benefit in treatment methods and formats in which it is advantageous to delay or precisely control expression of the target nucleic acid (e.g., to allow time for completion of surgery and/or healing following surgery; to allow time for the polynucleotide construct comprising the target nucleic acid to reach the site, cells, system, or tissue to be treated; to allow time for the graft containing cells transformed with the construct to become incorporated into the tissue or organ onto or into which it has been spliced or attached, etc.).

Bioinformatic systems are widely used in the art, and can be used to detect homology or similarity between different character strings, or can be used to perform other desirable functions such as to control output files, provide the basis for making presentations of information including the sequences and the like. Examples include BLAST, discussed supra. For example, commercially available databases, computers, computer readable media and systems may contain character strings corresponding to the sequence information herein for the CRN polypeptides and crn nucleic acids described herein. These sequences may include specifically the CRN or crn sequences listed herein and the various silent substitutions and conservative substitutions thereof.

The bioinformatic systems contain a wide variety of information that includes, for example, a complete sequence listings for the entire genome of an individual organism representing a species. Thus, for example, using the CRN or crn sequences as a basis for comparison, the bioinformatic systems may be used to compare different types of homology and similarity of various stringency and length on the basis of reported data. These comparisons are useful to identify homologs or orthologs where, for example, the basic crn gene ortholog is shown to be conserved across different organisms. Thus, the bioinformatic systems may be used to detect or recognize the homologs or orthologs, and to predict the function of recognized homologs or orthologs. By way of example, many homology determination methods have been designed for comparative analysis of sequences of biopolymers including nucleic acids, proteins, etc. With an understanding of hydrogen bonding between the principal nucleobases in natural polynucleotides, models that simulate annealing of complementary homologous polynucleotide strings can also be used as a foundation of sequence alignment or other operations typically performed on the character strings corresponding to the sequences herein. One example of a software package for calculating sequence similarity is BLAST, which can be adapted to the present invention by inputting character strings corresponding to the sequences herein. CLUSTAL provides another appropriate package.

Systems for analysis in the present invention typically include a digital computer with an appropriate data base and a sequence of the invention. Software for aligning sequences, as well as data sets entered into the software system comprising any of the sequences herein can be a feature of the invention. The computer can be, e.g., a PC (Intel x86 or Pentium chip-compatible DOS™, OS2™ WINDOWS™ WINDOWS NT™, WINDOWS95™, WINDOWS98™, WINDOWS2000™, WINDOWSME™, WINDOWSXP™, or LINUX based machine, a MACINTOSH™, Power PC, or a UNIX based (e.g., SUN™ work station or LINUX based machine) or other commercially common computer which is known to one of skill. Software for entering and aligning or otherwise manipulating sequences is available, or can easily be constructed by one of skill using a standard programming language such as Visualbasic, Fortran, Basic, Java, or the like.

Any controller or computer optionally includes a monitor which is often a cathode ray tube ("CRT") display, a flat panel display (e.g., active matrix liquid crystal display, liquid crystal display, etc.), or other display devices. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation.

The software can also include output elements for controlling nucleic acid synthesis (e.g., based upon a sequence or an alignment of a sequences herein) or other operations which occur downstream from an alignment or other operation performed using a character string corresponding to a sequence herein.

In an additional aspect, kits may embody any of the methods, compositions, systems or apparatus described above. Kits may optionally comprise one or more of the following: (1) a composition, system, or system component as described herein; (2) instructions for practicing the methods described herein, and/or for using the compositions or operating the system or system components herein; (3) one or more nuclease compositions or components; (4) a container for holding components or compositions, and, (5) packaging materials.

EXAMPLES

The nonlimiting examples that follow report general procedures, reagents and characterization methods that teach by way of example, and should not be construed in a narrowing manner that limits the disclosure to what is specifically disclosed. Those skilled in the art will understand that numerous modifications may be made and still the result will fall within the spirit and scope of the present invention. These examples show, for example, a variety of tests and procedures that may derive from use of assay kits incorporating CRN materials. Instructions for use of such materials may be prepared as detailed instructions for performing the protocols with use of the CRN materials.

Example 1

General Procedures

In these examples, any conventional procedure may be adapted to incorporate the CRN nucleases or related genetic materials as a subject of study. C. elegans strains were maintained using standard procedures following those used and reported by Brenner, S., The genetics of Caenorhabditis elegans. Genetics 77, 71-94 (1974). All strains used in this study have been described previously in Parrish et al. (2001), and Riddle, D. L., Blumenthal, T., Meyer, B. J., and Priess, J. R., eds., C. elegans II, Cold Spring Harbor, Cold Spring Harbor Laboratory (1997).

Bioinformatic systems were used to screen reported nucleic acid sequences, and to assess which sequences might function as nucleases. For each Open Reference Frame (ORF) identified n this way, a partial cDNA (>200 bp) was cloned into a bacterial dsRNA (double stranded RNA) expression vector (pPD129.36), the expression vector was introduced into a bacterial host, TH115, and RNAi experiments were carried out using a bacterial feeding protocol, as described by Parrish et al. (2001). L1 larval C. elegans animals were fed with bacteria expressing a specific dsRNA. L2 hermaphrodite larvae were transferred to plates seeded with bacteria expressing either control or crn-1 dsRNA and the progeny of treated animals were scored for RNAi phenotypes. More than 60 open reading frames (ORFs) tested using RNAi did not produce significant TUNEL or cell death phenotypes. The progeny of the treated animals were then scored for TUNEL and other cell death phenotypes. RNAi results for approximately 20% of the ORFs were verified using dsRNAs corresponding to the full-length cDNAs, and no differences in phenotypes were noted. Effects of RNAi on each ORF were tested in three genetic backgrounds, N2 (wild-type), cps-6(sm116), and nuc-1 (e1392), to identify genes that generate or resolve TUNEL-positive ends and to eliminate false positives. To further rule out false positives, ORFs that gave rise to TUNEL-phenotypes following RNAi treatment were retested in triplicate.

To obtain full-length cDNA clones corresponding to a specific ORF, total RNA was isolated from mixed-stage wild-type animals using TRI-Reagent (Sigma) at a ratio of 10:1 (TRI-Reagent:pelleted worms). The cDNAs were then PCR amplified using an Enhanced Avian RT-PCR kit (Sigma). Oligo-dT primers were used to reverse-transcribe 10 μg of total RNA and sequence-specific primers were used to amplify cDNAs by PCR from the resulting pool of the first strand cDNAs. Two crn-6 cDNAs (700 bp and 1.1 kb) were isolated using RT-PCR. The shorter cDNA clone is identical to yk720e2, a cDNA clone provided by Y. Kohara. The longer cDNA clone corresponded to the predicted crn-6 ORF and was used to make the GST fusion protein for protein binding studies.

GST fusion protein pull-down assays were performed as described in J. Parrish, H. Metters, L. Chen, D. Xue, Proc. Natl. Acad. Sci. U.S.A. 97, 11916 (2000). Purified GST or GST-fusion proteins (5 μg each) immobilized on glutathione sepharose beads were incubated with $^{35}$S-Methionine labeled proteins at 4° C. for 2 hours. The beads were washed extensively and the bound proteins were resolved on a 12% SDS-PAGE and visualized by autoradiography.

cDNAs corresponding to the ORFs were cloned into the pPD129.36 vector via its Nhe I and Xho I sites or the Xho I site alone. Full-length cDNAs were subcloned into the pGEX4T-2 vector for generating GST fusion proteins and for further protein purification and into the pcDNA3.1 vector for in vitro transcription/translation experiments.

$^{35}$S Methionine-labeled proteins were synthesized using Promega TNT rabbit reticulocyte lysate system as instructed by the manufacturer. GST-fusion proteins were prepared by growing bacterial BL21 (DE3)pLysS cells harboring the expression vector to an $OD_{595}$ of ~0.6 and then inducing the expression of the fusion protein with 0.2 mM IPTG for 12 hours at 15° C. Cells were harvested by centrifugation and lysed in the PBS buffer via sonication. Following centrifugation of the lysate, supernatant was incubated with Glutathione Sepharose resin (Amersham). Bound proteins were washed extensively using PBST buffer (PBS buffer with 1% Triton-X100) and eluted in PBST containing 20 mM reduced glutathione. Eluted proteins were dialyzed against buffers containing 50 mM Tris-HCl (pH 7.5), 100 mM NaCl, 1 mM DTT, and 15% glycerol and were stored at −80° C.

10 μg of the purified GST fusion protein was incubated with 5 μl $^{35}$S Methionine-labeled proteins in PBST (0.5% Triton-X100) at 4° C. for one hour. 10 μl of Glutathione Sepharose resin were then added to each reaction and allowed to equilibrate with the proteins at 4° C. for one additional hour. The resin was washed 3 times (10 minutes each) with PBST (1% Triton-X100) and the bound proteins were eluted with sample buffer and resolved on a 10% SDS-Polyacrylamide gel, which was then fixed and dried before being subjected to Phosphorimager analysis.

For plasmid cleavage assays, recombinant proteins were incubated with 1}1 g of plasmid DNA in 20 mM HEPES (pH 1.5), 10 mM KCl, 3 mM MgCl2, and 0.5 mM DTT for 0.5-1.5 ills at 31 C and reactions were resolved on 1% or 1.5% agarose gels. For example, an appropriate amount of purified protein was incubated with 1 μg of plasmid DNA in 20 mM HEPES (pH7.5), 10 mM NaCl, 3 mM MgCl$_2$, 1 mM DTT, 1 mM CaCl$_2$ and 2% glycerol at 37° C. for 2 hours. The reactions were then resolved on a 1.5% agarose gel and visualized with ethidium bromide.

The number of cell corpses in the head region of living *C. elegans* embryos and the number of extra cells in the anterior pharynx of L3-stage hermaphrodites were counted using Nomarski optics as previously described in Parrish et al. 2001.

TUNEL assays were carried out as described previously in Parrish et al. (2001) using an in situ cell death detection kit obtained on commercial order from Roche.

Early *C. elegans* embryos (one to four cell stage) were mounted on slides with agar pads in M9 and coverslips were sealed with mineral oil. Images in a 15 micron z series (1 micron/each layer) were captured every thirty seconds for 500 minutes using a Leica Nomarski microscope equipped with a Cohu CCD camera and Scion image 1.62c software. Images were compiled into a viewable 4D movie using a 4D Turnaround software and viewed using 4D Viewer.

Cell corpses in the head region of embryos or larvae and extra cells in anterior pharynges of L3 hermaphrodites were scored using the Nomarski optics. PLM survival was scored in the presence of an integrated array, bzIs8, using a Nomarski microscope equipped with epifluorescence. CRN-1 proteins (wild-type or mutant) or the CPS-6 protein were expressed under the control of the mec-7 promoter (S5) to assay their killing activities.

Germline transformation experiments were carried out as described in C. C. Mello, J. M. Krame, D. Stinchcomb, V. Ambros, *EMBO J.* 10, 3959 (1992). Constructs were injected into host strains (5-50}µg/ml) with pRP4 (50}µg/ml) as a co-injection marker.

Standard procedures following J. Sambrook, Fritsch, E. F., and Maniatis, T., *Molecular Cloning: A Laboratory Manual*, Cold Spring Harbor Laboratory Press, Cold Spring Harbor, N.Y., ed. 2nd, (1989) were used for plasmid construction and a Quick-change mutagenesis kit (Stratagene) was used to generate mutations. To generate P$_{crn-1}$crn-1:: gfp, the entire crn-1 coding region with 3491 bp of 5' untranslated region was Polymerase Chain Reaction (PCR) amplified using an expand long template PCR kit (Roche) and then subcloned into pPD95.77 via its Sph I and Sal I sites.

Recombinant His$_6$CPS-6, CRN-1-His$_6$, or GST-CRN-1 proteins were expressed in *E. coli* BL21(DE3)pLysS strain and purified using similar procedures as described in J. Parrish, H. Metters, L. Chen, D. Xue, *Proc. Natl. Acad. Sci. U.S.A.* 97, 11916 (2000).

For flap endonuclease assays, three oligonucleotides were annealed to generate a flap substrate, following the procedure of J. J. Harrington, M. R. Lieber, *EMBO J.* 13, 1235 (1994). These designations apply:

FLAP (5' gatgtcaagcagtcctaactttgaggcagagtcc 3'), SEQ ID NO. 52

FLAP-Br (5' ggactctgcctcaagacggtagtcaacgtg 3'), SEQ ID NO. 53 and

FLAP-Adj (5' cacgttgactaccgtc 3') SEQ ID NO. 54.

For exonuclease and gap-dependent endonuclease assays, these designations apply:

FLAP-Br long (5' ggactctgcctcaagacggtagtcaacgtggtgtg 3') SEQ ID NO. 55, and

FLAP-Blunt (5' cttgaggcagagtcc 3') SEQ ID NO. 56.

FLAP-Br long and FLAP-Blunt were annealed to generate a double-strand substrate with a 5' recessive end. FLAP 3' AS (5'cacaccacgttgactaccgt 3') SEQ ID NO. 57 or its derivatives with 1, 2 or 4 fewer nucleotides at the 3' end were annealed with FLAP-Br long and FLAP-Blunt to generate double stranded substrates with a nick or various single-stranded gaps. Prior to annealing, one of the oligonucleotides was either 5'-end labeled with ?-$^{32}$P-ATP using T4 polynucleotide kinase or 3'-end labeled with a-$^{32}$P cordycepin-5'-triphosphate using terminal deoxynucleotide transferase and subsequently purified on 1 M urea-polyacrylamide gels. For each substrate, 2 pmol of unlabeled oligonucleotides were mixed with 50 nmol of labeled oligonucleotides in 10 mM Tris (pH8.0), 50 mM KCl, and 1 mM EDTA, heated to 80 C, and slowly cooled to 25 C to facilitate annealing. Annealing efficiency was monitored on 5% non-denaturing polyacrylamide gels. Nuclease assays were carried out in 50 mM Tris (pH8.0), 5 mM MgCl$_2$, 0.5 mM B-mercaptoethanol, and 0.1 µg/ml BSA. 100 fmol of the labeled substrate was incubated with 0.2 µl of the indicated protein (synthesized using Promega TNT coupled reticulocyte lysate system). Reactions were incubated at 30 C for 45 minutes, resolved on 1M Urea/15% polyacrylamide gels, and analyzed using a phosphorimager (Molecular Dynamics).

Example 2

RNAI Screening to Identify Cell-Death Related Nucleases (CRN)

*C. elegans* deoxyribonucleases and ribonucleases were tested as well as cyclophilins and topoisomerases for potential roles in apoptotic DNA degradation. Bioinformatic systems used for the initial screening included INTERPRO and PFAM motif searches, for example, as described generally by Apweiler, R., Attwood, T. K., Bairoch, A., Bateman, A., Birney, E., Biswas, M., Bucher, P., Cerutti, L., Corpet, F., Croning, M. D., et al., *The InterPro database, an integrated documentation resource for protein families, domains and functional sites*. Nucleic Acids Res. 29, 37-40 (2001); and Sonnhammer, E. L., Eddy, S. R., and Durbin, R., *Pfam: a comprehensive database of protein domain families based on seed alignments*. Proteins 28, 405-420 (1997).

The search identified a total of 77 Open Reading Frames (ORFs) in the search categories. RNAi experiments on these 77 ORFs were conducted in three different genetic backgrounds, wild-type (N2), the cps-6(sm116) mutant, and/or the nuc-1(e1392) mutant, to identify an increase or decrease of TUNEL staining in these RNAi-treated animals versus control animals treated by RNAi. Table 1 shows the results of observations in the test population documenting twenty one instances of embryonic lethality, hermaphrodite sterility, and/or developmental defects in the test population.

TABLE 1

ORFs screened and their respective RNAi phenotypes

| Gene | Locus | Homology | Emb[a] | Ste[b] | ev[c] |
|---|---|---|---|---|---|
| | | Deoxyribonucleases | | | |
| AH9.2 | crn-4 | 3'-5' exonuclease | | | |
| B0432.8 | | TatD-related DNase | | | |
| C05C8.5 | | exonuclease | | | |
| C06A1.6 | | endonuclease III | | | |
| C07B5.5 | nuc-1 | DNaseII-like | | | |
| C08B6.6 | | | | | |
| C10G6.1 | | 3'-5' exonuclease | | | |
| C14A4.4 | crn-3 | 3'-5' exonuclease with HRDC domain | +/− | +/− | Gro |
| C41D11.8 | cps-6 | DNA/RNA non-specific endonuclease | | | |
| CD4.2 | crn-2 | TatD-related DNase | | | |
| F09G8.2 | yls-2 | DNaseII-related | | | |
| F10C2.4 | | DNA polymerase, exonuclease domain | + | + | |
| F10G7.2 | | Staphylococcal nuclease-like | | | |
| F21E9.1 | | AP-endonuclease | + | | |
| F31E3.4 | | Exonuclease, Ub. C-terminal hydorlase | | | |
| F33H2.5 | | DNA polymerase exonuclease domain | + | + | |
| F45G2.3 | | XPG-related nuclease | | | |
| F57B10.6 | | 5'-3' exonuclease, XPG-related | | | |
| H19N07.4 | | Endonuclease, O-acetyltransferase | | | |
| K04F10.5 | | AP-endonuclease | | | |
| K04H4.6a | crn-6 | DNase-II-related | | | |
| K05G3.1 | | 3'-5' exonuclease | | | |
| M02B7.2 | | exonuclease | | | |
| R02D3.8 | | exonuclease | | | |
| R09B3.1 | exo-3 | AP-endonuclease | | | |
| R10E4.5 | | Endonuclease III, HhH-GPD base-excision repair | | | |
| R11E3.3 | | AP-endonuclease | | | |
| T05H10.2 | apn-1 | AP-endonuclease | | | |
| T07A9.5a | | Exonuclease, SAP domain | | | |
| T12A2.8 | | 5'-3' exonuclease, XPG-related | | | |
| W05H12.2 | | 3'-5' exonuclease | | + | Gro |
| Y17G7B.12 | | exonuclease | | | |
| Y24F12A.1 | | TatD-related DNase | | | |
| Y37H2A.1 | | TatD-related DNase | | | |
| Y47D3A.29 | | DNA polymerase exonuclease domain | + | + | Lva |
| Y47G6A.8 | crn-1 | 5'-3' exonuclease, endonuclease, XPG-related | | + | Gro |
| Y56A3A.33 | | exonuclease | | | |
| Y57A10A.13 | | 3'-5' exonuclease | + | + | |
| Y63D3A.4 | | AP-endonuclease | | | |
| ZC302.1 | mre-11 | DNA repair exonuclease | | | |
| | | Ribonucleases | | | |
| B0564.1 | | 3'-5' exoribonuclease | | | |
| BE0003N10.1 | | 3'-5' exoribonuclease | | | |
| C04G2.6 | | Ribonuclease II | | +? | Sck, Sma |
| C14A4.5 | crn-5 | 3'-5' exoribonuclease | | | Gro |
| F31D4.1 | | 3'-5' exoribonuclease | | | Gro |
| F37C12.13 | | 3'-5' exoribonuclease | | | Lva |
| F48E8.6 | | Ribonuclease II | | | |
| K10C9.3 | | Ribonuclease T2 | | | |
| T13H5.7 | | Ribonuclease HII | | | |
| Y6D11A.1 | | 3'-5' exoribonuclease | | | Sck, Sma |
| ZK1098.3 | | Ribonuclease-D | | | |
| ZK1098.8 | mut-7 | Ribonuclease-D | | | |
| | | Cyclophilins[d] | | | |
| B0252.4 | cyp-10 | Peptidyl-prolyl cis-trans isomerase | | | |
| C34D4.12 | cyp-12 | Peptidyl-prolyl cis-trans isomerase | | | |
| D1009.2 | cyp-8 | Peptidyl-prolyl cis-trans isomerase | | | |
| F31C3.1 | cyp-5 | Peptidyl-prolyl cis-trans isomerase | | | |
| F39H2.2 | cyp-14 | Peptidyl-prolyl cis-trans isomerase | | | |
| F42G9.2 | cyp-6 | Peptidyl-prolyl cis-trans isomerase | | | |
| F59E10.2 | cyp-4 | Peptidyl-prolyl cis-trans isomerase | | | |
| T01B7.4 | cyp-11 | Peptidyl-prolyl cis-trans isomerase | +/− | | Gro |
| T27D1.1 | cyp-9 | Cyclophilin-related | | | |
| Y116A8C.34 | cyp-13 | Peptidyl-prolyl cis-trans isomerase | | | |
| Y17G7B.9 | cyp-16 | Peptidyl-prolyl cis-trans isomerase | | | |
| Y17G9B.4 | | Peptidyl-prolyl cis-trans isomerase | | | |
| Y49A3A.5 | cyp-1 | Peptidyl-prolyl cis-trans isomerase | | | |
| Y75B12B.2 | | Peptidyl-prolyl cis-trans isomerase | | +? | |
| Y75B12B.5 | cyp-3 | Peptidyl-prolyl cis-trans isomerase | | | |

TABLE 1-continued

ORFs screened and their respective RNAi phenotypes

| Gene | Locus | Homology | Emb[a] | Ste[b] | ev[c] |
|---|---|---|---|---|---|
| Y87G2A.6 | cyp-15 | Peptidyl-prolyl cis-trans isomerase | | | |
| ZC250.1 | cyp-17 | Peptidyl-prolyl cis-trans isomerase | | | |
| ZK520.5 | cyp-7 | Peptidyl-prolyl cis-trans isomerase | | | |
| | | Topoisomerases | | | |
| F31E8.6 | | Topoisomerase II | + | + | |
| F32A11.4 | | Topoisomerase II | | | |
| F32A11.5 | | Topoisomerase II | | + | |
| R05D3.1 | | Topoisomerase II | | | |
| Y42G9A.1 | | Topoisomerase II | | | Sck |
| Y46H3C.4 | | Topoisomerase IV | + | | |
| Y48C3A.14 | | Topoisomerase I | + | | |
| ZK1127.7 | | Topoisomerase II | + | | |

[a]F1 progeny of RNAi-treated hermaphrodites were examined for potential embryonic lethality (Emb) phenotypes which are classified as follows: "+/−" denotes less than 25% penetrance of embryonic lethality phenotype and "+" denotes more than 25% penetrance of embryonic lethality phenotype.
[b]F1 progeny of RNAi-treated hermaphrodites were examined for sterility (Ste) phenotypes and "+/−" or "+" denotes Ste phenotype with less than or more than 25% penetrance, respectively.
[c]P0 and F1 progeny of RNAi-treated hermaphrodites were monitored for a number of developmental defects (DEV) including dumpy (Dpy), uncoordinated (Unc), slow growth (Gro), larval arrest (Lva), sick (Sck), small (Sma), and long (Lon). Those that display more than 25% penetrance of these phenotypes are listed.
[d]Sequence for cyp-2 not available.

The RNAi treatment in the case of nine ORFs gave rise to TUNEL phenotypes that were indicative of involvement in apoptotic DNA degradation. As will be explained in greater detail below, the CRN nucleases have apoptotic activity, as illustrated in FIG. 1 and shown in Table 2 which show the results of TUNEL assays that provide an initial confirmation of CRN nuclease activity. Two of the ORFs, namely, C07B5.5 (nuc-1) and C41D11.8 (cps-6), were previously known to function in DNA degradation, demonstrating the effectiveness of the screen in comparison to other reports including Parrish et al. (2001); Sulston, J. E., *Post-embryonic development in the ventral cord of Caenorhabditis elegans*. Philos. Trans. R. Soc. Lond. B. Biol. Sci. 275, 287-297 (1976); and Wu, Y. C., Stanfield, G. M., and Horvitz, H. R., *NUC-1, a Caenorhabditis elegans DNase II homolog, functions in an intermediate step of DNA degradation during apoptosis*. Genes. Dev. 14, 536-548 (2000).

FIG. 1 shows 9 apoptotic nucleases identified from the *C. elegans* genome. The 77 ORFs screened for TUNEL phenotypes following RNAi treatment were categorized based on their chromosomal positions (Linkage Group; X-axis) and plotted according to the numbers of TUNEL-positive nuclei (on average) detected in 1.5-fold wild-type embryos (N2) treated with RNAi (Y-axis). RNAi of 68 ORFs (gray circles) resulted in TUNEL phenotypes that were not significantly different from that of N2 animals treated with control (RNAi) (black circle). RNAi of 9 ORFs resulted in significantly higher numbers of TUNEL-positive nuclei, including two genes (cps-6 and nuc-1) previously known to be involved in apoptotic DNA degradation (triangles), six new crn genes (cell death-related nucleases), and cyp-13, which was previously named (all in squares).

The remaining seven ORFs were novel in terms of their apoptotic phenotypes; including six previously uncharacterized genes, as shown in Table 2, and one cyclophilin homologue (cyp-13). RNAi of each of the nine genes led to an accumulation of TUNEL-positive nuclei that could be suppressed by a strong loss-of-function ced-3(n2433) mutation, which blocked most cell death in nematodes according to procedures following Ellis, H. M., and Horvitz, H. R., Genetic control of programmed cell death in the nematode *C. elegans*. Cell 44, 817-829 (1986). Furthermore, RNAi of crn-2 or crn-3 significantly enhanced the TUNEL phenotype of the cps-6(sm116) mutant, indicating that crn-2 and crn-3 function at least partially independently of cps-6, as shown in Table 2. However, double RNAi of crn-2 and crn-3 in N2, cps-6(sm 116), or nuc-1(e1392) animals did not result in a stronger TUNEL phenotype than either RNAi treatment alone. These results show that crn-2 and crn-3 may function in the same pathway to mediate apoptotic DNA degradation. Finally, RNAi of each of the seven new genes enhanced the TUNEL phenotype of nuc-1. These results show that nuc-1 functions in a different DNA degradation process from these seven genes, as shown in Table 2.

TABLE 2

TUNEL analysis of *C. elegans* genes involved in apoptotic DNA degradation

| ORF/Gene | | Strain treated by RNAi | | | | | | |
|---|---|---|---|---|---|---|---|---|
| | | N2 | | ced-3(n2433) | | cps-6(sm116) | | nuc-1(e1392) |
| ORF | Gene | TUNEL | n | TUNEL | n | TUNEL | n | TUNEL | n |
| Control | | 2.3 ± 2.1 | 16 | 0.3 ± 0.6 | 15 | 22.1 ± 2.1 | 15 | 35.2 ± 1.9 | 15 |
| C41D11.8 | cps-6 | 19.9 ± 1.9 | 15 | 1.7 ± 1.3 | 15 | 20.8 ± 2.6 | 15 | 46.7 ± 2.6 | 15 |
| C07B5.5 | nuc-1 | 30.9 ± 3.3 | 25 | 0.7 ± 1.2 | 15 | 43.7 ± 3.1 | 15 | 34.5 ± 1.9 | 15 |

TABLE 2-continued

TUNEL analysis of *C. elegans* genes involved in apoptotic DNA degradation

| ORF/Gene | | Strain treated by RNAi | | | | | | |
|---|---|---|---|---|---|---|---|---|
| | | N2 | | ced-3(n2433) | | cps-6(sm116) | | nuc-1(e1392) |
| ORF | Gene | TUNEL | n | TUNEL | n | TUNEL | n | TUNEL | n |
| Y47G6A.8 | crn-1 | 11.1 ± 2.9 | 10 | 2.1 ± 2.6 | 18 | 21.5 ± 2.9 | 10 | 45.6 ± 3.9 | 10 |
| CD4.2 | crn-2 | 14.3 ± 3.8 | 12 | 0.9 ± 1.1 | 10 | 27.8 ± 2.3 | 16 | 48.9 ± 2.8 | 14 |
| C14A4.4 | crn-3 | 11.8 ± 3.1 | 16 | 0.8 ± 1.2 | 13 | 29.3 ± 2.3 | 10 | 47.4 ± 3.6 | 13 |
| AH9.2 | crn-4 | 10.3 ± 3.5 | 11 | 1.1 ± 0.9 | 12 | 19.3 ± 2.5 | 11 | 45.8 ± 2.5 | 13 |
| C14A4.5 | crn-5 | 13.9 ± 3.4 | 13 | 1.5 ± 1.3 | 13 | 20.0 ± 2.4 | 10 | 42.6 ± 6.6 | 18 |
| K04H4.6a | crn-6 | 11.8 ± 2.9 | 17 | 1.3 ± 1.0 | 10 | 20.6 ± 2.3 | 11 | 44.8 ± 3.1 | 12 |
| Y116A8C.34 | cyp-13 | 17.1 ± 3.5 | 10 | 0.6 ± 0.7 | 16 | 19.8 ± 2.4 | 10 | 49.0 ± 3.4 | 15 |

The TUNEL assays were carried out as previously described in Parrish et al. (2001). TUNEL-reactive nuclei were scored in 1.5-fold stage embryos. "n" indicates the number of embryos scored.

Example 3

Identification of Mammalian Homologues of the CRN Nucleases

Bioinformatic sequence analysis of the crn genes and cyp-13 reveals insightful information regarding their functions, as illustrated in FIGS. 2A through 2F.

Figure 2A:
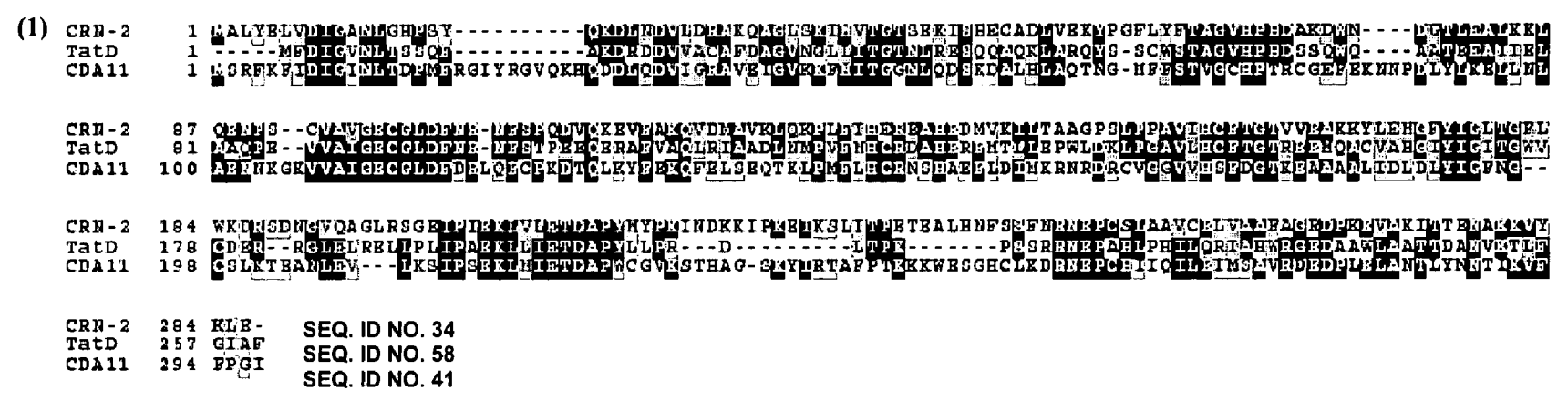
Figure 2B:
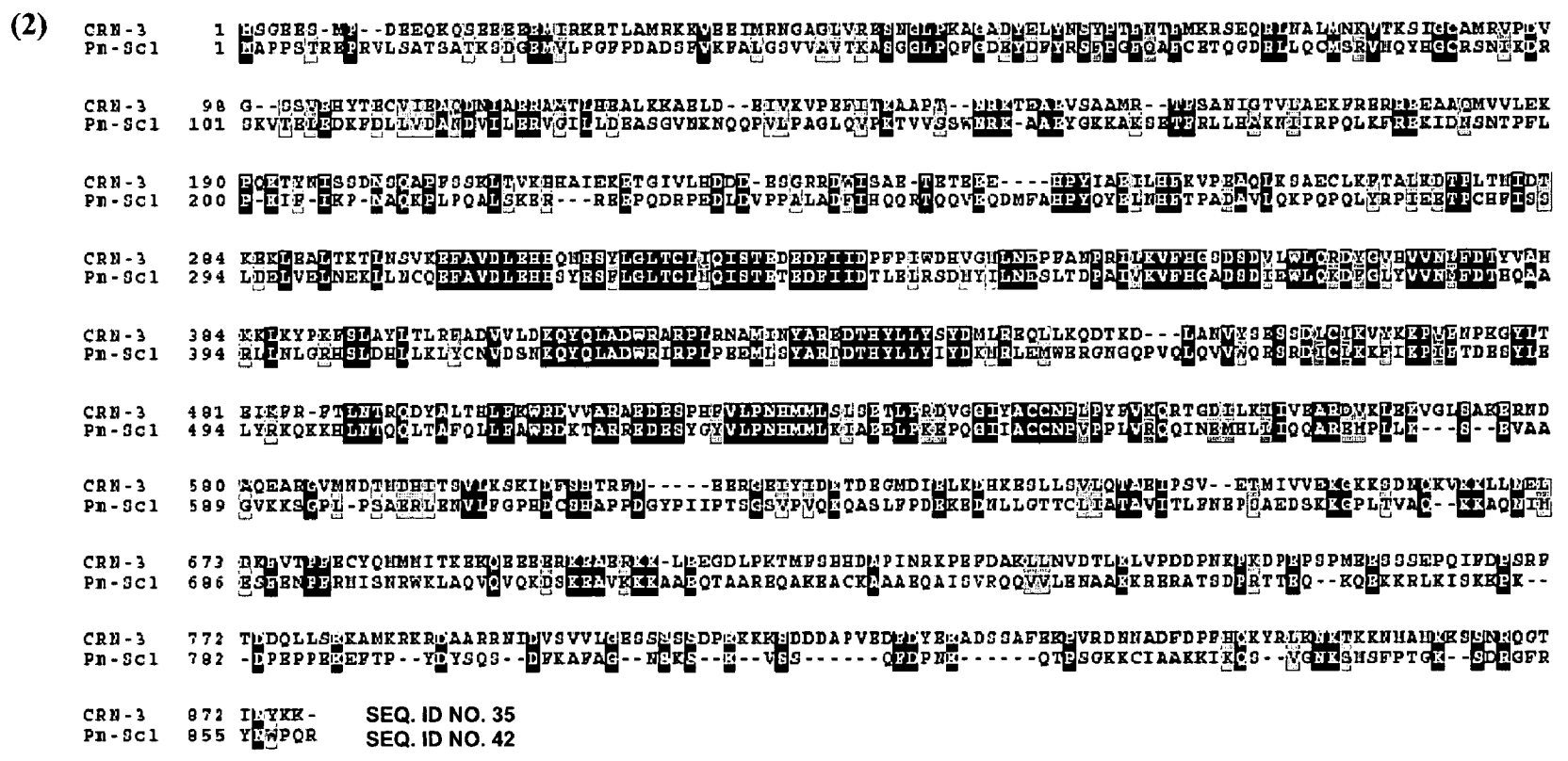
Figures 2C, 2D:
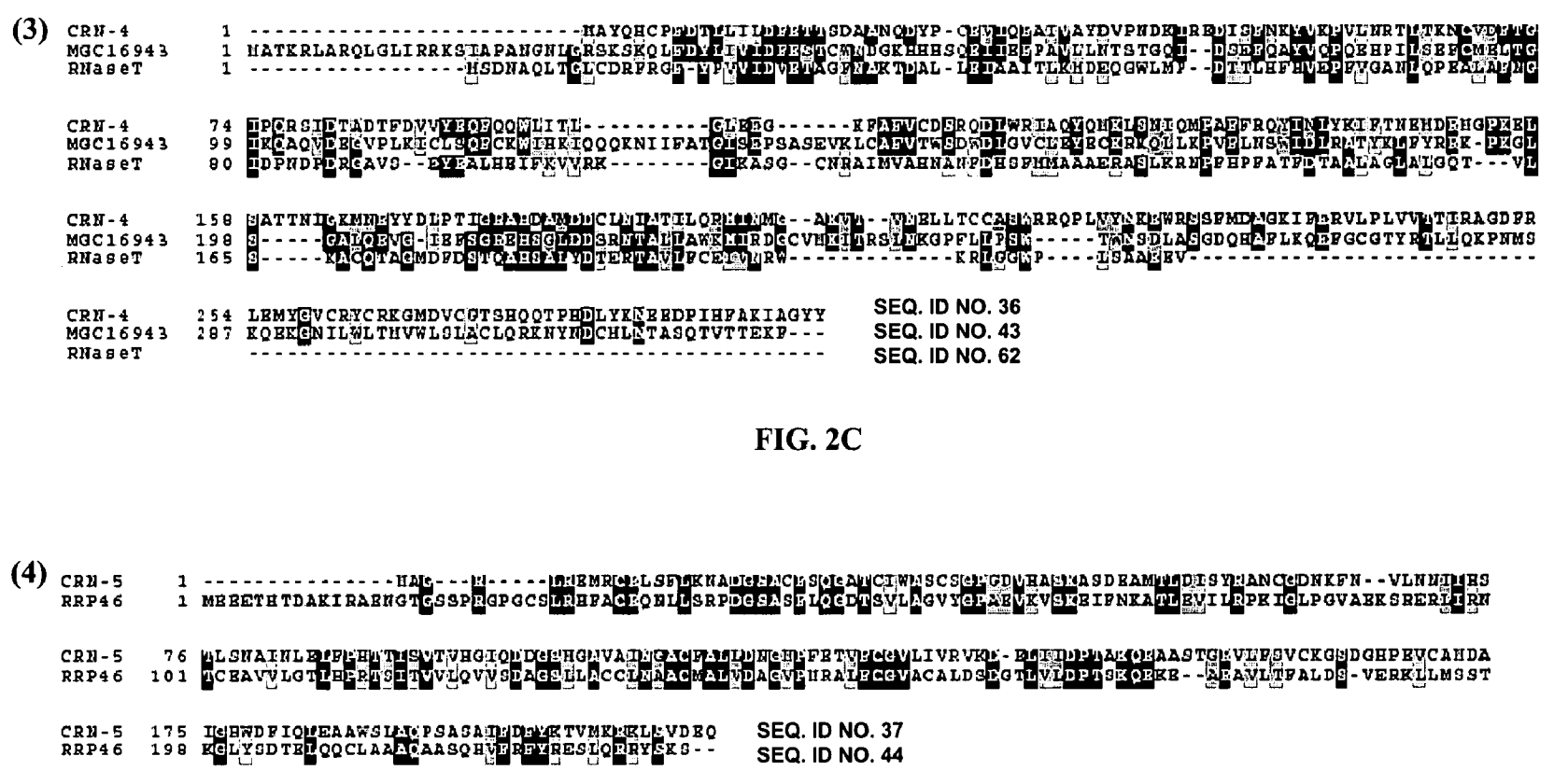
Figures 2E, 2F:
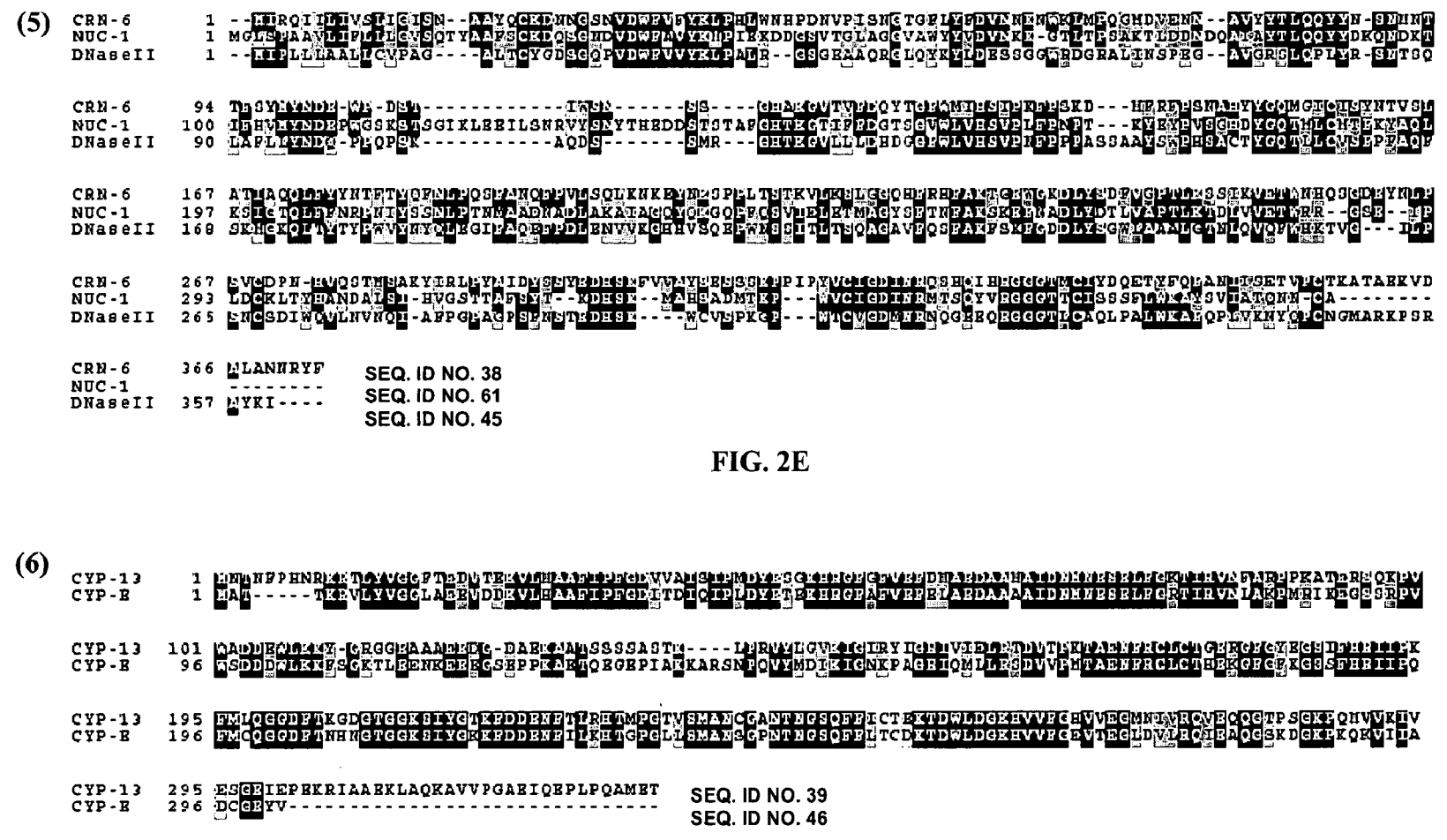

FIG. 2A shows alignment (1) of CRN-2, CDA11, a human protein, and TatD, an *E. coli* nuclease. FIG. 2B shows alignment (2) of CRN-3 and 100 kD human polymyositis/scleroderma autoantigen (PM/SCL). FIG. 2C shows alignment (3) of CRN-4, *E. coli* RNase T, and MGC16943, a predicted human DNA polymerase epsilon subunit. FIG. 2D shows alignment (4) of CRN-5 and human RRP46, an exonuclease component of the exosome. FIG. 2E shows alignment (5) of CRN-6, NUC-1 and human DNase II. FIG. 2F shows alignment (6) of CYP-13 and human cyclophilin E (CYP-E). Primary amino acid sequences of the indicated proteins were aligned using the ClustalW program and shaded using a Boxshade software. Identical residues are shaded in black and conserved residues are shaded in gray.

The crn-1 sequence encodes a homologue of flap endonuclease 1 (FEN-1), which is a mammalian nuclease involved with DNA replication and damage repair, for example, as reported in Harrington, J. J., and Lieber, M. R. *The characterization of a mammalian DNA structure-specific endonuclease.* Embo J. 13, 1235-1246 (1994); and Lieber, M. R. (1997). The FEN-1 family of structure-specific nucleases in eukaryotic DNA replication, recombination and repair. Bioessays 19, 233-240. The apoptotic activity observed in Table 2 for crn-1 may represent a critical switch between DNA replication/repair and apoptotic DNA degradation during apoptosis. crn-1 (RNAi) causes embryonic lethality in *C. elegans*, as shown in Table 1. These results show that crn-1 affects cell survival and, like FEN-1, may be involved in DNA replication/repair in *C. elegans*.

crn-2 encodes a homologue of the TatD nuclease, as shown in FIG. 2A(1). TatD is a poorly characterized *E. coli* magnesium-dependant nuclease previously reported by Wexler, M., Sargent, F., Jack, R. L., Stanley, N. R., Bogsch, E. G., Robinson, C., Berks, B. C., and Palmer, T., *TatD is a cytoplasmic protein with DNase activity. No requirement for TatD family proteins in sec-independent protein export.* J. Biol. Chem. 275, 16717-16722 (2000). Mammalian TatD homologues exist, but have no known function. The present findings support a role for TatD-like nucleases in mammalian apoptosis.

crn-3 and crn-5 encode homologues of the 100 kD polymyositis/scleroderma autoantigen PM/Scl-100 and Rrp46, as shown in FIGS. 2A(2) and 2(4). PM/Scl-100 and Rrp46 have been reported by Brouwer, R., Pruijn, G. J., and van Venrooij, W. J., *The human exosome: an autoantigenic complex of exoribonucleases in myositis and scleroderma*, Arthritis Res. 3, 102-106 (2001). Both PM/Scl-100 and Rrp46 are ribonuclease components of the exosome, which is a multi-exonuclease complex. The exosome functions in processing or degrading several types of RNAs and is crucial for the survival of yeast cells, as reported in Perumal, K., and Reddy, R., *The 3' end formation in small RNAs.* Gene Expr. 10, 59-78. (2002). Therefore, crn-3 and crn-5 appear to be shared components of two different machineries for RNA processing and for apoptotic DNA fragmentation. Both crn-3(RNAi) and crn-5(RNAi) cause retarded growth of treated animals. In the case of crn-3(RNAi), a low penetrance of embryonic lethality was observed and reported in Table 1. These observations are consistent with the potential roles of crn-3 and crn-S in RNA processing as components of the exosome in *C. elegans*, as confirmed by Table 1.

crn-4 is homologous to a family of 3' to 5' exonucleases including ribonuclease T and the epsilon subunit of DNA polymerase III, as shown in FIG. 2A(3). Ribonuclease T and the epsilon subunit of DNA polymerase III are involved in tRNA processing and DNA replication, respectively, as reported in Koonin, E. V., and Deutscher, M. P., *RNase T shares conserved sequence motifs with DNA proofreading exonucleases.* Nucleic Acids Res. 21, 2521-2522 (1993).

Like nuc-1, crn-6 encodes a type II DNase, as shown in FIG. 2A(5). CRN-6 and NUC-1 may function like an acid DNase implicated in degrading DNA from apoptotic cells engulfed by macrophages, as reported McIlroy, D., Tanaka, M., Sakahira, H., Fukuyama, H., Suzuki, M., Yamamura, K., Ohsawa, Y., Uchiyama, Y., and Nagata, S. *An auxiliary mode of apoptotic DNA fragmentation provided by phagocytes*, Genes. Dev. 14, 549-558 (2000).

Finally, cyp-13 is most homologous to mammalian cyclophilin E, as shown in FIG. 2B(6). Both sequences have a putative RNA-recognition motif (RRM) at the amino terminus and a peptidyl-prolyl cis-trans isomerase domain at the carboxyl terminus, where the mammalian sequence has bee observed by Andreeva, L., Heads, R., and Green, C. J., *Cyclophilins and their possible role in the stress response*, Int. J. Exp. Pathol. 80, 305-31 (1999). Cyclophilins have been implicated in apoptotic DNA degradation in mammalian cells, as reported in Montague, J. W., Hughes, F. M., Jr., and Cidlowski, J. A., *Native recombinant cyclophilins A, B, and C degrade DNA independently of peptidylprolyl cis-*

*trans-isomerase activity. Potential roles of cyclophilins in apoptosis*, J. Biol. Chem. 272, 6677-6684 (1997).

Figure 3A:
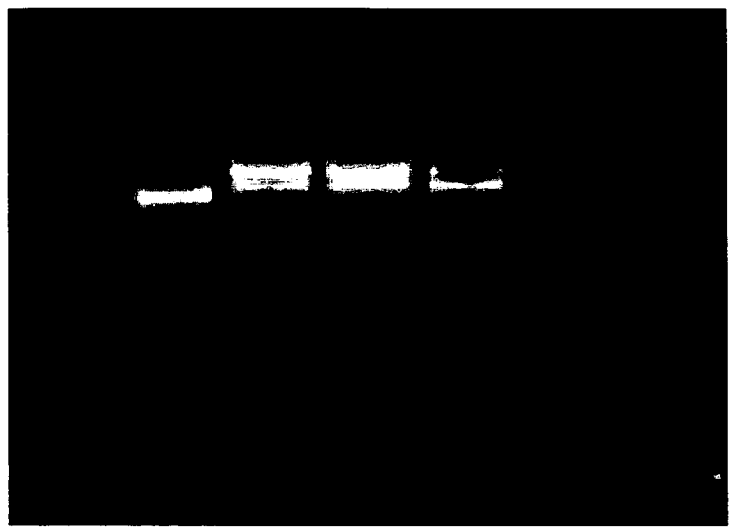
FIG. 3 shows data indicating that CYP-13 but not CYP-1 is a nuclease in vitro.
Figure 3B:
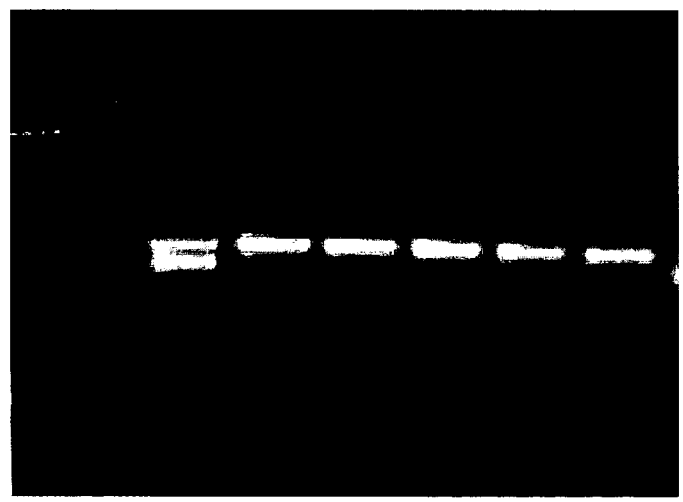

Like some other cyclophilins, CYP-13 is a nuclease in vitro, and may directly mediate DNA degradation, as shown in FIG. 3. Although the function of cyclophilin E is not understood, other cyclophilins have generally been implicated in facilitating cellular protein folding, as discussed in Andreeva et al. (1999). Furthermore, recent studies have shown that cyclophilin E is a component of the human spliceosome, for example, as reported in Zhou, Z., Licklider, L. J., Gygi, S. P., and Reed, R., *Comprehensive proteomic analysis of the human spliceosome*, Nature 419, 182-185 (2002). Therefore, cyp-13 may additionally be involved in RNA splicing in *C. elegans*. In summary, the identification of crn-6 and cyp-13 during the screening process confirms previous observations that their mammalian counterparts are likely involved in apoptotic DNA degradation in vivo and the identification of the other five genes (crn-1 to crn-5) may reveal novel functions for their mammalian homologues in apoptosis.

FIG. 3 shows data indicating that CYP-13 but not CYP-1 is a nuclease in vitro. Increasing concentrations of purified recombinant CYP-13 (A) or CYP-1 (B), another *C. elegans* cyclophilin homologue, were incubated with 1 μl of plasmid DNA at 37° C. for one hour and the reactions were resolved on 1% agarose gels. Bands with slower mobility relative to that of plasmid DNA control represent nicked plasmids.

Example 4

Figure 4A:
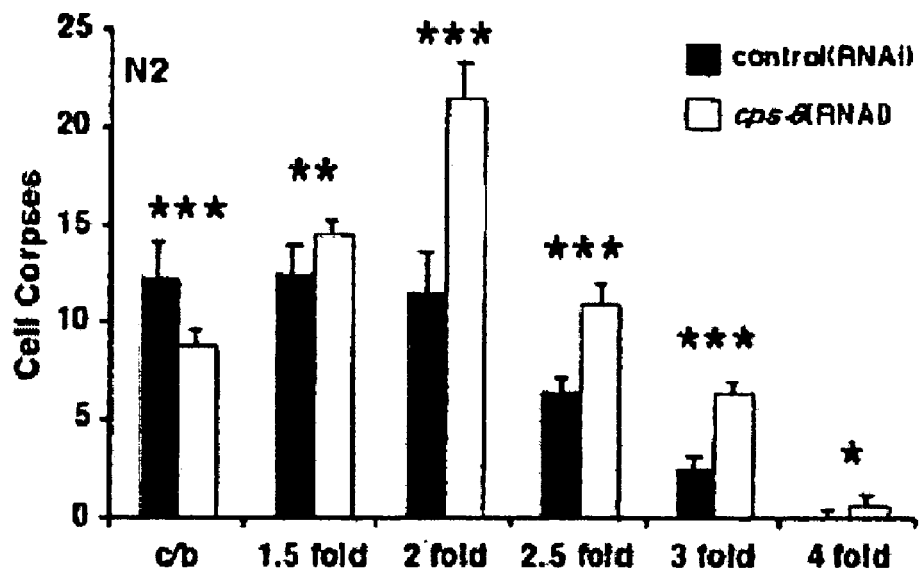
FIGS. 4A through 4J show a time-course analysis of embryonic cell corpses.
Figure 4B:
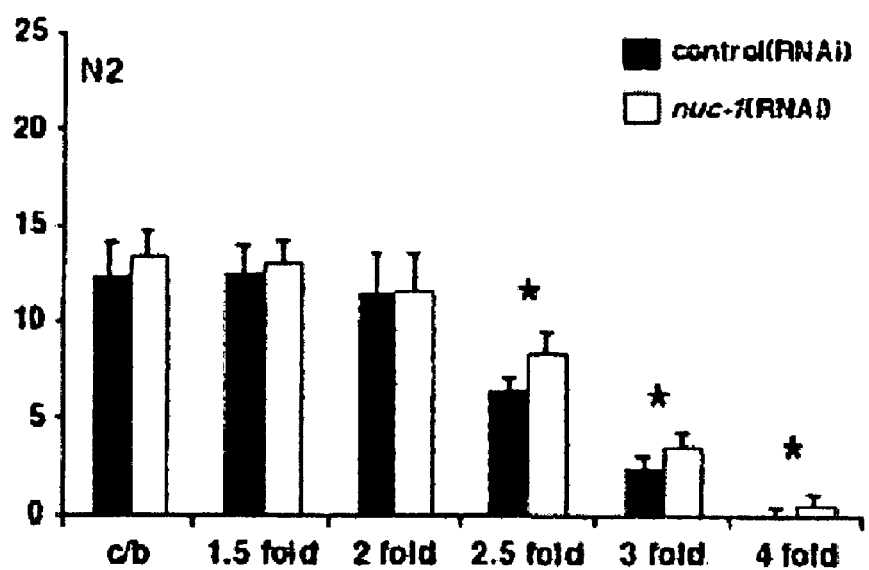
Figure 4C:
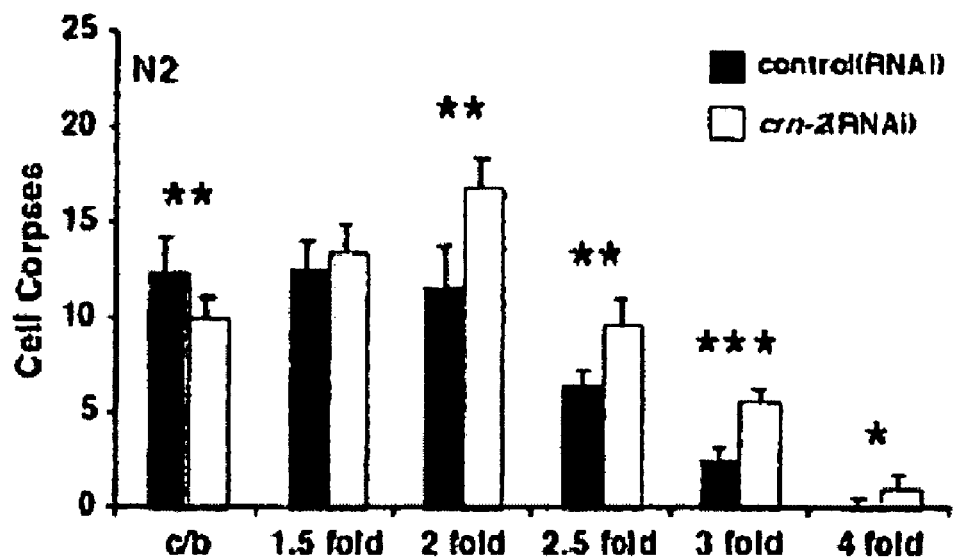
Figure 4D:
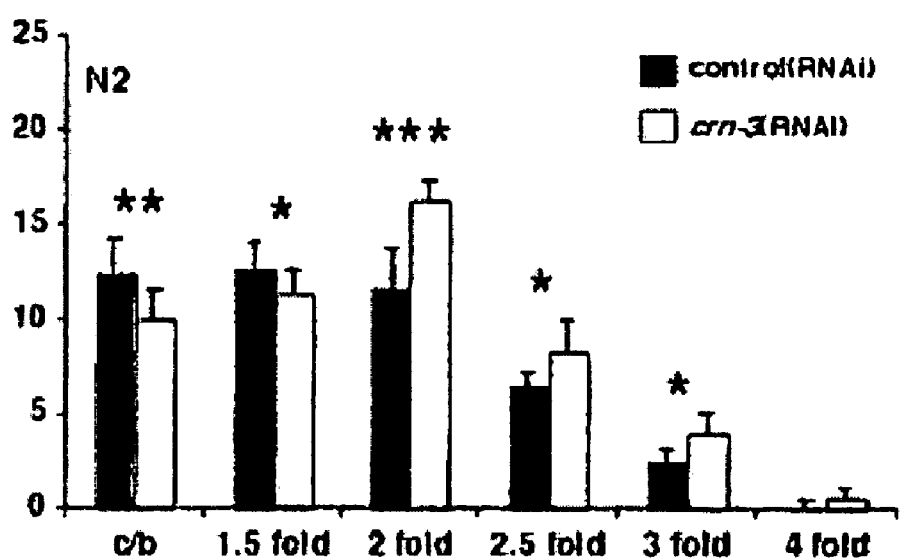
Figure 4E:
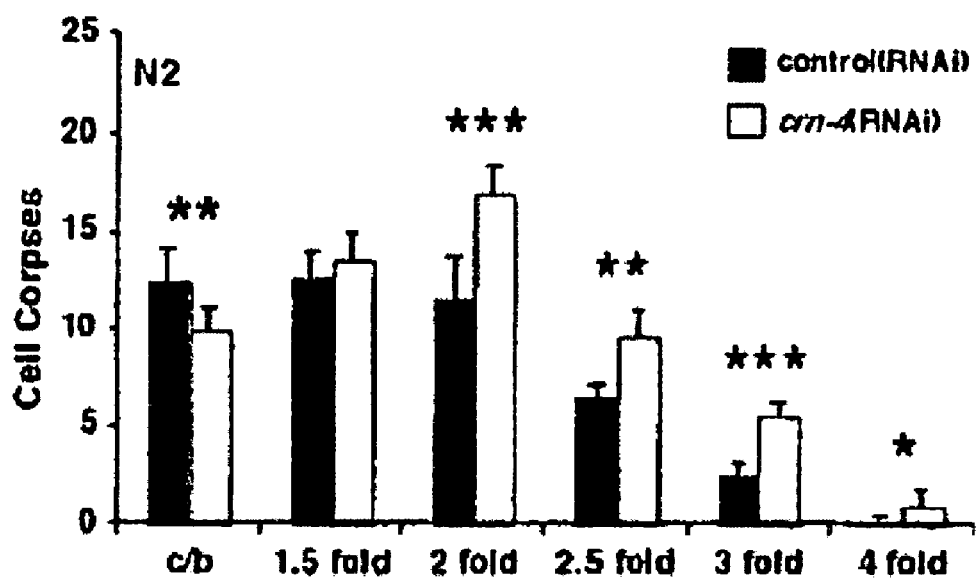
Figure 4F:
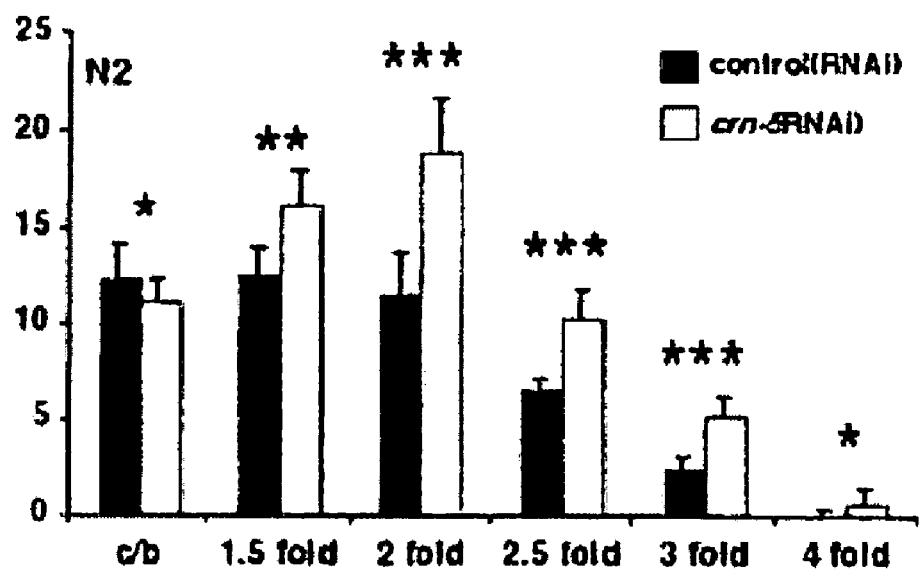
Figure 4G:
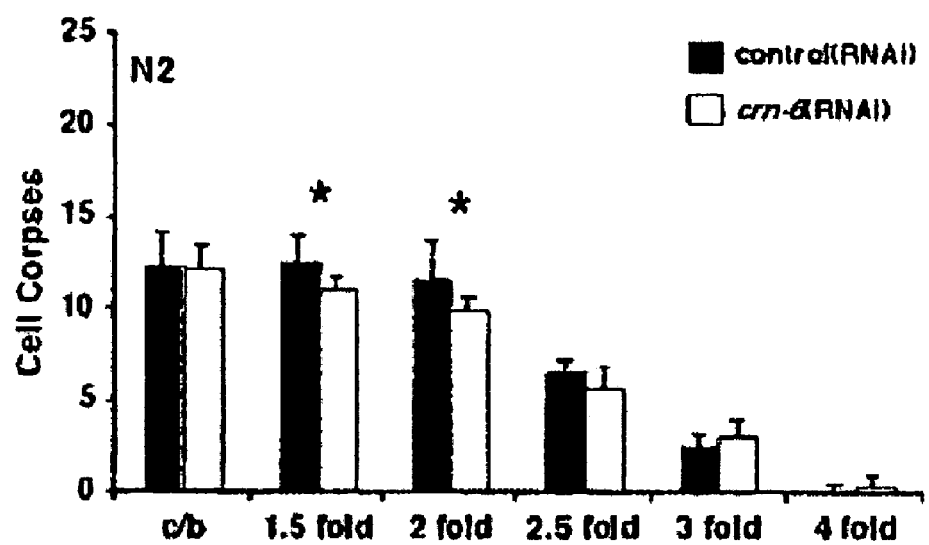
Figure 4H:
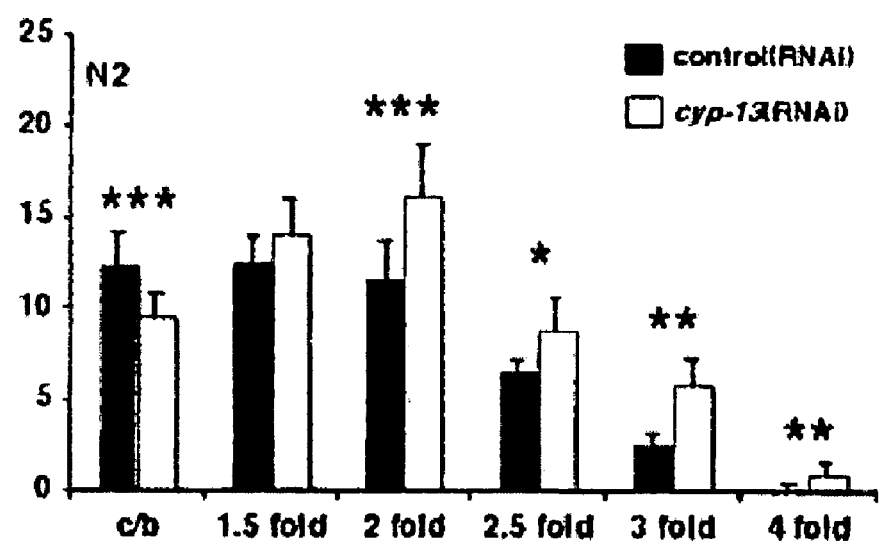

CRN Nucleases Affect Progression of Apoptosis in C. Elegans cps-6 is needed for normal progression of apoptosis, whereas nuc-1 appears dispensable for cell death, as reported in Parrish et al. (2001). Time-course analyses of embryonic cell corpses were conducted to determine whether cyp-13 and the six crn genes affect apoptosis in *C. elegans*, following the procedures of Parrish et al. (2001). RNAi of six genes, namely, crn-1, crn-2, crn-3, crn-4, crn-S and cyp-13, delayed appearance of embryonic cell corpses during development, generating profiles of embryonic cell corpses similar to that of cps-6(RNAi) animals. The peak of embryonic cell corpses shifted from the bean/comma stage in control(RNAi) animals to the 2-fold stage in cps-6 (RNAi)-treated animals (FIG. 4). In contrast, RNAi of four other ORFs (B0438.2, F09G8.2, M02B7.2, and Y57A10A.4) that did not yield any TUNEL phenotype in the screen had no effect on the appearance of embryonic cell corpses in N2 animals (data not shown). Interestingly, crn-6(RNAi), like nuc-1(RNAi), did not change the profile of cell corpses, as shown in FIGS. 4B and 4G. This result shows that crn-6 may be dispensable for apoptosis. Since crn-6 encodes a type-II DNase similar to NUC-1, these two nucleases may play a similar role in DNA degradation.

FIG. 4 shows a time-course analysis of embryonic cell corpses. L1 larvae from N2 (A-H) or cps-6(sm116) (I and J) animals were treated with control(RNAi) or (A) cps-6 (RNAi), (B) nuc-1(RNAi), (C) crn-2(RNAi), (D) crn-3 (RNAi), (E) crn-4(RNAi), (F) crn-5(RNAi), (G) crn-6 (RNAi), (H) cyp-13(RNAi), (I) crn-2(RNAi) or crn-3 (RNAi), or (J) crn-4(RNAi). Cell corpses were scored at six embryonic stages (comma/bean—c/b, 1.5 fold, 2 fold, 2.5 fold, 3 fold, and 4 fold) from progeny of RNAi-treated animals. The Y-axis represents the mean of cell corpses scored at the head region of embryos (at least 15 animals for each developmental stage) and error bars represent one standard error of the mean (S.E.M.). Data derived from control(RNAi) and RNAi treatment of crn genes, cps-6, or nuc-1 at the same stage were compared using unpaired t test.

\* denotes $P<0.05$, \*\* denotes $P<0.002$, and \*\*\* denotes $P<0.0005$. All other points had P values$>0.05$.

crn-6(RNAi) was tested to determine if it could phenocopy or enhance two other DNA degradation defects associated with the nuc-1 mutant. In these results, there was observed a failure to digest DNA of ingested bacteria in the intestine and inability of engulfing cells to degrade DNA derived from postembryonic cell deaths. The postembryonic cell death material existed as pycnotic bodies when stained with fluorescent DNA dye, such as Syto-11 (see Wu et al., 2000). It was determined that neither crn-6(RNAi) nor RNAi of any other crn gene or cyp-13 in either N2 or nuc-1(e1392) animals could phenocopy or enhance these two specific DNA degradation defects of nuc-1 (data not shown), showing that these six crn genes and cyp-13 are likely involved in DNA degradation specific for cell deaths.

Figure 4I:
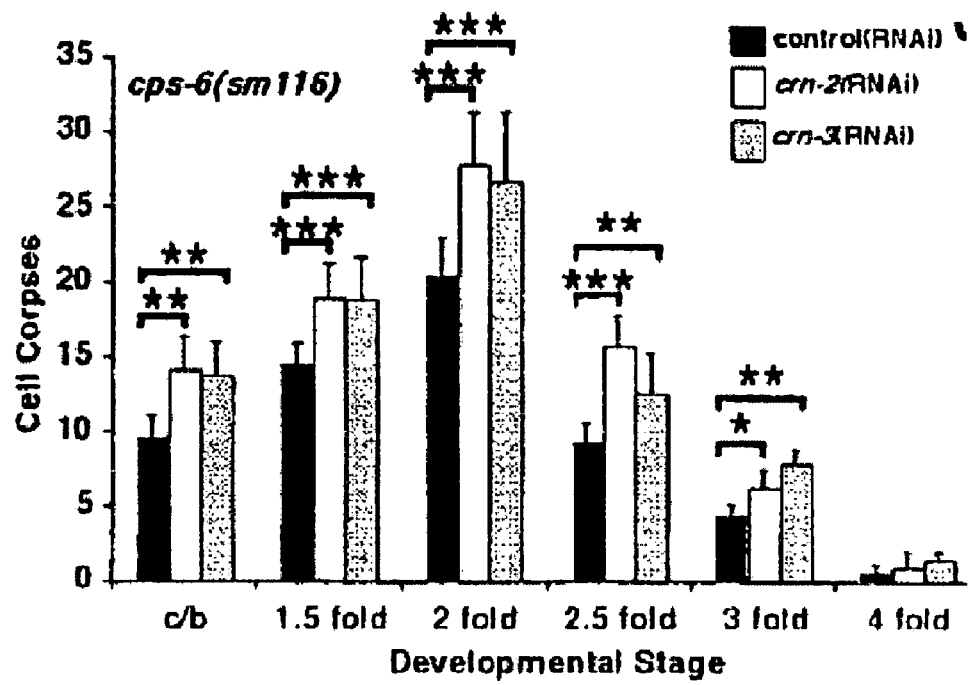
Figure 4J:
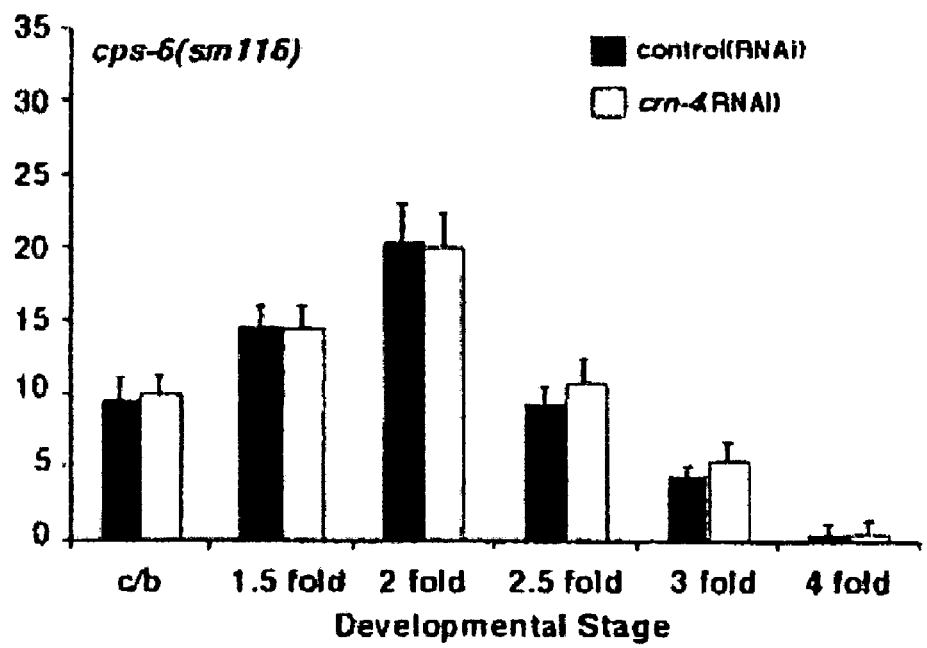

Since crn-2(RNAi) or crn-3(RNAi) enhanced the TUNEL phenotype of the cps-6(sm116) mutant, crn-2/crn-3 and cps-6 appear to function in two independent pathways, as confirmed by the results of Table 2. Intriguingly, more cell corpses were seen at every stage in cps-6(sm116); crn-2 (RNAi) or cps-6(sm116); crn-3(RNAi) embryos than in cps-6(sm116) control(RNAi) embryos, as illustrated in FIG. 4I. These results show that crn-2(RNAi) or crn-3(RNAi), when combined with cps-6(sm116), may impair cell corpse engulfment. RNAi of any other crn gene or cyp-13 did not affect the profile of cell corpse appearance in the cps-6 (sm116) mutant, which is consistent with the findings that some of these genes (crn-1, crn-4, crn-5 and cyp-13) function in the same pathway as cps-6 and some (crn-6 and nuc-1) act at a later stage of DNA degradation as confirmed by FIG. 4J and additional data that is not shown.

Example 5

CRN Nucleases Promote Cell Killing cps-6 promotes cell killing when assayed in sensitized genetic backgrounds, as reported in Parrish et al. (2001). The six crn genes and cyp-13 were similarly screened for cell killing modulation activity. Like the cps-6(sm116) mutation, RNAi of any of the six crn genes or cyp-13 alone has little effect on the deaths of 16 cells that normally occur in the anterior pharynx of animals. These results are observed as a cell count of no or few extra "undead" cells in the assayed region, as reported in Table 3; none of the six crn genes and cyp-13 alone can significantly contribute to cell killing. However, when combined with a weak ced-3(n2438) mutation, RNAi of any of these genes except crn-6 can significantly protect against cell deaths, generating a mean of 2.35 to 2.88 extra "undead" cells, compared with a mean of 1.56 extra cells seen in ced-3(n2438) animals treated with control (RNAi), as shown in Table 3. These observations indicate that five of the six crn genes (except crn-6) and cyp-13 can promote cell killing, just like cps-6.

Contributions of crn-2 and crn-4 to cell killing were examined in additional detail. These two genes act in two different DNA degradation pathways, with crn-4 and cps-6 being in the same pathway and crn-2 acting in a different one. It was determined that crn-2(RNAi), but not crn-4 (RNAi), can further increase the number of extra cells observed in cps-6(sm116); ced-3(n2447) or cps-6(sm116); ced-4(n2273) mutants. Results are shown in Table 3. This is further evidence that crn-2 functions in a different DNA degradation pathway from cps-6 and that the two DNA degradation pathways in nematodes can independently promote cell killing.

TABLE 3

Multiple crn genes and cyp-13 can contribute to cell killing

| Strain[a] | No. scored | Number of extra cells[b] Mean ± s.e.m. | Range | P value[d] |
|---|---|---|---|---|
| N2; control(RNAi) | 16 | 0 | 0 | N/A |
| N2; crn-2 (RNAi) | 17 | 0.06 ± 0.24 | 0-1 | 0.17 |
| N2; crn-3(RNAi) | 19 | 0.05 ± 0.23 | 0-1 | 0.18 |
| N2; crn-4 (RNAi) | 28 | 0.07 ± 0.26 | 0-1 | 0.14 |
| N2; crn-5(RNAi) | 21 | 0.05 ± 0.22 | 0-1 | 0.18 |
| N2; crn-6(RNAi) | 20 | 0 | 0 | N/A |
| N2; cyp-13(RNAi) | 15 | 0.07 ± 0.26 | 0-1 | 0.15 |
| ced-3(n2438); control(RNAi) | 16 | 1.56 ± 0.99 | 0-3 | N/A |
| ced-3(n2438); crn-2 (RNAi) | 17 | 2.88 ± 1.72 | 1-6 | 0.006 |
| ced-3(n2438); crn-3(RNAi) | 15 | 2.47 ± 1.25 | 1-4 | 0.006 |
| ced-3(n2438); crn-4 (RNAi) | 16 | 2.44 ± 1.36 | 0-5 | 0.02 |
| ced-3(n2438); crn-5(RNAi) | 15 | 2.35 ± 1.00 | 1-4 | 0.01 |
| ced-3(n2438); crn-6(RNAi) | 15 | 1.40 ± 0.91 | 0-3 | 0.41 |
| ced-3(n2438); cyp-13 (RNAi) | 15 | 2.53 ± 1.13 | 1-4 | 0.01 |
| cps-6(sm116); ced-3(n2447); control(RNAi)[c] | 16 | 2.63 ± 1.17 | 1-5 | N/A |
| cps-6(sm116); ced-3(n2447); crn-2 (RNAi)[c] | 13 | 3.38 ± 1.56 | 1-6 | 0.07 |
| cps-6(sm116); ced-3(n2447); crn-4 (RNAi)[c] | 15 | 2.67 ± 1.35 | 1-6 | 0.46 |
| cps-6(sm116); ced-4(n2273); control(RNAi)[c] | 17 | 3.65 ± 1.15 | 2-6 | N/A |
| cps-6(sm116); ced-4(n2273); crn-2 (RNAi)[c] | 11 | 4.55 ± 1.57 | 3-7 | 0.05 |
| cps-6(sm116); ced-4(n2273); crn-4 (RNAi)[c] | 15 | 3.80 ± 1.37 | 1-6 | 0.36 |

[a]Control(RNAi) indicates that animals were fed with bacteria containing an expression vector lacking an insert as a negative control.
[b]Extra cells were counted in the anterior pharynx of L3 hermaphrodites using Nomarski optics.
[c]These strains contain dpy-5(e61).
[d]P values were determined using student's t-tests. Data from RNAi-treated animals was compared to the appropriate RNAi control. N/A, not available.

Recently it has been shown that each of the two partially redundant cell corpse engulfment pathways in *C. elegans* independently contributes to cell killing, as reported in Hoeppner, D. J., Hengartner, M. O., and Schnabel, R., *Engulfment genes cooperate with ced-3 to promote cell death in Caenorhabditis elegans*. Nature 412, 202-206 (2001); and Reddien, P. W., Cameron, S., and Horvitz, H. R., *Phagocytosis promotes programmed cell death in C. elegans*, Nature 412, 198-202 (2001). Similarly, it has herein been shown that each of the two DNA degradation pathways represented by crn-2 and cps-6/crn-4 also independently contributes to cell killing. Further investigations were conducted to determine whether defects in both cell corpse engulfment pathways and both DNA degradation pathways could additively affect cell killing. Interestingly, when the functions of both engulfment pathways and both DNA degradation pathways are reduced by mutations or RNAi, for example, in cps-6(sm116); ced-7(n1892); ced-5(n1812); crn-2(RNAi) animals, a mean of 1.2 extra cells were seen, whereas reduction of activity in any of these pathways alone has little effect on cell killing, as shown in Table 4. These results indicate that the cell corpse engulfment and the DNA degradation pathways, and likely other cell death execution pathways, can independently and additively contribute to cell killing.

TABLE 4

DNA degradation and cell corpse engulfment pathways can additively contribute to cell killing

| Strain[a] | No. scored | Number of extra cells[b] Mean ± s.e.m. | Range |
|---|---|---|---|
| cps-6(sm116); control(RNAi) | 18 | 0.06 ± 0.26 | 0-1 |
| ced-5(n1812); control(RNAi) | 20 | 0.07 ± 0.26 | 0-1 |
| ced-7(n1892); control(RNAi) | 25 | 0.12 ± 0.41 | 0-1 |
| N2; crn-2 (RNAi) | 17 | 0.06 ± 0.24 | 0-1 |
| cps-6(sm116); ced-7(n1892); ced-5(n1812); crn-2(RNAi)[c] | 20 | 1.20 ± 0.69 | 0-2 |

[a]Control(RNAi) indicates that animals were fed with bacteria containing an expression vector lacking an insert as a negative control. cps-6 and crn-2 represent two different DNA degradation pathways. ced-5 and ced-7 represent two different cell corpse engulfment pathways.
[b]Extra cells were counted in the anterior pharynx of L3 hermaphrodites using Nomarski optics.
[c]This strain contains dpy-5(e61).

Example 6

Defects in Both DNA Degradation Pathways Affect Cell Corpse Engulfment

The cps-6(sm116) mutation and crn-2(RNAi) or crn-3(RNAi) cause a synthetic defect in cell corpse engulfment, which was verified by four-dimensional cell lineage analyses to examine the average duration of embryonic cell corpses. In N2 animals treated with control(RNAi), embryonic cell corpses persisted 21.9 minutes on average (Table 5). crn-2(RNAi) treatment of N2 animals or the cps-6(sm116) mutation with control(RNAi) did not prolong the persistence of embryonic cell corpses (Table 5). In contrast, crn-2(RNAi) treatment of the cps-6(sm116) mutant prolonged the persistence of embryonic cell corpses by 55%, indicative of a defect in cell corpse engulfment. To rule out the possibility that the observed differences in corpse durations resulted from different rates of development in different animals, the durations of four cell divisions in the MS cell lineage were simultaneously measured following the procedures of Sulston, J. E., Schierenberg, E., White, J. G., and Thomson, J. N., *The embryonic cell lineage of the nematode Caenorhabditis elegans*. Dev. Biol. 100, 64-119 (1983). The durations were found to be similar in all embryos analyzed, as shown in Table 5. These results show a significant, intrinsic connection between the apoptotic DNA degradation process and the cell corpse recognition/engulfment process.

TABLE 5

Inactivation of both cps-6 and crn-2 prolongs the persistence of cell corpses

| Strain | Corpse duration[a] (n) | Duration of Cell Divisions[a,b] |
|---|---|---|
| N2; control(RNAi) | 21.9 ± 3.2 (7) | 85.0 |
| N2; crn-2(RNAi) | 24.5 ± 1.7 (5) | 91.5 |
| cps-6(sm116); control (RNAi) | 23.4 ± 3.4 (7) | 93.0 |
| cps-6(sm116); crn-2(RNAi) | 34.0 ± 4.9 (7) | 91.5 |

[a]Corpse duration and duration of cell divisions are in minutes. At least three animals from each strain were examined and results from one representative animal are shown. "n" indicates the number of cell corpses examined in one embryo.
[b]The duration of four cell divisions in the MS cell lineage from the MS cell to the MSpppp cell (Sulston et al., 1983) was followed in embryos monitored for the duration of cell corpses.

cps-6 and CRN-1, as well as interactions among cps-6, CRN-4, CRN-5, and CYP-13. That these five nucleases may function together, possibly in a large complex along with non-nuclease components, for example, wah-1 as reported by Wang, X., Yang, C., Chai, J., Shi, Y., and Xue, D., *Mechanisms of AIF-Mediated Apoptotic DNA Degradation in Caenorhabditis elegans*, Science 298, 1587-1592 (2002). Complexing promotes apoptotic DNA degradation in vivo. These multi-nuclease complexes may be referred to as the "degradeosome." Only one interaction, namely, that of CRN-3/CRN-5, was identified between proteins functioning in two different DNA degradation pathways. The corresponding mammalian homologues interact in the exosome, as reported in Brouwer et al. (2001), indicating that the complex or interaction may be further implicated in a shared role for RNA processing. No strong interactions were observed between NUC-1 or CRN-6 and proteins acting in either the CPS-6 or CRN-2 pathways, consistent with NUC-1 and CRN-6 functioning in later stages of the DNA degradation process or in their own DNA degradation pathways.

Figure 5:
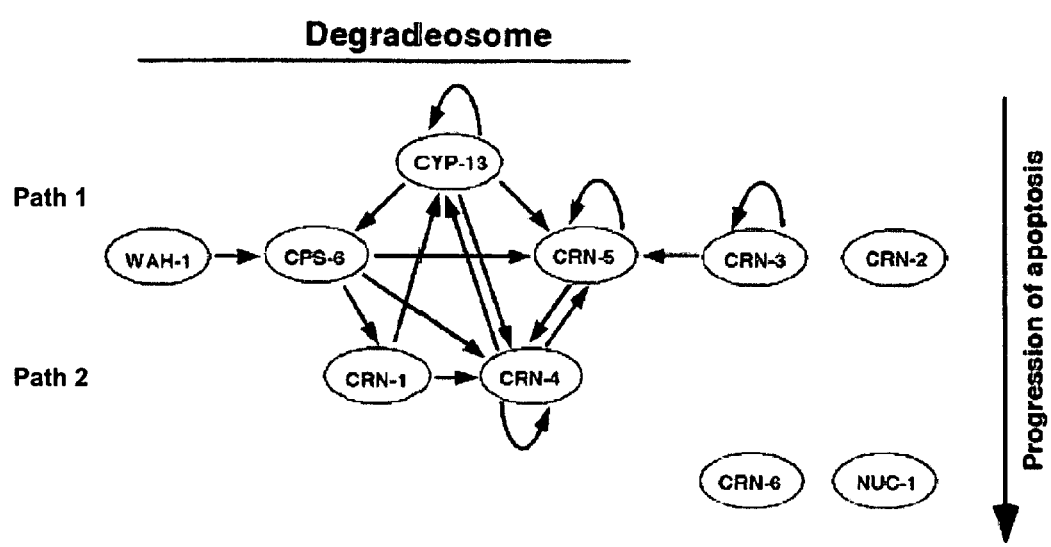
FIG. 5 shows an interaction map for nucleases involved in apoptotic DNA degradation in *C. elegans;*

FIG. 5 shows an interaction map for nucleases involved in apoptotic DNA degradation in *C. elegans*. Interactions between proteins were examined using GST fusion protein pulldown assays. An arrow indicates an interaction between a GST-fusion protein (pointed by the arrow) and a $^{35}$S Methionine-labeled protein. For example, GST-CPS-6 bound $^{35}$S-CYP-13. Only strong protein interactions are depicted. The interaction between cps-6 and wah-1 was described previously (Wang et al., 2002). NUC-1 and CRN-6 likely function at later stages of apoptosis.

Summary of in vitro interactions among CPS-6, NUC-1, CPY-13 and six CRN proteins

| $^{35}$S-Proteins | GST-fusion proteins[a] | | | | | | | | |
|---|---|---|---|---|---|---|---|---|---|
| | GST | CPS-6 | NUC-1 | CRN-1 | CRN-3 | CRN-4 | CRN-5 | CRN-6 | CYP-13 |
| Luciferase | – | – | – | – | – | – | – | – | – |
| CPS-6 | – | – | – | ++ | – | + | + | – | + |
| NUC-1 | – | – | – | – | – | – | – | – | – |
| CRN-1[b] | ++ | ND | ND | ND | ND | ND | ND | ND | ND |
| CRN-2 | – | – | – | – | – | – | – | – | + |
| CRN-3 | – | – | + | – | ++ | – | ++ | – | – |
| CRN-4 | – | ++ | + | + | – | ++ | + | – | – |
| CRN-5 | – | ++ | + | – | – | ++ | ++ | – | ++ |
| CRN-6 | – | – | – | – | – | – | – | – | – |
| CYP-13 | – | ++ | – | + | – | ++ | ++ | – | ++ |

[a]Interactions were evaluated relative to background binding of $^{35}$S-Methionine labeled Luciferase to GST-fusion proteins and $^{35}$S-Methionine labeled proteins to GST. "–" indicates no detectable binding, "+" indicates an interaction consistently observed above background levels, and "++" indicates a strong interaction.
[b]Because $^{35}$S-Methionine labeled CRN-1 binds GST tightly, it was not possible to evaluate interactions between $^{35}$S-CRN-1 and various GST-fusion proteins. ND, not determined.

Example 7

Multiple CRN Nucleases and CPS-6 Likely Interact to Form a DNA Degradation Complex Glutathione-S transferase (GST) fusion protein pull-down assays were performed to investigate how these nine nucleases affect apoptotic DNA degradation and potential protein-protein interactions among the nucleases. A number of in vitro interactions were identified among proteins functioning in the cps-6 pathway, as shown in FIG. 5 and Table 6. These interactions included interactions between Example 8

CRN-1: Assay Investigations Showing FLAP Endonuclease Ortholog Also Functions in Apoptosis Oligonucleosomal fragmentation of chromosomes in dying cells is a hallmark of apoptosis. Little is known about how fragmentation is executed or what cellular components are involved. The present example shows the foregoing going assay methods in use to confirm crn-1 switch functionality of crn-I both as a flap endonuclease and as a fragmentation material. crn-1 is a *C. elegans* homologue of human flap endonuclease 1 (FEN-1). FEN-1 is involved in DNA replication and repair, but is now also shown to be involved in apoptosis.

In summary, reduction of crn-1 activity by RNA interference resulted in cell death phenotypes similar to those displayed by a mutant lacking the mitochondrial endonuclease CPS-6/endonuclease G. CRN-1 localizes to nuclei and can associate and cooperate with CPS-6 to promote stepwise DNA fragmentation, utilizing the endonuclease activity of CPS-6 and both the 5'-3' exonuclease activity and a novel, gap-dependent endonuclease activity of CRN-1. These results show that CRN-1 and/or FEN-1 may play a facilitate switching the state of cells from DNA replication/repair to DNA degradation during apoptosis.

Two nucleases have been implicated in mediating apoptotic DNA degradation in mammals, namely, a 40 kD DNA fragmentation factor with caspase-activated deoxyribonuclease (DFF40/CAD) and mitochondrial endonuclease G (Endo G). DFF40/CAD is activated during apoptosis following caspase cleavage of its cognate inhibitor DFF45/ICAD. DFF40/CAD then associates with nuclear proteins, such as Histone HI and HMG proteins, to promote cleavage of internucleosomal DNA. Endo G is released from mitochondria during apoptosis and translocates to nuclei to mediate DNA fragmentation through a pathway that is independent of caspase and DFF40.

In *C. elegans*, the Endo G homologue is CPS-6. A type II DNase, NUC-I, has been implicated in apoptotic DNA degradation because TUNEL-positive nuclei accumulate in cps-6 or NUC-1 mutants. Additionally, reducing CPS-6 activity delays appearance of embryonic cell corpses and enhances the cell killing defect of other cell death mutants, which shows that CPS-6 may be used in normal progression of apoptosis and can promote cell killing. Since Endo G and/or CPS-6 define a conserved DNA degradation pathway, assays were run to investigate the mechanisms by which CPS-6 or Endo G affects apoptosis.

Figure 6A:
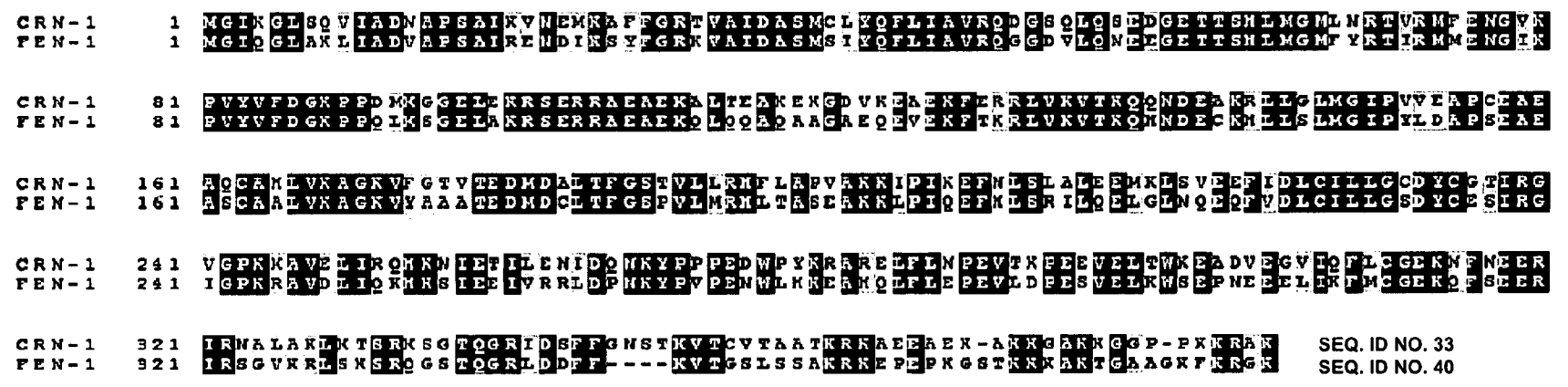
Figure 6B:
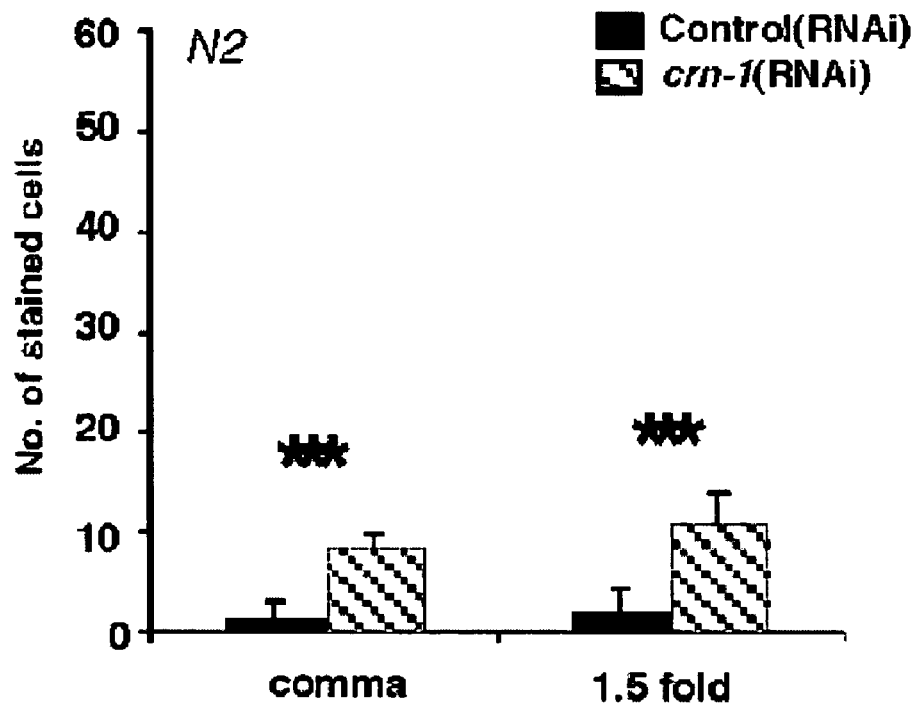
FIGS. 6B to 6E show results from TUNEL assays on *C. elegans* larvae.

FIG. 6A shows a comparison of sequence similarity confirming that crn-1 encodes a FEN-1-like nuclear protein-one that is involved in apoptosis. Alignment of CRN-1 and human FEN-I is shown where black shaded residues are identical and gray shaded residues are similar in two proteins.

FIGS. 6B to E show results from TUNEL assays in which N2 (B), cps-6(sm116) (C), nuc-1(e1392) (D), and ced-3 (n2433) (E) animals were treated with control(RNAi) (filled bars) or crn-1 (RNAi) (hatched bars) and their progeny were stained with TUNEL for examination of comma and 1.5 fold embryos. The y axis represents the mean number of TUNEL-positive cells present in the embryos. At least 12 embryos were scored at each stage.

FIGS. 6F to I show time course analysis of embryonic cell corpses where N2 (F), ced-8(n1891) (G), cps-6(sm116) (H), cps-6(sm116); ced-8(n1891) (I) animals were treated with control(RNAi) or crn-1 (RNAi) and their progeny were scored for cell corpses in comma, 1.5 fold, 2 fold, 2.5 fold, 3 fold, 4 fold stage embryos, as well as early L1 larvae, with at least 15 animals scored for each stage.

FIGS. 6J to M show data derived from control and crn-1(RNAi) treatment at the same stage with a comparison using an unpaired t test. The asterisk * denotes P<0.05,  denotes P<0.002, and * denotes P<0.0001. All other points have P values>0.05. Error bars indicate SEM.

FIGS. 6J to M show nuclear localization of CRN-1. Nomarski results are shown as FIGS. 6J and 6L for a 1.5-fold stage transgenic embryo. Fluorescent results are shown as FIGS. 6K and 6M for L1 transgenic larvae;

CRN-1 is a worm homologue of FEN-1, where the sequence comparison is illustrated in FIG. 6A. CRN-1 may be essential for nematode development; as crn-1 (RNAi)-treated L1 larvae developed normally but laid predominantly dead eggs (95% penetrance. Animals treated at later larval stages, L2 and L3 and thus with reduced exposure to crn-1 (RNAi), had many surviving progeny.

The viable crn-1(RNAi)-treated embryos accumulated TUNEL-positive nuclei. This TUNEL phenotype was suppressed by the ced-3(n2433) mutation, which blocks most *C. elegans* cell deaths. These results indicate that the TUNEL-positive nuclei observed in crn-1(RNAi) embryos correspond to apoptotic cells and that CRN-1 is involved in apoptotic DNA degradation, as confirmed by FIGS. 6B and 6E.

Figure 6C:
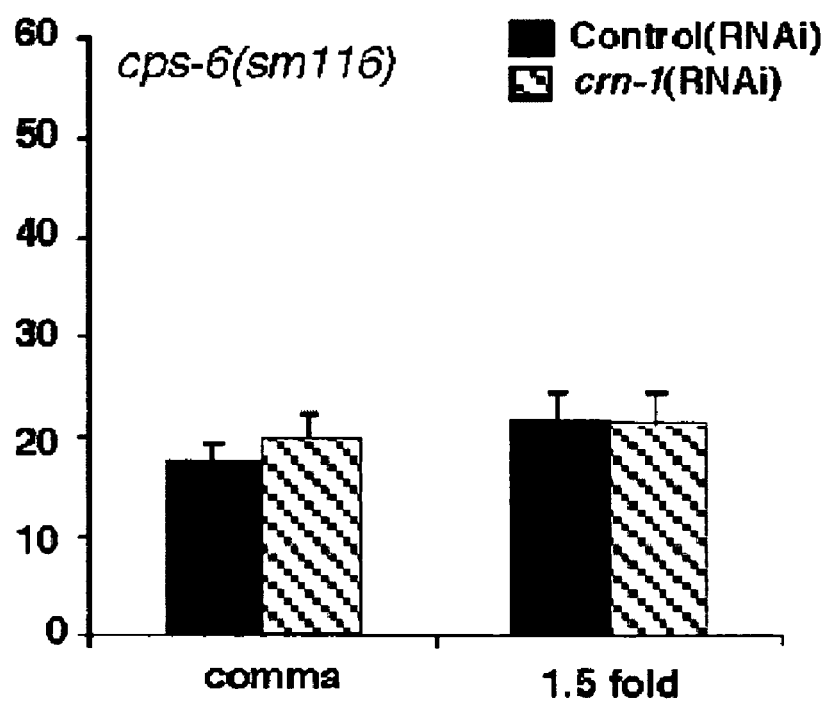
Figure 6D:
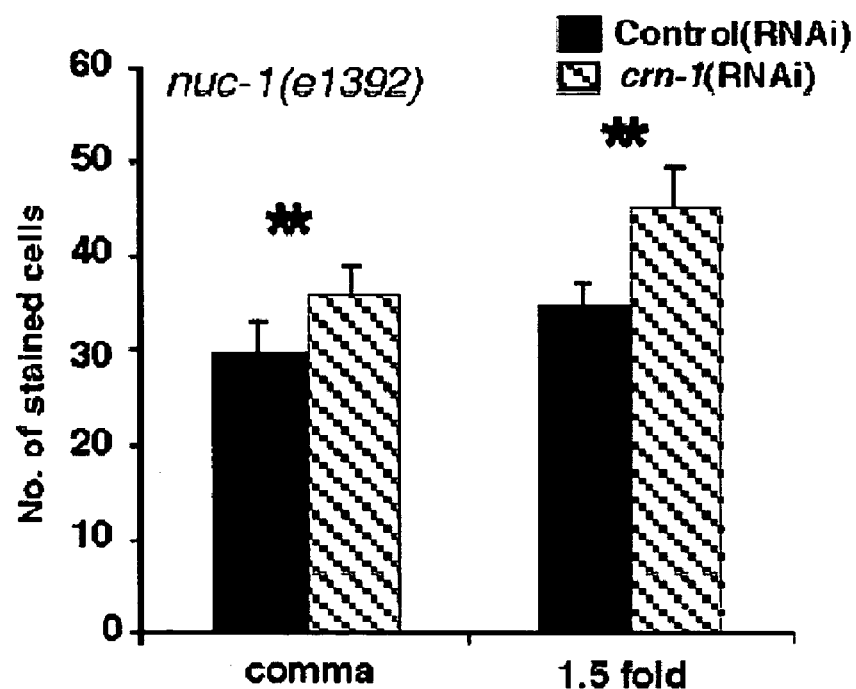
Figure 6E:
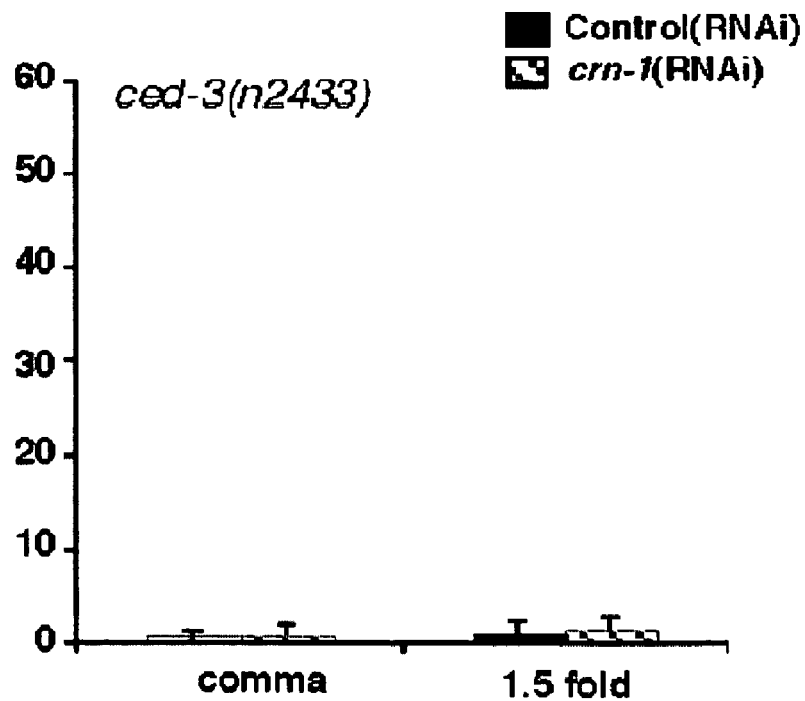

Interestingly, crn-1(RNAi) did not enhance the TUNEL phenotype of the cps-6(sm116) mutant but did so in nuc-1 (e1392) mutants, as shown in FIGS. 6C and 6D. These results show that CRN-1 functions in the same DNA degradation pathway as cps-6, which is different from that of nuc-1.

Figure 6F:
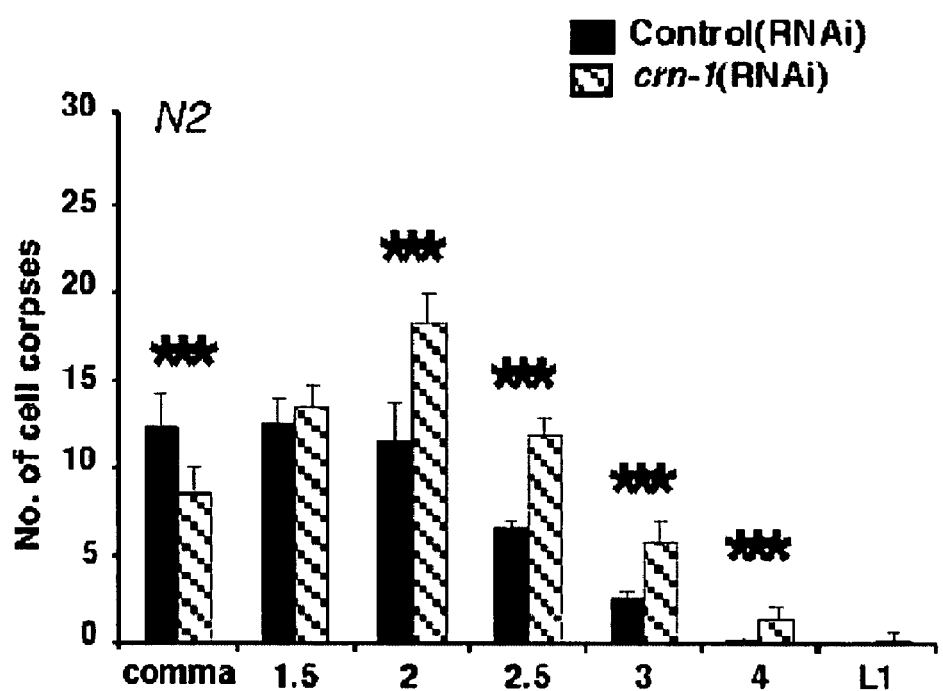
FIGS. 6F to I show time course analysis of embryonic cell corpses where N2 (F), ced-8(n1891) (G), cps-6(sml16) (H), cps-6(sml16); ced-8(n1891) (I) animals were treated with control (RNAi) or crn-1 (RNAi) and their progeny were scored for cell corpses in comma, 1.5 fold, 2 fold, 2.5 fold, 3 fold, 4 fold stage embryos, as well as early L1 larvae, with at least 15 animals scored for each stage.
Figure 6G:
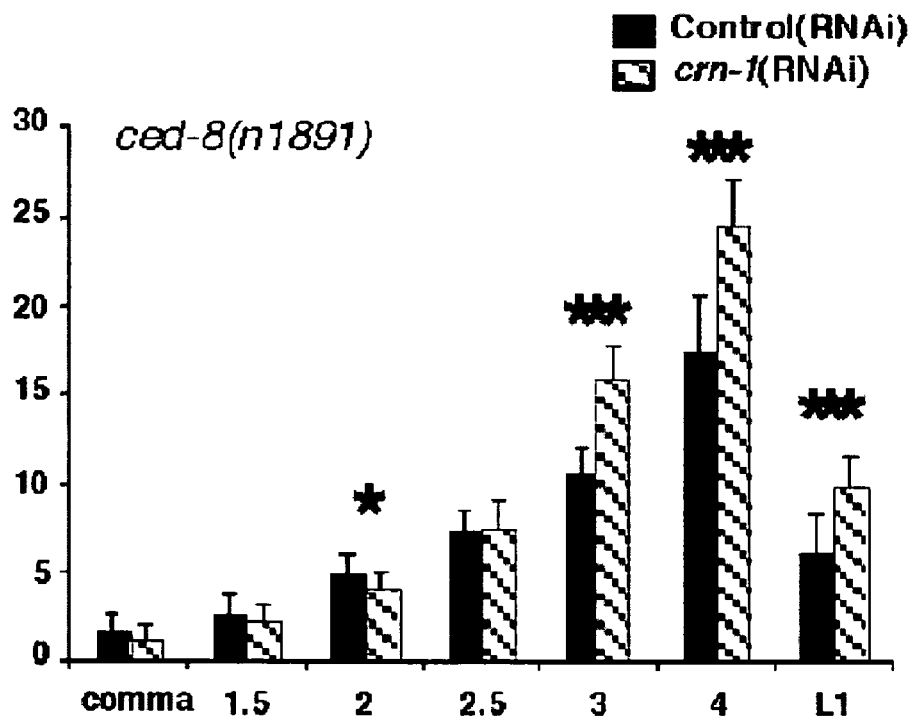
Figure 6H:
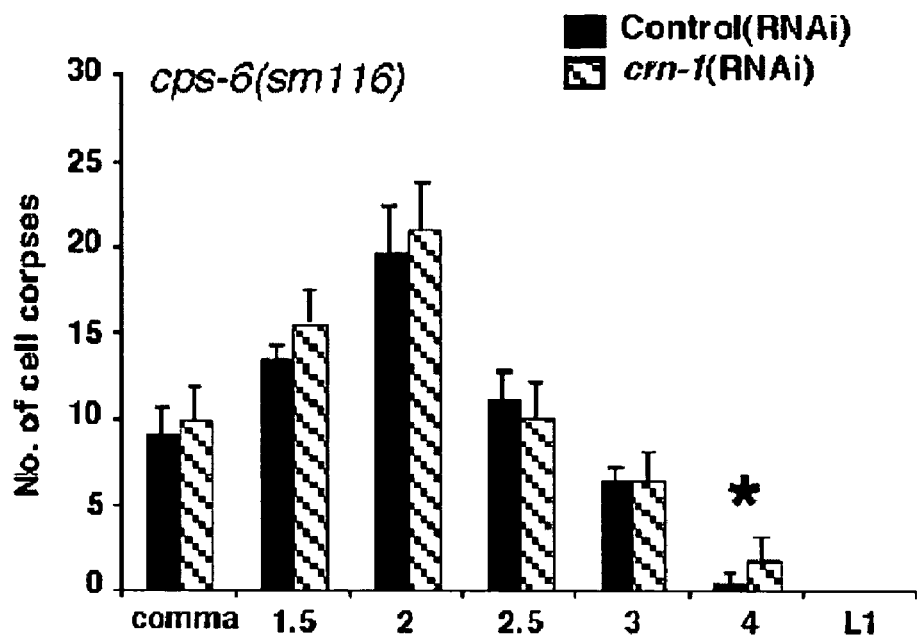
Figure 6I:
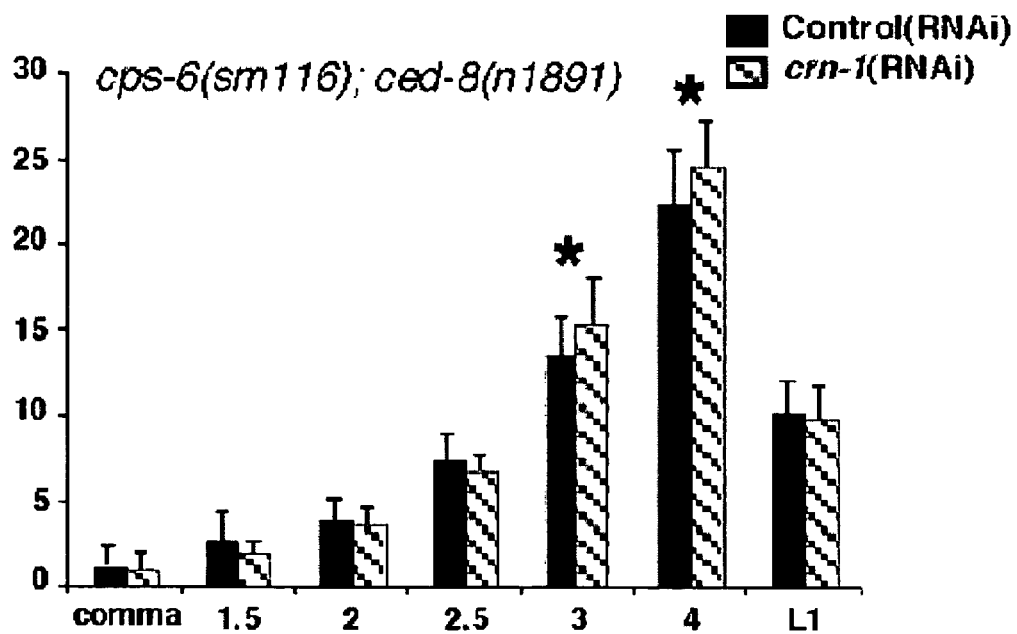
Figures 6J, 6K, 6L, 6M:
FIG. 6J to M show data derived from control and crn-1 (RNAi) treatment at the same stage with a comparison using an unpaired t test.

A time-course analysis of embryonic cell corpses indicate that CRN-1 affects the normal timing of apoptosis like cps-6. Specifically, crn-1 (RNAi) delays progression of apoptosis, shifting the peak of cell corpses from the comma embryonic stage in wild-type animal to the 2-fold embryonic stage in crn-1(RNAi) animals, as shown in FIG. 6F. crn-1(RNAi) also enhanced the delay-of-cell-death phenotype of the ced-8(n1891) mutant (13), further increasing the numbers of the late-appearing cell corpses in ced-8(n1891) embryos, as shown in FIG. 6G. However, crn-1(RNAi) treatment did not enhance the delayed corpse appearance phenotype of cps-6 (sm116) or cps-6(sm116); ced-8(n1891) mutants, as shown in FIGS. 6H and 6I. These results further show that CRN-1 and CSP-6 function in the same pathway to promote apoptosis.

Studies were performed to investigate whether crn-1 (RNAi) could prevent cell deaths and generate extra "undead" cells in the anterior pharynx of *C. elegans*. On its own, crn-1 (RNAi) did not block apoptosis, since few extra cells were seen in crn-1 (RNAi) animals, as shown in Table 7.

crn-1(RNAi) did enhance the cell killing defect of other cell death mutants, including mutants that were partially or strongly defective in two essential cell-killing genes, ced-3 and ced-4, as shown in Table 7. For example, a mean of only 1.6 extra cells was seen in the anterior pharynx of weak ced-3(n2447) mutants, compared to a mean of 2.7 extra cells seen in ced-3(n2447) for crn-1(RNAi) animals, as shown in Table 7. crn-1 (RNAi) similarly enhanced cell survival in several other mutants including weak ced-4(n2273) mutant and strong ced-3(n2433) and ced-4(n1162) mutants, as shown in Table 7. However, crn-1(RNAi) did not increase the number of extra cells observed in cps-6(sm116), cps-6 (sm116); ced-3(n2447), or cps-6(sml16), ced-4(n2273) mutants, as shown in Table 7. Taken together, these results show that crn-1 and cps-6 promote cell killing through the same cell death pathway.

TABLE 7

CRN-1 promotes cell killing in C. elegans.

| Strain* | Number Scored | Extra Cells‡ Mean ± s.e.m. | Range |
|---|---|---|---|
| N2; control(RNAi) | 18 | 0 | 0 |
| N2; crn-1(RNAi) | 22 | 0.09 ± 0.29 | 0 to 1 |
| ced-8(n1891); control(RNAi) | 16 | 0.87 ± 0.64 | 0 to 2 |
| ced-8(n1891),. crn-1(RNAi)§ | 15 | 1.50 ± 0.98 | 0 to 3 |
| ced-3(n2447); control(RNAi) | 16 | 1.56 ± 0.99 | 0 to 3 |
| ced-3(n2447); crn-1(RNAi) | 16 | 2.69 ± 1.10 | 1 to 4 |
| ced-3(n2433); control(RNAi) | 15 | 13.3 ± 1.63 | 11 to 16 |
| ced-3(n2433); crn-1(RNAi) | 15 | 14.2 ± 1.40 | 12 to 16 |
| ced-4(n2273); control(RNAi) | 15 | 3.04 ± 1.42 | 1 to 6 |
| ced-4(n2273); crn-1(RNAi)§ | 16 | 4.50 ± 1.50 | 2 to 7 |
| ced-4(n1162); control(RNAi) | 17 | 12.7 ± 1.77 | 10 to 15 |
| ced-4(n1162); crn-1(RNAi)§ | 15 | 13.7 ± 1.50 | 11 to 15 |
| cps-6(sml16); control(RNAi) | 18 | 0.06 ± 0.26 | 0 to 1 |
| cps-6(sml16); crn-1(RNAi) | 15 | 0.07 ± 0.26 | 0 to 1 |
| cps-6(sml16); ced-8(n1891); control(RNAi) | 17 | 1.35 ± 0.74 | 0 to 3 |
| cps-6(sml16); ced-8(n1891); crn-1(RNAi) | 16 | 1.31 ± 0.70 | 0 to 2 |
| cps-6(sml16); ced-3(n2447); control(RNAi)† | 16 | 2.63 ± 1.12 | 1 to 5 |
| cps-6(sml16); ced-3(n2447); crn-1(RNAi)† | 15 | 2.74 ± 1.10 | 1 to 5 |
| cps-6(sml16); ced-4(n2273); control(RNAI)† | 15 | 3.80 ± 1.14 | 2 to 6 |
| cps-6(sml16); ced-4(n2273); crn-1(RNAi)† | 15 | 4.00 ± 1.13 | 2 to 6 |

*RNAi experiments were carried out using a bacterial feeding protocol (6).
†These strains also contain dpy-5(e61).
‡Extra cells were scored in the anterior pharynx of L3 hermaphrodites using Nomarski optics as described (6).
§Numbers of extra cells from animals treated with control(RNAi) and crn-1 (RNAi) were compared using unpaired t test, P < 0.01. P < 0.002, unpaired t-test.

FEN-1 is know to be implicated in DNA replication, and participates in Okazaki fragment processing together with DNA damage repair including base excision repair. Loss-of-function mutations in Rad-27, the *S. cerivisiae* FEN-1 homologue can cause conditional lethality, a mutator phenotype, and sensitivity to genotoxic stress. These reports underscore the importance of FEN-1 in genome maintenance.

In *C. elegans*, CRN-1 is needed for developmental viability, and these results show a possible developmental role in DNA replication and repair. Results from CRN-1 expression using a fusion protein composed of CRN-1 and green fluorescent protein (CRN-1::GFP) under the control of its own promoter (P cm-I) show that CRN-1 is ubiquitously expressed in *C. elegans*, beginning early in embryogenesis and lasting until late larval stages. The CRN-1::GFP fusion protein was found exclusively in nuclei, as shown in FIGS. 6J to 6M. These results are consistent with CRN-1 having a role in mediating chromosome fragmentation during apoptosis and a possible role in DNA replication and repair.

Since cps-6 and CRN-1 appear to act in the same cell death pathway, as confirmed by FIG. 6 and Table 7, further tests wee performed to ascertain whether CPS-6 and CRN-1 directly interact. FIGS. 7A to 7D are, generally, Western blot results characterizing the activity of CPS-6 and CRN-1, for example, by use of a GST pull down assay.

Figure 7A:
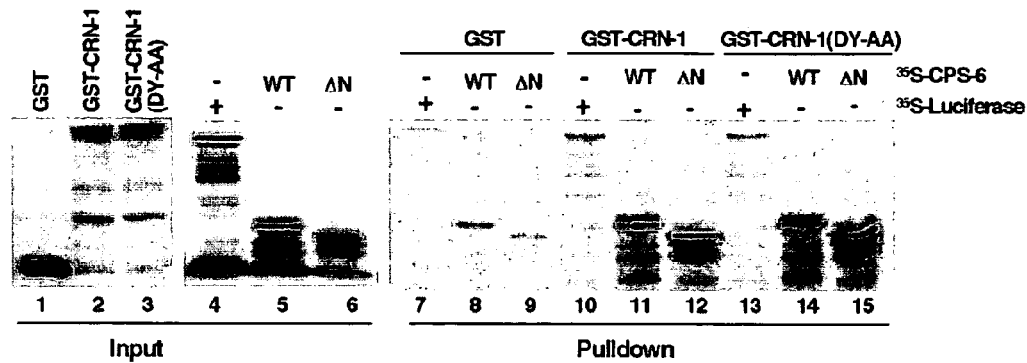
FIGS. 7A, 7B, 7C and 7D show results from GST pull down assays to characterize and compare activities of CRN-1 and CPS-6.

FIGS. 7A to 7D show nuclease activities of CRN-1 and its interaction with CPS-6, as results from a GST fusion protein pull down assay using a CRN-1 glutathione S-transferase (OST) fusion protein [OST-CRN-1(21-382)] bound full-length, with $^{35}$S-methionine labeled CPS-6. The observed CRN-1/CPS-6 interaction is specific, since OST alone did not bind CPS-6 and OST-CRN-1(21-382) did not pull down an unrelated protein, luciferase, as shown in FIG. 7A. Furthermore, CRN-1 interacted well with CPS-6(21-308), which is a truncated version of CPS-6 that lacks the mitochondria targeting sequence and localizes to nuclei instead of mitochondria.

FIG. 7A shows that CRN-1 binds CPS-6 in an assay using purified GST or GST-fusion proteins (5 μg each) to precipitate $^{35}$S-Methionine labeled proteins as indicated, where ?N denotes CPS-6(21-308) and 30% of input $^{35}$S-labeled proteins is shown.

Figures 7B, 7C, 7D:
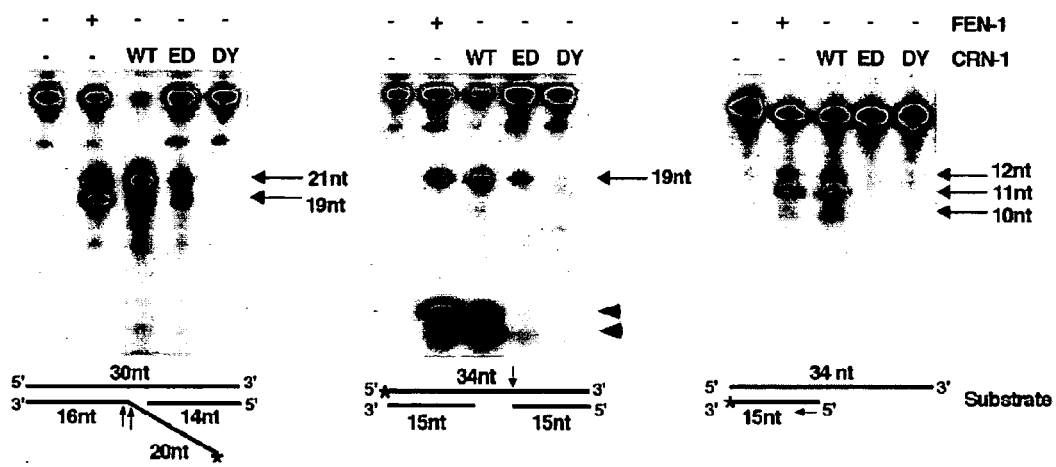

FIG. 7B shows CRN-1 has flap endonuclease activity where FEN-1 or CRN-1 proteins (wild type or mutant) synthesized in the reticulocyte lysate were incubated with the labeled flap substrate, which is schematized below the image (lengths of oligonucleotides are indicated and * indicates the position of 32P labeling), where 19 and 21 nt cleavage products and their respective cleavage sites on the substrate (1 nucleotide 5' or 3' of the branch point) are indicated by arrows. WT, wild-type CRN-1; ED, CRN-1 (EI60D); DY, CRN-1(DY-AA).

CRN-1 possesses a novel gap-dependent endonuclease activity, as represented in FIG. 7C. A different labeled substrate was incubated with FEN-1 or CRN-1 proteins. The 19 nt endonucleolytic cleavage product and its corresponding cleavage site on the substrate are indicated with an arrow. The bands (arrowheads) at the bottom of the gel are CRN-1 exonuclease products from the labeled 5' end.

CRN-1 5'-3' exonuclease activity is shown in FIG. 7D where a 3' end-labeled substrate was incubated with FEN-1 or CRN-1 proteins. The sizes of multiple cleavage products (indicated by arrows) are consistent with successive removal of 1 nt from the 5' end of the labeled strand by the exonuclease.

The mitochondria targeting sequence of Endo G, and likely CPS-6, is cleaved off following its importation into mitochondria, which suggests that the mature form of CPS-6 can interact with CRN-1 after it translocates from mitochondria to nuclei during apoptosis. These data further suggest that CPS-6 and CRN-1 may function together at the same step of apoptotic DNA degradation. FEN-1 is a structure-specific endonuclease that processes DNA flaps, bifurcated structures composed of double-stranded DNA and a displaced single-strand, and a 5'-3' exonuclease. Like FEN-I, CRN-1 cleaved a synthetic flap substrate, generating two characteristic cleavage products of 19 and 21 nucleotides, as shown in FIG. 7B. Furthermore, mutations in CRN-1 (D233A and Y234A; DY-AA) that alter conserved residues important for FEN-1 nuclease activities also abolished the flap endonuclease activity of CRN-1, as shown in FIG. 7B. These results confirm that CRN-1 has flap endonuclease activity like that of FEN-I.

Interestingly, both CRN-1 and FEN-1 possess a second substrate-specific endonuclease activity that has not been reported previously. Both proteins could endonucleotically cleave a double stranded DNA substrate with a 4 nt single stranded gap at the 3' end of the gap, as shown in FIG. 7C. This new gap-dependent endonuclease activity was also observed with a substrate that has 32 bp double stranded DNA flanking a similar 4 nt gap (8) and was lost in the CRN-1(DY-AA) mutant protein, as shown in FIG. 7C.

CRN-1 was tested for 5'-3' exonuclease activity like that of FEN-1. Both FEN-1 and CRN-1 can process a labeled 5' blunt end of a double-stranded oligonucleotide substrate to generate low molecular weight labeled nucleotides, indicative of 5'-3' exonuclease activity, as shown in FIG. 7C.

Additionally, both FEN-1 and CRN-1 cleaved a double-stranded substrate containing a 5' recessed end and a labeled 3' blunt end to generate a ladder of labeled products resulting from 5'-3' exonuclease digestion, as shown in FIG. 7D. In both assays, CRN-1(DY-AA) protein lacked 5'-3' exonuclease activity. as shown in FIGS. 7C and 7D. Interestingly, a mutation (E160D) in CRN-1 specifically abolished its 5'-3' exonuclease activity but not its flap or gap-dependent endonuclease activity, as shown in FIGS. 7B to 7D. The similarities between CRN-1 and FEN-1 in their nuclease activities suggest that CRN-1 is a functional homologue or ortholog of FEN-I.

Figure 8A:
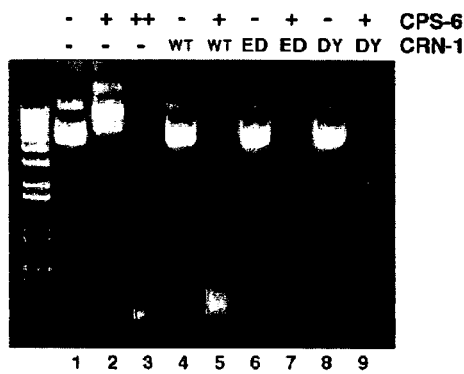
FIGS. 8A to 8D show a comparison of DNA degradation activity in a time-dependant introduction of CRN-1 and CPS-6.

Since CRN-1 and CPS-6 interacted in vitro, further tests were performed to assess whether they affect each other's activity using a plasmid cleavage assay. FIGS. 8A to 8D depict electrophoretic gels that show results from different time dependant uses of CRN-1 and CPS-6 confirming that CRN-1 and CPS-6 operate to promote DNA degradation. FIG. 8A shows results from a plasmid cleavage assay where CPS-6 ("+" denoting 50 ng and "++" denoting 250 ng) or CRN-1 proteins (250 ng each) were incubated either alone or together as indicated with plasmid DNA (1!-tg). WT, wild-type CRN-1; ED, CRN-1(EI60D); DY, CRN-1(DY-AA).

Figure 8B:
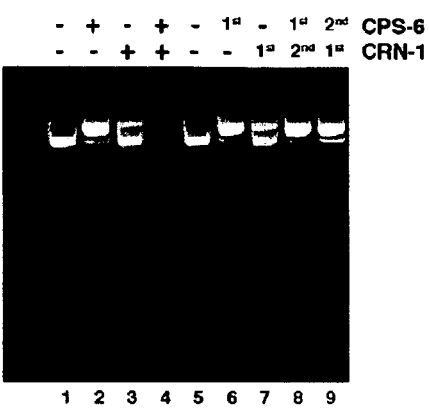

FIG. 8B shows that simultaneous presence of CRN-1 and CPS-6 enhances DNA degradation. In lanes 2-4, plasmid DNA was mock treated with buffer and passed over $Ni^{2+}$ NTA resin to simulate the depletion step. $His_6$ CPS-6 or CRN-1-$His_6$ was subsequently incubated either alone or together with plasmid DNA for 30 min. In lanes 6-9, $His_6$ CPS-6 (lanes 6 and 8) or CRN-1-$His_6$ (lanes 7 and 9) was first incubated with plasmid DNA for 30 min, depleted using $Ni^{2+}$ NTA resin (181), and plasmid DNA was subsequently incubated with CRN-1-$His_6$ (2nd; lane 8), or $His_6$CPS-6 (2nd; lane 9), or mock treated (buffer alone; "-") for another 30 min. 50 ng of $His_6$CPS-6 and 250 ng of CRN-1-$His_6$ were used in all reactions.

Figure 8C:
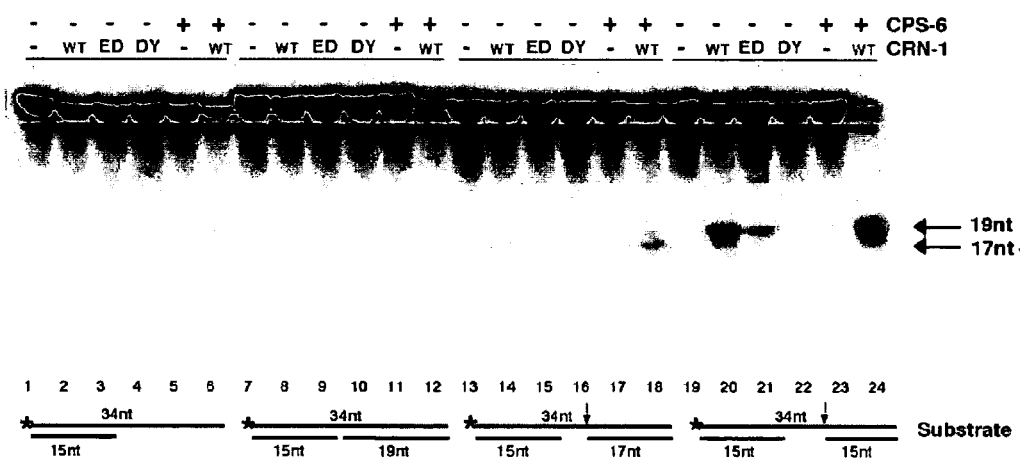

FIG. 8C shows that CPS-6 enhances CRN-1 gap-dependent endonuclease activity. CRN-proteins (WT or mutants) or CPS-6 were incubated either alone or together, as indicated, with different substrates (schematized below reactions in which they were used). The endonucleolytic product sizes (indicated with arrows) increase with the increasing lengths of the single stranded gaps in the substrates.

Figure 8D:
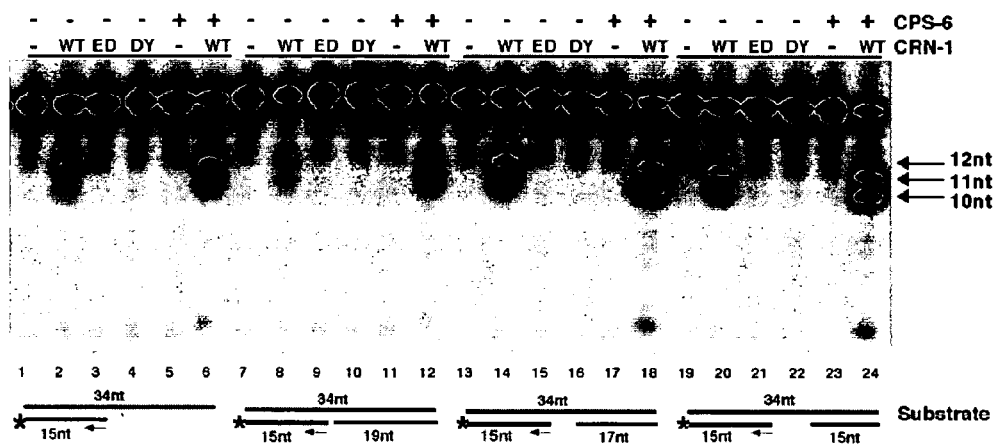

FIG. 8D shows that CPS-6 enhances CRN-1 5'-3' exonuclease activity. Reactions were carried out as in the case of FIG. 8C, except that substrates were 3'-end labeled to monitor 5'-3' exonuclease activity. 12, 11, and 10 nt exonucleolytic products were most prominent (indicated with arrows). In the presence of both CRN-1 and CPS-6, additional, smaller products were also visible.

At a low concentration, CPS-6 caused nicking of plasmid DNA, generating products with slower mobility, as shown in FIG. 8A. At a higher concentration, CPS-6 further fragmented plasmid DNA, generating a smear of smaller products, as shown in FIG. 8A.

CRN-1 alone had no detectable plasmid nicking or cleaving activity, even at high concentrations, as shown in FIG. 8A. However, adding CRN-1 to a reaction where CPS-6 alone only induced plasmid nicking resulted in complete plasmid degradation and approximately 500% increase in nuclease activity, as shown in FIG. 8A. These results shown that CRN-1 may potentate CPS-6 nuclease activity.

Interestingly, WAH-1, the *C. elegans* homologue of AIF (apoptosis-inducing factor), also enhances CPS-6 nuclease activity in vitro. However, WAH-1 did not affect CRN-1 activity alone and could not further stimulate CPS-6 activity in the presence of CRN-1, suggesting that CRN-1 and WAH-1 may use a similar mechanism to stimulate CPS-6 nuclease activity.

A test was performed to determine whether CRN-1 nuclease activities enhance CPS-6 nuclease activity using mutated proteins. The exonuclease-defective CRN-1(E 160D) protein or nuclease-defective CRN-1 (DY-AA) protein were used in plasmid cleavage reactions with CPS-6. Results show continuing enhancement of CPS-6 nuclease activity, though less potently than the wild type CRN-1 protein, as shown in FIG. 8A. These results indicate that CRN-1 can enhance CPS-6 nuclease activity through CRN-1 nuclease-dependent and -independent mechanisms. Interestingly, CRN-1(DY-AA) bound CPS-6 as well as did wild-type CRN-1, as shown in FIG. 7A, which indicates that association between CRN-1 and CPS-6 may be involved in CRN-1-mediated enhancement of CPS-6 nuclease activity.

Another test was performed to ascertain whether CPS-6 and CRN-1 act in a sequential manner to cleave DNA. The test entailed preincubating plasmid DNA with CPS-6 to deplete CPS-6 from the reaction before adding CRN-1, or reversing the incubation order of two CPS-6 and CRN-1. In both cases, there was no enhancement of the CPS-6 activity by CRN-1, as shown in FIG. 8B. These results indicate that CRN-1 and CPS-6 are preferably present at the same time for synergistic promotion of DNA degradation.

We also examined whether CPS-6 could enhance CRN-1 nuclease activities. Interestingly, CPS-6 had no effect on CRN-1 flap endonuclease activity, but could enhance the gap-dependent endonuclease activity of CRN-1, as shown in FIG. 8C. Ungapped single stranded DNA substrates (see lane 2, FIG. 8C) or double stranded DNA substrates with a nick (see no gap; lane 8, FIG. 8C) or a 1 nt gap were not endonucleotically cleaved by CRN-1. The gap-dependent endonuclease activity was apparent when the gap size was increased to 2 nt, and was enhanced when the gap size was increased to 4 nt (see lanes 14 and 20, FIG. 8C). Although CPS-6 was unable to process any of these substrates on its own, it enhanced the gap-dependent endonuclease activity of CRN-1 by more than 200% (see lanes 18 and 24, FIG. 8C).

Interestingly, CRN-1 had somewhat similar substrate preferences for its 5'-3' exonuclease activity. Although it could process 5' recessed ends (see lane 2, FIG. 8D) or 5' ends near a nick (see lane 8, FIG. 8D) or 1 nt gap in double stranded substrates, CRN-1 had stronger 5' to 3' exonuclease activity when the single stranded gap was 2 or 4 nt long (see lanes 14 and 20, FIG. 8D). In these latter two cases, addition of CPS-6 significantly enhanced CRN-1 exonuclease activity, generating smaller cleavage products (see lanes 8, and 24, FIG. 8D). Again, CPS-6 alone had no activity in processing any of the substrates, as shown in FIG. 8D. Taken together, these observations demonstrate that CPS-6 can enhance both the novel endonuclease and 5'-3' exonuclease activities of CRN-1 in a gap-dependent manner and offer important insights into the type of substrates or cleavage intermediates that CRN-1/CPS-6 might process or generate during apoptosis, providing the basis for a molecular model on how CRN-1 and CPS-6 may act together to promote stepwise chromosome fragmentation, as shown for example in FIG. 9.

Figure 9:
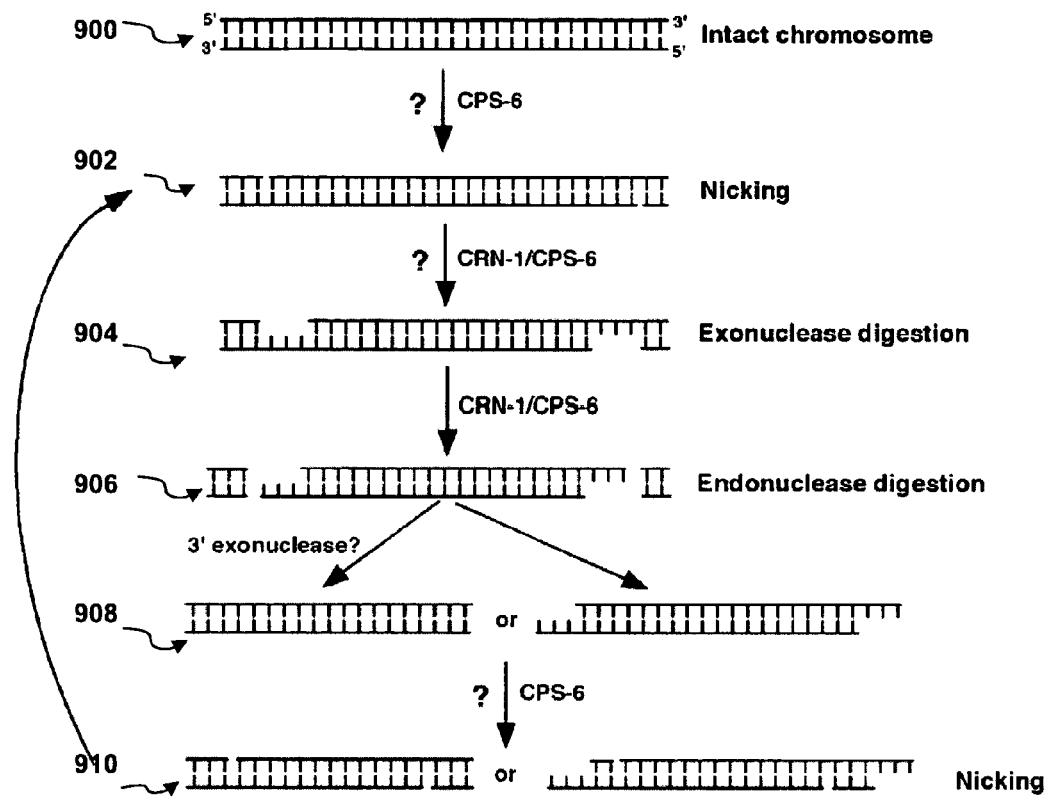
FIG. 9 is a schematic apoptotic pathway involving CRN-1 and CPS-6.

FIG. 9 shows a schematic molecular model for chromosome fragmentation during apoptosis that is supported by the results described above. In stage 900, intact chromosomal DNA is likely nicked by CPS-6 aided by CRN-1 and/or another nuclease. Following nicking, stage 902 shows that the 5'-3' exonuclease activities of CRN-1, aided by CPS-6 and possibly other exonucleases, turn the nicks into gaps. In stage 904, the resulting gapped substrates are cleaved by CRN-1 gap-dependent endonuclease activity (aided by CPS-6), resulting in fragmented substrates shown in stage 906, which either are further processed by a 3'-5' exonuclease in stage 908 or can be directly processed in stage 910 through similar steps (900 to 910) to generate smaller DNA fragments.

A study was performed to determine whether CRN-1 nuclease activities and CRN-1 interaction with CPS-6 are implicated in CRN-1 cell killing activity. Expression of CRN-1 in six non-essential touch receptor neurons under the control of the mec-7 gene promoter (P mec-7crn-1) (24) induced ectopic neuronal deaths, killing 16% to 20% of the test population when expressed from low copy transgenes, or 60% to 77% when expressed from high copy trans genes of the PLM touch receptor neurons, as reported in Table 8. Expression of CRN-1(E160D) or CRN-1(DY-AA) in touch cells weakly induced cell killing, as reported in Table 8. These results indicate that both the exonuclease and the endonuclease activities of CRN-1 are implicated in CRN-1 killing activity.

CRN-1-induced ectopic neuronal deaths were significantly inhibited by the CPS-6(sm116) or the ced-3(n2433) mutation, as reported in Table 8. These results indicate that CRN-1 induced cell death through existing apoptotic programs is mediated by cps-6 and ced-3. Furthermore, a nuclease-defective CPS-6 protein [CPS-6(D134A, Y135A)], which by itself had very weak cell killing activity, as reported in Table 8, significantly inhibited CRN-1 killing activity when co-expressed with CRN-1 in touch cells. These results indicate that the mutant CPS-6 protein may dominant-negatively inhibit CRN-1 cell killing, as shown in Table 8. These results provide further evidence that CPS-6 and CRN-1 function together to promote cell killing.

In summary, CRN-1 is newly discovered as an apoptotic nuclease that has been identified from a functional genomic screen. CRN-1 associates and cooperates with the mitochondrial nuclease CPS-6 to promote apoptotic DNA degradation. This conclusion is supported by the in vitro observations that CRN-1 bound CPS-6 and these two proteins mutually stimulated each other's nuclease activities and the in vivo observations that crn-1 (RNAi) caused cell death defects very similar to the cps-6(sm116) mutation and did not enhance the cell death defects observed in cps-6(sm116) mutants, and that crn-1 induced ectopic cell deaths in a cps-6-dependent manner.

Bioinformatic studies show that crn-1 encodes a homologue of human FEN-1 and yeast Rad27p. These nucleases are used for DNA replication and damage repair. The need for crn-1 in *C. elegans* embryonic development and the finding that CRN-1 possesses key biochemical properties characteristic of FEN-1 indicates that CRN-1 likely plays an important role in DNA replication/repair in *C. elegans*, in addition to its newly discovered role in apoptosis. Therefore, CRN-1 may serve as a critical switch between DNA replication/repair and degradation, two opposing biological events. Normally, CRN-1/FEN-1 assists in nuclear DNA replication and repair to maintain genome stability and fidelity. Pro-apoptotic stimuli could trigger translocation of CPS-6/Endo G from mitochondria to nuclei, facilitating association of CPS-6/EndoG with CRN-1/FEN-1 in nuclei, which transforms CRN-1/FEN-1 from a genome stabilizer to a genome destroyer.

In addition to CRN-1, several other CRN genes that normally appear to play important roles in RNA processing, splicing and protein folding are involved in apoptotic DNA degradation. Thus, CRN-1/FEN-1 as well as these CRN proteins could act as "double agents" like cytochrome c in regulating both cell survival and cell death.

TABLE 8

Overexpression of crn-1 induces ectopic cell killing.

| Strain* | High Concentration† | | Low Concentration† | |
|---|---|---|---|---|
| | Array | % PLM survival§ | Array | % PLM survival§ |
| N2 | | 100 | | |
| ced-3(n2433) | | 100 | | |
| cps-6(sm116) | | 100 | | |
| N2; P mec-7CRN-1 | 1 | 38 | 1 | 82 |
| | 2 | 40 | 2 | 84 |
| | 3 | 23 | 3 | 80 |
| N2; P mec-7CRN-1(EI60D) | 1 | 80 | 1 | 93 |
| | 2 | 90 | 2 | 90 |
| | 3 | 87 | 3 | 90 |
| N2; P mec-7CRN-1(DY-AA) | 1 | 83 | 1 | 100 |
| | 2 | 87 | 2 | 100 |
| | 3 | 90 | 3 | 97 |
| N2; P mec-7CPS-6(DY-AA) | 1 | 93 | 1 | 100 |
| | 2 | 93 | 2 | 97 |
| | 3 | 87 | 3 | 100 |
| N2; P mec-7CRN-I/P mec-7 CPS-6(DY-AA) | 1 | 69 | 1 | 97 |
| | 2 | 75 | 2 | 93 |
| | 3 | 67 | 3 | 100 |
| ced-3(n2433),. P mec-7CRN-1 | 1 | 75 | 1 | 97 |
| | 2 | 70 | 2 | 97 |
| | 3 | 69 | 3 | 100 |
| cps-6(sml16),. mec-7-7CRN-1 | 1 | 66 | 1 | 93 |
| | 2 | 72 | 2 | 93 |
| | 3 | 60 | 3 | 97 |

*All strains contain an integrated trans gene, bzIs8, which directs GFP expression in six mechanosensory neurons under the control of the mec-4 gene promoter and is used to help identify the PLML/R neurons. N2 is the wild-type strain. CPS-6(DY-AA) denotes CPS-6(DI34A, YI35A). CRN-1 (DY-AA) denotes CRN-1(D233A, Y234A).
†Transgenes were injected at a concentration of 50 μg/ml (high concentration) or 5 μg/ml (low concentration) with pRF4 (at 50 μg/ml), a dominant co-injection marker (26).
§PLM survival was scored in transgenic L4 larvae based on the number of fluorescent PLMR/L neurons detected using a fluorescent Nomarski microscope. At least 15 animals were scored for each transgenic line.

Example 9

CRN-1: Use of Bioinformatic Systems

The attached Sequence Listing contains evidence of comparison studies that commercially available bioinformatic systems can produce. Sequencing projects are currently underway to sequence the entire genomes of various organisms, and the genomes of certain organisms have been entirely sequenced. It is common practice to place this genetic information into commercially available bioinformatic databases for study and analysis. Although the data is available, there remains much to be learned from these genomic databases. Table 9 below shows the results of genomic comparisons that confirms conservation of homologous genes encoding the CRN nucleases across a wide variety of species including nematodes, humans, and plants. The comparison results shown in Table 9 were obtained using commercially available bioinformatic databases to compare sequences confirming high identity in comparison to the CRN materials that were isolated from *C. elegans* and confirmed by TUNEL analysis, as described above in Example 1.

TABLE 9

Trans-species conservation of CRN homologs.

C. elegans CRN Material or Homolog as shown in SEQ ID NO.

| Species | CRN-1 | CRN-2 | CRN-3 | CRN-4 | CRN-5 | CRN-6 | CYP-13 |
|---|---|---|---|---|---|---|---|
| C. elegans | 1, 2, 33 | 3, 4, 34 | 5, 6, 7, 8, 35 | 9, 10, 36 | 11, 12, 37 | 13, 14, 15, 16, 38 | 17, 18, 39 |
| Homo sapiens | 19, 20, 40 (FEN-1) | 21, 22, 41 (CDA11) | 23, 24, 42 (PM-SCL-100) | 25, 26, 43 (MGC16943) | 27, 28, 44 (RRP46) | 29, 30, 45 (DNaseII) | 31, 32, 46 (Cycliphilin E) |
| Arabidopsis thaliana | | 47 | 48 | 49 | 50 | 51 | |

One significance of observing highly conserved genetic sequences across plants, lower animals, and higher animals (and even bacteria) it that one homolog or ortholog may be substituted for another, for example, as FEN-1 may be substituted for CRN-1. These substitutions may modulate the activity of apoptotic complexes, cofactors, time dependant relationships, or synergystic cooperation of different nucleases in the degradeosome pathways, for example, as illustrated in FIG. 5. Furthermore, when these substitutions are made and subsequent assay observations indicate that activity of the substituted combinations has been altered, selected polynucleic acid portions of one homolog may be spliced, grafted or fused into counterpart nucleases to produce synthetic gene materials having still different activities.

Figure 10:
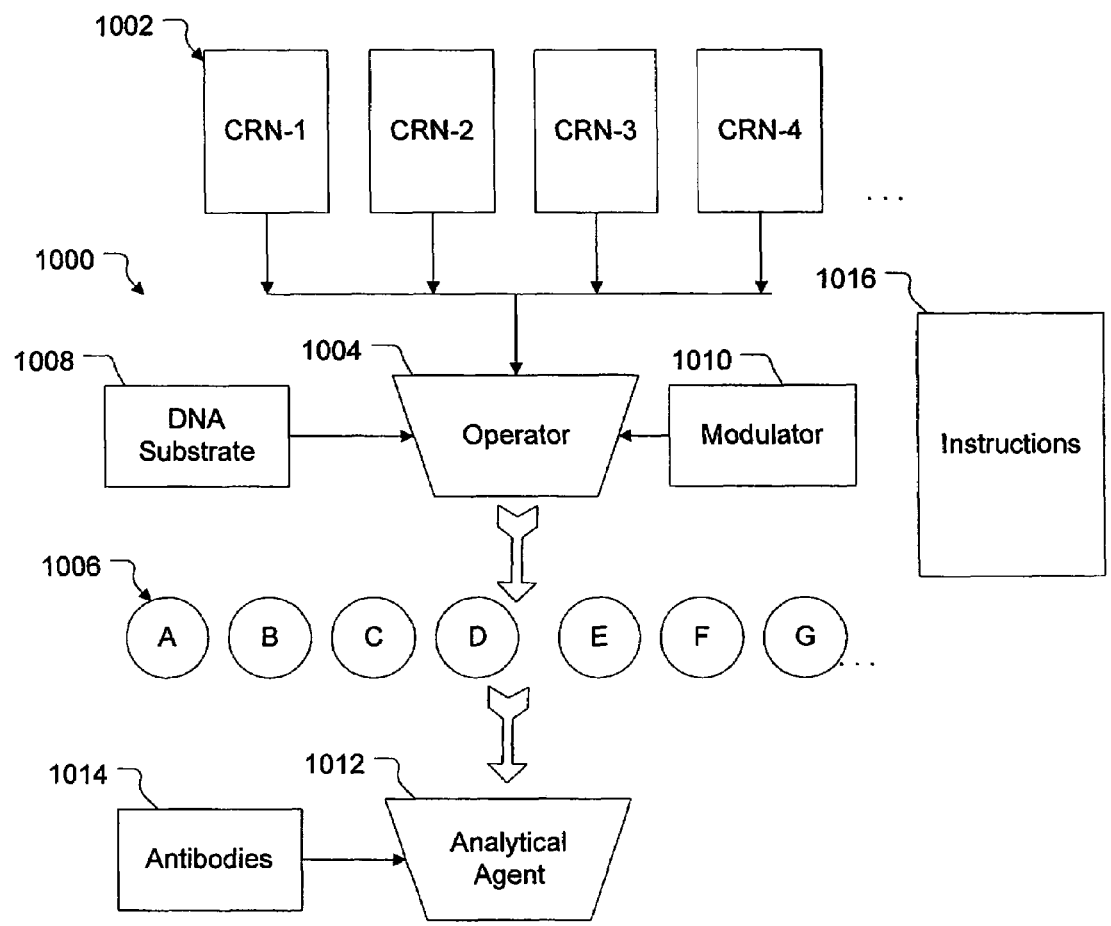
FIG. 10 depicts an assay kit in use to perform DNA degradation studies.

FIG. 10 shows an assay kit 1000 that may be used according to the instrumentalities described herein. A plurality of CRN materials 1002 may include, for example, polypeptide or polynucleotide described in SEQ ID NOs. 1-15. These materials may, for example, be expressed and harvested from C. elegans according to procedures described above. For example, purification may be by affinity chromatography with the purified materials being diluted 50% in glycerol and stored indefinitely at a low temperature, such as −50° C.

An operator 1004 is not necessarily included in the assay kit and may be a laboratory technician, a computer assisted robotic device, and/or other laboratory equipment commonly used in procedures generally of the type described above. The operator 1004 may combine the CRN materials 1002 in any combination, at any concentration, or at any level of expression in a host organism, for use in any number of reactors 1006. By way of example, the reactors 1006 may be cell cultures, host organisms, or reaction beakers. Where the CRN materials 1002 include crn polynucleotides, the operator 1004 may transform a host organism to express one or more of the CRN materials as the reactors 1006. The operator 1004 may further contact the reactors 1006 with CRN polypeptides. Optionally, the operator 1004 may mix a DNA substrate 1008 into the reactors 1006 to observe DNA degradation. The assay kit 1000 may also contain a modulator composition 1010, or the operator 1004 may provide the modulator composition 1008 independently of the assay kit 1000. Suitable modulator compositions may include, for example, RNAi materials, small molecules designed by biochemists to interfere or enhance direct or indirect DNA degradation activity of the CRN materials 1002, small molecules that bind or react with the CRN materials 1002 to impair or enhance activity of the CRN materials 1002, bioactive chemicals that function as modulators, or a deactivated nuclease that may compete with the CRN materials 1002 or impair access of the CRN materials 1002 to the DNA substrate 1008.

An analytical agent 1012 is not necessarily part of assay kit 1000, and may be a laboratory technician, optical instrumentation, and/or other laboratory analytical equipment commonly used in procedures generally of the type described above. The analytical agent 1012 may use, for example, antibodies 1014 to assess the concentration of CRN materials 1012 and associated products in the reactors 1006.

Instructions 1016 may contain, for example, instructions for storage and use of the CRN materials 1002 according to any experimental protocol or any protocol for diagnosing a disease.

While the foregoing instrumentalities have been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

REFERENCES

Additional information is found in the following publications and references cited within:

Andreeva, L., Heads, R., and Green, C. J. (1999). Cyclophilins and their possible role in the stress response. Int. J. Exp. Pathol. 80, 305-315.

Apweiler, R., Attwood, T. K., Bairoch, A., Bateman, A., Birney, E., Biswas, M., Bucher, P., Cerutti, L., Corpet, F., Croning, M. D., et al. (2001). The InterPro database, an integrated documentation resource for protein families, domains and functional sites. Nucleic Acids Res. 29, 37-40.

Arnold, Protein engineering for unusual environments, Current Opinion in Biotechnology 4:450-455 (1993);

Bass et al., Mutant Trp repressors with new DNA-binding specificities, Science 242:240-245 (1988);

Bell, D. A., Morrison, B., and VandenBygaart, P. (1990). Immunogenic DNA-related factors. Nucleosomes spontaneously released from normal murine lymphoid cells stimulate proliferation and immunoglobulin synthesis of normal mouse lymphocytes. J. Clin. Invest. 85, 1487-1496.

Blumenthal, T., Evans, D., Link, C. D., Guffanti, A., Lawson, D., Thierry-Mieg, J., Thierry-Mieg, D., Chiu, W. L., Duke, K., Kiraly, M., and Kim, S. K. (2002). A global analysis of *Caenorhabditis elegans* operons. Nature 417, 851-854.

Botstein & Shortle, Strategies and applications of in vitro mutagenesis, Science 229:1193-1201(1985);

Boulton, S. J., Gartner, A., Reboul, J., Vaglio, P., Dyson, N., Hill, D. E., and Vidal, M. (2002). *Combined functional genomic maps of the C. elegans DNA damage response.* Science 295, 127-131.

Brenner, S. (1974). *he genetics of Caenorhabditis elegans.* Genetics 77, 71-94.

Brouwer, R., Pruijn, G. J., and van Venrooij, W. J. (2001). *The human exosome: an autoantigenic complex of exoribonucleases in myositis and scleroderma.* Arthritis Res. 3, 102-106.

Carter et al., *Improved oligonucleotide site-directed mutagenesis using M13 vectors*, Nucl. Acids Res. 13: 4431-4443 (1985);

Carter, *Improved oligonucleotide-directed mutagenesis using M13 vectors*, Methods in Enzymol. 154: 382-403 (1987);

Carter, *Site-directed mutagenesis*, Biochem. J. 237:1-7 (1986);

Consortium, T. C. e. S. (1998). *Genome sequence of the nematode C. elegans: a platform for investigating biology.* The *C. elegans* Sequencing Consortium. Science 282, 2012-2018.

Dale et al., *Oligonucleotide-directed random mutagenesis using the phosphorothioate method*, Methods Mol. Biol. 57:369-374 (1996);

Eghtedarzadeh & Henikoff, Use of oligonucleotides to generate large deletions, Nucl. Acids Res. 14: 5115 (1986);

Ellis, H. M., and Horvitz, H. R. (1986). *Genetic control of programmed cell death in the nematode C. elegans.* Cell 44, 817-829.

Enari, M., Sakahira, H., Yokoyama, H., Okawa, K., Iwamatsu, A., and Nagata, S. (1998). *A caspase-activated DNase that degrades DNA during apoptosis, and its inhibitor ICAD.* Nature 391, 43-50.

Fire, A., Xu, S., Montgomery, M. K., Kostas, S. A., Driver, S. E., and Mello, C. C. (1998). *Potent and specific genetic interference by double-stranded RNA in Caenorhabditis elegans.* Nature 391, 806-811.

Fraser, A. G., Kamath, R. S., Zipperlen, P., Martinez-Campos, M., Sohrmann, M., and Ahringer, J. (2000). *Functional genomic analysis of C. elegans chromosome I by systematic RNA interference.* Nature 408, 325-330.

Fritz et al., *Oligonucleotide-directed construction of mutations: a gapped duplex DNA procedure without enzymatic reactions in vitro*, Nucl. Acids Res. 16: 6987-6999 (1988);

Gonczy, P., Echeverri, C., Oegema, K., Coulson, A., Jones, S. J., Copley, R. R., Duperon, J., Oegema, J., Brehm, M., Cassin, E., et al. (2000). *Functional genomic analysis of cell division in C. elegans using RNAi of genes on chromosome III.* Nature 408, 331-336.

Grundström et al., *Oligonucleotide-directed mutagenesis by microscale 'shot-gun' gene synthesis*, Nucl. Acids Res. 13: 3305-3316 (1985);

Halenbeck, R., MacDonald, H., Roulston, A., Chen, T. T., Conroy, L., and Williams, L. T. (1998). *CPAN, a human nuclease regulated by the caspase-sensitive inhibitor DFF45.* Curr. Biol. 8, 537-540.

Harrington, J. J., and Lieber, M. R. (1994). *The characterization of a mammalian DNA structure-specific endonuclease.* Embo J. 13, 1235-1246.

Hoeppner, D. J., Hengartner, M. O., and Schnabel, R. (2001). *Engulfment genes cooperate withced-3 to promote cell death in Caenorhabditis elegans.* Nature 412, 202-206.

Klein, J. A., Longo-Guess, C. M., Rossmann, M. P., Seburn, K. L., Hurd, R. E., Frankel, W. N., Bronson, R. T., and Ackerman, S. L. (2002). *The harlequin mouse mutation downregulates apoptosis-inducing factor.* Nature 419, 367-374.

Koonin, E. V., and Deutscher, M. P. (1993). *RNase T shares conserved sequence motifs with DNA proofreading exonucleases.* Nucleic Acids Res. 21, 2521-2522.

Kramer & Fritz *Oligonucleotide-directed construction of mutations via gapped duplex DNA*, Methods in Enzymol. 154:350-367 (1987);

Kramer et al., *Point Mismatch Repair*, Cell 38:879-887 (1984); Kramer et al., *Improved enzymatic in vitro reactions in the gapped duplex DNA approach to oligonucleotide-directed construction of mutations*, Nucl. Acids Res. 16: 7207 (1988);

Kramer et al., *The gapped duplex DNA approach to oligonucleotide-directed mutation construction*, Nucl. Acids Res. 12: 9441-9456 (1984);

Kunkel et al., *Rapid and efficient site-specific mutagenesis without phenotypic selection*, Methods in Enzymol. 154, 367-382 (1987);

Kunkel, *Rapid and efficient site-specific mutagenesis without phenotypic selection*, Proc. Natl. Acad. Sci. USA 82:488-492 (1985);

Kunkel, *The efficiency of oligonucleotide directed mutagenesis, in Nucleic Acids & Molecular Biology* (Eckstein, F. and Lilley, D. M. J. eds., Springer Verlag, Berlin)) (1987);

Li, L. Y., Luo, X., and Wang, X. (2001). *Endonuclease G is an apoptotic DNase when released from mitochondria.* Nature 412, 95-99.

Lieber, M. R. (1997). *The FEN-1 family of structure-specific nucleases in eukaryotic DNA replication, recombination and repair.* Bioessays 19, 233-240.

Ling et al., *Approaches to DNA mutagenesis: an overview*, Anal Biochem. 254(2): 157-178 (1997);

Liu, X., Kim, C. N., Yang, J., Jemmerson, R., and Wang, X. (1996). *Induction of apoptotic program in cell-free extracts: requirement for dATP and cytochrome c.* Cell 86, 147-157.

Liu, X., L1, P., Widlak, P., Zou, H., Luo, X., Garrard, W. T., and Wang, X. (1998). *The 40-kDa subunit of DNA fragmentation factor induces DNA fragmentation and chromatin condensation during apoptosis.* Proc. Natl. Acad. Sci. USA 95, 8461-8466.

Liu, X., Zou, H., Slaughter, C., and Wang, X. (1997). *DFF, a heterodimeric protein that functions downstream of caspase-3 to trigger DNA fragmentation during apoptosis.* Cell 89, 175-184.

Lorimer and Pastan Nucleic Acids Res. 23, 3067-8 (1995);

Mandecki, *Oligonucleotide-directed double-strand break repair in plasmids of Escherichia coli: a method for site-specific mutagenesis*, Proc. Natl. Acad. Sci. USA, 83:7177-7181 (1986);

McIlroy, D., Tanaka, M., Sakahira, H., Fukuyama, H., Suzuki, M., Yamamura, K., Ohsawa, Y., Uchiyama, Y., and Nagata, S. (2000). *An auxiliary mode of apoptotic DNA fragmentation provided by phagocytes.* Genes. Dev. 14, 549-558.

Mi, H., Kops, O., Zimmermann, E., Jaschke, A., and Tropschug, M. (1996). *A nuclear RNA-binding cyclophilin in human T cells*. FEBS Lett. 398, 201-205.

Montague, J. W., Hughes, F. M., Jr., and Cidlowski, J. A. (1997). *Native recombinant cyclophilins A, B, and C degrade DNA independently of peptidylprolyl cis-trans-isomerase activity. Potential roles of cyclophilins in apoptosis*. J. Biol. Chem. 272, 6677-6684.

Nakamaye & Eckstein, *Inhibition of restriction endonuclease Nci I cleavage by phosphorothioate groups and its application to oligonucleotide-directed mutagenesis*, Nucl. Acids Res. 14: 9679-9698 (1986);

Nambiar et al., *Total synthesis and cloning of a gene coding for the ribonuclease S protein*, Science 223: 1299-1301 (1984);

Parrish, J., Li, L., Klotz, K., Ledwich, D., Wang, X., and Xue, D. (2001). *Mitochondrial endonuclease G is important for apoptosis in C. elegans*. Nature 412, 90-94.

Perumal, K., and Reddy, R. (2002). *The 3' end formation in small RNAs*. Gene Expr. 10, 59-78.

Platt, N., da Silva, R. P., and Gordon, S. (1998). *Recognizing death: the phagocytosis of apoptotic cells*. Trends Cell Biol. 8, 365-372.

Reddien, P. W., Cameron, S., and Horvitz, H. R. (2001). *Phagocytosis promotes programmed cell death in C. elegans*. Nature 412, 198-202.

Reed, J. C. (1997). *Cytochrome c: can't live with it—can't live without it*. Cell 91, 559-562.

Riddle, D. L., Blumenthal, T., Meyer, B. J., and Priess, J. R., eds. (1997). *C. elegans II* (Cold Spring Harbor, Cold Spring Harbor Laboratory).

Sakamar and Khorana, *Total synthesis and expression of a gene for the a-subunit of bovine rod outer segment guanine nucleotide-binding protein (transducin)*, Nucl. Acids Res. 14: 6361-6372 (1988);

Samejima, K., Tone, S., and Earnshaw, W. C. (2001). *CAD/DFF40 nuclease is dispensable for high molecular weight DNA cleavage and stage I chromatin condensation in apoptosis*. J. Biol. Chem. 276, 45427-45432.

Sayers et al., *Strand specific cleavage of phosphorothioate-containing DNA by reaction with restriction endonucleases in the presence of ethidium bromide*, (1988) Nucl. Acids Res. 16: 803-814;

Sayers et al., *Y-T Exonucleases in phosphorothioate-based oligonucleotide-directed mutagenesis*, Nucl. Acids Res. 16:791-802 (1988);

Sieber, et al., *Nature Biotechnology*, 19:456-460 (2001); Smith, *In vitro mutagenesis*, Ann. Rev. Genet. 19:423-462 (1985); Methods in Enzymol. 100: 468-500 (1983); Methods in Enzymol. 154: 329-350 (1987);

Sonnhammer, E. L., Eddy, S. R., and Durbin, R. (1997). *Pfam: a comprehensive database of protein domain families based on seed alignments*. Proteins 28, 405-420.

Steller, H. (1995). *Mechanisms and genes of cellular suicide*. Science 267, 1445-1449.

Stemmer, Nature 370, 389-91 (1994); Taylor et al., *The use of phosphorothioate-modified DNA in restriction enzyme reactions to prepare nicked DNA*, Nucl. Acids Res. 13: 8749-8764 (1985);

Sulston, J. E. (1976). *Post-embryonic development in the ventral cord of Caenorhabditis elegans*. Philos. Trans. R. Soc. Lond. B. Biol. Sci. 275, 287-297.

Sulston, J. E., Schierenberg, E., White, J. G., and Thomson, J. N. (1983). *The embryonic cell lineage of the nematode Caenorhabditis elegans*. Dev. Biol. 100, 64-119.

Susin, S. A., Lorenzo, H. K., Zamzami, N., Marzo, I., Snow, B. E., Brothers, G. M., Mangion, J., Jacotot, E., Costantini, P., Loeffler, M., et al. (1999). *Molecular characterization of mitochondrial apoptosis-inducing factor*. Nature 397, 441-446.

Taylor et al., *The rapid generation of oligonucleotide-directed mutations at high frequency using phosphorothioate-modified DNA*, Nucl. Acids Res. 13: 8765-8787 (1985);

Vaux, D. L., and Korsmeyer, S. J. (1999). *Cell death in development*. Cell 96, 245-254.

Walhout, A. J., Sordella, R., Lu, X., Hartley, J. L., Temple, G. F., Brasch, M. A., Thierry-Mieg, N., and Vidal, M. (2000). *Protein interaction mapping in C. elegans using proteins involved in vulval development*. Science 287, 116-122.

Wang, X., Yang, C., Chai, J., Shi, Y., and Xue, D. (2002). *Mechanisms of AIF-Mediated Apoptotic DNA Degradation in Caenorhabditis elegans*. Science 298, 1587-1592.

Wells et al., *Importance of hydrogen-bond formation in stabilizing the transition state of subtilisin*, Phil. Trans. R. Soc. Lond. A 317: 415-423 (1986); Wells et al., *Cassette mutagenesis: an efficient method for generation of multiple mutations at defined sites*, Gene 34:315-323 (1985);

Wexler, M., Sargent, F., Jack, R. L., Stanley, N. R., Bogsch, E. G., Robinson, C., Berks, B. C., and Palmer, T. (2000). *TatD is a cytoplasmic protein with DNase activity. No requirement for TatD family proteins in sec-independent protein export*. J. Biol. Chem. 275, 16717-16722.

Wu, Y. C., Stanfield, G. M., and Horvitz, H. R. (2000). *NUC-1, a Caenorhabditis elegans DNase II homolog, functions in an intermediate step of DNA degradation during apoptosis*. Genes. Dev. 14, 536-548.

Wyllie, A. H. (1980). *Glucocorticoid-induced thymocyte apoptosis is associated with endogenous endonuclease activation*. Nature 284, 555-556.

Zhang, J., and Xu, M. (2002). *Apoptotic DNA fragmentation and tissue homeostasis*. Trends Cell Biol. 12, 84-89.

Zhang, J., Liu, X., Scherer, D. C., van Kaer, L., Wang, X., and Xu, M. (1998). *Resistance to DNA fragmentation and chromatin condensation in mice lacking the DNA fragmentation factor 45*. Proc. Natl. Acad. Sci. U.S.A. 95, 12480-12485.

Zhou, Z., Licklider, L. J., Gygi, S. P., and Reed, R. (2002). *Comprehensive proteomic analysis of the human spliceosome*. Nature 419, 182-185.

Zoller & Smith, *Oligonucleotide-directed mutagenesis of DNA fragments cloned into M13 vectors*, Methods in Enzymol. 100:468-500 (1983); and Zoller & Smith, *Oligonucleotide-directed mutagenesis using M13-derived vectors: an efficient and general procedure for the production of point mutations in any DNA fragment*, Nucleic Acids Res. 10:6487-6500 (1982);

Zoller & Smith, *Oligonucleotide-directed mutagenesis: a simple method using two oligonucleotide primers and a single-stranded DNA template*, Methods in Enzymol. 154:329-350 (1987). Additional details on many of the above methods can be found in Methods in Enzymology Volume 154, which also describes useful controls for trouble-shooting problems with various mutagenesis methods.

Zou, H., Henzel, W. J., Liu, X., Lutschg, A., and Wang, X. (1997). *Apaf-1, a human protein homologous to C. elegans CED-4, participates in cytochrome c-dependent activation of caspase-3*. Cell 90, 405-413.

Zou, H., Li, Y., Liu, X., and Wang, X. (1999). *An APAF-1.Cytochrome c multimeric complex is a functional apoptosome that activates procaspase-9*. J. Biol. Chem. 274, 11549-11556.

We claim:

1. A method of screening for an apoptosis modulator by using cell death-related nucleases (CRN), the method comprising:
   (a) contacting at least one candidate apoptosis modulator with a CRN material comprising a polypeptide having nuclease activity and at least 98% sequence identity with respect to SEQ ID NO:2 or a fragment thereof; and
   (b) detecting a modulated activity and/or level of said polypeptide, thereby identifying the apoptosis modulator.

2. The method of claim 1, wherein the step of detecting comprises detecting DNA degradation.

3. The method of claim 1, wherein the CRN material comprises the polypeptides of SEQ ID NO. 2.

4. The method of claim 1, further comprising steps of isolating the apoptosis modulator; and
   converting the apoptosis modulator into a dosage form in an effective amount for modulating apoptosis in an organism.

* * * * *

SEQUENCE LISTING

<160> NUMBER OF SEQ ID NOS: 62

<210> SEQ ID NO 1
<211> LENGTH: 1149
<212> TYPE: DNA
<213> ORGANISM: Caenorhabditis elegans
<220> FEATURE:
<221> NAME/KEY: CDS
<222> LOCATION: (1)..(1149)
<223> OTHER INFORMATION: crn-1/CRN-1

<400> SEQUENCE: 1

```
atg gga att aaa gga ctc tcc caa gtg att gct gat aat gct ccc tcc        48
Met Gly Ile Lys Gly Leu Ser Gln Val Ile Ala Asp Asn Ala Pro Ser
1               5                  10                  15 gcg att aaa gtc aac gag atg aag gcg ttc ttc gga aga aca gta gca        96
Ala Ile Lys Val Asn Glu Met Lys Ala Phe Phe Gly Arg Thr Val Ala
            20                  25                  30 atc gac gca tca atg tgc ctc tac caa ttc ctc att gct gtt cgt caa       144
Ile Asp Ala Ser Met Cys Leu Tyr Gln Phe Leu Ile Ala Val Arg Gln
        35                  40                  45 gat ggt tcc cag ctt caa agt gaa gat gga gaa acc aca agt cac ttg       192
Asp Gly Ser Gln Leu Gln Ser Glu Asp Gly Glu Thr Thr Ser His Leu
    50                  55                  60 atg gga atg ctg aat cgt acg gtt cga atg ttc gag aac gga gtg aag       240
Met Gly Met Leu Asn Arg Thr Val Arg Met Phe Glu Asn Gly Val Lys
65                  70                  75                  80 cct gtc tac gtt ttc gac gga aaa cca ccg gat atg aag ggt gga gag       288
Pro Val Tyr Val Phe Asp Gly Lys Pro Pro Asp Met Lys Gly Gly Glu
                85                  90                  95 ctt gaa aaa cgt tcc gag cgt cgt gct gaa gca gaa aaa gcg ctg act       336
Leu Glu Lys Arg Ser Glu Arg Arg Ala Glu Ala Glu Lys Ala Leu Thr
            100                 105                 110 gag gcc aag gag aag gga gat gtt aag gaa gcg gag aag ttc gag aga       384
Glu Ala Lys Glu Lys Gly Asp Val Lys Glu Ala Glu Lys Phe Glu Arg
        115                 120                 125 aga ctc gta aaa gtc aca aaa caa cag aac gac gag gcg aag cgt ttg       432
Arg Leu Val Lys Val Thr Lys Gln Gln Asn Asp Glu Ala Lys Arg Leu
    130                 135                 140 ctg gga tta atg gga att cca gtt gtc gag gct cca tgc gag gca gaa       480
Leu Gly Leu Met Gly Ile Pro Val Val Glu Ala Pro Cys Glu Ala Glu
145                 150                 155                 160 gct cag tgt gct cat ctc gtg aaa gct gga aaa gta ttc gga act gtc       528
Ala Gln Cys Ala His Leu Val Lys Ala Gly Lys Val Phe Gly Thr Val
                165                 170                 175 act gag gat atg gac gcg ctg acc ttc ggc tcc acg gtt ctt ctc aga       576
Thr Glu Asp Met Asp Ala Leu Thr Phe Gly Ser Thr Val Leu Leu Arg
            180                 185                 190 cat ttc ctg gct cca gtc gcc aag aaa atc ccg atc aag gag ttc aat       624
His Phe Leu Ala Pro Val Ala Lys Lys Ile Pro Ile Lys Glu Phe Asn
        195                 200                 205 ctt tct ttg gct ctc gaa gaa atg aag cta agc gtt gag gaa ttt att       672
Leu Ser Leu Ala Leu Glu Glu Met Lys Leu Ser Val Glu Glu Phe Ile
    210                 215                 220 gat ttg tgt att ctt ctc ggc tgt gac tat tgt gga act att cga ggc       720
Asp Leu Cys Ile Leu Leu Gly Cys Asp Tyr Cys Gly Thr Ile Arg Gly
225                 230                 235                 240 gtc ggg cct aag aag gct gtt gag ctg atc aga cag cac aag aat att       768
Val Gly Pro Lys Lys Ala Val Glu Leu Ile Arg Gln His Lys Asn Ile
                245                 250                 255
```

```
gag acg att ctt gag aat atc gat caa aat aaa tac cca cca cca gag       816
Glu Thr Ile Leu Glu Asn Ile Asp Gln Asn Lys Tyr Pro Pro Pro Glu
            260                 265                 270 gat tgg cca tac aag cgt gct cgt gag ctt ttc ctc aat cca gaa gtg       864
Asp Trp Pro Tyr Lys Arg Ala Arg Glu Leu Phe Leu Asn Pro Glu Val
                275                 280                 285 aca aaa ccg gaa gaa gtt gaa ctg aca tgg aag gaa gcc gat gtc gaa       912
Thr Lys Pro Glu Glu Val Glu Leu Thr Trp Lys Glu Ala Asp Val Glu
290                 295                 300 ggt gtc att cag ttc ttg tgc gga gag aag aac ttc aat gag gag cgc       960
Gly Val Ile Gln Phe Leu Cys Gly Glu Lys Asn Phe Asn Glu Glu Arg
305                 310                 315                 320 atc cga aac gcg ttg gca aaa ctg aag act agc cgt aaa tct gga aca      1008
Ile Arg Asn Ala Leu Ala Lys Leu Lys Thr Ser Arg Lys Ser Gly Thr
                325                 330                 335 caa gga cga att gac tcg ttc ttc gga aac tcg acc aag gtt aca tgt      1056
Gln Gly Arg Ile Asp Ser Phe Phe Gly Asn Ser Thr Lys Val Thr Cys
                340                 345                 350 gtg aca gct gcg aca aaa cga aag gcg gag gaa gct gag aag gcg aag      1104
Val Thr Ala Ala Thr Lys Arg Lys Ala Glu Glu Ala Glu Lys Ala Lys
        355                 360                 365 aag gga gca aag aag ggt gga cca ccg aag aag aga gcc aag tag          1149
Lys Gly Ala Lys Lys Gly Gly Pro Pro Lys Lys Arg Ala Lys
370                 375                 380

<210> SEQ ID NO 2
<211> LENGTH: 382
<212> TYPE: PRT
<213> ORGANISM: Caenorhabditis elegans

<400> SEQUENCE: 2

Met Gly Ile Lys Gly Leu Ser Gln Val Ile Ala Asp Asn Ala Pro Ser
1               5                   10                  15

Ala Ile Lys Val Asn Glu Met Lys Ala Phe Phe Gly Arg Thr Val Ala
            20                  25                  30

Ile Asp Ala Ser Met Cys Leu Tyr Gln Phe Leu Ile Ala Val Arg Gln
        35                  40                  45

Asp Gly Ser Gln Leu Gln Ser Glu Asp Gly Glu Thr Thr Ser His Leu
    50                  55                  60

Met Gly Met Leu Asn Arg Thr Val Arg Met Phe Glu Asn Gly Val Lys
65                  70                  75                  80

Pro Val Tyr Val Phe Asp Gly Lys Pro Pro Asp Met Lys Gly Gly Glu
                85                  90                  95

Leu Glu Lys Arg Ser Glu Arg Arg Ala Glu Ala Glu Lys Ala Leu Thr
            100                 105                 110

Glu Ala Lys Glu Lys Gly Asp Val Lys Glu Ala Glu Lys Phe Glu Arg
        115                 120                 125

Arg Leu Val Lys Val Thr Lys Gln Gln Asn Asp Glu Ala Lys Arg Leu
    130                 135                 140

Leu Gly Leu Met Gly Ile Pro Val Val Glu Ala Pro Cys Glu Ala Glu
145                 150                 155                 160

Ala Gln Cys Ala His Leu Val Lys Ala Gly Lys Val Phe Gly Thr Val
                165                 170                 175

Thr Glu Asp Met Asp Ala Leu Thr Phe Gly Ser Thr Val Leu Leu Arg
            180                 185                 190

His Phe Leu Ala Pro Val Ala Lys Lys Ile Pro Ile Lys Glu Phe Asn
        195                 200                 205
```

-continued

```
Leu Ser Leu Ala Leu Glu Glu Met Lys Leu Ser Val Glu Glu Phe Ile
    210                 215                 220

Asp Leu Cys Ile Leu Leu Gly Cys Asp Tyr Cys Gly Thr Ile Arg Gly
225                 230                 235                 240

Val Gly Pro Lys Lys Ala Val Glu Leu Ile Arg Gln His Lys Asn Ile
                245                 250                 255

Glu Thr Ile Leu Glu Asn Ile Asp Gln Asn Lys Tyr Pro Pro Pro Glu
            260                 265                 270

Asp Trp Pro Tyr Lys Arg Ala Arg Glu Leu Phe Leu Asn Pro Glu Val
        275                 280                 285

Thr Lys Pro Glu Glu Val Glu Leu Thr Trp Lys Glu Ala Asp Val Glu
    290                 295                 300

Gly Val Ile Gln Phe Leu Cys Gly Glu Lys Asn Phe Asn Glu Glu Arg
305                 310                 315                 320

Ile Arg Asn Ala Leu Ala Lys Leu Lys Thr Ser Arg Lys Ser Gly Thr
                325                 330                 335

Gln Gly Arg Ile Asp Ser Phe Phe Gly Asn Ser Thr Lys Val Thr Cys
            340                 345                 350

Val Thr Ala Ala Thr Lys Arg Lys Ala Glu Glu Ala Glu Lys Ala Lys
        355                 360                 365

Lys Gly Ala Lys Lys Gly Gly Pro Pro Lys Lys Arg Ala Lys
    370                 375                 380

<210> SEQ ID NO 3
<211> LENGTH: 861
<212> TYPE: DNA
<213> ORGANISM: Caenorhabditis elegans
<220> FEATURE:
<221> NAME/KEY: CDS
<222> LOCATION: (1)..(861)
<223> OTHER INFORMATION: crn-2/CRN-2

<400> SEQUENCE: 3 atg gcg ttg tac gaa ctc gtc gac atc gga gcc aat ctg ggt cat cct      48
Met Ala Leu Tyr Glu Leu Val Asp Ile Gly Ala Asn Leu Gly His Pro
1               5                   10                  15 tca tat caa aag gat ttg aat gat gtg ctc gat cgt gcc aag caa gcc      96
Ser Tyr Gln Lys Asp Leu Asn Asp Val Leu Asp Arg Ala Lys Gln Ala
                20                  25                  30 ggg ttg tcg aaa att atg gtt act gga acc agc gaa aaa att agt cat     144
Gly Leu Ser Lys Ile Met Val Thr Gly Thr Ser Glu Lys Ile Ser His
            35                  40                  45 gaa tgt gca gat ctc gtt gaa aag tat ccg gga ttt ttg tat ttt act     192
Glu Cys Ala Asp Leu Val Glu Lys Tyr Pro Gly Phe Leu Tyr Phe Thr
        50                  55                  60 gca ggc gtt cat ccg cac gat gcc aag gat tgg aat gat gga aca ttg     240
Ala Gly Val His Pro His Asp Ala Lys Asp Trp Asn Asp Gly Thr Leu
65                  70                  75                  80 gaa gct ctc aaa aaa tta caa gaa aac ccg agt tgc gtg gct gtt ggc     288
Glu Ala Leu Lys Lys Leu Gln Glu Asn Pro Ser Cys Val Ala Val Gly
                85                  90                  95 gaa tgt ggt ctc gat ttt aat cgc aac ttt tct cca caa gat gtg caa     336
Glu Cys Gly Leu Asp Phe Asn Arg Asn Phe Ser Pro Gln Asp Val Gln
            100                 105                 110 aaa gaa gtg ttc gca aag caa gta gat atg gct gta aag ctt cag aaa     384
Lys Glu Val Phe Ala Lys Gln Val Asp Met Ala Val Lys Leu Gln Lys
        115                 120                 125 cca ttg ttc att cac gaa aga gaa gct cat gaa gat atg gtt aaa ata     432
```

```
Pro Leu Phe Ile His Glu Arg Glu Ala His Glu Asp Met Val Lys Ile
    130                 135                 140 tta aca gct gcc gga cct tcc ctt cca ccc gca gtc att cat tgc ttc        480
Leu Thr Ala Ala Gly Pro Ser Leu Pro Pro Ala Val Ile His Cys Phe
145                 150                 155                 160 act ggg acc gta gtg gag gcg aag aaa tat ttg gaa atg ggg ttc tac        528
Thr Gly Thr Val Val Glu Ala Lys Lys Tyr Leu Glu Met Gly Phe Tyr
                165                 170                 175 atc gga ttg aca ggg ttc ctc tgg aaa gat aga tca gat aat gga gtg        576
Ile Gly Leu Thr Gly Phe Leu Trp Lys Asp Arg Ser Asp Asn Gly Val
            180                 185                 190 cag gca ggg ctt cga tct gga gaa att ccg att gaa aag ctg gtt ctt        624
Gln Ala Gly Leu Arg Ser Gly Glu Ile Pro Ile Glu Lys Leu Val Leu
        195                 200                 205 gaa act gat gca cct tat atg tac ccg aaa atc aac gat aaa aag att        672
Glu Thr Asp Ala Pro Tyr Met Tyr Pro Lys Ile Asn Asp Lys Lys Ile
    210                 215                 220 cca aaa gaa atc aaa agc cta att acc ccg gaa acc gaa gcg ctt cac        720
Pro Lys Glu Ile Lys Ser Leu Ile Thr Pro Glu Thr Glu Ala Leu His
225                 230                 235                 240 aat ttc tct tcg ttc aat cgg aat gag ccg tgt tct cta gca gcc gtc        768
Asn Phe Ser Ser Phe Asn Arg Asn Glu Pro Cys Ser Leu Ala Ala Val
                245                 250                 255 tgt gag ctt gtc gct gct ttt gcc ggt cga gat ccg aag gaa gtt gcg        816
Cys Glu Leu Val Ala Ala Phe Ala Gly Arg Asp Pro Lys Glu Val Ala
            260                 265                 270 aag att acg acg gaa aat gcg aag aaa gtt tac aaa cta gaa tga            861
Lys Ile Thr Thr Glu Asn Ala Lys Lys Val Tyr Lys Leu Glu
        275                 280                 285
```

<210> SEQ ID NO 4
<211> LENGTH: 286
<212> TYPE: PRT
<213> ORGANISM: Caenorhabditis elegans

<400> SEQUENCE: 4

```
Met Ala Leu Tyr Glu Leu Val Asp Ile Gly Ala Asn Leu Gly His Pro
1               5                   10                  15

Ser Tyr Gln Lys Asp Leu Asn Asp Val Leu Asp Arg Ala Lys Gln Ala
                20                  25                  30

Gly Leu Ser Lys Ile Met Val Thr Gly Thr Ser Glu Lys Ile Ser His
            35                  40                  45

Glu Cys Ala Asp Leu Val Glu Lys Tyr Pro Gly Phe Leu Tyr Phe Thr
        50                  55                  60

Ala Gly Val His Pro His Asp Ala Lys Asp Trp Asn Asp Gly Thr Leu
65                  70                  75                  80

Glu Ala Leu Lys Lys Leu Gln Glu Asn Pro Ser Cys Val Ala Val Gly
                85                  90                  95

Glu Cys Gly Leu Asp Phe Asn Arg Asn Phe Ser Pro Gln Asp Val Gln
            100                 105                 110

Lys Glu Val Phe Ala Lys Gln Val Asp Met Ala Val Lys Leu Gln Lys
        115                 120                 125

Pro Leu Phe Ile His Glu Arg Glu Ala His Glu Asp Met Val Lys Ile
    130                 135                 140

Leu Thr Ala Ala Gly Pro Ser Leu Pro Pro Ala Val Ile His Cys Phe
145                 150                 155                 160

Thr Gly Thr Val Val Glu Ala Lys Lys Tyr Leu Glu Met Gly Phe Tyr
                165                 170                 175
```

```
Ile Gly Leu Thr Gly Phe Leu Trp Lys Asp Arg Ser Asp Asn Gly Val
            180                 185                 190

Gln Ala Gly Leu Arg Ser Gly Glu Ile Pro Ile Glu Lys Leu Val Leu
        195                 200                 205

Glu Thr Asp Ala Pro Tyr Met Tyr Pro Lys Ile Asn Asp Lys Lys Ile
    210                 215                 220

Pro Lys Glu Ile Lys Ser Leu Ile Thr Pro Glu Thr Glu Ala Leu His
225                 230                 235                 240

Asn Phe Ser Ser Phe Asn Arg Asn Glu Pro Cys Ser Leu Ala Ala Val
                245                 250                 255

Cys Glu Leu Val Ala Ala Phe Ala Gly Arg Asp Pro Lys Glu Val Ala
            260                 265                 270

Lys Ile Thr Thr Glu Asn Ala Lys Lys Val Tyr Lys Leu Glu
        275                 280                 285

<210> SEQ ID NO 5
<211> LENGTH: 2631
<212> TYPE: DNA
<213> ORGANISM: Caenorhabditis elegans
<220> FEATURE:
<221> NAME/KEY: CDS
<222> LOCATION: (1)..(2631)
<223> OTHER INFORMATION: crn-3/CRN-3 (876 isoform)

<400> SEQUENCE: 5 atg tca gga gaa gaa tca atg ccc gat gaa gag cag aag caa tct gag      48
Met Ser Gly Glu Glu Ser Met Pro Asp Glu Glu Gln Lys Gln Ser Glu
1               5                   10                  15 gaa gaa gag gaa atg ata aga aaa aga acg tta gcg atg agg aaa aaa      96
Glu Glu Glu Glu Met Ile Arg Lys Arg Thr Leu Ala Met Arg Lys Lys
            20                  25                  30 gtc gaa gaa att atg aga aat ggc gcc ggg ctt gtt cgt gaa tca aat     144
Val Glu Glu Ile Met Arg Asn Gly Ala Gly Leu Val Arg Glu Ser Asn
        35                  40                  45 ggt ttg ccg aaa gct ggt gcg gat tat gag ctc tac aac tcg tat ccg     192
Gly Leu Pro Lys Ala Gly Ala Asp Tyr Glu Leu Tyr Asn Ser Tyr Pro
    50                  55                  60 aca ttc aac acg ttt atg aag cga tcc gag cag aga ttg aat gca ctc     240
Thr Phe Asn Thr Phe Met Lys Arg Ser Glu Gln Arg Leu Asn Ala Leu
65                  70                  75                  80 atg aac aaa gtc acc aag tca ata gga tgt gca atg cga gtt cca gat     288
Met Asn Lys Val Thr Lys Ser Ile Gly Cys Ala Met Arg Val Pro Asp
                85                  90                  95 gtc ggt tca tca gtc gaa cat tac aca gaa tgt gtt atc gag gct cag     336
Val Gly Ser Ser Val Glu His Tyr Thr Glu Cys Val Ile Glu Ala Gln
            100                 105                 110 gac aac att gca gaa cgt gca gca act ctc cat gaa gcg ctg aaa aaa     384
Asp Asn Ile Ala Glu Arg Ala Ala Thr Leu His Glu Ala Leu Lys Lys
        115                 120                 125 gcc gag cta gat gag ata gtc aaa gtt cca gaa ttc att aca aaa gcc     432
Ala Glu Leu Asp Glu Ile Val Lys Val Pro Glu Phe Ile Thr Lys Ala
    130                 135                 140 gcc cca aca aat cga aaa acc gaa gca gaa gtt tca gcg gca atg aga     480
Ala Pro Thr Asn Arg Lys Thr Glu Ala Glu Val Ser Ala Ala Met Arg
145                 150                 155                 160 acg ttt tca gcg aat att gga acg gtt ttg gcg gag aag ttt aga gaa     528
Thr Phe Ser Ala Asn Ile Gly Thr Val Leu Ala Glu Lys Phe Arg Glu
                165                 170                 175 cga aga gaa gaa gct gct cag atg gtt gtg ttg gaa aaa cca cag aag     576
```

```
Arg Arg Glu Glu Ala Ala Gln Met Val Val Leu Glu Lys Pro Gln Lys
        180                 185                 190 acg tat aac atc agt tcg gac aac tca caa gct cct ttt tct tct aaa        624
Thr Tyr Asn Ile Ser Ser Asp Asn Ser Gln Ala Pro Phe Ser Ser Lys
        195                 200                 205 ttg act gtt aaa cat cat gcc att gaa aaa cga acg ggt att gtt ctc        672
Leu Thr Val Lys His His Ala Ile Glu Lys Arg Thr Gly Ile Val Leu
    210                 215                 220 cac gat gac gat gag tct gga aga aga gat tgg ata agt gct gaa aca        720
His Asp Asp Asp Glu Ser Gly Arg Arg Asp Trp Ile Ser Ala Glu Thr
225                 230                 235                 240 gaa act gaa gag gaa cat cca tat atc gct gaa att ctt cac ttc aaa        768
Glu Thr Glu Glu Glu His Pro Tyr Ile Ala Glu Ile Leu His Phe Lys
                245                 250                 255 gtt cca gaa gct cag ctg aaa tct gca gag tgt tta aaa ttc aca gca        816
Val Pro Glu Ala Gln Leu Lys Ser Ala Glu Cys Leu Lys Phe Thr Ala
            260                 265                 270 ttg aag gat act cca ttg aca atg att gat act aag gag aag ctt gaa        864
Leu Lys Asp Thr Pro Leu Thr Met Ile Asp Thr Lys Glu Lys Leu Glu
        275                 280                 285 gca tta acg aaa act ttg aat tct gta aaa gag ttc gca gtc gac ttg        912
Ala Leu Thr Lys Thr Leu Asn Ser Val Lys Glu Phe Ala Val Asp Leu
    290                 295                 300 gag cat cac caa atg cga tcg tat ctt gga ttg acc tgc ctt att caa        960
Glu His His Gln Met Arg Ser Tyr Leu Gly Leu Thr Cys Leu Ile Gln
305                 310                 315                 320 att tca aca aga gat gaa gac ttt atc att gat ccc ttc cca ata tgg       1008
Ile Ser Thr Arg Asp Glu Asp Phe Ile Ile Asp Pro Phe Pro Ile Trp
                325                 330                 335 gat cat gtt gga atg ctc aat gag cca ttt gca aat cca cgt att ctc       1056
Asp His Val Gly Met Leu Asn Glu Pro Phe Ala Asn Pro Arg Ile Leu
            340                 345                 350 aaa gtt ttt cac ggt tct gac agt gat gtt ctc tgg cta caa agg gat       1104
Lys Val Phe His Gly Ser Asp Ser Asp Val Leu Trp Leu Gln Arg Asp
        355                 360                 365 tat gga gtt cat gtt gtt aat tta ttt gat aca tat gtt gcc atg aaa       1152
Tyr Gly Val His Val Val Asn Leu Phe Asp Thr Tyr Val Ala Met Lys
    370                 375                 380 aag ctg aag tat cct aaa ttc agt ctt gcc tac ctc act ctc cga ttt       1200
Lys Leu Lys Tyr Pro Lys Phe Ser Leu Ala Tyr Leu Thr Leu Arg Phe
385                 390                 395                 400 gcc gac gtt gtt ctg gac aaa caa tat caa ctg gct gac tgg aga gca       1248
Ala Asp Val Val Leu Asp Lys Gln Tyr Gln Leu Ala Asp Trp Arg Ala
                405                 410                 415 cgg cct cta cga aat gcg atg ata aac tac gcg aga gag gat act cat       1296
Arg Pro Leu Arg Asn Ala Met Ile Asn Tyr Ala Arg Glu Asp Thr His
            420                 425                 430 tac ctt ttg tat agt tat gat atg ctc cga gag caa ctt ctg aaa caa       1344
Tyr Leu Leu Tyr Ser Tyr Asp Met Leu Arg Glu Gln Leu Leu Lys Gln
        435                 440                 445 gat acc aag gat ttg gcc aac gtc tac tca gag tct agc gat ctt tgc       1392
Asp Thr Lys Asp Leu Ala Asn Val Tyr Ser Glu Ser Ser Asp Leu Cys
    450                 455                 460 ata aaa gta tac aag aaa cca gtg ttc aat ccg aaa gga tat ttg acg       1440
Ile Lys Val Tyr Lys Lys Pro Val Phe Asn Pro Lys Gly Tyr Leu Thr
465                 470                 475                 480 gaa ata aaa ttc cga ttc aca ctg aat act cga cag gac tat gca ctt       1488
Glu Ile Lys Phe Arg Phe Thr Leu Asn Thr Arg Gln Asp Tyr Ala Leu
                485                 490                 495
```

```
aca cat ctt ttc aaa tgg aga gat gta gta gct aga gca gaa gat gag      1536
Thr His Leu Phe Lys Trp Arg Asp Val Val Ala Arg Ala Glu Asp Glu
        500                 505                 510 agc cca cat ttt gta ctt cca aat cat atg atg cta tca ctt tct gag      1584
Ser Pro His Phe Val Leu Pro Asn His Met Met Leu Ser Leu Ser Glu
        515                 520                 525 aca tta cca cga gat gtt gga ggt atc tac gcg tgt tgt aac ccg tta      1632
Thr Leu Pro Arg Asp Val Gly Gly Ile Tyr Ala Cys Cys Asn Pro Leu
530                 535                 540 ccg tac ttt gtg aaa cag cga act ggt gat att ttg aaa ata att gtg      1680
Pro Tyr Phe Val Lys Gln Arg Thr Gly Asp Ile Leu Lys Ile Ile Val
545                 550                 555                 560 gag gcc aga gat gtg aag ctt gag aaa gtg gga ttg tcg gcg aaa gaa      1728
Glu Ala Arg Asp Val Lys Leu Glu Lys Val Gly Leu Ser Ala Lys Glu
                565                 570                 575 aga aat gat gca cag gaa gca cga ggt gta atg aac gat act atg gat      1776
Arg Asn Asp Ala Gln Glu Ala Arg Gly Val Met Asn Asp Thr Met Asp
                580                 585                 590 cat atc act tca gtt tta aaa tca aaa atc gac ttt tca cac act aga      1824
His Ile Thr Ser Val Leu Lys Ser Lys Ile Asp Phe Ser His Thr Arg
                595                 600                 605 ttt gac gaa gaa cgc gga gaa att tat att gat aag aca gat gaa gga      1872
Phe Asp Glu Glu Arg Gly Glu Ile Tyr Ile Asp Lys Thr Asp Glu Gly
610                 615                 620 atg gat atc gag ctg aaa gat cat aaa gaa tca ttg tta tca gtg ctc      1920
Met Asp Ile Glu Leu Lys Asp His Lys Glu Ser Leu Leu Ser Val Leu
625                 630                 635                 640 caa acg gct gaa att cca agt gtg gaa act atg att gtt gtg gaa aaa      1968
Gln Thr Ala Glu Ile Pro Ser Val Glu Thr Met Ile Val Val Glu Lys
                645                 650                 655 gga aag aaa tcg gat aat cag aaa gtt aaa aag ttg ttg aat gaa ctt      2016
Gly Lys Lys Ser Asp Asn Gln Lys Val Lys Lys Leu Leu Asn Glu Leu
                660                 665                 670 gac aaa ttt gta act cca ttt gaa tgt tat caa atg atg att aca          2064
Asp Lys Phe Val Thr Pro Phe Glu Cys Tyr Gln Met Met Met Ile Thr
                675                 680                 685 aaa gaa aag caa gaa gaa gaa gag aga aaa gag gct gag aga aag aaa      2112
Lys Glu Lys Gln Glu Glu Glu Glu Arg Lys Glu Ala Glu Arg Lys Lys
690                 695                 700 ttg gag gaa ggt gat cta ccg aag act atg ttc tca cat cat gat gct     2160
Leu Glu Glu Gly Asp Leu Pro Lys Thr Met Phe Ser His His Asp Ala
705                 710                 715                 720 ccg att aat aga aaa cct gaa ttc gat gcg aag ctt cta aac gtt gat      2208
Pro Ile Asn Arg Lys Pro Glu Phe Asp Ala Lys Leu Leu Asn Val Asp
                725                 730                 735 aca ctg aag ctg gtc cca gat gat ccg aac aag ccg aaa gat cca gaa      2256
Thr Leu Lys Leu Val Pro Asp Asp Pro Asn Lys Pro Lys Asp Pro Glu
                740                 745                 750 cct tca cca atg gaa gaa tct tca tcg gaa cct caa atc ttc gat cca      2304
Pro Ser Pro Met Glu Glu Ser Ser Ser Glu Pro Gln Ile Phe Asp Pro
        755                 760                 765 tct cgt ttt acc gac gac cag cta ctg tca aag aag gca atg aaa aga      2352
Ser Arg Phe Thr Asp Asp Gln Leu Leu Ser Lys Lys Ala Met Lys Arg
        770                 775                 780 aag aga gat gct gct cga cga aat ata gat gtt tct gtt gtg ctc ggc      2400
Lys Arg Asp Ala Ala Arg Arg Asn Ile Asp Val Ser Val Val Leu Gly
785                 790                 795                 800 gag tcg tcg agt agt tca gat cca aaa aag aaa aaa tct gat gat gat      2448
Glu Ser Ser Ser Ser Ser Asp Pro Lys Lys Lys Lys Ser Asp Asp Asp
                805                 810                 815
```

```
gct ccc gtt gaa gat ttt gat tat gaa aaa gct gat agt agt gca ttt      2496
Ala Pro Val Glu Asp Phe Asp Tyr Glu Lys Ala Asp Ser Ser Ala Phe
            820                 825                 830 gaa aaa cct gtt cga gac aac aac gcc gat ttc gat cca ttc cat caa      2544
Glu Lys Pro Val Arg Asp Asn Asn Ala Asp Phe Asp Pro Phe His Gln
835                 840                 845 aaa tat cga ttg aag aac aag aca aag aag aat atg gct atg aaa aaa      2592
Lys Tyr Arg Leu Lys Asn Lys Thr Lys Lys Asn Met Ala Met Lys Lys
    850                 855                 860 tca tcg aat cga caa gga acc atc aac tac aaa aaa tga                  2631
Ser Ser Asn Arg Gln Gly Thr Ile Asn Tyr Lys Lys
865                 870                 875

<210> SEQ ID NO 6
<211> LENGTH: 876
<212> TYPE: PRT
<213> ORGANISM: Caenorhabditis elegans

<400> SEQUENCE: 6

Met Ser Gly Glu Glu Ser Met Pro Asp Glu Glu Gln Lys Gln Ser Glu
1               5                   10                  15

Glu Glu Glu Glu Met Ile Arg Lys Arg Thr Leu Ala Met Arg Lys Lys
                20                  25                  30

Val Glu Glu Ile Met Arg Asn Gly Ala Gly Leu Val Arg Glu Ser Asn
            35                  40                  45

Gly Leu Pro Lys Ala Gly Ala Asp Tyr Glu Leu Tyr Asn Ser Tyr Pro
        50                  55                  60

Thr Phe Asn Thr Phe Met Lys Arg Ser Glu Gln Arg Leu Asn Ala Leu
65                  70                  75                  80

Met Asn Lys Val Thr Lys Ser Ile Gly Cys Ala Met Arg Val Pro Asp
                85                  90                  95

Val Gly Ser Ser Val Glu His Tyr Thr Glu Cys Val Ile Glu Ala Gln
            100                 105                 110

Asp Asn Ile Ala Glu Arg Ala Ala Thr Leu His Glu Ala Leu Lys Lys
        115                 120                 125

Ala Glu Leu Asp Glu Ile Val Lys Val Pro Glu Phe Ile Thr Lys Ala
130                 135                 140

Ala Pro Thr Asn Arg Lys Thr Glu Ala Glu Val Ser Ala Ala Met Arg
145                 150                 155                 160

Thr Phe Ser Ala Asn Ile Gly Thr Val Leu Ala Glu Lys Phe Arg Glu
                165                 170                 175

Arg Arg Glu Glu Ala Ala Gln Met Val Val Leu Glu Lys Pro Gln Lys
            180                 185                 190

Thr Tyr Asn Ile Ser Ser Asp Asn Ser Gln Ala Pro Phe Ser Ser Lys
        195                 200                 205

Leu Thr Val Lys His His Ala Ile Glu Lys Arg Thr Gly Ile Val Leu
210                 215                 220

His Asp Asp Asp Glu Ser Gly Arg Arg Asp Trp Ile Ser Ala Glu Thr
225                 230                 235                 240

Glu Thr Glu Glu Glu His Pro Tyr Ile Ala Glu Ile Leu His Phe Lys
                245                 250                 255

Val Pro Glu Ala Gln Leu Lys Ser Ala Glu Cys Leu Lys Phe Thr Ala
            260                 265                 270

Leu Lys Asp Thr Pro Leu Thr Met Ile Asp Thr Lys Glu Lys Leu Glu
        275                 280                 285
```

-continued

```
Ala Leu Thr Lys Thr Leu Asn Ser Val Lys Glu Phe Ala Val Asp Leu
290                 295                 300

Glu His His Gln Met Arg Ser Tyr Leu Gly Leu Thr Cys Leu Ile Gln
305                 310                 315                 320

Ile Ser Thr Arg Asp Glu Asp Phe Ile Ile Asp Pro Phe Pro Ile Trp
                325                 330                 335

Asp His Val Gly Met Leu Asn Glu Pro Phe Ala Asn Pro Arg Ile Leu
                340                 345                 350

Lys Val Phe His Gly Ser Asp Ser Asp Val Leu Trp Leu Gln Arg Asp
                355                 360                 365

Tyr Gly Val His Val Val Asn Leu Phe Asp Thr Tyr Val Ala Met Lys
370                 375                 380

Lys Leu Lys Tyr Pro Lys Phe Ser Leu Ala Tyr Leu Thr Leu Arg Phe
385                 390                 395                 400

Ala Asp Val Val Leu Asp Lys Gln Tyr Gln Leu Ala Asp Trp Arg Ala
                405                 410                 415

Arg Pro Leu Arg Asn Ala Met Ile Asn Tyr Ala Arg Glu Asp Thr His
                420                 425                 430

Tyr Leu Leu Tyr Ser Tyr Asp Met Leu Arg Glu Gln Leu Leu Lys Gln
                435                 440                 445

Asp Thr Lys Asp Leu Ala Asn Val Tyr Ser Glu Ser Ser Asp Leu Cys
450                 455                 460

Ile Lys Val Tyr Lys Lys Pro Val Phe Asn Pro Lys Gly Tyr Leu Thr
465                 470                 475                 480

Glu Ile Lys Phe Arg Phe Thr Leu Asn Thr Arg Gln Asp Tyr Ala Leu
                485                 490                 495

Thr His Leu Phe Lys Trp Arg Asp Val Val Ala Arg Ala Glu Asp Glu
                500                 505                 510

Ser Pro His Phe Val Leu Pro Asn His Met Met Leu Ser Leu Ser Glu
                515                 520                 525

Thr Leu Pro Arg Asp Val Gly Gly Ile Tyr Ala Cys Cys Asn Pro Leu
530                 535                 540

Pro Tyr Phe Val Lys Gln Arg Thr Gly Asp Ile Leu Lys Ile Ile Val
545                 550                 555                 560

Glu Ala Arg Asp Val Lys Leu Glu Lys Val Gly Leu Ser Ala Lys Glu
                565                 570                 575

Arg Asn Asp Ala Gln Glu Ala Arg Gly Val Met Asn Asp Thr Met Asp
                580                 585                 590

His Ile Thr Ser Val Leu Lys Ser Lys Ile Asp Phe Ser His Thr Arg
                595                 600                 605

Phe Asp Glu Glu Arg Gly Glu Ile Tyr Ile Asp Lys Thr Asp Glu Gly
610                 615                 620

Met Asp Ile Glu Leu Lys Asp His Lys Glu Ser Leu Leu Ser Val Leu
625                 630                 635                 640

Gln Thr Ala Glu Ile Pro Ser Val Glu Thr Met Ile Val Val Glu Lys
                645                 650                 655

Gly Lys Lys Ser Asp Asn Gln Lys Lys Leu Leu Asn Glu Leu
                660                 665                 670

Asp Lys Phe Val Thr Pro Phe Glu Cys Tyr Gln Met Met Met Ile Thr
                675                 680                 685

Lys Glu Lys Gln Glu Glu Glu Arg Lys Glu Ala Glu Arg Lys Lys
690                 695                 700

Leu Glu Glu Gly Asp Leu Pro Lys Thr Met Phe Ser His His Asp Ala
```

-continued

```
          705                 710                 715                 720
Pro Ile Asn Arg Lys Pro Glu Phe Asp Ala Lys Leu Leu Asn Val Asp
                725                 730                 735

Thr Leu Lys Leu Val Pro Asp Asp Pro Asn Lys Pro Lys Asp Pro Glu
            740                 745                 750

Pro Ser Pro Met Glu Glu Ser Ser Glu Pro Gln Ile Phe Asp Pro
        755                 760                 765

Ser Arg Phe Thr Asp Asp Gln Leu Leu Ser Lys Lys Ala Met Lys Arg
    770                 775                 780

Lys Arg Asp Ala Arg Arg Asn Ile Asp Val Ser Val Leu Gly
785                 790                 795                 800

Glu Ser Ser Ser Ser Asp Pro Lys Lys Lys Ser Asp Asp Asp
                805                 810                 815

Ala Pro Val Glu Asp Phe Asp Tyr Glu Lys Ala Asp Ser Ser Ala Phe
            820                 825                 830

Glu Lys Pro Val Arg Asp Asn Asn Ala Asp Phe Asp Pro Phe His Gln
        835                 840                 845

Lys Tyr Arg Leu Lys Asn Lys Thr Lys Lys Asn Met Ala Met Lys Lys
    850                 855                 860

Ser Ser Asn Arg Gln Gly Thr Ile Asn Tyr Lys Lys
865                 870                 875

<210> SEQ ID NO 7
<211> LENGTH: 1785
<212> TYPE: DNA
<213> ORGANISM: Caenorhabditis elegans
<220> FEATURE:
<221> NAME/KEY: CDS
<222> LOCATION: (1)..(1785)
<223> OTHER INFORMATION: crn-3/CRN-3 (594 isoform)

<400> SEQUENCE: 7 atg tca gga gaa gaa tca atg ccc gat gaa gag cag aag caa tct gag       48
Met Ser Gly Glu Glu Ser Met Pro Asp Glu Glu Gln Lys Gln Ser Glu
1               5                   10                  15 gaa gaa gag gaa atg ata aga aaa aga acg tta gcg atg agg aaa aaa       96
Glu Glu Glu Glu Met Ile Arg Lys Arg Thr Leu Ala Met Arg Lys Lys
            20                  25                  30 gtc gaa gaa att atg aga aat ggc gcc ggg ctt gtt cgt gaa tca aat      144
Val Glu Glu Ile Met Arg Asn Gly Ala Gly Leu Val Arg Glu Ser Asn
        35                  40                  45 ggt ttg ccg aaa gct ggt gcg gat tat gag ctc tac aac tcg tat ccg      192
Gly Leu Pro Lys Ala Gly Ala Asp Tyr Glu Leu Tyr Asn Ser Tyr Pro
    50                  55                  60 aca ttc aac acg ttt atg aag cga tcc gag cag aga ttg aat gca ctc      240
Thr Phe Asn Thr Phe Met Lys Arg Ser Glu Gln Arg Leu Asn Ala Leu
65                  70                  75                  80 atg aac aaa gtc acc aag tca ata gga tgt gca atg cga gtt cca gat      288
Met Asn Lys Val Thr Lys Ser Ile Gly Cys Ala Met Arg Val Pro Asp
                85                  90                  95 gtc ggt tca tca gtc gaa cat tac aca gaa tgt gtt atc gag gct cag      336
Val Gly Ser Ser Val Glu His Tyr Thr Glu Cys Val Ile Glu Ala Gln
            100                 105                 110 gac aac att gca gaa cgt gca gca act ctc cat gaa gcg ctg aaa aaa      384
Asp Asn Ile Ala Glu Arg Ala Ala Thr Leu His Glu Ala Leu Lys Lys
        115                 120                 125 gcc gag cta gat gag ata gtc aaa gtt cca gaa ttc att aca aaa gcc      432
Ala Glu Leu Asp Glu Ile Val Lys Val Pro Glu Phe Ile Thr Lys Ala
    130                 135                 140
```

-continued

```
gcc cca aca aat cga aaa acc gaa gca gaa gtt tca gcg gca atg aga    480
Ala Pro Thr Asn Arg Lys Thr Glu Ala Glu Val Ser Ala Ala Met Arg
145                 150                 155                 160 acg ttt tca gcg aat att gga acg gtt ttg gcg gag aag ttt aga gaa    528
Thr Phe Ser Ala Asn Ile Gly Thr Val Leu Ala Glu Lys Phe Arg Glu
                165                 170                 175 cga aga gaa gaa gct gct cag atg gtt gtg ttg gaa aaa cca cag aag    576
Arg Arg Glu Glu Ala Ala Gln Met Val Val Leu Glu Lys Pro Gln Lys
            180                 185                 190 acg tat aac atc agt tcg gac aac tca caa gct cct ttt tct tct aaa    624
Thr Tyr Asn Ile Ser Ser Asp Asn Ser Gln Ala Pro Phe Ser Ser Lys
        195                 200                 205 ttg act gtt aaa cat cat gcc att gaa aaa cga acg ggt att gtt ctc    672
Leu Thr Val Lys His His Ala Ile Glu Lys Arg Thr Gly Ile Val Leu
    210                 215                 220 cac gat gac gat gag tct gga aga aga gat tgg ata agt gct gaa aca    720
His Asp Asp Asp Glu Ser Gly Arg Arg Asp Trp Ile Ser Ala Glu Thr
225                 230                 235                 240 gaa act gaa gag gaa cat cca tat atc gct gaa att ctt cac ttc aaa    768
Glu Thr Glu Glu Glu His Pro Tyr Ile Ala Glu Ile Leu His Phe Lys
                245                 250                 255 gtt cca gaa gct cag ctg aaa tct gca gag tgt tta aaa ttc aca gca    816
Val Pro Glu Ala Gln Leu Lys Ser Ala Glu Cys Leu Lys Phe Thr Ala
            260                 265                 270 ttg aag gat act cca ttg aca atg att gat act aag gag aag ctt gaa    864
Leu Lys Asp Thr Pro Leu Thr Met Ile Asp Thr Lys Glu Lys Leu Glu
        275                 280                 285 gca tta acg aaa act ttg aat tct gta aaa gag ttc gca gtc gac ttg    912
Ala Leu Thr Lys Thr Leu Asn Ser Val Lys Glu Phe Ala Val Asp Leu
    290                 295                 300 gag cat cac caa atg cga tcg tat ctt gga ttg acc tgc ctt att caa    960
Glu His His Gln Met Arg Ser Tyr Leu Gly Leu Thr Cys Leu Ile Gln
305                 310                 315                 320 att tca aca aga gat gaa gac ttt atc att gat ccc ttc cca ata tgg   1008
Ile Ser Thr Arg Asp Glu Asp Phe Ile Ile Asp Pro Phe Pro Ile Trp
                325                 330                 335 gat cat gtt gga atg ctc aat gag cca ttt gca aat cca cgt att ctc   1056
Asp His Val Gly Met Leu Asn Glu Pro Phe Ala Asn Pro Arg Ile Leu
            340                 345                 350 aaa gtt ttt cac ggt tct gac agt gat gtt ctc tgg cta caa agg gat   1104
Lys Val Phe His Gly Ser Asp Ser Asp Val Leu Trp Leu Gln Arg Asp
        355                 360                 365 tat gga gtt cat gtt gtt aat tta ttt gat aca tat gtt aaa gtt aaa   1152
Tyr Gly Val His Val Val Asn Leu Phe Asp Thr Tyr Val Lys Val Lys
    370                 375                 380 aag ttg ttg aat gaa ctt gac aaa ttt gta act cca ttt gaa tgt tat   1200
Lys Leu Leu Asn Glu Leu Asp Lys Phe Val Thr Pro Phe Glu Cys Tyr
385                 390                 395                 400 caa atg atg atg att aca aaa gaa aag caa gaa gaa gag aga aaa        1248
Gln Met Met Met Ile Thr Lys Glu Lys Gln Glu Glu Glu Arg Lys
                405                 410                 415 gag gct gag aga aag aaa ttg gag gaa ggt gat cta ccg aag act atg   1296
Glu Ala Glu Arg Lys Lys Leu Glu Glu Gly Asp Leu Pro Lys Thr Met
            420                 425                 430 ttc tca cat cat gat gct ccg att aat aga aaa cct gaa ttc gat gcg   1344
Phe Ser His His Asp Ala Pro Ile Asn Arg Lys Pro Glu Phe Asp Ala
        435                 440                 445 aag ctt cta aac gtt gat aca ctg aag ctg gtc cca gat gat ccg aac   1392
Lys Leu Leu Asn Val Asp Thr Leu Lys Leu Val Pro Asp Asp Pro Asn
```

-continued

```
                450                 455                 460
aag ccg aaa gat cca gaa cct tca cca atg gaa gaa tct tca tcg gaa      1440
Lys Pro Lys Asp Pro Glu Pro Ser Pro Met Glu Glu Ser Ser Ser Glu
465                 470                 475                 480 cct caa atc ttc gat cca tct cgt ttt acc gac gac cag cta ctg tca      1488
Pro Gln Ile Phe Asp Pro Ser Arg Phe Thr Asp Asp Gln Leu Leu Ser
                485                 490                 495 aag aag gca atg aaa aga aag aga gat gct gct cga cga aat ata gat      1536
Lys Lys Ala Met Lys Arg Lys Arg Asp Ala Ala Arg Arg Asn Ile Asp
            500                 505                 510 gtt tct gtt gtg ctc ggc gag tcg tcg agt agt tca gat cca aaa aag      1584
Val Ser Val Val Leu Gly Glu Ser Ser Ser Ser Ser Asp Pro Lys Lys
        515                 520                 525 aaa aaa tct gat gat gat gct ccc gtt gaa gat ttt gat tat gaa aaa      1632
Lys Lys Ser Asp Asp Asp Ala Pro Val Glu Asp Phe Asp Tyr Glu Lys
530                 535                 540 gct gat agt agt gca ttt gaa aaa cct gtt cga gac aac aac gcc gat      1680
Ala Asp Ser Ser Ala Phe Glu Lys Pro Val Arg Asp Asn Asn Ala Asp
545                 550                 555                 560 ttc gat cca ttc cat caa aaa tat cga ttg aag aac aag aca aag aag      1728
Phe Asp Pro Phe His Gln Lys Tyr Arg Leu Lys Asn Lys Thr Lys Lys
                565                 570                 575 aat atg gct atg aaa aaa tca tcg aat cga caa gga acc atc aac tac      1776
Asn Met Ala Met Lys Lys Ser Ser Asn Arg Gln Gly Thr Ile Asn Tyr
            580                 585                 590 aaa aaa tga                                                           1785
Lys Lys <210> SEQ ID NO 8
<211> LENGTH: 594
<212> TYPE: PRT
<213> ORGANISM: Caenorhabditis elegans

<400> SEQUENCE: 8

Met Ser Gly Glu Glu Ser Met Pro Asp Glu Glu Gln Lys Gln Ser Glu
1               5                   10                  15

Glu Glu Glu Glu Met Ile Arg Lys Arg Thr Leu Ala Met Arg Lys Lys
                20                  25                  30

Val Glu Glu Ile Met Arg Asn Gly Ala Gly Leu Val Arg Glu Ser Asn
            35                  40                  45

Gly Leu Pro Lys Ala Gly Ala Asp Tyr Glu Leu Tyr Asn Ser Tyr Pro
        50                  55                  60

Thr Phe Asn Thr Phe Met Lys Arg Ser Glu Gln Arg Leu Asn Ala Leu
65                  70                  75                  80

Met Asn Lys Val Thr Lys Ser Ile Gly Cys Ala Met Arg Val Pro Asp
                85                  90                  95

Val Gly Ser Ser Val Glu His Tyr Thr Glu Cys Val Ile Glu Ala Gln
            100                 105                 110

Asp Asn Ile Ala Glu Arg Ala Ala Thr Leu His Glu Ala Leu Lys Lys
        115                 120                 125

Ala Glu Leu Asp Glu Ile Val Lys Val Pro Glu Phe Ile Thr Lys Ala
    130                 135                 140

Ala Pro Thr Asn Arg Lys Thr Glu Ala Glu Val Ser Ala Ala Met Arg
145                 150                 155                 160

Thr Phe Ser Ala Asn Ile Gly Thr Val Leu Ala Glu Lys Phe Arg Glu
                165                 170                 175

Arg Arg Glu Glu Ala Ala Gln Met Val Val Leu Glu Lys Pro Gln Lys
```

-continued

```
                180                 185                 190
Thr Tyr Asn Ile Ser Ser Asp Asn Ser Gln Ala Pro Phe Ser Ser Lys
            195                 200                 205
Leu Thr Val Lys His His Ala Ile Glu Lys Arg Thr Gly Ile Val Leu
        210                 215                 220
His Asp Asp Glu Ser Gly Arg Arg Asp Trp Ile Ser Ala Glu Thr
225                 230                 235                 240
Glu Thr Glu Glu Glu His Pro Tyr Ile Ala Glu Ile Leu His Phe Lys
                245                 250                 255
Val Pro Glu Ala Gln Leu Lys Ser Ala Glu Cys Leu Lys Phe Thr Ala
            260                 265                 270
Leu Lys Asp Thr Pro Leu Thr Met Ile Asp Thr Lys Glu Lys Leu Glu
        275                 280                 285
Ala Leu Thr Lys Thr Leu Asn Ser Val Lys Glu Phe Ala Val Asp Leu
        290                 295                 300
Glu His His Gln Met Arg Ser Tyr Leu Gly Leu Thr Cys Leu Ile Gln
305                 310                 315                 320
Ile Ser Thr Arg Asp Glu Asp Phe Ile Ile Asp Pro Phe Pro Ile Trp
                325                 330                 335
Asp His Val Gly Met Leu Asn Glu Pro Phe Ala Asn Pro Arg Ile Leu
            340                 345                 350
Lys Val Phe His Gly Ser Asp Ser Asp Val Leu Trp Leu Gln Arg Asp
        355                 360                 365
Tyr Gly Val His Val Val Asn Leu Phe Asp Thr Tyr Val Lys Val Lys
    370                 375                 380
Lys Leu Leu Asn Glu Leu Asp Lys Phe Val Thr Pro Phe Glu Cys Tyr
385                 390                 395                 400
Gln Met Met Met Ile Thr Lys Glu Lys Gln Glu Glu Glu Arg Lys
                405                 410                 415
Glu Ala Glu Arg Lys Lys Leu Glu Glu Gly Asp Leu Pro Lys Thr Met
            420                 425                 430
Phe Ser His His Asp Ala Pro Ile Asn Arg Lys Pro Glu Phe Asp Ala
        435                 440                 445
Lys Leu Leu Asn Val Asp Thr Leu Lys Leu Val Pro Asp Asp Pro Asn
    450                 455                 460
Lys Pro Lys Asp Pro Glu Pro Ser Pro Met Glu Glu Ser Ser Ser Glu
465                 470                 475                 480
Pro Gln Ile Phe Asp Pro Ser Arg Phe Thr Asp Gln Leu Leu Ser
                485                 490                 495
Lys Lys Ala Met Lys Arg Lys Asp Ala Ala Arg Arg Asn Ile Asp
            500                 505                 510
Val Ser Val Val Leu Gly Glu Ser Ser Ser Ser Asp Pro Lys Lys
        515                 520                 525
Lys Lys Ser Asp Asp Asp Ala Pro Val Glu Asp Phe Asp Tyr Glu Lys
    530                 535                 540
Ala Asp Ser Ser Ala Phe Glu Lys Pro Val Arg Asp Asn Asn Ala Asp
545                 550                 555                 560
Phe Asp Pro Phe His Gln Lys Tyr Arg Leu Lys Asn Lys Thr Lys Lys
                565                 570                 575
Asn Met Ala Met Lys Lys Ser Ser Asn Arg Gln Gly Thr Ile Asn Tyr
            580                 585                 590
Lys Lys
```

<210> SEQ ID NO 9
<211> LENGTH: 897
<212> TYPE: DNA
<213> ORGANISM: Caenorhabditis elegans
<220> FEATURE:
<221> NAME/KEY: CDS
<222> LOCATION: (1)..(897)
<223> OTHER INFORMATION: crn-4/CRN-4

<400> SEQUENCE: 9

```
atg gct tac caa cac tgt ccg ttt gat act tta ttg att ctc gac ttt    48
Met Ala Tyr Gln His Cys Pro Phe Asp Thr Leu Leu Ile Leu Asp Phe
1               5                   10                  15 gag aca aca tcc gat gct gct aat caa gat tac ccg tgc gaa gtc att    96
Glu Thr Thr Ser Asp Ala Ala Asn Gln Asp Tyr Pro Cys Glu Val Ile
            20                  25                  30 cag ttc gcg atc gtt gcc tat gat gtc cca aat gat aaa att cgt gag   144
Gln Phe Ala Ile Val Ala Tyr Asp Val Pro Asn Asp Lys Ile Arg Glu
        35                  40                  45 gac att agt ttc aac aag tac gtc aaa cct gtt ctc aat cgg act ttg   192
Asp Ile Ser Phe Asn Lys Tyr Val Lys Pro Val Leu Asn Arg Thr Leu
    50                  55                  60 aca aag aac tgt gtc gat ttt acc gga atc ccg caa cgt tcc att gac   240
Thr Lys Asn Cys Val Asp Phe Thr Gly Ile Pro Gln Arg Ser Ile Asp
65                  70                  75                  80 acc gcc gac acc ttt gat gtg gtc tac gag cag ttc cag cag tgg ctc   288
Thr Ala Asp Thr Phe Asp Val Val Tyr Glu Gln Phe Gln Gln Trp Leu
                85                  90                  95 atc acg ctt gga ttg gaa gaa gga aag ttc gct ttc gtc tgt gac agt   336
Ile Thr Leu Gly Leu Glu Glu Gly Lys Phe Ala Phe Val Cys Asp Ser
            100                 105                 110 cgt cag gat ttg tgg cgt att gct cag tat cag atg aaa ctg tcc aat   384
Arg Gln Asp Leu Trp Arg Ile Ala Gln Tyr Gln Met Lys Leu Ser Asn
        115                 120                 125 atc caa atg cca gct ttc ttc cgt cag tac atc aat ttg tac aag att   432
Ile Gln Met Pro Ala Phe Phe Arg Gln Tyr Ile Asn Leu Tyr Lys Ile
    130                 135                 140 ttc acg aat gag atg gat cga atg ggc ccc aaa gag ctt tct gcg acg   480
Phe Thr Asn Glu Met Asp Arg Met Gly Pro Lys Glu Leu Ser Ala Thr
145                 150                 155                 160 acc aac atc ggc aag atg aac gaa tac tac gat ctg cca acc atc gga   528
Thr Asn Ile Gly Lys Met Asn Glu Tyr Tyr Asp Leu Pro Thr Ile Gly
                165                 170                 175 cgt gct cat gat gcc atg gat gac tgt ctg aat att gct act att ctc   576
Arg Ala His Asp Ala Met Asp Asp Cys Leu Asn Ile Ala Thr Ile Leu
            180                 185                 190 cag cga atg att aac atg ggc gca aaa gtt act gtg aac gag ctg ctg   624
Gln Arg Met Ile Asn Met Gly Ala Lys Val Thr Val Asn Glu Leu Leu
        195                 200                 205 acc tgt tgt gct tcg tgg cgc aga caa ccg ctg gtc tac aac aaa gaa   672
Thr Cys Cys Ala Ser Trp Arg Arg Gln Pro Leu Val Tyr Asn Lys Glu
    210                 215                 220 tgg aga agc agc ttc atg gac gct gga aag att ttc gaa aga gtc ctg   720
Trp Arg Ser Ser Phe Met Asp Ala Gly Lys Ile Phe Glu Arg Val Leu
225                 230                 235                 240 cca ctt gtc gtg act aca att cgc gca ggc gac ttt cgt ctc gag atg   768
Pro Leu Val Val Thr Thr Ile Arg Ala Gly Asp Phe Arg Leu Glu Met
                245                 250                 255 tac gga gtc tgc cgc tat tgc cgc aaa gga atg gat gtg tgt gga aca   816
Tyr Gly Val Cys Arg Tyr Cys Arg Lys Gly Met Asp Val Cys Gly Thr
            260                 265                 270
```

```
agt cat cag cag aca cca cat gat ctc tac aaa aat gag gag gat cct    864
Ser His Gln Gln Thr Pro His Asp Leu Tyr Lys Asn Glu Glu Asp Pro
    275                 280                 285 atc cac ttt gcc aaa att gcc ggt tac tac tag                        897
Ile His Phe Ala Lys Ile Ala Gly Tyr Tyr
    290                 295

<210> SEQ ID NO 10
<211> LENGTH: 298
<212> TYPE: PRT
<213> ORGANISM: Caenorhabditis elegans

<400> SEQUENCE: 10

Met Ala Tyr Gln His Cys Pro Phe Asp Thr Leu Leu Ile Leu Asp Phe
1               5                   10                  15

Glu Thr Thr Ser Asp Ala Ala Asn Gln Asp Tyr Pro Cys Glu Val Ile
            20                  25                  30

Gln Phe Ala Ile Val Ala Tyr Asp Val Pro Asn Asp Lys Ile Arg Glu
        35                  40                  45

Asp Ile Ser Phe Asn Lys Tyr Val Lys Pro Val Leu Asn Arg Thr Leu
    50                  55                  60

Thr Lys Asn Cys Val Asp Phe Thr Gly Ile Pro Gln Arg Ser Ile Asp
65                  70                  75                  80

Thr Ala Asp Thr Phe Asp Val Val Tyr Glu Gln Phe Gln Gln Trp Leu
                85                  90                  95

Ile Thr Leu Gly Leu Glu Glu Gly Lys Phe Ala Phe Val Cys Asp Ser
            100                 105                 110

Arg Gln Asp Leu Trp Arg Ile Ala Gln Tyr Gln Met Lys Leu Ser Asn
        115                 120                 125

Ile Gln Met Pro Ala Phe Phe Arg Gln Tyr Ile Asn Leu Tyr Lys Ile
    130                 135                 140

Phe Thr Asn Glu Met Asp Arg Met Gly Pro Lys Glu Leu Ser Ala Thr
145                 150                 155                 160

Thr Asn Ile Gly Lys Met Asn Glu Tyr Tyr Asp Leu Pro Thr Ile Gly
                165                 170                 175

Arg Ala His Asp Ala Met Asp Asp Cys Leu Asn Ile Ala Thr Ile Leu
            180                 185                 190

Gln Arg Met Ile Asn Met Gly Ala Lys Val Thr Val Asn Glu Leu Leu
        195                 200                 205

Thr Cys Cys Ala Ser Trp Arg Arg Gln Pro Leu Val Tyr Asn Lys Glu
    210                 215                 220

Trp Arg Ser Ser Phe Met Asp Ala Gly Lys Ile Phe Glu Arg Val Leu
225                 230                 235                 240

Pro Leu Val Val Thr Thr Ile Arg Ala Gly Asp Phe Arg Leu Glu Met
                245                 250                 255

Tyr Gly Val Cys Arg Tyr Cys Arg Lys Gly Met Asp Val Cys Gly Thr
            260                 265                 270

Ser His Gln Gln Thr Pro His Asp Leu Tyr Lys Asn Glu Glu Asp Pro
        275                 280                 285

Ile His Phe Ala Lys Ile Ala Gly Tyr Tyr
    290                 295

<210> SEQ ID NO 11
<211> LENGTH: 645
<212> TYPE: DNA
<213> ORGANISM: Caenorhabditis elegans
```

<220> FEATURE:
<221> NAME/KEY: CDS
<222> LOCATION: (1)..(645)
<223> OTHER INFORMATION: crn-5/CRN-5

<400> SEQUENCE: 11

| | | | | | | | | | | | | | | | | |
|---|---|---|---|---|---|---|---|---|---|---|---|---|---|---|---|---|
| atg | gcc | ggc | aga | ctt | cgt | gaa | atg | cgt | tgt | gag | ctc | tcg | ttc | ctc | aaa | 48 |
| Met | Ala | Gly | Arg | Leu | Arg | Glu | Met | Arg | Cys | Glu | Leu | Ser | Phe | Leu | Lys | |
| 1 | | | | 5 | | | | | 10 | | | | | 15 | | |

| aac | gcg | gat | ggc | tcg | gca | tgc | ttc | tcc | cag | ggt | gcc | acg | tgt | att | tgg | 96 |
|---|---|---|---|---|---|---|---|---|---|---|---|---|---|---|---|---|
| Asn | Ala | Asp | Gly | Ser | Ala | Cys | Phe | Ser | Gln | Gly | Ala | Thr | Cys | Ile | Trp | |
| | | | 20 | | | | | 25 | | | | | 30 | | | |

| gct | tca | tgc | agt | ggt | cct | gga | gat | gtt | cac | gct | tcg | aaa | gca | agt | gat | 144 |
|---|---|---|---|---|---|---|---|---|---|---|---|---|---|---|---|---|
| Ala | Ser | Cys | Ser | Gly | Pro | Gly | Asp | Val | His | Ala | Ser | Lys | Ala | Ser | Asp | |
| | | 35 | | | | | 40 | | | | | 45 | | | | |

| gag | gct | atg | act | ctg | gat | att | agt | tat | aga | gca | aat | tgt | gga | gat | aac | 192 |
|---|---|---|---|---|---|---|---|---|---|---|---|---|---|---|---|---|
| Glu | Ala | Met | Thr | Leu | Asp | Ile | Ser | Tyr | Arg | Ala | Asn | Cys | Gly | Asp | Asn | |
| 50 | | | | | 55 | | | | | 60 | | | | | | |

| aag | ttc | aat | gtg | ctg | aac | aat | atc | att | cat | tct | act | cta | tcc | aat | gca | 240 |
|---|---|---|---|---|---|---|---|---|---|---|---|---|---|---|---|---|
| Lys | Phe | Asn | Val | Leu | Asn | Asn | Ile | Ile | His | Ser | Thr | Leu | Ser | Asn | Ala | |
| 65 | | | | 70 | | | | | 75 | | | | | 80 | | |

| atc | aat | ctc | gaa | ttg | ttt | ccc | cac | aca | aca | att | tct | gtc | aca | gta | cat | 288 |
|---|---|---|---|---|---|---|---|---|---|---|---|---|---|---|---|---|
| Ile | Asn | Leu | Glu | Leu | Phe | Pro | His | Thr | Thr | Ile | Ser | Val | Thr | Val | His | |
| | | | | 85 | | | | | 90 | | | | | 95 | | |

| gga | att | cag | gat | gat | gga | agt | atg | gga | gct | gta | gcg | ata | aat | gga | gct | 336 |
|---|---|---|---|---|---|---|---|---|---|---|---|---|---|---|---|---|
| Gly | Ile | Gln | Asp | Asp | Gly | Ser | Met | Gly | Ala | Val | Ala | Ile | Asn | Gly | Ala | |
| | | | | 100 | | | | | 105 | | | | | 110 | | |

| tgt | ttt | gct | cta | ctt | gac | aat | gga | atg | cca | ttc | gaa | aca | gtc | ttc | tgt | 384 |
|---|---|---|---|---|---|---|---|---|---|---|---|---|---|---|---|---|
| Cys | Phe | Ala | Leu | Leu | Asp | Asn | Gly | Met | Pro | Phe | Glu | Thr | Val | Phe | Cys | |
| | | | 115 | | | | | 120 | | | | | 125 | | | |

| ggt | gtc | ctt | att | gtt | cgt | gtc | aaa | gat | gag | ctg | att | att | gat | ccg | aca | 432 |
|---|---|---|---|---|---|---|---|---|---|---|---|---|---|---|---|---|
| Gly | Val | Leu | Ile | Val | Arg | Val | Lys | Asp | Glu | Leu | Ile | Ile | Asp | Pro | Thr | |
| | | 130 | | | | | 135 | | | | | 140 | | | | |

| gca | aaa | caa | gaa | gct | gca | tcg | act | gga | aga | gtg | ctc | ttt | tca | gtg | tgc | 480 |
|---|---|---|---|---|---|---|---|---|---|---|---|---|---|---|---|---|
| Ala | Lys | Gln | Glu | Ala | Ala | Ser | Thr | Gly | Arg | Val | Leu | Phe | Ser | Val | Cys | |
| 145 | | | | | 150 | | | | | 155 | | | | | 160 | |

| aaa | gga | tcc | gat | gga | cat | cca | gaa | gtg | tgt | gcg | atg | gac | gct | ata | gga | 528 |
|---|---|---|---|---|---|---|---|---|---|---|---|---|---|---|---|---|
| Lys | Gly | Ser | Asp | Gly | His | Pro | Glu | Val | Cys | Ala | Met | Asp | Ala | Ile | Gly | |
| | | | | 165 | | | | | 170 | | | | | 175 | | |

| cat | tgg | gat | ttt | att | cag | ctg | gaa | gcc | gcg | tgg | tca | ttg | gca | caa | cca | 576 |
|---|---|---|---|---|---|---|---|---|---|---|---|---|---|---|---|---|
| His | Trp | Asp | Phe | Ile | Gln | Leu | Glu | Ala | Ala | Trp | Ser | Leu | Ala | Gln | Pro | |
| | | | 180 | | | | | 185 | | | | | 190 | | | |

| tct | gcc | agt | gct | att | ttt | gat | ttc | tac | aaa | act | gtg | atg | aag | agg | aag | 624 |
|---|---|---|---|---|---|---|---|---|---|---|---|---|---|---|---|---|
| Ser | Ala | Ser | Ala | Ile | Phe | Asp | Phe | Tyr | Lys | Thr | Val | Met | Lys | Arg | Lys | |
| | | 195 | | | | | 200 | | | | | 205 | | | | |

| ctt | tcg | gtt | gat | gag | caa | tag | | | | | | | | | | 645 |
|---|---|---|---|---|---|---|---|---|---|---|---|---|---|---|---|---|
| Leu | Ser | Val | Asp | Glu | Gln | | | | | | | | | | | |
| | 210 | | | | | | | | | | | | | | | |

<210> SEQ ID NO 12
<211> LENGTH: 214
<212> TYPE: PRT
<213> ORGANISM: Caenorhabditis elegans

<400> SEQUENCE: 12

| Met | Ala | Gly | Arg | Leu | Arg | Glu | Met | Arg | Cys | Glu | Leu | Ser | Phe | Leu | Lys |
|---|---|---|---|---|---|---|---|---|---|---|---|---|---|---|---|
| 1 | | | | 5 | | | | | 10 | | | | | 15 | |

| Asn | Ala | Asp | Gly | Ser | Ala | Cys | Phe | Ser | Gln | Gly | Ala | Thr | Cys | Ile | Trp |
|---|---|---|---|---|---|---|---|---|---|---|---|---|---|---|---|
| | | | 20 | | | | | 25 | | | | | 30 | | |

| Ala | Ser | Cys | Ser | Gly | Pro | Gly | Asp | Val | His | Ala | Ser | Lys | Ala | Ser | Asp |
|---|---|---|---|---|---|---|---|---|---|---|---|---|---|---|---|
| | | 35 | | | | | 40 | | | | | 45 | | | |

-continued

```
Glu Ala Met Thr Leu Asp Ile Ser Tyr Arg Ala Asn Cys Gly Asp Asn
 50                  55                  60

Lys Phe Asn Val Leu Asn Asn Ile Ile His Ser Thr Leu Ser Asn Ala
 65                  70                  75                  80

Ile Asn Leu Glu Leu Phe Pro His Thr Thr Ile Ser Val Thr Val His
                 85                  90                  95

Gly Ile Gln Asp Asp Gly Ser Met Gly Ala Val Ala Ile Asn Gly Ala
            100                 105                 110

Cys Phe Ala Leu Leu Asp Asn Gly Met Pro Phe Glu Thr Val Phe Cys
        115                 120                 125

Gly Val Leu Ile Val Arg Val Lys Asp Glu Leu Ile Ile Asp Pro Thr
130                 135                 140

Ala Lys Gln Glu Ala Ala Ser Thr Gly Arg Val Leu Phe Ser Val Cys
145                 150                 155                 160

Lys Gly Ser Asp Gly His Pro Glu Val Cys Ala Met Asp Ala Ile Gly
                165                 170                 175

His Trp Asp Phe Ile Gln Leu Glu Ala Ala Trp Ser Leu Ala Gln Pro
            180                 185                 190

Ser Ala Ser Ala Ile Phe Asp Phe Tyr Lys Thr Val Met Lys Arg Lys
        195                 200                 205

Leu Ser Val Asp Glu Gln
    210
```

<210> SEQ ID NO 13
<211> LENGTH: 1122
<212> TYPE: DNA
<213> ORGANISM: Caenorhabditis elegans
<220> FEATURE:
<221> NAME/KEY: CDS
<222> LOCATION: (1)..(1122)
<223> OTHER INFORMATION: crn-6/CRN-6 (373 isoform)

<400> SEQUENCE: 13

```
atg att cgt caa att atc ttg ata gtt tca ctt att ggg ata tca aat        48
Met Ile Arg Gln Ile Ile Leu Ile Val Ser Leu Ile Gly Ile Ser Asn
 1               5                  10                  15 gcc gcg tac caa tgc aag gat aat aat gga agt aat gta gat tgg ttc        96
Ala Ala Tyr Gln Cys Lys Asp Asn Asn Gly Ser Asn Val Asp Trp Phe
                20                  25                  30 gtc ttc tac aaa ctt cca cat ctt tgg aat cat cca gac aat gta cca       144
Val Phe Tyr Lys Leu Pro His Leu Trp Asn His Pro Asp Asn Val Pro
         35                  40                  45 att tca aat gga act gga ttc ttg tat ttt gat gtc aat aat aaa aat       192
Ile Ser Asn Gly Thr Gly Phe Leu Tyr Phe Asp Val Asn Asn Lys Asn
 50                  55                  60 tgg aaa ctt atg cca caa gga atg gat gtt gag aat aat gcc gta tat       240
Trp Lys Leu Met Pro Gln Gly Met Asp Val Glu Asn Asn Ala Val Tyr
 65                  70                  75                  80 tat acc ctc caa cag tac tat aac tcg aat atg aat acg aca ttc agc       288
Tyr Thr Leu Gln Gln Tyr Tyr Asn Ser Asn Met Asn Thr Thr Phe Ser
                 85                  90                  95 tac atg tac aat gac gag tgg cct gat agc aca atc tgg agt aat agt       336
Tyr Met Tyr Asn Asp Glu Trp Pro Asp Ser Thr Ile Trp Ser Asn Ser
            100                 105                 110 tca gga cat gca aag ggt gtt act gta ttt gat caa tac acc gga ttc       384
Ser Gly His Ala Lys Gly Val Thr Val Phe Asp Gln Tyr Thr Gly Phe
        115                 120                 125 tgg atg att cac agt att cca aag ttc ccg agt aaa gat atg ttc cga       432
```

```
Trp Met Ile His Ser Ile Pro Lys Phe Pro Ser Lys Asp Met Phe Arg
        130                 135                 140 ttc cca tca aat gcg cat tat tat ggg caa atg gga att tgt att tct    480
Phe Pro Ser Asn Ala His Tyr Tyr Gly Gln Met Gly Ile Cys Ile Ser
145                 150                 155                 160 tac aat acg gtt tcc ttg gca act att gct caa caa ctc ttc tac tac    528
Tyr Asn Thr Val Ser Leu Ala Thr Ile Ala Gln Gln Leu Phe Tyr Tyr
                165                 170                 175 aac aca ttc act tat cag ttc aat ttg cca cag agt ttt gca aac cag    576
Asn Thr Phe Thr Tyr Gln Phe Asn Leu Pro Gln Ser Phe Ala Asn Gln
            180                 185                 190 ttt cct gtt tta tct caa ttg aaa aat aag gaa tat aac aag agt cca    624
Phe Pro Val Leu Ser Gln Leu Lys Asn Lys Glu Tyr Asn Lys Ser Pro
        195                 200                 205 cca ctc act tcc acg aag gtt ttg aaa tca ctt ggt ggc caa cac ttc    672
Pro Leu Thr Ser Thr Lys Val Leu Lys Ser Leu Gly Gly Gln His Phe
    210                 215                 220 cga cat ttc gcg aaa acc ggt gaa tgg gga aaa gat ctc tac agc gat    720
Arg His Phe Ala Lys Thr Gly Glu Trp Gly Lys Asp Leu Tyr Ser Asp
225                 230                 235                 240 ttt gtc ggt cct aca ttg aag tct tcg atc aaa gtt gaa aca tgg aat    768
Phe Val Gly Pro Thr Leu Lys Ser Ser Ile Lys Val Glu Thr Trp Asn
                245                 250                 255 cat cag agc gga gat gag tat aat ctc cca tca gtt tgt gat ccc aat    816
His Gln Ser Gly Asp Glu Tyr Asn Leu Pro Ser Val Cys Asp Pro Asn
            260                 265                 270 cat gtt cag tcg aca atg agt gca aaa tac att cgt ctt cca tat gca    864
His Val Gln Ser Thr Met Ser Ala Lys Tyr Ile Arg Leu Pro Tyr Ala
        275                 280                 285 atc gat tac tcc agc tat gaa gat cat tca aag ttc gtc gtg gca tat    912
Ile Asp Tyr Ser Ser Tyr Glu Asp His Ser Lys Phe Val Val Ala Tyr
    290                 295                 300 agt gaa agc tcc tca aag cca cca att cca tac gtt tgt att gga gat    960
Ser Glu Ser Ser Lys Pro Pro Ile Pro Tyr Val Cys Ile Gly Asp
305                 310                 315                 320 atc aat cgt cag agt cat caa atc cat cgt ggc ggt gga aca atg tgc    1008
Ile Asn Arg Gln Ser His Gln Ile His Arg Gly Gly Gly Thr Met Cys
                325                 330                 335 atc tac gat caa gaa aca tac ttc caa ttc gca aat atc atc agt gaa    1056
Ile Tyr Asp Gln Glu Thr Tyr Phe Gln Phe Ala Asn Ile Ile Ser Glu
            340                 345                 350 aca gtg cct tgc aca aaa gca acg gct gaa aag gta gat gcg ctt gcc    1104
Thr Val Pro Cys Thr Lys Ala Thr Ala Glu Lys Val Asp Ala Leu Ala
        355                 360                 365 aac aat cga tat ttc tag                                            1122
Asn Asn Arg Tyr Phe
    370

<210> SEQ ID NO 14
<211> LENGTH: 373
<212> TYPE: PRT
<213> ORGANISM: Caenorhabditis elegans

<400> SEQUENCE: 14

Met Ile Arg Gln Ile Ile Leu Ile Val Ser Leu Ile Gly Ile Ser Asn
1               5                   10                  15

Ala Ala Tyr Gln Cys Lys Asp Asn Asn Gly Ser Asn Val Asp Trp Phe
                20                  25                  30

Val Phe Tyr Lys Leu Pro His Leu Trp Asn His Pro Asp Asn Val Pro
            35                  40                  45
```

-continued

```
Ile Ser Asn Gly Thr Gly Phe Leu Tyr Phe Asp Val Asn Asn Lys Asn
         50                  55                  60

Trp Lys Leu Met Pro Gln Gly Met Asp Val Glu Asn Asn Ala Val Tyr
 65                  70                  75                  80

Tyr Thr Leu Gln Gln Tyr Tyr Asn Ser Asn Met Asn Thr Thr Phe Ser
                 85                  90                  95

Tyr Met Tyr Asn Asp Glu Trp Pro Asp Ser Thr Ile Trp Ser Asn Ser
            100                 105                 110

Ser Gly His Ala Lys Gly Val Thr Val Phe Asp Gln Tyr Thr Gly Phe
        115                 120                 125

Trp Met Ile His Ser Ile Pro Lys Phe Pro Ser Lys Asp Met Phe Arg
    130                 135                 140

Phe Pro Ser Asn Ala His Tyr Tyr Gly Gln Met Gly Ile Cys Ile Ser
145                 150                 155                 160

Tyr Asn Thr Val Ser Leu Ala Thr Ile Ala Gln Gln Leu Phe Tyr Tyr
                165                 170                 175

Asn Thr Phe Thr Tyr Gln Phe Asn Leu Pro Gln Ser Phe Ala Asn Gln
            180                 185                 190

Phe Pro Val Leu Ser Gln Leu Lys Asn Lys Glu Tyr Asn Lys Ser Pro
        195                 200                 205

Pro Leu Thr Ser Thr Lys Val Leu Lys Ser Leu Gly Gly Gln His Phe
    210                 215                 220

Arg His Phe Ala Lys Thr Gly Glu Trp Gly Lys Asp Leu Tyr Ser Asp
225                 230                 235                 240

Phe Val Gly Pro Thr Leu Lys Ser Ser Ile Lys Val Glu Thr Trp Asn
                245                 250                 255

His Gln Ser Gly Asp Glu Tyr Asn Leu Pro Ser Val Cys Asp Pro Asn
            260                 265                 270

His Val Gln Ser Thr Met Ser Ala Lys Tyr Ile Arg Leu Pro Tyr Ala
        275                 280                 285

Ile Asp Tyr Ser Ser Tyr Glu Asp His Ser Lys Phe Val Val Ala Tyr
    290                 295                 300

Ser Glu Ser Ser Ser Lys Pro Pro Ile Pro Tyr Val Cys Ile Gly Asp
305                 310                 315                 320

Ile Asn Arg Gln Ser His Gln Ile His Arg Gly Gly Gly Thr Met Cys
                325                 330                 335

Ile Tyr Asp Gln Glu Thr Tyr Phe Gln Phe Ala Asn Ile Ile Ser Glu
            340                 345                 350

Thr Val Pro Cys Thr Lys Ala Thr Ala Glu Lys Val Asp Ala Leu Ala
        355                 360                 365

Asn Asn Arg Tyr Phe
    370
```

<210> SEQ ID NO 15
<211> LENGTH: 1137
<212> TYPE: DNA
<213> ORGANISM: Caenorhabditis elegans
<220> FEATURE:
<221> NAME/KEY: CDS
<222> LOCATION: (1)..(1137)
<223> OTHER INFORMATION: crn-6/CRN-6 (378 isoform)

<400> SEQUENCE: 15

```
atg att cgt caa att atc ttg ata gtt tca ctt att ggg ata tca aat    48
Met Ile Arg Gln Ile Ile Leu Ile Val Ser Leu Ile Gly Ile Ser Asn
 1               5                  10                  15
```

```
gcc gcg tac caa tgc aag gat aat aat gga agt aat gta gat tgg ttc      96
Ala Ala Tyr Gln Cys Lys Asp Asn Asn Gly Ser Asn Val Asp Trp Phe
         20                  25                  30 gtc ttc tac aaa ctt cca cat ctt tgg aat cat cca gac aat gta cca     144
Val Phe Tyr Lys Leu Pro His Leu Trp Asn His Pro Asp Asn Val Pro
     35                  40                  45 att tca aat gga act gga ttc ttg tat ttt gat gtc aat aat aaa aat     192
Ile Ser Asn Gly Thr Gly Phe Leu Tyr Phe Asp Val Asn Asn Lys Asn
 50                  55                  60 tgg aaa ctt atg cca caa gga atg gat gtt gag aat aat gcc gta tat     240
Trp Lys Leu Met Pro Gln Gly Met Asp Val Glu Asn Asn Ala Val Tyr
 65                  70                  75                  80 tat acc ctc caa cag tac tat aac tcg aat atg aat acg aca ttc agc     288
Tyr Thr Leu Gln Gln Tyr Tyr Asn Ser Asn Met Asn Thr Thr Phe Ser
                 85                  90                  95 tac atg tac aat gac gag tgg cct gat agc aca atc tgg agt aat agt     336
Tyr Met Tyr Asn Asp Glu Trp Pro Asp Ser Thr Ile Trp Ser Asn Ser
            100                 105                 110 tca gga cat gca aag ggt gtt act gta ttt gat caa tac acc gga ttc     384
Ser Gly His Ala Lys Gly Val Thr Val Phe Asp Gln Tyr Thr Gly Phe
        115                 120                 125 tgg atg att cac agt att cca aag ttc ccg agt aaa gat atg ttc cga     432
Trp Met Ile His Ser Ile Pro Lys Phe Pro Ser Lys Asp Met Phe Arg
    130                 135                 140 ttc cca tca aat gcg cat tat tat ggg caa atg gga att tgt att tct     480
Phe Pro Ser Asn Ala His Tyr Tyr Gly Gln Met Gly Ile Cys Ile Ser
145                 150                 155                 160 tac aat acg gtt tcc ttg gca act att gct caa caa ctc ttc tac tac     528
Tyr Asn Thr Val Ser Leu Ala Thr Ile Ala Gln Gln Leu Phe Tyr Tyr
                165                 170                 175 aac aca ttc act tat cag ttc aat ttg cca cag agt ttt gca aac cag     576
Asn Thr Phe Thr Tyr Gln Phe Asn Leu Pro Gln Ser Phe Ala Asn Gln
            180                 185                 190 ttt cct gtt tta tct caa ttg aaa aat aag gaa tat aac aag agt cca     624
Phe Pro Val Leu Ser Gln Leu Lys Asn Lys Glu Tyr Asn Lys Ser Pro
        195                 200                 205 cca ctc act tcc acg aag gtt ttg aaa tca ctt ggt ggc caa cac ttc     672
Pro Leu Thr Ser Thr Lys Val Leu Lys Ser Leu Gly Gly Gln His Phe
    210                 215                 220 cga cat ttc gcg aaa acc ggt gaa tgg gga aaa gat ctc tac agc gat     720
Arg His Phe Ala Lys Thr Gly Glu Trp Gly Lys Asp Leu Tyr Ser Asp
225                 230                 235                 240 ttt gtc ggt cct aca ttg aag tct tcg atc aaa gtt gaa aca tgg aat     768
Phe Val Gly Pro Thr Leu Lys Ser Ser Ile Lys Val Glu Thr Trp Asn
                245                 250                 255 cat cag agc gga gat gag tat aat ctc cca tca gtt tgt gat ccc aat     816
His Gln Ser Gly Asp Glu Tyr Asn Leu Pro Ser Val Cys Asp Pro Asn
            260                 265                 270 cat gtt cag tcg aca atg agt gca aaa tac att cgt ctt cca tat gca     864
His Val Gln Ser Thr Met Ser Ala Lys Tyr Ile Arg Leu Pro Tyr Ala
        275                 280                 285 atc gat tac tcc agc tat gaa gat cat tca aag ttc gtc gtg gca tat     912
Ile Asp Tyr Ser Ser Tyr Glu Asp His Ser Lys Phe Val Val Ala Tyr
    290                 295                 300 agt gaa agc tcc tca aag cca cca att cca tac gtt tgt att gga gat     960
Ser Glu Ser Ser Ser Lys Pro Pro Ile Pro Tyr Val Cys Ile Gly Asp
305                 310                 315                 320 atc aat cgt cag agt cat caa atc cat cgt ggc ggt gga aca atg tgc    1008
Ile Asn Arg Gln Ser His Gln Ile His Arg Gly Gly Gly Thr Met Cys
```

```
                   325                 330                 335
atc tac gat caa gaa aca tac ttc caa ttc gca aat atc atc agt gaa    1056
Ile Tyr Asp Gln Glu Thr Tyr Phe Gln Phe Ala Asn Ile Ile Ser Glu
            340                 345                 350 aca gtg cct tgc aca aaa gca acg gct gaa aag gcg acc cta aca gtt    1104
Thr Val Pro Cys Thr Lys Ala Thr Ala Glu Lys Ala Thr Leu Thr Val
        355                 360                 365 ctt ctt atc gca att ata acc ttc ttt aag tga                        1137
Leu Leu Ile Ala Ile Ile Thr Phe Phe Lys
    370                 375

<210> SEQ ID NO 16
<211> LENGTH: 378
<212> TYPE: PRT
<213> ORGANISM: Caenorhabditis elegans

<400> SEQUENCE: 16

Met Ile Arg Gln Ile Ile Leu Ile Val Ser Leu Ile Gly Ile Ser Asn
1               5                   10                  15

Ala Ala Tyr Gln Cys Lys Asp Asn Asn Gly Ser Asn Val Asp Trp Phe
            20                  25                  30

Val Phe Tyr Lys Leu Pro His Leu Trp Asn His Pro Asp Asn Val Pro
        35                  40                  45

Ile Ser Asn Gly Thr Gly Phe Leu Tyr Phe Asp Val Asn Asn Lys Asn
    50                  55                  60

Trp Lys Leu Met Pro Gln Gly Met Asp Val Glu Asn Asn Ala Val Tyr
65                  70                  75                  80

Tyr Thr Leu Gln Gln Tyr Tyr Asn Ser Asn Met Asn Thr Thr Phe Ser
                85                  90                  95

Tyr Met Tyr Asn Asp Glu Trp Pro Asp Ser Thr Ile Trp Ser Asn Ser
            100                 105                 110

Ser Gly His Ala Lys Gly Val Thr Val Phe Asp Gln Tyr Thr Gly Phe
        115                 120                 125

Trp Met Ile His Ser Ile Pro Lys Phe Pro Ser Lys Asp Met Phe Arg
    130                 135                 140

Phe Pro Ser Asn Ala His Tyr Tyr Gly Gln Met Gly Ile Cys Ile Ser
145                 150                 155                 160

Tyr Asn Thr Val Ser Leu Ala Thr Ile Ala Gln Gln Leu Phe Tyr Tyr
                165                 170                 175

Asn Thr Phe Thr Tyr Gln Phe Asn Leu Pro Gln Ser Phe Ala Asn Gln
            180                 185                 190

Phe Pro Val Leu Ser Gln Leu Lys Asn Lys Glu Tyr Asn Lys Ser Pro
        195                 200                 205

Pro Leu Thr Ser Thr Lys Val Leu Lys Ser Leu Gly Gln His Phe
    210                 215                 220

Arg His Phe Ala Lys Thr Gly Glu Trp Gly Lys Asp Leu Tyr Ser Asp
225                 230                 235                 240

Phe Val Gly Pro Thr Leu Lys Ser Ser Ile Lys Val Glu Thr Trp Asn
                245                 250                 255

His Gln Ser Gly Asp Glu Tyr Asn Leu Pro Ser Val Cys Asp Pro Asn
            260                 265                 270

His Val Gln Ser Thr Met Ser Ala Lys Tyr Ile Arg Leu Pro Tyr Ala
        275                 280                 285

Ile Asp Tyr Ser Ser Tyr Glu Asp His Ser Lys Phe Val Val Ala Tyr
    290                 295                 300
```

```
Ser Glu Ser Ser Ser Lys Pro Pro Ile Pro Tyr Val Cys Ile Gly Asp
305                 310                 315                 320

Ile Asn Arg Gln Ser His Gln Ile His Arg Gly Gly Gly Thr Met Cys
            325                 330                 335

Ile Tyr Asp Gln Glu Thr Tyr Phe Gln Phe Ala Asn Ile Ile Ser Glu
        340                 345                 350

Thr Val Pro Cys Thr Lys Ala Thr Ala Glu Lys Ala Thr Leu Thr Val
            355                 360                 365

Leu Leu Ile Ala Ile Ile Thr Phe Phe Lys
    370                 375
```

<210> SEQ ID NO 17
<211> LENGTH: 996
<212> TYPE: DNA
<213> ORGANISM: Caenorhabditis elegans
<220> FEATURE:
<221> NAME/KEY: CDS
<222> LOCATION: (1)..(996)
<223> OTHER INFORMATION: cyp-13/CYP-13

<400> SEQUENCE: 17

```
atg aac acg aat ttt cca cac aat cgg aaa aga acg ctc tac gtc gga      48
Met Asn Thr Asn Phe Pro His Asn Arg Lys Arg Thr Leu Tyr Val Gly
1               5                   10                  15 ggt ttc acc gag gat gtc act gaa aaa gtg ttg atg gcc gcg ttc att      96
Gly Phe Thr Glu Asp Val Thr Glu Lys Val Leu Met Ala Ala Phe Ile
            20                  25                  30 ccg ttt gga gac gtc gtt gcc atc tcg att ccg atg gat tac gag tcg     144
Pro Phe Gly Asp Val Val Ala Ile Ser Ile Pro Met Asp Tyr Glu Ser
        35                  40                  45 gga aag cat cgt ggc ttc gga ttc gtc gaa ttc gat atg gct gag gat     192
Gly Lys His Arg Gly Phe Gly Phe Val Glu Phe Asp Met Ala Glu Asp
    50                  55                  60 gcg gcg atg gcg att gat aat atg aac gag agc gag ctg ttc gga aag     240
Ala Ala Met Ala Ile Asp Asn Met Asn Glu Ser Glu Leu Phe Gly Lys
65                  70                  75                  80 act att cgt gtc aac ttt gct cgt cca cca aaa gcc acc gaa cgc tca     288
Thr Ile Arg Val Asn Phe Ala Arg Pro Pro Lys Ala Thr Glu Arg Ser
                85                  90                  95 cag aaa cct gtc tgg gca gac gac gaa tgg ctc aaa aag tat gga aga     336
Gln Lys Pro Val Trp Ala Asp Asp Glu Trp Leu Lys Lys Tyr Gly Arg
            100                 105                 110 ggt gga gaa gct gct gcg gaa gaa gac gga gac gct gaa aaa gcc gcc     384
Gly Gly Glu Ala Ala Ala Glu Glu Asp Gly Asp Ala Glu Lys Ala Ala
        115                 120                 125 acg tca tcg tcg tca gcc tcg acg aag ctt cca cgt gtc tat ctg gga     432
Thr Ser Ser Ser Ser Ala Ser Thr Lys Leu Pro Arg Val Tyr Leu Gly
    130                 135                 140 gtg aag att gga att cga tat att gga cga ata gtg atc gag tta aga     480
Val Lys Ile Gly Ile Arg Tyr Ile Gly Arg Ile Val Ile Glu Leu Arg
145                 150                 155                 160 act gac gtt aca ccg aaa act gcc gaa aac ttc aga tgt ttg tgc aca     528
Thr Asp Val Thr Pro Lys Thr Ala Glu Asn Phe Arg Cys Leu Cys Thr
                165                 170                 175 gga gaa cga gga ttc ggt tat gaa gga tcg ata ttt cat cgg att att     576
Gly Glu Arg Gly Phe Gly Tyr Glu Gly Ser Ile Phe His Arg Ile Ile
            180                 185                 190 cca aaa ttt atg ctt caa ggc ggt gac ttt acg aaa gga gac gga acc     624
Pro Lys Phe Met Leu Gln Gly Gly Asp Phe Thr Lys Gly Asp Gly Thr
        195                 200                 205
```

```
ggc ggg aag tcg atc tat gga acg aaa ttt gat gat gag aat ttc acg    672
Gly Gly Lys Ser Ile Tyr Gly Thr Lys Phe Asp Asp Glu Asn Phe Thr
210                 215                 220 ctc cgc cac aca atg ccc ggc aca gtt tca atg gcg aac tgc ggt gcg    720
Leu Arg His Thr Met Pro Gly Thr Val Ser Met Ala Asn Cys Gly Ala
225                 230                 235                 240 aac aca aat ggc tca caa ttc ttc att tgc acc gag aaa acc gat tgg    768
Asn Thr Asn Gly Ser Gln Phe Phe Ile Cys Thr Glu Lys Thr Asp Trp
                245                 250                 255 ctt gac gga aaa cac gta gtg ttc ggt cat gtt gtt gaa gga atg aat    816
Leu Asp Gly Lys His Val Val Phe Gly His Val Val Glu Gly Met Asn
            260                 265                 270 att gta cga caa gtc gaa cag caa gga act ccg tct ggc aaa cct cag    864
Ile Val Arg Gln Val Glu Gln Gln Gly Thr Pro Ser Gly Lys Pro Gln
        275                 280                 285 atg gtt gtg aaa atc gtg gaa agc ggg gaa att gag ccg gaa aaa cgg    912
Met Val Val Lys Ile Val Glu Ser Gly Glu Ile Glu Pro Glu Lys Arg
    290                 295                 300 att gcc gcc gaa aaa ttg gcc cag aag gca gtt gtt ccg gga gcc gag    960
Ile Ala Ala Glu Lys Leu Ala Gln Lys Ala Val Val Pro Gly Ala Glu
305                 310                 315                 320 att cag gag ccg ctt ccg cag gct atg gag act taa                    996
Ile Gln Glu Pro Leu Pro Gln Ala Met Glu Thr
                325                 330

<210> SEQ ID NO 18
<211> LENGTH: 331
<212> TYPE: PRT
<213> ORGANISM: Caenorhabditis elegans

<400> SEQUENCE: 18

Met Asn Thr Asn Phe Pro His Asn Arg Lys Arg Thr Leu Tyr Val Gly
1               5                   10                  15

Gly Phe Thr Glu Asp Val Thr Glu Lys Val Leu Met Ala Ala Phe Ile
                20                  25                  30

Pro Phe Gly Asp Val Val Ala Ile Ser Ile Pro Met Asp Tyr Glu Ser
            35                  40                  45

Gly Lys His Arg Gly Phe Gly Phe Val Glu Phe Asp Met Ala Glu Asp
        50                  55                  60

Ala Ala Met Ala Ile Asp Asn Met Asn Glu Ser Glu Leu Phe Gly Lys
65                  70                  75                  80

Thr Ile Arg Val Asn Phe Ala Arg Pro Pro Lys Ala Thr Glu Arg Ser
                85                  90                  95

Gln Lys Pro Val Trp Ala Asp Asp Glu Trp Leu Lys Lys Tyr Gly Arg
            100                 105                 110

Gly Gly Glu Ala Ala Ala Glu Glu Asp Gly Asp Ala Glu Lys Ala Ala
        115                 120                 125

Thr Ser Ser Ser Ala Ser Thr Lys Leu Pro Arg Val Tyr Leu Gly
    130                 135                 140

Val Lys Ile Gly Ile Arg Tyr Ile Gly Arg Ile Val Ile Glu Leu Arg
145                 150                 155                 160

Thr Asp Val Thr Pro Lys Thr Ala Glu Asn Phe Arg Cys Leu Cys Thr
                165                 170                 175

Gly Glu Arg Gly Phe Gly Tyr Glu Gly Ser Ile Phe His Arg Ile Ile
            180                 185                 190

Pro Lys Phe Met Leu Gln Gly Gly Asp Phe Thr Lys Gly Asp Gly Thr
        195                 200                 205
```

-continued

```
Gly Gly Lys Ser Ile Tyr Gly Thr Lys Phe Asp Asp Glu Asn Phe Thr
            210                 215                 220

Leu Arg His Thr Met Pro Gly Thr Val Ser Met Ala Asn Cys Gly Ala
225                 230                 235                 240

Asn Thr Asn Gly Ser Gln Phe Phe Ile Cys Thr Glu Lys Thr Asp Trp
                245                 250                 255

Leu Asp Gly Lys His Val Val Phe Gly His Val Val Glu Gly Met Asn
            260                 265                 270

Ile Val Arg Gln Val Glu Gln Gln Gly Thr Pro Ser Gly Lys Pro Gln
        275                 280                 285

Met Val Val Lys Ile Val Glu Ser Gly Glu Ile Glu Pro Glu Lys Arg
    290                 295                 300

Ile Ala Ala Glu Lys Leu Ala Gln Lys Ala Val Val Pro Gly Ala Glu
305                 310                 315                 320

Ile Gln Glu Pro Leu Pro Gln Ala Met Glu Thr
                325                 330
```

<210> SEQ ID NO 19
<211> LENGTH: 2022
<212> TYPE: DNA
<213> ORGANISM: Homo sapiens
<220> FEATURE:
<221> NAME/KEY: CDS
<222> LOCATION: (130)..(1272)
<223> OTHER INFORMATION: fen-1/FEN-1 (Human crn-2 homolog)

<400> SEQUENCE: 19

```
caggccaccc gccgctaagc tgagaaggga gagcgagctt aggaccgcct gcccggggca      60
accccgaacc aagctttagc cgccgaggcc gcgtgtccca aaggccagtc atccctcctc     120 tgtgttgcc atg gga att caa ggc ctg gcc aaa cta att gct gat gtg gcc     171
           Met Gly Ile Gln Gly Leu Ala Lys Leu Ile Ala Asp Val Ala
               1               5                  10 ccc agt gcc atc cgg gag aat gac atc aag agc tac ttt ggc cgt aag      219
Pro Ser Ala Ile Arg Glu Asn Asp Ile Lys Ser Tyr Phe Gly Arg Lys
 15              20                  25                  30 gtg gcc att gat gcc tct atg agc att tat cag ttc ctg att gct gtt      267
Val Ala Ile Asp Ala Ser Met Ser Ile Tyr Gln Phe Leu Ile Ala Val
                35                  40                  45 cgc cag ggt ggg gat gtg ctg cag aat gag gag ggt gag acc acc agc      315
Arg Gln Gly Gly Asp Val Leu Gln Asn Glu Glu Gly Glu Thr Thr Ser
            50                  55                  60 cac ctg atg ggc atg ttc tac cgc acc att cgc atg atg gag aac ggc      363
His Leu Met Gly Met Phe Tyr Arg Thr Ile Arg Met Met Glu Asn Gly
        65                  70                  75 atc aag ccc gtg tat gtc ttt gat ggc aag ccg cca cag ctc aag tca      411
Ile Lys Pro Val Tyr Val Phe Asp Gly Lys Pro Pro Gln Leu Lys Ser
    80                  85                  90 ggc gag ctg gcc aaa cgc agt gag cgg cgg gct gag gca gag aag cag      459
Gly Glu Leu Ala Lys Arg Ser Glu Arg Arg Ala Glu Ala Glu Lys Gln
 95                 100                 105                 110 ctg cag cag gct cag gct gct ggg gcc gag cag gag gtg gaa aaa ttc      507
Leu Gln Gln Ala Gln Ala Ala Gly Ala Glu Gln Glu Val Glu Lys Phe
                115                 120                 125 act aag cgg ctg gtg aag gtc act aag cag cac aat gat gag tgc aaa      555
Thr Lys Arg Leu Val Lys Val Thr Lys Gln His Asn Asp Glu Cys Lys
            130                 135                 140 cat ctg ctg agc ctc atg ggc atc cct tat ctt gat gca ccc agt gag      603
His Leu Leu Ser Leu Met Gly Ile Pro Tyr Leu Asp Ala Pro Ser Glu
        145                 150                 155
```

| | | | | | | | | | | | | | | |
|---|---|---|---|---|---|---|---|---|---|---|---|---|---|---|
| gca | gag | gcc | agc | tgt | gct | gcc | ctg | gtg | aag | gct | ggc | aaa | gtc | tat | gct | 651 |
| Ala | Glu | Ala | Ser | Cys | Ala | Ala | Leu | Val | Lys | Ala | Gly | Lys | Val | Tyr | Ala |
| 160 | | | | 165 | | | | | 170 | | | | | | gca gag gcc agc tgt gct gcc ctg gtg aag gct ggc aaa gtc tat gct    651
Ala Glu Ala Ser Cys Ala Ala Leu Val Lys Ala Gly Lys Val Tyr Ala
    160             165                 170 gcg gct acc gag gac atg gac tgc ctc acc ttc ggc agc cct gtg cta    699
Ala Ala Thr Glu Asp Met Asp Cys Leu Thr Phe Gly Ser Pro Val Leu
175             180                 185                 190 atg cga cac ctg act gcc agt gaa gcc aaa aag ctg cca atc cag gaa    747
Met Arg His Leu Thr Ala Ser Glu Ala Lys Lys Leu Pro Ile Gln Glu
                195                 200                 205 ttc cac ctg agc cgg att ctg cag gag ctg ggc ctg aac cag gaa cag    795
Phe His Leu Ser Arg Ile Leu Gln Glu Leu Gly Leu Asn Gln Glu Gln
            210                 215                 220 ttt gtg gat ctg tgc atc ctg cta ggc agt gac tac tgt gag agt atc    843
Phe Val Asp Leu Cys Ile Leu Leu Gly Ser Asp Tyr Cys Glu Ser Ile
        225                 230                 235 cgg ggt att ggg ccc aag cgg gct gtg gac ctc atc cag aag cac aag    891
Arg Gly Ile Gly Pro Lys Arg Ala Val Asp Leu Ile Gln Lys His Lys
    240                 245                 250 agc atc gag gag atc gtg cgg cga ctt gac ccc aac aag tac cct gtg    939
Ser Ile Glu Glu Ile Val Arg Arg Leu Asp Pro Asn Lys Tyr Pro Val
255                 260                 265                 270 cca gaa aat tgg ctc cac aag gag gct cac cag ctc ttc ttg gaa cct    987
Pro Glu Asn Trp Leu His Lys Glu Ala His Gln Leu Phe Leu Glu Pro
                275                 280                 285 gag gtg ctg gac cca gag tct gtg gag ctg aag tgg agc gag cca aat    1035
Glu Val Leu Asp Pro Glu Ser Val Glu Leu Lys Trp Ser Glu Pro Asn
            290                 295                 300 gaa gaa gag ctg atc aag ttc atg tgt ggt gaa aag cag ttc tct gag    1083
Glu Glu Glu Leu Ile Lys Phe Met Cys Gly Glu Lys Gln Phe Ser Glu
        305                 310                 315 gag cga atc cgc agt ggg gtc aag agg ctg agt aag agc cgc caa ggc    1131
Glu Arg Ile Arg Ser Gly Val Lys Arg Leu Ser Lys Ser Arg Gln Gly
    320                 325                 330 agc acc cag ggc cgc ctg gat gat ttc ttc aag gtg acc ggc tca ctc    1179
Ser Thr Gln Gly Arg Leu Asp Asp Phe Phe Lys Val Thr Gly Ser Leu
335                 340                 345                 350 tct tca gct aag cgc aag gag cca gaa ccc aag gga tcc act aag aag    1227
Ser Ser Ala Lys Arg Lys Glu Pro Glu Pro Lys Gly Ser Thr Lys Lys
                355                 360                 365 aag gca aag act ggg gca gca ggg aag ttt aaa agg gga aaa taa       1272
Lys Ala Lys Thr Gly Ala Ala Gly Lys Phe Lys Arg Gly Lys
            370                 375                 380 atgtgtttcc ccattatacc tccttcaccc cagaatattt gccgtcttgt acccttaaga   1332
gctacagcta gagaaacctt cacggggtgg agagaggatt ctaaggcttt tctagcgtga   1392
cccttttcag tagtgctagt ccctttttta cttgatctta atggcaagaa ggccacagag   1452
gtacttttcc ttttttagct caggaaaata tgtcaggctc aaaccacttc tcaggcagtt   1512
taatggacac taagtccatt gttacatgaa agtgatagat agcaacaagt tttggagaag   1572
agagagggag ataaaagggg gagacaaaag atgtacagaa atgatttcct ggctggccaa   1632
ctggtggcca gtgggaggtg atggtggacc tagactgtgc ttttctgtct tgttcagcct   1692
tgacccacct tgagagagag ccaccaggaa ggcgcatctt agcagatggg aggaactgct   1752
gagagaagat gggcagaaag ctggagcccc tggagttggc tgtgtctgtg tttgtgactg   1812
attactggct gtgtcttggg tgggcagaaa ctcgaacttg ctatgtaatt tgtgtctagt   1872
tattcagagg agtaagatgg tgatgttcac ctggcaatca gctgagttga gactttggaa   1932

```
taagacactg gttttcatgc gctgttttg ttttaaagtt atgaagaaaa aagtcaataa    1992
aattctaaaa gtaaaaaaaa aaaaaaaaaa                                    2022
```

<210> SEQ ID NO 20
<211> LENGTH: 380
<212> TYPE: PRT
<213> ORGANISM: Homo sapiens

<400> SEQUENCE: 20

```
Met Gly Ile Gln Gly Leu Ala Lys Leu Ile Ala Asp Val Ala Pro Ser
1               5                   10                  15

Ala Ile Arg Glu Asn Asp Ile Lys Ser Tyr Phe Gly Arg Lys Val Ala
            20                  25                  30

Ile Asp Ala Ser Met Ser Ile Tyr Gln Phe Leu Ile Ala Val Arg Gln
        35                  40                  45

Gly Gly Asp Val Leu Gln Asn Glu Gly Glu Thr Thr Ser His Leu
    50                  55                  60

Met Gly Met Phe Tyr Arg Thr Ile Arg Met Met Glu Asn Gly Ile Lys
65                  70                  75                  80

Pro Val Tyr Val Phe Asp Gly Lys Pro Pro Gln Leu Lys Ser Gly Glu
                85                  90                  95

Leu Ala Lys Arg Ser Glu Arg Arg Ala Glu Ala Glu Lys Gln Leu Gln
            100                 105                 110

Gln Ala Gln Ala Ala Gly Ala Glu Gln Glu Val Glu Lys Phe Thr Lys
        115                 120                 125

Arg Leu Val Lys Val Thr Lys Gln His Asn Asp Glu Cys Lys His Leu
    130                 135                 140

Leu Ser Leu Met Gly Ile Pro Tyr Leu Asp Ala Pro Ser Glu Ala Glu
145                 150                 155                 160

Ala Ser Cys Ala Ala Leu Val Lys Ala Gly Lys Val Tyr Ala Ala Ala
                165                 170                 175

Thr Glu Asp Met Asp Cys Leu Thr Phe Gly Ser Pro Val Leu Met Arg
            180                 185                 190

His Leu Thr Ala Ser Glu Ala Lys Lys Leu Pro Ile Gln Glu Phe His
        195                 200                 205

Leu Ser Arg Ile Leu Gln Glu Leu Gly Leu Asn Gln Glu Gln Phe Val
    210                 215                 220

Asp Leu Cys Ile Leu Leu Gly Ser Asp Tyr Cys Glu Ser Ile Arg Gly
225                 230                 235                 240

Ile Gly Pro Lys Arg Ala Val Asp Leu Ile Gln Lys His Lys Ser Ile
                245                 250                 255

Glu Glu Ile Val Arg Arg Leu Asp Pro Asn Lys Tyr Pro Val Pro Glu
            260                 265                 270

Asn Trp Leu His Lys Glu Ala His Gln Leu Phe Leu Glu Pro Glu Val
        275                 280                 285

Leu Asp Pro Glu Ser Val Glu Leu Lys Trp Ser Pro Asn Glu Glu
    290                 295                 300

Glu Leu Ile Lys Phe Met Cys Gly Glu Lys Gln Phe Ser Glu Glu Arg
305                 310                 315                 320

Ile Arg Ser Gly Val Lys Arg Leu Ser Lys Ser Arg Gln Gly Ser Thr
                325                 330                 335

Gln Gly Arg Leu Asp Asp Phe Phe Lys Val Thr Gly Ser Leu Ser Ser
            340                 345                 350

Ala Lys Arg Lys Glu Pro Glu Pro Lys Gly Ser Thr Lys Lys Lys Ala
```

```
                     355                 360                 365
Lys Thr Gly Ala Ala Gly Lys Phe Lys Arg Gly Lys
            370                 375                 380

<210> SEQ ID NO 21
<211> LENGTH: 1039
<212> TYPE: DNA
<213> ORGANISM: Homo sapiens
<220> FEATURE:
<221> NAME/KEY: CDS
<222> LOCATION: (26)..(919)
<223> OTHER INFORMATION: cda11/CDA11 (Human crn-2 homolog)

<400> SEQUENCE: 21
atggggaggt cctccatgcg cagtc atg agt cgc ttc aag ttt atc gat att       52
                             Met Ser Arg Phe Lys Phe Ile Asp Ile
                              1               5 ggt atc aac ttg act gac cct atg ttc aga gga att tat agg ggg gtt      100
Gly Ile Asn Leu Thr Asp Pro Met Phe Arg Gly Ile Tyr Arg Gly Val
 10              15                  20                  25 caa aag cat caa gat gac tta cag gat gta ata ggg aga gct gtc gag      148
Gln Lys His Gln Asp Asp Leu Gln Asp Val Ile Gly Arg Ala Val Glu
                 30                  35                  40 att ggt gtt aaa aag ttt atg att aca ggt gga aat cta caa gac agt      196
Ile Gly Val Lys Lys Phe Met Ile Thr Gly Gly Asn Leu Gln Asp Ser
             45                  50                  55 aaa gat gca ctg cat ttg gca caa aca aat ggt atg ttt ttc agt aca      244
Lys Asp Ala Leu His Leu Ala Gln Thr Asn Gly Met Phe Phe Ser Thr
         60                  65                  70 gtt gga tgt cat cct aca aga tgt ggt gaa ttt gaa aag aat aac cct      292
Val Gly Cys His Pro Thr Arg Cys Gly Glu Phe Glu Lys Asn Asn Pro
     75                  80                  85 gat ctt tac tta aag gag ttg cta aat ctt gct gaa aac aat aaa ggg      340
Asp Leu Tyr Leu Lys Glu Leu Leu Asn Leu Ala Glu Asn Asn Lys Gly
 90                  95                 100                 105 aaa gtt gtg gca ata gga gaa tgc gga ctt gat ttt gac cga ctg cag      388
Lys Val Val Ala Ile Gly Glu Cys Gly Leu Asp Phe Asp Arg Leu Gln
                110                 115                 120 ttt tgt ccc aaa gat act caa ctc aaa tat ttt gaa aaa cag ttt gaa      436
Phe Cys Pro Lys Asp Thr Gln Leu Lys Tyr Phe Glu Lys Gln Phe Glu
            125                 130                 135 ctg tca gaa caa aca aaa tta cca atg ttt ctt cat tgt cga aac tca      484
Leu Ser Glu Gln Thr Lys Leu Pro Met Phe Leu His Cys Arg Asn Ser
        140                 145                 150 cat gct gaa ttt ctg gac ata atg aaa aga aat aga gat cgg tgt gta      532
His Ala Glu Phe Leu Asp Ile Met Lys Arg Asn Arg Asp Arg Cys Val
    155                 160                 165 ggg gga gtg gtg cat tca ttt gat ggt acc aag gaa gca gca gct gct      580
Gly Gly Val Val His Ser Phe Asp Gly Thr Lys Glu Ala Ala Ala Ala
170                 175                 180                 185 ttg att gac ttg gat ctt tat ata gga ttt aat ggt tgc tca ctg aaa      628
Leu Ile Asp Leu Asp Leu Tyr Ile Gly Phe Asn Gly Cys Ser Leu Lys
                190                 195                 200 act gaa gct aat ttg gaa gtt ttg aag tca att cct agt gaa aaa tta      676
Thr Glu Ala Asn Leu Glu Val Leu Lys Ser Ile Pro Ser Glu Lys Leu
            205                 210                 215 atg att gag aca gat gca cct tgg tgt gga gtc aaa agt aca cat gct      724
Met Ile Glu Thr Asp Ala Pro Trp Cys Gly Val Lys Ser Thr His Ala
        220                 225                 230 gga tca aaa tat ata aga act gca ttt cct acc aaa aag aag tgg gaa      772
Gly Ser Lys Tyr Ile Arg Thr Ala Phe Pro Thr Lys Lys Lys Trp Glu
```

```
                235                 240                 245
agt ggg cac tgc tta aaa gac aga aat gaa ccc tgc cat ata att caa    820
Ser Gly His Cys Leu Lys Asp Arg Asn Glu Pro Cys His Ile Ile Gln
250                 255                 260                 265 ata ttg gag ata atg tca gca gtg aga gat gag gat cca ctg gaa tta    868
Ile Leu Glu Ile Met Ser Ala Val Arg Asp Glu Asp Pro Leu Glu Leu
                270                 275                 280 gcc aat aca cta tat aac aat act att aaa gta ttt ttt cct gga ata    916
Ala Asn Thr Leu Tyr Asn Asn Thr Ile Lys Val Phe Phe Pro Gly Ile
                285                 290                 295 taa ttggtatatg tcttccactt tccatcatgt atgtaaaatt tcatagtaaa        969
acttcctgat agtttcaata agaaattat ctgcaaaaaa aaaaaaaaaa aaaaaaaaa    1029 aaaaaaaaaa                                                        1039

<210> SEQ ID NO 22
<211> LENGTH: 297
<212> TYPE: PRT
<213> ORGANISM: Homo sapiens

<400> SEQUENCE: 22

Met Ser Arg Phe Lys Phe Ile Asp Ile Gly Ile Asn Leu Thr Asp Pro
1               5                   10                  15

Met Phe Arg Gly Ile Tyr Arg Gly Val Gln Lys His Gln Asp Asp Leu
                20                  25                  30

Gln Asp Val Ile Gly Arg Ala Val Glu Ile Gly Val Lys Lys Phe Met
            35                  40                  45

Ile Thr Gly Gly Asn Leu Gln Asp Ser Lys Asp Ala Leu His Leu Ala
        50                  55                  60

Gln Thr Asn Gly Met Phe Ser Thr Val Gly Cys His Pro Thr Arg
65                  70                  75                  80

Cys Gly Glu Phe Glu Lys Asn Asn Pro Asp Leu Tyr Leu Lys Glu Leu
                85                  90                  95

Leu Asn Leu Ala Glu Asn Asn Lys Gly Lys Val Val Ala Ile Gly Glu
            100                 105                 110

Cys Gly Leu Asp Phe Asp Arg Leu Gln Phe Cys Pro Lys Asp Thr Gln
        115                 120                 125

Leu Lys Tyr Phe Glu Lys Gln Phe Glu Leu Ser Glu Gln Thr Lys Leu
    130                 135                 140

Pro Met Phe Leu His Cys Arg Asn Ser His Ala Glu Phe Leu Asp Ile
145                 150                 155                 160

Met Lys Arg Asn Arg Asp Arg Cys Val Gly Gly Val Val His Ser Phe
                165                 170                 175

Asp Gly Thr Lys Glu Ala Ala Ala Leu Ile Asp Leu Asp Leu Tyr
            180                 185                 190

Ile Gly Phe Asn Gly Cys Ser Leu Lys Thr Glu Ala Asn Leu Glu Val
        195                 200                 205

Leu Lys Ser Ile Pro Ser Glu Lys Leu Met Ile Glu Thr Asp Ala Pro
    210                 215                 220

Trp Cys Gly Val Lys Ser Thr His Ala Gly Ser Lys Tyr Ile Arg Thr
225                 230                 235                 240

Ala Phe Pro Thr Lys Lys Lys Trp Glu Ser Gly His Cys Leu Lys Asp
                245                 250                 255

Arg Asn Glu Pro Cys His Ile Ile Gln Ile Leu Glu Ile Met Ser Ala
            260                 265                 270
```

```
                Val Arg Asp Glu Asp Pro Leu Glu Leu Ala Asn Thr Leu Tyr Asn Asn
                            275                 280                 285

Thr Ile Lys Val Phe Phe Pro Gly Ile
                    290                 295

<210> SEQ ID NO 23
<211> LENGTH: 2583
<212> TYPE: DNA
<213> ORGANISM: Homo sapiens
<220> FEATURE:
<221> NAME/KEY: CDS
<222> LOCATION: (1)..(2580)
<223> OTHER INFORMATION: pm-scl-100/PM-SCL-100 (Human crn-3 homolog)

<400> SEQUENCE: 23 atg gcg cca ccc agt acc cgg gag ccc agg gtc ctg tcg gcg acc agc        48
Met Ala Pro Pro Ser Thr Arg Glu Pro Arg Val Leu Ser Ala Thr Ser
1               5                   10                  15 gca acc aaa tcc gac gga gag atg gtg ctg cca ggc ttc ccg gac gcc        96
Ala Thr Lys Ser Asp Gly Glu Met Val Leu Pro Gly Phe Pro Asp Ala
                20                  25                  30 gac agc ttt gtg aag ttt gct ctt ggg tcc gtg gtg gca gtc acc aag       144
Asp Ser Phe Val Lys Phe Ala Leu Gly Ser Val Val Ala Val Thr Lys
            35                  40                  45 gca tct ggg ggc cta cca cag ttt ggc gat gag tat gat ttt tac cga       192
Ala Ser Gly Gly Leu Pro Gln Phe Gly Asp Glu Tyr Asp Phe Tyr Arg
        50                  55                  60 agt ttt cct ggc ttc caa gca ttt tgc gaa aca cag gga gac agg ttg       240
Ser Phe Pro Gly Phe Gln Ala Phe Cys Glu Thr Gln Gly Asp Arg Leu
65                  70                  75                  80 ctt cag tgc atg agc aga gta atg cag tac cat ggg tgt cgc agc aac       288
Leu Gln Cys Met Ser Arg Val Met Gln Tyr His Gly Cys Arg Ser Asn
                85                  90                  95 att aag gat cga agt aaa gtg act gag ctg gaa gac aag ttt gat tta       336
Ile Lys Asp Arg Ser Lys Val Thr Glu Leu Glu Asp Lys Phe Asp Leu
                100                 105                 110 cta gtt gat gcc aat gat gta att ctg gag aga gtg ggt att tta ctg       384
Leu Val Asp Ala Asn Asp Val Ile Leu Glu Arg Val Gly Ile Leu Leu
            115                 120                 125 gat gaa gcc tca ggt gta aac aag aat caa cag cct gtc ctc cct gcc       432
Asp Glu Ala Ser Gly Val Asn Lys Asn Gln Gln Pro Val Leu Pro Ala
        130                 135                 140 ggc ttg cag gtc ccc aaa acg gta gtg tcc agc tgg aac cgt aag gca       480
Gly Leu Gln Val Pro Lys Thr Val Val Ser Ser Trp Asn Arg Lys Ala
145                 150                 155                 160 gca gaa tat ggc aaa aaa gca aaa tct gaa act ttc cgg ctg ctt cat       528
Ala Glu Tyr Gly Lys Lys Ala Lys Ser Glu Thr Phe Arg Leu Leu His
                165                 170                 175 gca aaa aat atc atc cga cct cag ctc aag ttt cga gag aag att gac       576
Ala Lys Asn Ile Ile Arg Pro Gln Leu Lys Phe Arg Glu Lys Ile Asp
            180                 185                 190 aat tcc aac aca cca ttt ctt cct aaa atc ttc atc aaa ccc aat gct       624
Asn Ser Asn Thr Pro Phe Leu Pro Lys Ile Phe Ile Lys Pro Asn Ala
        195                 200                 205 cag aaa cct ctc cct caa gct ctc tct aag gaa agg cgg gaa cgc cca       672
Gln Lys Pro Leu Pro Gln Ala Leu Ser Lys Glu Arg Arg Glu Arg Pro
    210                 215                 220 cag gat cgt cct gag gac ttg gac gtc ccc cct gca ctg gct gat ttc       720
Gln Asp Arg Pro Glu Asp Leu Asp Val Pro Pro Ala Leu Ala Asp Phe
225                 230                 235                 240 atc cat cag cag aga acc cag cag gtt gag caa gac atg ttt gca cat       768
```

```
Ile His Gln Gln Arg Thr Gln Gln Val Glu Gln Asp Met Phe Ala His
            245                 250                 255 cct tat caa tat gaa cta aat cac ttt acc cca gca gat gca gtg ctt        816
Pro Tyr Gln Tyr Glu Leu Asn His Phe Thr Pro Ala Asp Ala Val Leu
            260                 265                 270 caa aag cca caa ccc cag tta tac aga cct ata gaa gag aca cca tgc        864
Gln Lys Pro Gln Pro Gln Leu Tyr Arg Pro Ile Glu Glu Thr Pro Cys
            275                 280                 285 cat ttc ata tcc tcc ctg gat gaa ctc gtg gaa ctc aac gaa aag ctc        912
His Phe Ile Ser Ser Leu Asp Glu Leu Val Glu Leu Asn Glu Lys Leu
            290                 295                 300 ttg aat tgt cag gaa ttt gca gtt gac ttg gag cac cac tct tac agg        960
Leu Asn Cys Gln Glu Phe Ala Val Asp Leu Glu His His Ser Tyr Arg
305                 310                 315                 320 agc ttc ctg gga ctg acc tgc ctg atg caa att tct act cgg acg gaa       1008
Ser Phe Leu Gly Leu Thr Cys Leu Met Gln Ile Ser Thr Arg Thr Glu
            325                 330                 335 gac ttc atc att gac acc ctc gag ctt cga agt gac atg tac att ctc       1056
Asp Phe Ile Ile Asp Thr Leu Glu Leu Arg Ser Asp Met Tyr Ile Leu
            340                 345                 350 aat gag agc ctc aca gac cca gcc atc gtt aag gtc ttt cat ggt gct       1104
Asn Glu Ser Leu Thr Asp Pro Ala Ile Val Lys Val Phe His Gly Ala
            355                 360                 365 gat tca gac ata gaa tgg cta cag aaa gac ttt ggg ttg tat gta gta       1152
Asp Ser Asp Ile Glu Trp Leu Gln Lys Asp Phe Gly Leu Tyr Val Val
370                 375                 380 aac atg ttt gat act cat cag gca gca cgc ctt ctt aac ctg ggc agg       1200
Asn Met Phe Asp Thr His Gln Ala Ala Arg Leu Leu Asn Leu Gly Arg
385                 390                 395                 400 cac tca ctc gat cat ctc ctg aaa ctc tac tgc aac gtg gac tca aac       1248
His Ser Leu Asp His Leu Leu Lys Leu Tyr Cys Asn Val Asp Ser Asn
            405                 410                 415 aag caa tat cag ctg gct gat tgg aga ata cgc cct ctg ccc gag gag       1296
Lys Gln Tyr Gln Leu Ala Asp Trp Arg Ile Arg Pro Leu Pro Glu Glu
            420                 425                 430 atg ctc agc tac gcc cgg gat gac acc cat tac ctg cta tat atc tat       1344
Met Leu Ser Tyr Ala Arg Asp Asp Thr His Tyr Leu Leu Tyr Ile Tyr
            435                 440                 445 gac aaa atg agg ctg gag atg tgg gag cgc ggc aac ggg cag ccc gtg       1392
Asp Lys Met Arg Leu Glu Met Trp Glu Arg Gly Asn Gly Gln Pro Val
            450                 455                 460 cag ctg cag gtg gtg tgg caa cgg agc agg gac atc tgc ctc aag aaa       1440
Gln Leu Gln Val Val Trp Gln Arg Ser Arg Asp Ile Cys Leu Lys Lys
465                 470                 475                 480 ttc atc aaa cct atc ttc acg gat gag tcc tac ctt gaa ctc tat agg       1488
Phe Ile Lys Pro Ile Phe Thr Asp Glu Ser Tyr Leu Glu Leu Tyr Arg
            485                 490                 495 aag cag aag aag cac ctt aac aca cag cag ttg aca gcc ttt cag ctg       1536
Lys Gln Lys Lys His Leu Asn Thr Gln Gln Leu Thr Ala Phe Gln Leu
            500                 505                 510 ctg ttt gcc tgg agg gat aaa aca gct cgc agg gaa gat gaa agt tac       1584
Leu Phe Ala Trp Arg Asp Lys Thr Ala Arg Arg Glu Asp Glu Ser Tyr
            515                 520                 525 gga tat gta ctg cca aac cac atg atg ctg aaa ata gct gaa gaa ctg       1632
Gly Tyr Val Leu Pro Asn His Met Met Leu Lys Ile Ala Glu Glu Leu
            530                 535                 540 cct aag gaa cct cag ggc atc ata gct tgc tgc aac cca gta ccg ccc       1680
Pro Lys Glu Pro Gln Gly Ile Ile Ala Cys Cys Asn Pro Val Pro Pro
545                 550                 555                 560
```

```
ctt gtg cgg cag cag atc aac gaa atg cac ctt tta atc cag cag gcc      1728
Leu Val Arg Gln Gln Ile Asn Glu Met His Leu Leu Ile Gln Gln Ala
            565                 570                 575 cga gag atg ccc ctg ctc aag tct gaa gtt gca gcc gga gtg aag aag      1776
Arg Glu Met Pro Leu Leu Lys Ser Glu Val Ala Ala Gly Val Lys Lys
        580                 585                 590 agc gga ccg ctg ccc agt gct gag aga ttg gag aat gtt ctc ttt gga      1824
Ser Gly Pro Leu Pro Ser Ala Glu Arg Leu Glu Asn Val Leu Phe Gly
    595                 600                 605 cct cac gac tgc tcc cat gcc cct ccg gat ggc tat cca atc atc cca      1872
Pro His Asp Cys Ser His Ala Pro Pro Asp Gly Tyr Pro Ile Ile Pro
610                 615                 620 acc agt gga tct gtg cca gtt cag aag cag gcg agc ctc ttc cct gat      1920
Thr Ser Gly Ser Val Pro Val Gln Lys Gln Ala Ser Leu Phe Pro Asp
625                 630                 635                 640 gaa aaa gaa gat aac ttg ctg ggt acc aca tgc ctg att gcc aca gct      1968
Glu Lys Glu Asp Asn Leu Leu Gly Thr Thr Cys Leu Ile Ala Thr Ala
            645                 650                 655 gtc atc acg tta ttt aat gaa cct agt gct gaa gac agt aaa aag ggt      2016
Val Ile Thr Leu Phe Asn Glu Pro Ser Ala Glu Asp Ser Lys Lys Gly
        660                 665                 670 cca ttg aca gtt gca cag aaa aaa gcc cag aac atc atg gag tcc ttt      2064
Pro Leu Thr Val Ala Gln Lys Lys Ala Gln Asn Ile Met Glu Ser Phe
    675                 680                 685 gaa aat cca ttt agg atg atc agc aac cgt tgg aag ctg gcc cag gta      2112
Glu Asn Pro Phe Arg Met Ile Ser Asn Arg Trp Lys Leu Ala Gln Val
690                 695                 700 caa gta caa aaa gac tct aaa gaa gct gtc aag aag aag gca gct gag      2160
Gln Val Gln Lys Asp Ser Lys Glu Ala Val Lys Lys Lys Ala Ala Glu
705                 710                 715                 720 caa aca gct gcc cgg gaa cag gca aag gag gcg tgc aaa gct gca gca      2208
Gln Thr Ala Ala Arg Glu Gln Ala Lys Glu Ala Cys Lys Ala Ala Ala
            725                 730                 735 gaa cag gcc atc tcc gtc cga cag cag gtc gtg cta gaa aat gct gca      2256
Glu Gln Ala Ile Ser Val Arg Gln Gln Val Val Leu Glu Asn Ala Ala
        740                 745                 750 aag aag aga gag cga gca aca agc gac cca agg acc aca gaa cag aaa      2304
Lys Lys Arg Glu Arg Ala Thr Ser Asp Pro Arg Thr Thr Glu Gln Lys
    755                 760                 765 caa gag aag aaa cga ctc aaa att tcc aag aag cca aag gac cca gag      2352
Gln Glu Lys Lys Arg Leu Lys Ile Ser Lys Lys Pro Lys Asp Pro Glu
770                 775                 780 cca cca gaa aaa gag ttt acg cct tac gac tac agc cag tca gac ttc      2400
Pro Pro Glu Lys Glu Phe Thr Pro Tyr Asp Tyr Ser Gln Ser Asp Phe
785                 790                 795                 800 aag gct ttt gct gga aac agc aaa tcc aaa gtt tct tct cag ttt gat      2448
Lys Ala Phe Ala Gly Asn Ser Lys Ser Lys Val Ser Ser Gln Phe Asp
            805                 810                 815 cca aat aaa cag acc ccg tct ggc aag aaa tgc att gca gcc aaa aaa      2496
Pro Asn Lys Gln Thr Pro Ser Gly Lys Lys Cys Ile Ala Ala Lys Lys
        820                 825                 830 att aaa cag tcg gtg gga aac aaa agc atg tcc ttt cca act gga aag      2544
Ile Lys Gln Ser Val Gly Asn Lys Ser Met Ser Phe Pro Thr Gly Lys
    835                 840                 845 tca gac aga ggc ttc agg tac aac tgg cca cag aga tag                  2583
Ser Asp Arg Gly Phe Arg Tyr Asn Trp Pro Gln Arg
    850                 855                 860

<210> SEQ ID NO 24
<211> LENGTH: 860
```

-continued

```
<212> TYPE: PRT
<213> ORGANISM: Homo sapiens

<400> SEQUENCE: 24

Met Ala Pro Pro Ser Thr Arg Glu Pro Arg Val Leu Ser Ala Thr Ser
1               5                   10                  15

Ala Thr Lys Ser Asp Gly Glu Met Val Leu Pro Gly Phe Pro Asp Ala
            20                  25                  30

Asp Ser Phe Val Lys Phe Ala Leu Gly Ser Val Val Ala Val Thr Lys
        35                  40                  45

Ala Ser Gly Gly Leu Pro Gln Phe Gly Asp Glu Tyr Asp Phe Tyr Arg
    50                  55                  60

Ser Phe Pro Gly Phe Gln Ala Phe Cys Glu Thr Gln Gly Asp Arg Leu
65                  70                  75                  80

Leu Gln Cys Met Ser Arg Val Met Gln Tyr His Gly Cys Arg Ser Asn
                85                  90                  95

Ile Lys Asp Arg Ser Lys Val Thr Glu Leu Glu Asp Lys Phe Asp Leu
            100                 105                 110

Leu Val Asp Ala Asn Asp Val Ile Leu Glu Arg Val Gly Ile Leu Leu
        115                 120                 125

Asp Glu Ala Ser Gly Val Asn Lys Asn Gln Gln Pro Val Leu Pro Ala
    130                 135                 140

Gly Leu Gln Val Pro Lys Thr Val Val Ser Ser Trp Asn Arg Lys Ala
145                 150                 155                 160

Ala Glu Tyr Gly Lys Lys Ala Lys Ser Glu Thr Phe Arg Leu Leu His
                165                 170                 175

Ala Lys Asn Ile Ile Arg Pro Gln Leu Lys Phe Arg Glu Lys Ile Asp
            180                 185                 190

Asn Ser Asn Thr Pro Phe Leu Pro Lys Ile Phe Ile Lys Pro Asn Ala
        195                 200                 205

Gln Lys Pro Leu Pro Gln Ala Leu Ser Lys Glu Arg Arg Glu Arg Pro
    210                 215                 220

Gln Asp Arg Pro Glu Asp Leu Asp Val Pro Pro Ala Leu Ala Asp Phe
225                 230                 235                 240

Ile His Gln Gln Arg Thr Gln Gln Val Glu Gln Asp Met Phe Ala His
                245                 250                 255

Pro Tyr Gln Tyr Glu Leu Asn His Phe Thr Pro Ala Asp Ala Val Leu
            260                 265                 270

Gln Lys Pro Gln Pro Gln Leu Tyr Arg Pro Ile Glu Glu Thr Pro Cys
        275                 280                 285

His Phe Ile Ser Ser Leu Asp Glu Leu Val Glu Leu Asn Glu Lys Leu
    290                 295                 300

Leu Asn Cys Gln Glu Phe Ala Val Asp Leu Glu His Ser Tyr Arg
305                 310                 315                 320

Ser Phe Leu Gly Leu Thr Cys Leu Met Gln Ile Ser Thr Arg Thr Glu
                325                 330                 335

Asp Phe Ile Ile Asp Thr Leu Glu Leu Arg Ser Asp Met Tyr Ile Leu
            340                 345                 350

Asn Glu Ser Leu Thr Asp Pro Ala Ile Val Lys Val Phe His Gly Ala
        355                 360                 365

Asp Ser Asp Ile Glu Trp Leu Gln Lys Asp Phe Gly Leu Tyr Val Val
    370                 375                 380

Asn Met Phe Asp Thr His Gln Ala Ala Arg Leu Leu Asn Leu Gly Arg
385                 390                 395                 400
```

-continued

```
His Ser Leu Asp His Leu Leu Lys Leu Tyr Cys Asn Val Asp Ser Asn
                405                 410                 415
Lys Gln Tyr Gln Leu Ala Asp Trp Arg Ile Arg Pro Leu Pro Glu Glu
            420                 425                 430
Met Leu Ser Tyr Ala Arg Asp Asp Thr His Tyr Leu Leu Tyr Ile Tyr
        435                 440                 445
Asp Lys Met Arg Leu Glu Met Trp Glu Arg Gly Asn Gly Gln Pro Val
    450                 455                 460
Gln Leu Gln Val Val Trp Gln Arg Ser Arg Asp Ile Cys Leu Lys Lys
465                 470                 475                 480
Phe Ile Lys Pro Ile Phe Thr Asp Glu Ser Tyr Leu Glu Leu Tyr Arg
                485                 490                 495
Lys Gln Lys Lys His Leu Asn Thr Gln Gln Leu Thr Ala Phe Gln Leu
            500                 505                 510
Leu Phe Ala Trp Arg Asp Lys Thr Ala Arg Arg Glu Asp Glu Ser Tyr
        515                 520                 525
Gly Tyr Val Leu Pro Asn His Met Met Leu Lys Ile Ala Glu Glu Leu
    530                 535                 540
Pro Lys Glu Pro Gln Gly Ile Ile Ala Cys Cys Asn Pro Val Pro Pro
545                 550                 555                 560
Leu Val Arg Gln Gln Ile Asn Glu Met His Leu Leu Ile Gln Gln Ala
                565                 570                 575
Arg Glu Met Pro Leu Leu Lys Ser Glu Val Ala Ala Gly Val Lys Lys
            580                 585                 590
Ser Gly Pro Leu Pro Ser Ala Glu Arg Leu Glu Asn Val Leu Phe Gly
        595                 600                 605
Pro His Asp Cys Ser His Ala Pro Pro Asp Gly Tyr Pro Ile Ile Pro
    610                 615                 620
Thr Ser Gly Ser Val Pro Val Gln Lys Gln Ala Ser Leu Phe Pro Asp
625                 630                 635                 640
Glu Lys Glu Asp Asn Leu Leu Gly Thr Thr Cys Leu Ile Ala Thr Ala
                645                 650                 655
Val Ile Thr Leu Phe Asn Glu Pro Ser Ala Glu Asp Ser Lys Lys Gly
            660                 665                 670
Pro Leu Thr Val Ala Gln Lys Lys Ala Gln Asn Ile Met Glu Ser Phe
        675                 680                 685
Glu Asn Pro Phe Arg Met Ile Ser Asn Arg Trp Lys Leu Ala Gln Val
    690                 695                 700
Gln Val Gln Lys Asp Ser Lys Glu Ala Val Lys Lys Ala Ala Glu
705                 710                 715                 720
Gln Thr Ala Ala Arg Glu Gln Ala Lys Glu Ala Cys Lys Ala Ala Ala
                725                 730                 735
Glu Gln Ala Ile Ser Val Arg Gln Gln Val Val Leu Glu Asn Ala Ala
            740                 745                 750
Lys Lys Arg Glu Arg Ala Thr Ser Asp Pro Arg Thr Thr Glu Gln Lys
        755                 760                 765
Gln Glu Lys Lys Arg Leu Lys Ile Ser Lys Lys Pro Lys Asp Pro Glu
    770                 775                 780
Pro Pro Glu Lys Glu Phe Thr Pro Tyr Asp Tyr Ser Gln Ser Asp Phe
785                 790                 795                 800
Lys Ala Phe Ala Gly Asn Ser Lys Ser Lys Val Ser Ser Gln Phe Asp
                805                 810                 815
```

```
Pro Asn Lys Gln Thr Pro Ser Gly Lys Lys Cys Ile Ala Ala Lys Lys
        820                 825                 830

Ile Lys Gln Ser Val Gly Asn Lys Ser Met Ser Phe Pro Thr Gly Lys
        835                 840                 845

Ser Asp Arg Gly Phe Arg Tyr Asn Trp Pro Gln Arg
        850                 855                 860

<210> SEQ ID NO 25
<211> LENGTH: 1503
<212> TYPE: DNA
<213> ORGANISM: Homo sapiens
<220> FEATURE:
<221> NAME/KEY: CDS
<222> LOCATION: (44)..(1027)
<223> OTHER INFORMATION: mgc16943/MGC16943 (Human crn-4 homolog)

<400> SEQUENCE: 25
```

| | | |
|---|---|---|
| cgacttccgg cagctggact tggaaaagca aggagtgtcg gga atg gcg acc aag<br>                                                      Met Ala Thr Lys<br>                                                        1 | | 55 |
| cgg ctc gcg cgg cag ctt gga tta att agg aga aag tca att gcg cca<br>Arg Leu Ala Arg Gln Leu Gly Leu Ile Arg Arg Lys Ser Ile Ala Pro<br>  5              10                  15                  20 | | 103 |
| gca aat gga aat ctc gga aga agc aaa tcc aag cag ttg ttt gac tac<br>Ala Asn Gly Asn Leu Gly Arg Ser Lys Ser Lys Gln Leu Phe Asp Tyr<br>              25                  30                  35 | | 151 |
| tta att gtc att gat ttt gaa tcg aca tgc tgg aat gat ggg aag cac<br>Leu Ile Val Ile Asp Phe Glu Ser Thr Cys Trp Asn Asp Gly Lys His<br>          40                  45                  50 | | 199 |
| cac cat agc cag gaa ata att gag ttt cca gca gtg ttg ctg aac aca<br>His His Ser Gln Glu Ile Ile Glu Phe Pro Ala Val Leu Leu Asn Thr<br>      55                  60                  65 | | 247 |
| tca act gga cag att gac tct gag ttc cag gct tat gtt caa cct cag<br>Ser Thr Gly Gln Ile Asp Ser Glu Phe Gln Ala Tyr Val Gln Pro Gln<br>  70                  75                  80 | | 295 |
| gaa cat cca att ctt tca gaa ttt tgc atg gaa ttg aca ggc ata aag<br>Glu His Pro Ile Leu Ser Glu Phe Cys Met Glu Leu Thr Gly Ile Lys<br>85                  90                  95                 100 | | 343 |
| cag gct caa gtt gat gaa gga gtc cct ctg aag att tgc tta tct cag<br>Gln Ala Gln Val Asp Glu Gly Val Pro Leu Lys Ile Cys Leu Ser Gln<br>                 105                 110                 115 | | 391 |
| ttc tgt aaa tgg att cat aag att cag caa cag aag aac att att ttt<br>Phe Cys Lys Trp Ile His Lys Ile Gln Gln Gln Lys Asn Ile Ile Phe<br>             120                 125                 130 | | 439 |
| gct act ggg att tca gag cct tct gct tct gaa gta aaa tta tgt gca<br>Ala Thr Gly Ile Ser Glu Pro Ser Ala Ser Glu Val Lys Leu Cys Ala<br>         135                 140                 145 | | 487 |
| ttt gtt act tgg tca gac tgg gac ttg ggg gtt tgc ctg gag tat gag<br>Phe Val Thr Trp Ser Asp Trp Asp Leu Gly Val Cys Leu Glu Tyr Glu<br>     150                 155                 160 | | 535 |
| tgt aaa aga aaa cag ctg tta aaa cct gtg ttt tta aat tct tgg att<br>Cys Lys Arg Lys Gln Leu Leu Lys Pro Val Phe Leu Asn Ser Trp Ile<br>165                 170                 175                 180 | | 583 |
| gat ctc aga gca act tac aag ctt ttc tat agg aga aaa cca aaa gga<br>Asp Leu Arg Ala Thr Tyr Lys Leu Phe Tyr Arg Arg Lys Pro Lys Gly<br>                 185                 190                 195 | | 631 |
| cta agt ggt gcc ttg cag gaa gta gga ata gaa ttc tca gga cga gaa<br>Leu Ser Gly Ala Leu Gln Glu Val Gly Ile Glu Phe Ser Gly Arg Glu<br>             200                 205                 210 | | 679 |
| cat tct ggg ttg gac gat tct cgg aat act gcc ctt ctt gct tgg aaa<br>His Ser Gly Leu Asp Asp Ser Arg Asn Thr Ala Leu Leu Ala Trp Lys | | 727 |

```
                215                 220                 225
atg atc aga gat ggt tgt gta atg aaa att aca agg tcg ttg aac aag    775
Met Ile Arg Asp Gly Cys Val Met Lys Ile Thr Arg Ser Leu Asn Lys
    230                 235                 240 ggt ccc ttc ctc ttg cct tcg tgg acc tgg aac agt gat ctg gcc tca    823
Gly Pro Phe Leu Leu Pro Ser Trp Thr Trp Asn Ser Asp Leu Ala Ser
245                 250                 255                 260 ggg gac cag cat gct ttt ctt aag caa gaa ttt ggc tgt gga acc tac    871
Gly Asp Gln His Ala Phe Leu Lys Gln Glu Phe Gly Cys Gly Thr Tyr
                265                 270                 275 aga acc tta ctt cag aag ccc aat atg agt aaa cag gaa aag ggg aat    919
Arg Thr Leu Leu Gln Lys Pro Asn Met Ser Lys Gln Glu Lys Gly Asn
            280                 285                 290 att ctc tgg ttg aca atg gtg tgg ctg tca ctg gca tgt ctg caa agg    967
Ile Leu Trp Leu Thr Met Val Trp Leu Ser Leu Ala Cys Leu Gln Arg
        295                 300                 305 aaa aac tac aat gac tgc atg tta aac aca gca tca cag act gtt acc    1015
Lys Asn Tyr Asn Asp Cys Met Leu Asn Thr Ala Ser Gln Thr Val Thr
    310                 315                 320 act gaa aaa ttt tgagaagctc tccacttgaa cctcttcatg tcatgaatca        1067
Thr Glu Lys Phe
325 ggtgccagtg gcttagcttg aattacaggg taaaagccat cactttctct atccttttag  1127 gtgctttcta gaatcaaaac taaactttgt catcaaaggc ccatttataa tagctgcttt  1187 cctagctttt tattctatga taaagaagga ttgaagcatt tttaaaactt gagatttta   1247 tcatacctcc agcagagtaa ggagtctgtg tgatcttgca atcatggata aggaagaatt  1307 ttcccttcc ctcccctatg gatgctttaa aatgtgatt tttaaaaatg agtatgttaa    1367 tacaatacat gttagtaaaa gccatgggta ctgatgggcc aacacactac agcctactgg  1427 caaaatctga cttgcctctt gtttctgtaa ataaaatgtt attgcccatt caaaaaaaaa  1487 aaaaaaaaaa aaaaaa                                                  1503

<210> SEQ ID NO 26
<211> LENGTH: 328
<212> TYPE: PRT
<213> ORGANISM: Homo sapiens

<400> SEQUENCE: 26

Met Ala Thr Lys Arg Leu Ala Arg Gln Leu Gly Leu Ile Arg Arg Lys
1               5                   10                  15

Ser Ile Ala Pro Ala Asn Gly Asn Leu Gly Arg Ser Lys Ser Lys Gln
            20                  25                  30

Leu Phe Asp Tyr Leu Ile Val Ile Asp Phe Glu Ser Thr Cys Trp Asn
        35                  40                  45

Asp Gly Lys His His His Ser Gln Glu Ile Ile Glu Phe Pro Ala Val
    50                  55                  60

Leu Leu Asn Thr Ser Thr Gly Gln Ile Asp Ser Glu Phe Gln Ala Tyr
65                  70                  75                  80

Val Gln Pro Gln Glu His Pro Ile Leu Ser Glu Phe Cys Met Glu Leu
                85                  90                  95

Thr Gly Ile Lys Gln Ala Gln Val Asp Glu Gly Val Pro Leu Lys Ile
            100                 105                 110

Cys Leu Ser Gln Phe Cys Lys Trp Ile His Lys Ile Gln Gln Gln Lys
        115                 120                 125

Asn Ile Ile Phe Ala Thr Gly Ile Ser Glu Pro Ser Ala Ser Glu Val
```

```
                   130                 135                 140
Lys Leu Cys Ala Phe Val Thr Trp Ser Asp Trp Asp Leu Gly Val Cys
145                 150                 155                 160

Leu Glu Tyr Glu Cys Lys Arg Lys Gln Leu Leu Lys Pro Val Phe Leu
                165                 170                 175

Asn Ser Trp Ile Asp Leu Arg Ala Thr Tyr Lys Leu Phe Tyr Arg Arg
            180                 185                 190

Lys Pro Lys Gly Leu Ser Gly Ala Leu Gln Glu Val Gly Ile Glu Phe
        195                 200                 205

Ser Gly Arg Glu His Ser Gly Leu Asp Asp Ser Arg Asn Thr Ala Leu
    210                 215                 220

Leu Ala Trp Lys Met Ile Arg Asp Gly Cys Val Met Lys Ile Thr Arg
225                 230                 235                 240

Ser Leu Asn Lys Gly Pro Phe Leu Leu Pro Ser Trp Thr Trp Asn Ser
                245                 250                 255

Asp Leu Ala Ser Gly Asp Gln His Ala Phe Leu Lys Gln Glu Phe Gly
            260                 265                 270

Cys Gly Thr Tyr Arg Thr Leu Leu Gln Lys Pro Asn Met Ser Lys Gln
        275                 280                 285

Glu Lys Gly Asn Ile Leu Trp Leu Thr Met Val Trp Leu Ser Leu Ala
    290                 295                 300

Cys Leu Gln Arg Lys Asn Tyr Asn Asp Cys Met Leu Asn Thr Ala Ser
305                 310                 315                 320

Gln Thr Val Thr Thr Glu Lys Phe
                325

<210> SEQ ID NO 27
<211> LENGTH: 999
<212> TYPE: DNA
<213> ORGANISM: Homo sapiens
<220> FEATURE:
<221> NAME/KEY: CDS
<222> LOCATION: (16)..(720)
<223> OTHER INFORMATION: rrp46/RRP46 (Human crn-5 homolog)

<400> SEQUENCE: 27
ggcacgaggg gcgcg atg gag gag gag atg cat act gac gcc aaa atc cgt        51
                Met Glu Glu Glu Met His Thr Asp Ala Lys Ile Arg
                 1               5                  10 gct gaa aat gga aca ggg tcc agc cct cgg ggt cct ggc tgc agc ctc         99
Ala Glu Asn Gly Thr Gly Ser Ser Pro Arg Gly Pro Gly Cys Ser Leu
            15                  20                  25 cgg cac ttt gcc tgc gaa cag aac ctg ctg tcg cgg cca gat ggc tct        147
Arg His Phe Ala Cys Glu Gln Asn Leu Leu Ser Arg Pro Asp Gly Ser
        30                  35                  40 gct tcc ttc ctg caa ggt gac acc tct gtc ctg gcg ggt gtg tac ggg        195
Ala Ser Phe Leu Gln Gly Asp Thr Ser Val Leu Ala Gly Val Tyr Gly
45                  50                  55                  60 ccg gcc gag gtg aag gtc agc aaa gag att ttc aac aag gcc aca ctc        243
Pro Ala Glu Val Lys Val Ser Lys Glu Ile Phe Asn Lys Ala Thr Leu
                65                  70                  75 gaa gtg atc ctg agg ccg aag att ggg ctg cct ggt gtt gca gag aag        291
Glu Val Ile Leu Arg Pro Lys Ile Gly Leu Pro Gly Val Ala Glu Lys
            80                  85                  90 agc cgg gag cgg ctg atc agg aac acg tgc gag gcg gtg gtg ctg ggc        339
Ser Arg Glu Arg Leu Ile Arg Asn Thr Cys Glu Ala Val Val Leu Gly
        95                 100                 105 acg ttg cac ccc gcc acc tcc atc acc gtg gtg ctg cag gtt gtc agc        387
```

```
Thr Leu His Pro Arg Thr Ser Ile Thr Val Val Leu Gln Val Val Ser
    110                 115                 120 gat gcc ggc tct ctc ctg gcc tgt tgt ctg aat gcc gcc tgc atg gca    435
Asp Ala Gly Ser Leu Leu Ala Cys Cys Leu Asn Ala Ala Cys Met Ala
125                 130                 135                 140 ttg gtg gat gca ggt gtg ccc atg cgg gct ctc ttc tgt ggg gtc gcc    483
Leu Val Asp Ala Gly Val Pro Met Arg Ala Leu Phe Cys Gly Val Ala
                145                 150                 155 tgc gcc ctg gac tct gat ggg acc ctc gtg ctg gat cct aca tcc aag    531
Cys Ala Leu Asp Ser Asp Gly Thr Leu Val Leu Asp Pro Thr Ser Lys
                    160                 165                 170 caa gaa aag gag gcc cgg gca gtc ctg acc ttt gcc ctg gac agc gtg    579
Gln Glu Lys Glu Ala Arg Ala Val Leu Thr Phe Ala Leu Asp Ser Val
            175                 180                 185 gaa cgg aag ctg ctg atg tcc agc acc aag ggg ctc tac tca gac act    627
Glu Arg Lys Leu Leu Met Ser Ser Thr Lys Gly Leu Tyr Ser Asp Thr
        190                 195                 200 gag ctc cag cag tgc ctg gct gcg gcc cag gcc gct tcg caa cac gtc    675
Glu Leu Gln Gln Cys Leu Ala Ala Ala Gln Ala Ala Ser Gln His Val
205                 210                 215                 220 ttc cgt ttc tac cgg gaa tcg ctg cag agg cgt tac tcc aag agc       720
Phe Arg Phe Tyr Arg Glu Ser Leu Gln Arg Arg Tyr Ser Lys Ser
                    225                 230                 235 tgaggcaagc tggggcaagg ggccgctccc attgcctcca cccactcacc ccctacagcc    780
tgaagcaaac cagcagccca gccttgcctc tctgacccat gggctccttg agcctgcagc    840
tctgtaacca cagggctcct gtggggaggc cttggcctgt gacagccccc aggcctgggg    900
gcacagatcc ccccagcaag ataacattc aaaggagctc acatttatgg aatggatgaa    960
tcaataaatt aattcacttt aaaaaaaaaa aaaaaaaa                            999

<210> SEQ ID NO 28
<211> LENGTH: 235
<212> TYPE: PRT
<213> ORGANISM: Homo sapiens

<400> SEQUENCE: 28

Met Glu Glu Glu Met His Thr Asp Ala Lys Ile Arg Ala Glu Asn Gly
1               5                   10                  15

Thr Gly Ser Ser Pro Arg Gly Pro Gly Cys Ser Leu Arg His Phe Ala
                20                  25                  30

Cys Glu Gln Asn Leu Leu Ser Arg Pro Asp Gly Ser Ala Ser Phe Leu
            35                  40                  45

Gln Gly Asp Thr Ser Val Leu Ala Gly Val Tyr Gly Pro Ala Glu Val
        50                  55                  60

Lys Val Ser Lys Glu Ile Phe Asn Lys Ala Thr Leu Glu Val Ile Leu
65                  70                  75                  80

Arg Pro Lys Ile Gly Leu Pro Gly Val Ala Glu Lys Ser Arg Glu Arg
                85                  90                  95

Leu Ile Arg Asn Thr Cys Glu Ala Val Val Leu Gly Thr Leu His Pro
            100                 105                 110

Arg Thr Ser Ile Thr Val Val Leu Gln Val Val Ser Asp Ala Gly Ser
        115                 120                 125

Leu Leu Ala Cys Cys Leu Asn Ala Ala Cys Met Ala Leu Val Asp Ala
    130                 135                 140

Gly Val Pro Met Arg Ala Leu Phe Cys Gly Val Ala Cys Ala Leu Asp
145                 150                 155                 160
```

```
Ser Asp Gly Thr Leu Val Leu Asp Pro Thr Ser Lys Gln Glu Lys Glu
            165                 170                 175

Ala Arg Ala Val Leu Thr Phe Ala Leu Asp Ser Val Glu Arg Lys Leu
            180                 185                 190

Leu Met Ser Ser Thr Lys Gly Leu Tyr Ser Asp Thr Glu Leu Gln Gln
            195                 200                 205

Cys Leu Ala Ala Gln Ala Ala Ser Gln His Val Phe Arg Phe Tyr
            210                 215                 220

Arg Glu Ser Leu Gln Arg Arg Tyr Ser Lys Ser
225                 230                 235

<210> SEQ ID NO 29
<211> LENGTH: 1751
<212> TYPE: DNA
<213> ORGANISM: Homo sapiens
<220> FEATURE:
<221> NAME/KEY: CDS
<222> LOCATION: (77)..(1156)
<223> OTHER INFORMATION: DNaseII (Human crn-6 homolog)

<400> SEQUENCE: 29
ccagtcctgg cctctgatgt aacccagcgc cccgcagtcc cgacacagat tcctggatct      60
cagccccata gcagct atg atc ccg ctg ctg ctg gca gcg ctg ctg tgc gtc    112
               Met Ile Pro Leu Leu Leu Ala Ala Leu Leu Cys Val
                1               5                   10 ccc gcc ggg gcc ctg acc tgc tac ggg gac tcc ggg cag cct gta gac    160
Pro Ala Gly Ala Leu Thr Cys Tyr Gly Asp Ser Gly Gln Pro Val Asp
            15                  20                  25 tgg ttc gtg gtc tac aag ctg cca gct ctt aga ggg tcc ggg gag gcg    208
Trp Phe Val Val Tyr Lys Leu Pro Ala Leu Arg Gly Ser Gly Glu Ala
        30                  35                  40 gcg cag aga ggg ctg cag tac aag tat ctg gac gag agc tcc gga ggc    256
Ala Gln Arg Gly Leu Gln Tyr Lys Tyr Leu Asp Glu Ser Ser Gly Gly
45                  50                  55                  60 tgg cgg gac ggc agg gca ctc atc aac agc ccg gag ggg gcc gtg ggc    304
Trp Arg Asp Gly Arg Ala Leu Ile Asn Ser Pro Glu Gly Ala Val Gly
                65                  70                  75 cga agc ctg cag ccg ctg tac cgg agc aac acc agc cag ctc gcc ttc    352
Arg Ser Leu Gln Pro Leu Tyr Arg Ser Asn Thr Ser Gln Leu Ala Phe
            80                  85                  90 ctg ctc tac aat gac caa ccg cct caa ccc agc aag gct cag gac tct    400
Leu Leu Tyr Asn Asp Gln Pro Pro Gln Pro Ser Lys Ala Gln Asp Ser
        95                  100                 105 tcc atg cgt ggg cac acg aag ggt gtc ctg ctc ctt gac cac gat ggg    448
Ser Met Arg Gly His Thr Lys Gly Val Leu Leu Leu Asp His Asp Gly
    110                 115                 120 ggc ttc tgg ctg gtc cac agt gta cct aac ttc cct cca ccg gcc tcc    496
Gly Phe Trp Leu Val His Ser Val Pro Asn Phe Pro Pro Pro Ala Ser
125                 130                 135                 140 tct gct gca tac agc tgg cct cat agc gcc tgt acc tac ggg cag acc    544
Ser Ala Ala Tyr Ser Trp Pro His Ser Ala Cys Thr Tyr Gly Gln Thr
                145                 150                 155 ctg ctc tgt gtg tct ttt ccc ttc gct cag ttc tcg aag atg ggc aag    592
Leu Leu Cys Val Ser Phe Pro Phe Ala Gln Phe Ser Lys Met Gly Lys
            160                 165                 170 cag ctg acc tac acc tac ccc tgg gtc tat aac tac cag ctg gaa ggg    640
Gln Leu Thr Tyr Thr Tyr Pro Trp Val Tyr Asn Tyr Gln Leu Glu Gly
        175                 180                 185 atc ttt gcc cag gaa ttc ccc gac ttg gag aat gtg gtc aag ggc cac    688
Ile Phe Ala Gln Glu Phe Pro Asp Leu Glu Asn Val Val Lys Gly His
    190                 195                 200
```

```
                190                 195                 200
cac gtt agc caa gaa ccc tgg aac agc agc atc aca ctc aca tcc cag      736
His Val Ser Gln Glu Pro Trp Asn Ser Ser Ile Thr Leu Thr Ser Gln
205                 210                 215                 220 gcc ggg gct gtt ttc cag agc ttt gcc aag ttc agc aaa ttt gga gat      784
Ala Gly Ala Val Phe Gln Ser Phe Ala Lys Phe Ser Lys Phe Gly Asp
                225                 230                 235 gac ctg tac tcc ggc tgg ttg gca gca gcc ctt ggt acc aac ctg cag      832
Asp Leu Tyr Ser Gly Trp Leu Ala Ala Ala Leu Gly Thr Asn Leu Gln
        240                 245                 250 gtc cag ttc tgg cac aaa act gta ggc atc ctg ccc tct aac tgc tcg      880
Val Gln Phe Trp His Lys Thr Val Gly Ile Leu Pro Ser Asn Cys Ser
                255                 260                 265 gat atc tgg cag gtt ctg aat gtg aac cag ata gct ttc cct gga cca      928
Asp Ile Trp Gln Val Leu Asn Val Asn Gln Ile Ala Phe Pro Gly Pro
        270                 275                 280 gcc ggc cca agc ttc aac agc aca gag gac cac tcc aaa tgg tgc gtg      976
Ala Gly Pro Ser Phe Asn Ser Thr Glu Asp His Ser Lys Trp Cys Val
285                 290                 295                 300 tcc cca aaa ggg ccc tgg acc tgc gtg ggt gac atg aat cgg aac cag     1024
Ser Pro Lys Gly Pro Trp Thr Cys Val Gly Asp Met Asn Arg Asn Gln
                305                 310                 315 gga gag gag caa cgg ggt ggg ggc aca ctg tgt gcc cag ctg cca gcc     1072
Gly Glu Glu Gln Arg Gly Gly Gly Thr Leu Cys Ala Gln Leu Pro Ala
        320                 325                 330 ctc tgg aaa gcc ttc cag ccg ctg gtg aag aac tac cag ccc tgt aat     1120
Leu Trp Lys Ala Phe Gln Pro Leu Val Lys Asn Tyr Gln Pro Cys Asn
                335                 340                 345 ggc atg gcc agg aag ccc agc aga gct tat aag atc taacccttat         1166
Gly Met Ala Arg Lys Pro Ser Arg Ala Tyr Lys Ile
        350                 355                 360 ggccaggtgc agtggctcac gtatgtaatc ccagcacttt gggaagccaa ggagggagga   1226
tcacttgaac tcaggaattc gagaccagcc tgggctacat agtgagacca catctctact   1286
agaacttaaa aaaagttagc caggcacggt gataaatgcc tgtagtccca gccactgaag   1346
ccagaggatc gattgaacca gggagatcat ggtcacagtg aactatgatt acgccaacct   1406
gggtcacata gcaagactct gtttcaaaaa aaaggggggg gcgggggacg ggtgggtgca   1466
gtggctcaca tctgtaaccc cagcactttg ggaggctgag atgggcagat cacttgaggt   1526
caggagttcg agaccagcct ggccaacatg gtgaaacccc atatccatta aaaatattta   1586
aaaattagcc agacatggtg gcacgcgtct gtggtcctag ctcctcggga ggctgaggca   1646
ggagaatcgc ttgaactcgg gaggcagagg ttgtcatgag ctgagctaac accacggcac   1706
ttcagcctgg gtgacagaat gagactctgt gtcaaaaaaa taaaa                  1751
```

<210> SEQ ID NO 30
<211> LENGTH: 360
<212> TYPE: PRT
<213> ORGANISM: Homo sapiens

<400> SEQUENCE: 30

```
Met Ile Pro Leu Leu Ala Ala Leu Leu Cys Val Pro Ala Gly Ala
1               5                   10                  15

Leu Thr Cys Tyr Gly Asp Ser Gly Gln Pro Val Asp Trp Phe Val
            20                  25                  30

Tyr Lys Leu Pro Ala Leu Arg Gly Ser Gly Glu Ala Ala Gln Arg Gly
        35                  40                  45
```

```
Leu Gln Tyr Lys Tyr Leu Asp Glu Ser Ser Gly Gly Trp Arg Asp Gly
 50                  55                  60

Arg Ala Leu Ile Asn Ser Pro Glu Gly Ala Val Gly Arg Ser Leu Gln
 65                  70                  75                  80

Pro Leu Tyr Arg Ser Asn Thr Ser Gln Leu Ala Phe Leu Leu Tyr Asn
                 85                  90                  95

Asp Gln Pro Pro Gln Pro Ser Lys Ala Gln Asp Ser Ser Met Arg Gly
                100                 105                 110

His Thr Lys Gly Val Leu Leu Asp His Asp Gly Phe Trp Leu
            115                 120                 125

Val His Ser Val Pro Asn Phe Pro Pro Ala Ser Ser Ala Ala Tyr
    130                 135                 140

Ser Trp Pro His Ser Ala Cys Thr Tyr Gly Gln Thr Leu Leu Cys Val
145                 150                 155                 160

Ser Phe Pro Phe Ala Gln Phe Ser Lys Met Gly Lys Gln Leu Thr Tyr
                165                 170                 175

Thr Tyr Pro Trp Val Tyr Asn Tyr Gln Leu Glu Gly Ile Phe Ala Gln
                180                 185                 190

Glu Phe Pro Asp Leu Glu Asn Val Val Lys Gly His His Val Ser Gln
            195                 200                 205

Glu Pro Trp Asn Ser Ser Ile Thr Leu Thr Ser Gln Ala Gly Ala Val
    210                 215                 220

Phe Gln Ser Phe Ala Lys Phe Ser Lys Phe Gly Asp Asp Leu Tyr Ser
225                 230                 235                 240

Gly Trp Leu Ala Ala Ala Leu Gly Thr Asn Leu Gln Val Gln Phe Trp
                245                 250                 255

His Lys Thr Val Gly Ile Leu Pro Ser Asn Cys Ser Asp Ile Trp Gln
                260                 265                 270

Val Leu Asn Val Asn Gln Ile Ala Phe Pro Gly Pro Ala Gly Pro Ser
            275                 280                 285

Phe Asn Ser Thr Glu Asp His Ser Lys Trp Cys Val Ser Pro Lys Gly
    290                 295                 300

Pro Trp Thr Cys Val Gly Asp Met Asn Arg Asn Gln Gly Glu Glu Gln
305                 310                 315                 320

Arg Gly Gly Gly Thr Leu Cys Ala Gln Leu Pro Ala Leu Trp Lys Ala
                325                 330                 335

Phe Gln Pro Leu Val Lys Asn Tyr Gln Pro Cys Asn Gly Met Ala Arg
                340                 345                 350

Lys Pro Ser Arg Ala Tyr Lys Ile
            355                 360

<210> SEQ ID NO 31
<211> LENGTH: 1273
<212> TYPE: DNA
<213> ORGANISM: Homo sapiens
<220> FEATURE:
<221> NAME/KEY: CDS
<222> LOCATION: (7)..(909)
<223> OTHER INFORMATION: Cycliphilin E (Human cyp-13 homolog)

<400> SEQUENCE: 31 agcaag atg gcc acc acc aag cgc gtc ttg tac gtg ggt gga ctg gca        48
       Met Ala Thr Thr Lys Arg Val Leu Tyr Val Gly Gly Leu Ala
        1               5                  10 gag gaa gtg gac gac aaa gtt ctt cat gct gcg ttc att cct ttt gga      96
Glu Glu Val Asp Asp Lys Val Leu His Ala Ala Phe Ile Pro Phe Gly
 15                  20                  25                  30
```

```
gac atc aca gat att cag att cct ctg gat tat gaa aca gaa aag cac    144
Asp Ile Thr Asp Ile Gln Ile Pro Leu Asp Tyr Glu Thr Glu Lys His
             35                  40                  45 cga gga ttt gct ttt gtt gaa ttt gag ttg gca gag gat gct gca gca    192
Arg Gly Phe Ala Phe Val Glu Phe Glu Leu Ala Glu Asp Ala Ala Ala
         50                  55                  60 gct atc gac aac atg aat gaa tct gag ctt ttt gga cgt aca att cgt    240
Ala Ile Asp Asn Met Asn Glu Ser Glu Leu Phe Gly Arg Thr Ile Arg
             65                  70                  75 gtc aat ttg gcc aaa cca atg aga att aag gaa ggc tct tcc agg cca    288
Val Asn Leu Ala Lys Pro Met Arg Ile Lys Glu Gly Ser Ser Arg Pro
         80                  85                  90 gtt tgg tca gat gat gac tgg ttg aag aag ttt tct ggg aag acg ctt    336
Val Trp Ser Asp Asp Asp Trp Leu Lys Lys Phe Ser Gly Lys Thr Leu
 95                 100                 105                 110 gaa gag aat aaa gag gaa gaa ggg tca gag cct ccc aaa gca gag acc    384
Glu Glu Asn Lys Glu Glu Glu Gly Ser Glu Pro Pro Lys Ala Glu Thr
                115                 120                 125 cag gag gga gag ccc att gct aaa aag gcc cgc tca aat cct cag gtg    432
Gln Glu Gly Glu Pro Ile Ala Lys Lys Ala Arg Ser Asn Pro Gln Val
            130                 135                 140 tac atg gac atc aag att ggg aac aag ccg gct ggc cgc atc cag atg    480
Tyr Met Asp Ile Lys Ile Gly Asn Lys Pro Ala Gly Arg Ile Gln Met
            145                 150                 155 ctc ctg cgt tct gat gtc gtg ccc atg aca gca gag aat ttc cgc tgc    528
Leu Leu Arg Ser Asp Val Val Pro Met Thr Ala Glu Asn Phe Arg Cys
        160                 165                 170 ctg tgc act cat gaa aag ggc ttt ggc ttt aag gga agc agc ttc cac    576
Leu Cys Thr His Glu Lys Gly Phe Gly Phe Lys Gly Ser Ser Phe His
175                 180                 185                 190 cgc atc atc ccc cag ttc atg tgc cag ggc ggt gat ttc aca aac cac    624
Arg Ile Ile Pro Gln Phe Met Cys Gln Gly Gly Asp Phe Thr Asn His
                195                 200                 205 aat ggc act ggg ggc aag tcc atc tat ggg aag aag ttc gat gat gaa    672
Asn Gly Thr Gly Gly Lys Ser Ile Tyr Gly Lys Lys Phe Asp Asp Glu
            210                 215                 220 aac ttt atc ctc aag cat acg gga cca ggt cta cta tcc atg gcc aac    720
Asn Phe Ile Leu Lys His Thr Gly Pro Gly Leu Leu Ser Met Ala Asn
        225                 230                 235 tct ggc cca aac acc aat ggc tct cag ttc ttc ctg aca tgt gac aag    768
Ser Gly Pro Asn Thr Asn Gly Ser Gln Phe Phe Leu Thr Cys Asp Lys
    240                 245                 250 aca gac tgg ctg gat ggc aag cat gtg gtg ttt gga gag gtc acc gaa    816
Thr Asp Trp Leu Asp Gly Lys His Val Val Phe Gly Glu Val Thr Glu
255                 260                 265                 270 ggc cta gat gtc ttg cgg caa att gag gcc cag ggc agc aag gac ggg    864
Gly Leu Asp Val Leu Arg Gln Ile Glu Ala Gln Gly Ser Lys Asp Gly
                275                 280                 285 aag cca aag cag aag gtg atc atc gcc gac tgt ggg gag tac gtg        909
Lys Pro Lys Gln Lys Val Ile Ile Ala Asp Cys Gly Glu Tyr Val
            290                 295                 300 tgaggcggca ctctctctgc ttccccctcc gctcttgacc ctgcatatcc aggaaggaac    969
tgccagcctc agaggaggca gcaccgaggg tgcctgtttg aagcaagcag catttgggat   1029
atgtgccctt cctcagggtc tgcttggagc agctcctctg caggcacagc ctggactatt   1089
cccaggcaca gctgtgggcc caggagccag ctcaggtgct cccctccacc atgggcaggc   1149
tgtgcaaaaa gccactggct tttctcagca tttgctgctg ggcctctcct gggactacca   1209
```

```
gtgtggctct tacgtgtttt ctttgctaaa ataaaccta gttcttaaaa aaaaaaaaaa      1269
aaaa                                                                 1273
```

<210> SEQ ID NO 32
<211> LENGTH: 301
<212> TYPE: PRT
<213> ORGANISM: Homo sapiens

<400> SEQUENCE: 32

```
Met Ala Thr Thr Lys Arg Val Leu Tyr Val Gly Gly Leu Ala Glu Glu
1               5                   10                  15

Val Asp Asp Lys Val Leu His Ala Ala Phe Ile Pro Phe Gly Asp Ile
            20                  25                  30

Thr Asp Ile Gln Ile Pro Leu Asp Tyr Glu Thr Glu Lys His Arg Gly
        35                  40                  45

Phe Ala Phe Val Glu Phe Glu Leu Ala Glu Asp Ala Ala Ala Ala Ile
    50                  55                  60

Asp Asn Met Asn Glu Ser Glu Leu Phe Gly Arg Thr Ile Arg Val Asn
65                  70                  75                  80

Leu Ala Lys Pro Met Arg Ile Lys Glu Gly Ser Ser Arg Pro Val Trp
                85                  90                  95

Ser Asp Asp Asp Trp Leu Lys Lys Phe Ser Gly Lys Thr Leu Glu Glu
            100                 105                 110

Asn Lys Glu Glu Glu Gly Ser Glu Pro Pro Lys Ala Glu Thr Gln Glu
        115                 120                 125

Gly Glu Pro Ile Ala Lys Lys Ala Arg Ser Asn Pro Gln Val Tyr Met
    130                 135                 140

Asp Ile Lys Ile Gly Asn Lys Pro Ala Gly Arg Ile Gln Met Leu Leu
145                 150                 155                 160

Arg Ser Asp Val Val Pro Met Thr Ala Glu Asn Phe Arg Cys Leu Cys
                165                 170                 175

Thr His Glu Lys Gly Phe Gly Phe Lys Gly Ser Ser Phe His Arg Ile
            180                 185                 190

Ile Pro Gln Phe Met Cys Gln Gly Gly Asp Phe Thr Asn His Asn Gly
        195                 200                 205

Thr Gly Gly Lys Ser Ile Tyr Gly Lys Lys Phe Asp Asp Glu Asn Phe
    210                 215                 220

Ile Leu Lys His Thr Gly Pro Gly Leu Leu Ser Met Ala Asn Ser Gly
225                 230                 235                 240

Pro Asn Thr Asn Gly Ser Gln Phe Phe Leu Thr Cys Asp Lys Thr Asp
                245                 250                 255

Trp Leu Asp Gly Lys His Val Val Phe Gly Glu Val Thr Glu Gly Leu
            260                 265                 270

Asp Val Leu Arg Gln Ile Glu Ala Gln Gly Ser Lys Asp Gly Lys Pro
        275                 280                 285

Lys Gln Lys Val Ile Ile Ala Asp Cys Gly Glu Tyr Val
    290                 295                 300
```

<210> SEQ ID NO 33
<211> LENGTH: 382
<212> TYPE: PRT
<213> ORGANISM: Caenorhabditis elegans
<220> FEATURE:
<221> NAME/KEY: MISC_FEATURE
<222> LOCATION: (1)..(382)
<223> OTHER INFORMATION: CRN-1

```
<400> SEQUENCE: 33

Met Gly Ile Lys Gly Leu Ser Gln Val Ile Ala Asp Asn Ala Pro Ser
1               5                   10                  15

Ala Ile Lys Val Asn Glu Met Lys Ala Phe Phe Gly Arg Thr Val Ala
            20                  25                  30

Ile Asp Ala Ser Met Cys Leu Tyr Gln Phe Leu Ile Ala Val Arg Gln
        35                  40                  45

Asp Gly Ser Gln Leu Gln Ser Glu Asp Gly Glu Thr Thr Ser His Leu
    50                  55                  60

Met Gly Met Leu Asn Arg Thr Val Arg Met Phe Glu Asn Gly Val Lys
65                  70                  75                  80

Pro Val Tyr Val Phe Asp Gly Lys Pro Pro Asp Met Lys Gly Gly Glu
                85                  90                  95

Leu Glu Lys Arg Ser Glu Arg Arg Ala Glu Ala Lys Ala Leu Thr
            100                 105                 110

Glu Ala Lys Glu Lys Gly Asp Val Lys Glu Ala Glu Lys Phe Glu Arg
            115                 120                 125

Arg Leu Val Lys Val Thr Lys Gln Gln Asn Asp Glu Ala Lys Arg Leu
    130                 135                 140

Leu Gly Leu Met Gly Ile Pro Val Val Glu Ala Pro Cys Glu Ala Glu
145                 150                 155                 160

Ala Gln Cys Ala His Leu Val Lys Ala Gly Lys Val Phe Gly Thr Val
                165                 170                 175

Thr Glu Asp Met Asp Ala Leu Thr Phe Gly Ser Thr Val Leu Leu Arg
            180                 185                 190

His Phe Leu Ala Pro Val Ala Lys Lys Ile Pro Ile Lys Glu Phe Asn
    195                 200                 205

Leu Ser Leu Ala Leu Glu Glu Met Lys Leu Ser Val Glu Glu Phe Ile
            210                 215                 220

Asp Leu Cys Ile Leu Leu Gly Cys Asp Tyr Cys Gly Thr Ile Arg Gly
225                 230                 235                 240

Val Gly Pro Lys Lys Ala Val Glu Leu Ile Arg Gln His Lys Asn Ile
                245                 250                 255

Glu Thr Ile Leu Glu Asn Ile Asp Gln Asn Lys Tyr Pro Pro Pro Glu
            260                 265                 270

Asp Trp Pro Tyr Lys Arg Ala Arg Glu Leu Phe Leu Asn Pro Glu Val
    275                 280                 285

Thr Lys Pro Glu Glu Val Glu Leu Thr Trp Lys Glu Ala Asp Val Glu
            290                 295                 300

Gly Val Ile Gln Phe Leu Cys Gly Glu Lys Asn Phe Asn Glu Glu Arg
305                 310                 315                 320

Ile Arg Asn Ala Leu Ala Lys Leu Lys Thr Ser Arg Lys Ser Gly Thr
                325                 330                 335

Gln Gly Arg Ile Asp Ser Phe Phe Gly Asn Ser Thr Lys Val Thr Cys
            340                 345                 350

Val Thr Ala Ala Thr Lys Arg Lys Ala Glu Glu Ala Glu Lys Ala Lys
    355                 360                 365

Lys Gly Ala Lys Lys Gly Gly Pro Pro Lys Lys Arg Ala Lys
    370                 375                 380

<210> SEQ ID NO 34
<211> LENGTH: 286
<212> TYPE: PRT
<213> ORGANISM: Caenorhabditis elegans
```

```
<220> FEATURE:
<221> NAME/KEY: MISC_FEATURE
<222> LOCATION: (1)..(286)
<223> OTHER INFORMATION: CRN-2

<400> SEQUENCE: 34
```

| | | | | | | | | | | | | | | |
|---|---|---|---|---|---|---|---|---|---|---|---|---|---|---|
| Met | Ala | Leu | Tyr | Glu | Leu | Val | Asp | Ile | Gly | Ala | Asn | Leu | Gly | His | Pro |
| 1 | | | | 5 | | | | | 10 | | | | | 15 | |

Ser Tyr Gln Lys Asp Leu Asn Asp Val Leu Asp Arg Ala Lys Gln Ala
            20                  25                  30

Gly Leu Ser Lys Ile Met Val Thr Gly Thr Ser Glu Lys Ile Ser His
            35                  40                  45

Glu Cys Ala Asp Leu Val Glu Lys Tyr Pro Gly Phe Leu Tyr Phe Thr
 50                  55                  60

Ala Gly Val His Pro His Asp Ala Lys Asp Trp Asn Asp Gly Thr Leu
65                  70                  75                  80

Glu Ala Leu Lys Lys Leu Gln Glu Asn Pro Ser Cys Val Ala Val Gly
                85                  90                  95

Glu Cys Gly Leu Asp Phe Asn Arg Asn Phe Ser Pro Gln Asp Val Gln
            100                 105                 110

Lys Glu Val Phe Ala Lys Gln Val Asp Met Ala Val Lys Leu Gln Lys
            115                 120                 125

Pro Leu Phe Ile His Glu Arg Glu Ala His Glu Asp Met Val Lys Ile
130                 135                 140

Leu Thr Ala Ala Gly Pro Ser Leu Pro Pro Ala Val Ile His Cys Phe
145                 150                 155                 160

Thr Gly Thr Val Val Glu Ala Lys Lys Tyr Leu Glu Met Gly Phe Tyr
                165                 170                 175

Ile Gly Leu Thr Gly Phe Leu Trp Lys Asp Arg Ser Asp Asn Gly Val
            180                 185                 190

Gln Ala Gly Leu Arg Ser Gly Glu Ile Pro Ile Glu Lys Leu Val Leu
            195                 200                 205

Glu Thr Asp Ala Pro Tyr Met Tyr Pro Lys Ile Asn Asp Lys Lys Ile
210                 215                 220

Pro Lys Glu Ile Lys Ser Leu Ile Thr Pro Glu Thr Glu Ala Leu His
225                 230                 235                 240

Asn Phe Ser Ser Phe Asn Arg Asn Glu Pro Cys Ser Leu Ala Ala Val
                245                 250                 255

Cys Glu Leu Val Ala Ala Phe Ala Gly Arg Asp Pro Lys Glu Val Ala
            260                 265                 270

Lys Ile Thr Thr Glu Asn Ala Lys Lys Val Tyr Lys Leu Glu
            275                 280                 285

```
<210> SEQ ID NO 35
<211> LENGTH: 876
<212> TYPE: PRT
<213> ORGANISM: Caenorhabditis elegans
<220> FEATURE:
<221> NAME/KEY: MISC_FEATURE
<223> OTHER INFORMATION: CRN-3

<400> SEQUENCE: 35
```

Met Ser Gly Glu Glu Ser Met Pro Asp Glu Glu Gln Lys Gln Ser Glu
1               5                   10                  15

Glu Glu Glu Glu Met Ile Arg Lys Arg Thr Leu Ala Met Arg Lys Lys
            20                  25                  30

Val Glu Glu Ile Met Arg Asn Gly Ala Gly Leu Val Arg Glu Ser Asn

-continued

```
               35                  40                  45
Gly Leu Pro Lys Ala Gly Ala Asp Tyr Glu Leu Tyr Asn Ser Tyr Pro
             50                  55                  60

Thr Phe Asn Thr Phe Met Lys Arg Ser Glu Gln Arg Leu Asn Ala Leu
 65                  70                  75                  80

Met Asn Lys Val Thr Lys Ser Ile Gly Cys Ala Met Arg Val Pro Asp
                 85                  90                  95

Val Gly Ser Ser Val Glu His Tyr Thr Glu Cys Val Ile Glu Ala Gln
             100                 105                 110

Asp Asn Ile Ala Glu Arg Ala Ala Thr Leu His Glu Ala Leu Lys Lys
             115                 120                 125

Ala Glu Leu Asp Glu Ile Val Lys Val Pro Glu Phe Ile Thr Lys Ala
130                 135                 140

Ala Pro Thr Asn Arg Lys Thr Glu Ala Glu Val Ser Ala Ala Met Arg
145                 150                 155                 160

Thr Phe Ser Ala Asn Ile Gly Thr Val Leu Ala Glu Lys Phe Arg Glu
                165                 170                 175

Arg Arg Glu Glu Ala Ala Gln Met Val Val Leu Glu Lys Pro Gln Lys
             180                 185                 190

Thr Tyr Asn Ile Ser Ser Asp Asn Ser Gln Ala Pro Phe Ser Ser Lys
             195                 200                 205

Leu Thr Val Lys His His Ala Ile Glu Lys Arg Thr Gly Ile Val Leu
    210                 215                 220

His Asp Asp Glu Ser Gly Arg Arg Asp Trp Ile Ser Ala Glu Thr
225                 230                 235                 240

Glu Thr Glu Glu Glu His Pro Tyr Ile Ala Glu Ile Leu His Phe Lys
                245                 250                 255

Val Pro Glu Ala Gln Leu Lys Ser Ala Glu Cys Leu Lys Phe Thr Ala
            260                 265                 270

Leu Lys Asp Thr Pro Leu Thr Met Ile Asp Thr Lys Glu Lys Leu Glu
            275                 280                 285

Ala Leu Thr Lys Thr Leu Asn Ser Val Lys Glu Phe Ala Val Asp Leu
290                 295                 300

Glu His His Gln Met Arg Ser Tyr Leu Gly Leu Thr Cys Leu Ile Gln
305                 310                 315                 320

Ile Ser Thr Arg Asp Glu Asp Phe Ile Ile Asp Pro Phe Pro Ile Trp
                325                 330                 335

Asp His Val Gly Met Leu Asn Glu Pro Phe Ala Asn Pro Arg Ile Leu
            340                 345                 350

Lys Val Phe His Gly Ser Asp Ser Asp Val Leu Trp Leu Gln Arg Asp
            355                 360                 365

Tyr Gly Val His Val Val Asn Leu Phe Asp Thr Tyr Val Ala Met Lys
    370                 375                 380

Lys Leu Lys Tyr Pro Lys Phe Ser Leu Ala Tyr Leu Thr Leu Arg Phe
385                 390                 395                 400

Ala Asp Val Val Leu Asp Lys Gln Tyr Gln Leu Ala Asp Trp Arg Ala
                405                 410                 415

Arg Pro Leu Arg Asn Ala Met Ile Asn Tyr Ala Arg Glu Asp Thr His
            420                 425                 430

Tyr Leu Leu Tyr Ser Tyr Asp Met Leu Arg Glu Gln Leu Leu Lys Gln
            435                 440                 445

Asp Thr Lys Asp Leu Ala Asn Val Tyr Ser Glu Ser Ser Asp Leu Cys
450                 455                 460
```

```
Ile Lys Val Tyr Lys Lys Pro Val Phe Asn Pro Lys Gly Tyr Leu Thr
465                 470                 475                 480

Glu Ile Lys Phe Arg Phe Thr Leu Asn Thr Arg Gln Asp Tyr Ala Leu
            485                 490                 495

Thr His Leu Phe Lys Trp Arg Asp Val Val Ala Arg Ala Glu Asp Glu
                500                 505                 510

Ser Pro His Phe Val Leu Pro Asn His Met Met Leu Ser Leu Ser Glu
            515                 520                 525

Thr Leu Pro Arg Asp Val Gly Gly Ile Tyr Ala Cys Cys Asn Pro Leu
530                 535                 540

Pro Tyr Phe Val Lys Gln Arg Thr Gly Asp Ile Leu Lys Ile Ile Val
545                 550                 555                 560

Glu Ala Arg Asp Val Lys Leu Glu Lys Val Gly Leu Ser Ala Lys Glu
                565                 570                 575

Arg Asn Asp Ala Gln Glu Ala Arg Gly Val Met Asn Asp Thr Met Asp
            580                 585                 590

His Ile Thr Ser Val Leu Lys Ser Lys Ile Asp Phe Ser His Thr Arg
            595                 600                 605

Phe Asp Glu Glu Arg Gly Glu Ile Tyr Ile Asp Lys Thr Asp Glu Gly
610                 615                 620

Met Asp Ile Glu Leu Lys Asp His Lys Glu Ser Leu Leu Ser Val Leu
625                 630                 635                 640

Gln Thr Ala Glu Ile Pro Ser Val Glu Thr Met Ile Val Val Glu Lys
                645                 650                 655

Gly Lys Lys Ser Asp Asn Gln Lys Val Lys Leu Leu Asn Glu Leu
            660                 665                 670

Asp Lys Phe Val Thr Pro Phe Glu Cys Tyr Gln Met Met Met Ile Thr
            675                 680                 685

Lys Glu Lys Gln Glu Glu Glu Arg Lys Glu Ala Glu Arg Lys Lys
            690                 695                 700

Leu Glu Glu Gly Asp Leu Pro Lys Thr Met Phe Ser His His Asp Ala
705                 710                 715                 720

Pro Ile Asn Arg Lys Pro Glu Phe Asp Ala Lys Leu Leu Asn Val Asp
                725                 730                 735

Thr Leu Lys Leu Val Pro Asp Asp Pro Asn Lys Pro Lys Asp Pro Glu
            740                 745                 750

Pro Ser Pro Met Glu Glu Ser Ser Glu Pro Gln Ile Phe Asp Pro
            755                 760                 765

Ser Arg Phe Thr Asp Asp Gln Leu Leu Ser Lys Lys Ala Met Lys Arg
770                 775                 780

Lys Arg Asp Ala Ala Arg Arg Asn Ile Asp Val Ser Val Val Leu Gly
785                 790                 795                 800

Glu Ser Ser Ser Ser Asp Pro Lys Lys Lys Ser Asp Asp Asp
                805                 810                 815

Ala Pro Val Glu Asp Phe Asp Tyr Glu Lys Ala Asp Ser Ser Ala Phe
                820                 825                 830

Glu Lys Pro Val Arg Asp Asn Asn Ala Asp Phe Asp Pro Phe His Gln
            835                 840                 845

Lys Tyr Arg Leu Lys Asn Lys Thr Lys Lys Asn Met Ala Met Lys Lys
            850                 855                 860

Ser Ser Asn Arg Gln Gly Thr Ile Asn Tyr Lys Lys
865                 870                 875
```

<210> SEQ ID NO 36
<211> LENGTH: 298
<212> TYPE: PRT
<213> ORGANISM: Caenorhabditis elegans
<220> FEATURE:
<221> NAME/KEY: MISC_FEATURE
<222> LOCATION: (1)..(298)
<223> OTHER INFORMATION: CRN-4

<400> SEQUENCE: 36

```
Met Ala Tyr Gln His Cys Pro Phe Asp Thr Leu Leu Ile Leu Asp Phe
1               5                   10                  15

Glu Thr Thr Ser Asp Ala Ala Asn Gln Asp Tyr Pro Cys Glu Val Ile
            20                  25                  30

Gln Phe Ala Ile Val Ala Tyr Asp Val Pro Asn Asp Lys Ile Arg Glu
        35                  40                  45

Asp Ile Ser Phe Asn Lys Tyr Val Lys Pro Val Leu Asn Arg Thr Leu
    50                  55                  60

Thr Lys Asn Cys Val Asp Phe Thr Gly Ile Pro Gln Arg Ser Ile Asp
65                  70                  75                  80

Thr Ala Asp Thr Phe Asp Val Val Tyr Glu Gln Phe Gln Gln Trp Leu
                85                  90                  95

Ile Thr Leu Gly Leu Glu Glu Gly Lys Phe Ala Phe Val Cys Asp Ser
            100                 105                 110

Arg Gln Asp Leu Trp Arg Ile Ala Gln Tyr Gln Met Lys Leu Ser Asn
        115                 120                 125

Ile Gln Met Pro Ala Phe Phe Arg Gln Tyr Ile Asn Leu Tyr Lys Ile
    130                 135                 140

Phe Thr Asn Glu Met Asp Arg Met Gly Pro Lys Glu Leu Ser Ala Thr
145                 150                 155                 160

Thr Asn Ile Gly Lys Met Asn Glu Tyr Tyr Asp Leu Pro Thr Ile Gly
                165                 170                 175

Arg Ala His Asp Ala Met Asp Asp Cys Leu Asn Ile Ala Thr Ile Leu
            180                 185                 190

Gln Arg Met Ile Asn Met Gly Ala Lys Val Thr Val Asn Glu Leu Leu
        195                 200                 205

Thr Cys Cys Ala Ser Trp Arg Arg Gln Pro Leu Val Tyr Asn Lys Glu
    210                 215                 220

Trp Arg Ser Ser Phe Met Asp Ala Gly Lys Ile Phe Glu Arg Val Leu
225                 230                 235                 240

Pro Leu Val Val Thr Thr Ile Arg Ala Gly Asp Phe Arg Leu Glu Met
                245                 250                 255

Tyr Gly Val Cys Arg Tyr Cys Arg Lys Gly Met Asp Val Cys Gly Thr
            260                 265                 270

Ser His Gln Gln Thr Pro His Asp Leu Tyr Lys Asn Glu Glu Asp Pro
        275                 280                 285

Ile His Phe Ala Lys Ile Ala Gly Tyr Tyr
    290                 295
```

<210> SEQ ID NO 37
<211> LENGTH: 214
<212> TYPE: PRT
<213> ORGANISM: Caenorhabditis elegans
<220> FEATURE:
<221> NAME/KEY: MISC_FEATURE
<222> LOCATION: (1)..(214)
<223> OTHER INFORMATION: CRN-5

```
<400> SEQUENCE: 37

Met Ala Gly Arg Leu Arg Glu Met Arg Cys Glu Leu Ser Phe Leu Lys
1               5                   10                  15

Asn Ala Asp Gly Ser Ala Cys Phe Ser Gln Gly Ala Thr Cys Ile Trp
                20                  25                  30

Ala Ser Cys Ser Gly Pro Gly Asp Val His Ala Ser Lys Ala Ser Asp
            35                  40                  45

Glu Ala Met Thr Leu Asp Ile Ser Tyr Arg Ala Asn Cys Gly Asp Asn
50                  55                  60

Lys Phe Asn Val Leu Asn Asn Ile Ile His Ser Thr Leu Ser Asn Ala
65                  70                  75                  80

Ile Asn Leu Glu Leu Phe Pro His Thr Thr Ile Ser Val Thr Val His
                85                  90                  95

Gly Ile Gln Asp Asp Gly Ser Met Gly Ala Val Ala Ile Asn Gly Ala
            100                 105                 110

Cys Phe Ala Leu Leu Asp Asn Gly Met Pro Phe Glu Thr Val Phe Cys
        115                 120                 125

Gly Val Leu Ile Val Arg Val Lys Asp Glu Leu Ile Ile Asp Pro Thr
130                 135                 140

Ala Lys Gln Glu Ala Ala Ser Thr Gly Arg Val Leu Phe Ser Val Cys
145                 150                 155                 160

Lys Gly Ser Asp Gly His Pro Glu Val Cys Ala Met Asp Ala Ile Gly
                165                 170                 175

His Trp Asp Phe Ile Gln Leu Gly Ala Ala Trp Ser Leu Ala Gln Pro
            180                 185                 190

Ser Ala Ser Ala Ile Phe Asp Phe Tyr Lys Thr Val Met Lys Arg Lys
        195                 200                 205

Leu Ser Val Asp Glu Gln
        210

<210> SEQ ID NO 38
<211> LENGTH: 373
<212> TYPE: PRT
<213> ORGANISM: Caenorhabditis elegans
<220> FEATURE:
<221> NAME/KEY: MISC_FEATURE
<222> LOCATION: (1)..(373)
<223> OTHER INFORMATION: CRN-6

<400> SEQUENCE: 38

Met Ile Arg Gln Ile Ile Leu Ile Val Ser Leu Ile Gly Ile Ser Asn
1               5                   10                  15

Ala Ala Tyr Gln Cys Lys Asp Asn Asn Gly Ser Asn Val Asp Trp Phe
                20                  25                  30

Val Phe Tyr Lys Leu Pro His Leu Trp Asn His Pro Asp Asn Val Pro
            35                  40                  45

Ile Ser Asn Gly Thr Gly Phe Leu Tyr Phe Asp Val Asn Asn Lys Asn
50                  55                  60

Trp Lys Leu Met Pro Gln Gly Met Asp Val Glu Asn Asn Ala Val Tyr
65                  70                  75                  80

Tyr Thr Leu Gln Gln Tyr Tyr Asn Ser Asn Met Asn Thr Thr Phe Ser
                85                  90                  95

Tyr Met Tyr Asn Asp Glu Trp Pro Asp Ser Thr Ile Trp Ser Asn Ser
            100                 105                 110

Ser Gly His Ala Lys Gly Val Thr Val Phe Asp Gln Tyr Thr Gly Phe
        115                 120                 125
```

```
Trp Met Ile His Ser Ile Pro Lys Phe Pro Ser Lys Asp Met Phe Arg
    130                 135                 140

Phe Pro Ser Asn Ala His Tyr Tyr Gly Gln Met Gly Ile Cys Ile Ser
145                 150                 155                 160

Tyr Asn Thr Val Ser Leu Ala Thr Ile Ala Gln Gln Leu Phe Tyr Tyr
                165                 170                 175

Asn Thr Phe Thr Tyr Gln Phe Asn Leu Pro Gln Ser Phe Ala Asn Gln
            180                 185                 190

Phe Pro Val Leu Ser Gln Leu Lys Asn Lys Glu Tyr Asn Lys Ser Pro
        195                 200                 205

Pro Leu Thr Ser Thr Lys Val Leu Lys Ser Leu Gly Gly Gln His Phe
    210                 215                 220

Arg His Phe Ala Lys Thr Gly Glu Trp Gly Lys Asp Leu Tyr Ser Asp
225                 230                 235                 240

Phe Val Gly Pro Thr Leu Lys Ser Ser Ile Lys Val Glu Thr Trp Asn
                245                 250                 255

His Gln Ser Gly Asp Glu Tyr Asn Leu Pro Ser Val Cys Asp Pro Asn
            260                 265                 270

His Val Gln Ser Thr Met Ser Ala Lys Tyr Ile Arg Leu Pro Tyr Ala
        275                 280                 285

Ile Asp Tyr Ser Ser Tyr Glu Asp His Ser Lys Phe Val Val Ala Tyr
    290                 295                 300

Ser Glu Ser Ser Ser Lys Pro Pro Ile Pro Tyr Val Cys Ile Gly Asp
305                 310                 315                 320

Ile Asn Arg Gln Ser His Gln Ile His Arg Gly Gly Thr Met Cys
                325                 330                 335

Ile Tyr Asp Gln Glu Thr Tyr Phe Gln Phe Ala Asn Ile Ile Ser Glu
            340                 345                 350

Thr Val Pro Cys Thr Lys Ala Thr Ala Glu Lys Val Asp Ala Leu Ala
        355                 360                 365

Asn Asn Arg Tyr Phe
    370

<210> SEQ ID NO 39
<211> LENGTH: 331
<212> TYPE: PRT
<213> ORGANISM: Caenorhabditis elegans
<220> FEATURE:
<221> NAME/KEY: MISC_FEATURE
<222> LOCATION: (1)..(331)
<223> OTHER INFORMATION: CYP-13

<400> SEQUENCE: 39

Met Asn Thr Asn Phe Pro His Asn Arg Lys Arg Thr Leu Tyr Val Gly
1               5                   10                  15

Gly Phe Thr Glu Asp Val Thr Glu Lys Val Leu Met Ala Ala Phe Ile
            20                  25                  30

Pro Phe Gly Asp Val Val Ala Ile Ser Ile Pro Met Asp Tyr Glu Ser
        35                  40                  45

Gly Lys His Arg Gly Phe Gly Phe Val Glu Phe Asp Met Ala Glu Asp
    50                  55                  60

Ala Ala Met Ala Ile Asp Asn Met Asn Glu Ser Glu Leu Phe Gly Lys
65                  70                  75                  80

Thr Ile Arg Val Asn Phe Ala Arg Pro Pro Lys Ala Thr Glu Arg Ser
                85                  90                  95
```

-continued

```
Gln Lys Pro Val Trp Ala Asp Glu Trp Leu Lys Lys Tyr Gly Arg
            100                 105                 110

Gly Gly Glu Ala Ala Ala Glu Asp Gly Asp Ala Glu Lys Ala Ala
            115                 120                 125

Thr Ser Ser Ser Ala Ser Thr Lys Leu Pro Arg Val Tyr Leu Gly
            130                 135                 140

Val Lys Ile Gly Ile Arg Tyr Ile Gly Arg Ile Val Ile Glu Leu Arg
145                 150                 155                 160

Thr Asp Val Thr Pro Lys Thr Ala Glu Asn Phe Arg Cys Leu Cys Thr
                    165                 170                 175

Gly Glu Arg Gly Phe Gly Tyr Glu Gly Ser Ile Phe His Arg Ile Ile
            180                 185                 190

Pro Lys Phe Met Leu Gln Gly Gly Asp Phe Thr Lys Gly Asp Gly Thr
            195                 200                 205

Gly Gly Lys Ser Ile Tyr Gly Thr Lys Phe Asp Asp Glu Asn Phe Thr
            210                 215                 220

Leu Arg His Thr Met Pro Gly Thr Val Ser Met Ala Asn Cys Gly Ala
225                 230                 235                 240

Asn Thr Asn Gly Ser Gln Phe Phe Ile Cys Thr Glu Lys Thr Asp Trp
                    245                 250                 255

Leu Asp Gly Lys His Val Val Phe Gly His Val Val Glu Gly Met Asn
            260                 265                 270

Ile Val Arg Gln Val Glu Gln Gln Gly Thr Pro Ser Gly Lys Pro Gln
            275                 280                 285

Met Val Val Lys Ile Val Glu Ser Gly Glu Ile Glu Pro Glu Lys Arg
            290                 295                 300

Ile Ala Ala Glu Lys Leu Ala Gln Lys Ala Val Val Pro Gly Ala Glu
305                 310                 315                 320

Ile Gln Glu Pro Leu Pro Gln Ala Met Glu Thr
                    325                 330

<210> SEQ ID NO 40
<211> LENGTH: 380
<212> TYPE: PRT
<213> ORGANISM: Homo sapiens
<220> FEATURE:
<221> NAME/KEY: MISC_FEATURE
<222> LOCATION: (1)..(380)
<223> OTHER INFORMATION: FEN-1 (Human CRN-1 homolog)

<400> SEQUENCE: 40

Met Gly Ile Gln Gly Leu Ala Lys Leu Ile Ala Asp Val Ala Pro Ser
1               5                   10                  15

Ala Ile Arg Glu Asn Asp Ile Lys Ser Tyr Phe Gly Lys Val Ala
            20                  25                  30

Ile Asp Ala Ser Met Ser Ile Tyr Gln Phe Leu Ile Ala Val Arg Gln
            35                  40                  45

Gly Gly Asp Val Leu Gln Asn Glu Glu Gly Glu Thr Thr Ser His Leu
            50                  55                  60

Met Gly Met Phe Tyr Arg Thr Ile Arg Met Met Glu Asn Gly Ile Lys
65                  70                  75                  80

Pro Val Tyr Val Phe Asp Gly Lys Pro Pro Gln Leu Lys Ser Gly Glu
                85                  90                  95

Leu Ala Lys Arg Ser Glu Arg Arg Ala Glu Ala Glu Lys Gln Leu Gln
            100                 105                 110

Gln Ala Gln Ala Ala Gly Ala Glu Gln Glu Val Glu Lys Phe Thr Lys
```

-continued

```
                115                 120                 125
Arg Leu Val Lys Val Thr Lys Gln His Asn Asp Glu Cys Lys His Leu
    130                 135                 140

Leu Ser Leu Met Gly Ile Pro Tyr Leu Asp Ala Pro Ser Glu Ala Glu
145                 150                 155                 160

Ala Ser Cys Ala Ala Leu Val Lys Ala Gly Lys Val Tyr Ala Ala Ala
                165                 170                 175

Thr Glu Asp Met Asp Cys Leu Thr Phe Gly Ser Pro Val Leu Met Arg
            180                 185                 190

His Leu Thr Ala Ser Glu Ala Lys Lys Leu Pro Ile Gln Glu Phe His
        195                 200                 205

Leu Ser Arg Ile Leu Gln Glu Leu Gly Leu Asn Gln Glu Gln Phe Val
    210                 215                 220

Asp Leu Cys Ile Leu Leu Gly Ser Asp Tyr Cys Glu Ser Ile Arg Gly
225                 230                 235                 240

Ile Gly Pro Lys Arg Ala Val Asp Leu Ile Gln Lys His Lys Ser Ile
                245                 250                 255

Glu Glu Ile Val Arg Arg Leu Asp Pro Asn Lys Tyr Pro Val Pro Glu
            260                 265                 270

Asn Trp Leu His Lys Glu Ala His Gln Leu Phe Leu Glu Pro Glu Val
        275                 280                 285

Leu Asp Pro Glu Ser Val Glu Leu Lys Trp Ser Pro Asn Glu Glu
    290                 295                 300

Glu Leu Ile Lys Phe Met Cys Gly Glu Lys Gln Phe Ser Glu Glu Arg
305                 310                 315                 320

Ile Arg Ser Gly Val Lys Arg Leu Ser Lys Ser Arg Gln Gly Ser Thr
                325                 330                 335

Gln Gly Arg Leu Asp Asp Phe Phe Lys Val Thr Gly Ser Leu Ser Ser
            340                 345                 350

Ala Lys Arg Lys Glu Pro Glu Pro Lys Gly Ser Thr Lys Lys Lys Ala
        355                 360                 365

Lys Thr Gly Ala Ala Gly Lys Phe Lys Arg Gly Lys
    370                 375                 380
```

<210> SEQ ID NO 41
<211> LENGTH: 297
<212> TYPE: PRT
<213> ORGANISM: Homo sapiens
<220> FEATURE:
<221> NAME/KEY: MISC_FEATURE
<222> LOCATION: (1)..(297)
<223> OTHER INFORMATION: CDA11 (Human CRN-2 homolog)

<400> SEQUENCE: 41

```
Met Ser His Phe Lys Phe Ile Asp Ile Val Ile Asn Leu Thr Asp Thr
1               5                   10                  15

Met Phe Arg Gly Ile Tyr Arg Gly Val Gln Lys His Gln Asp Asp Leu
            20                  25                  30

Gln Asp Val Thr Gly Arg Ala Val Glu Ile Gly Val Lys Lys Phe Met
        35                  40                  45

Ile Thr Gly Gly Asn Leu Gln Asp Ser Lys Asp Ala Leu His Leu Ala
    50                  55                  60

Gln Thr Asn His Met Phe Phe Ser Thr Ala Gly Cys His Pro Thr Arg
65                  70                  75                  80

Cys Gly Lys Phe Glu Lys Asn Asn Pro Asp Leu Tyr Leu Lys Glu Leu
                85                  90                  95
```

Leu Asn Leu Asp Glu Asn Asn Lys Gly Lys Val Val Ala Val Gly Glu
            100                 105                 110

Cys Gly Leu Asp Phe Asp Arg Leu His Phe Cys Pro Lys Asp Thr Gln
            115                 120                 125

Leu Lys Tyr Cys Glu Lys Gln Phe Glu Leu Ser Glu Gln Thr Lys Leu
        130                 135                 140

Pro Met Phe Leu His Cys Arg Asn Ser His Ala Glu Phe Leu Asp Ile
145                 150                 155                 160

Ile Lys Arg Asn Arg Asp Arg Cys Val Glu Gly Val Val His Ser Phe
                165                 170                 175

Asp Gly Thr Lys Glu Ala Ala Ala Leu Ile Asp Leu Asp Leu Tyr
            180                 185                 190

Ile Gly Phe Asn Gly Cys Ser Leu Lys Thr Glu Thr Asn Leu Glu Val
                195                 200                 205

Leu Lys Ser Ile Pro Ser Glu Lys Leu Met Ile Glu Thr Asp Ala Pro
        210                 215                 220

Trp Cys Gly Val Lys Ser Thr His Ala Gly Ser Lys Tyr Ile Lys Thr
225                 230                 235                 240

Ala Phe Pro Thr Lys Lys Lys Trp Glu Ser Gly His Cys Leu Lys Asp
                245                 250                 255

Arg Asn Glu Pro Cys His Ile Ile Gln Ile Leu Glu Ile Met Ser Ala
                260                 265                 270

Val Arg Asp Glu Asp Pro Leu Glu Ser Ala Asn Thr Leu Tyr Asn Asn
        275                 280                 285

Thr Ile Lys Val Phe Phe Pro Gly Ile
    290                 295

<210> SEQ ID NO 42
<211> LENGTH: 860
<212> TYPE: PRT
<213> ORGANISM: Homo sapiens
<220> FEATURE:
<221> NAME/KEY: MISC_FEATURE
<222> LOCATION: (1)..(860)
<223> OTHER INFORMATION: PM-SCL-100 (Human CRN-3 homolog)

<400> SEQUENCE: 42

Met Ala Pro Pro Ser Thr Arg Glu Pro Arg Val Leu Ser Ala Thr Ser
1               5                   10                  15

Ala Thr Lys Ser Asp Gly Glu Met Val Leu Pro Gly Phe Pro Asp Ala
            20                  25                  30

Asp Ser Phe Val Lys Phe Ala Leu Gly Ser Val Val Ala Val Thr Lys
        35                  40                  45

Ala Ser Gly Gly Leu Pro Gln Phe Gly Asp Glu Tyr Asp Phe Tyr Arg
    50                  55                  60

Ser Phe Pro Gly Phe Gln Ala Phe Cys Glu Thr Gln Gly Asp Arg Leu
65                  70                  75                  80

Leu Gln Cys Met Ser Arg Val Met Gln Tyr His Gly Cys Arg Ser Asn
                85                  90                  95

Ile Lys Asp Arg Ser Lys Val Thr Glu Leu Glu Asp Lys Phe Asp Leu
            100                 105                 110

Leu Val Asp Ala Asn Asp Val Ile Leu Glu Arg Val Gly Ile Leu Leu
        115                 120                 125

Asp Glu Ala Ser Gly Val Asn Lys Asn Gln Gln Pro Val Leu Pro Ala
    130                 135                 140

```
Gly Leu Gln Val Pro Lys Thr Val Val Ser Ser Trp Asn Arg Lys Ala
145                 150                 155                 160

Ala Glu Tyr Gly Lys Lys Ala Lys Ser Glu Thr Phe Arg Leu Leu His
            165                 170                 175

Ala Lys Asn Ile Ile Arg Pro Gln Leu Lys Phe Arg Glu Lys Ile Asp
            180                 185                 190

Asn Ser Asn Thr Pro Phe Leu Pro Lys Ile Phe Ile Lys Pro Asn Ala
            195                 200                 205

Gln Lys Pro Leu Pro Gln Ala Leu Ser Lys Glu Arg Arg Glu Arg Pro
            210                 215                 220

Gln Asp Arg Pro Glu Asp Leu Asp Val Pro Pro Ala Leu Ala Asp Phe
225                 230                 235                 240

Ile His Gln Gln Arg Thr Gln Gln Val Glu Gln Asp Met Phe Ala His
            245                 250                 255

Pro Tyr Gln Tyr Glu Leu Asn His Phe Thr Pro Ala Asp Ala Val Leu
            260                 265                 270

Gln Lys Pro Gln Pro Gln Leu Tyr Arg Pro Ile Glu Glu Thr Pro Cys
            275                 280                 285

His Phe Ile Ser Ser Leu Asp Glu Leu Val Glu Leu Asn Glu Lys Leu
            290                 295                 300

Leu Asn Cys Gln Glu Phe Ala Val Asp Leu Glu His His Ser Tyr Arg
305                 310                 315                 320

Ser Phe Leu Gly Leu Thr Cys Leu Met Gln Ile Ser Thr Arg Thr Glu
            325                 330                 335

Asp Phe Ile Ile Asp Thr Leu Glu Leu Arg Ser Asp Met Tyr Ile Leu
            340                 345                 350

Asn Glu Ser Leu Thr Asp Pro Ala Ile Val Lys Val Phe His Gly Ala
            355                 360                 365

Asp Ser Asp Ile Glu Trp Leu Gln Lys Asp Phe Gly Leu Tyr Val Val
            370                 375                 380

Asn Met Phe Asp Thr His Gln Ala Ala Arg Leu Leu Asn Leu Gly Arg
385                 390                 395                 400

His Ser Leu Asp His Leu Leu Lys Leu Tyr Cys Asn Val Asp Ser Asn
            405                 410                 415

Lys Gln Tyr Gln Leu Ala Asp Trp Arg Ile Arg Pro Leu Pro Glu Glu
            420                 425                 430

Met Leu Ser Tyr Ala Arg Asp Thr His Tyr Leu Leu Tyr Ile Tyr
            435                 440                 445

Asp Lys Met Arg Leu Glu Met Trp Glu Arg Gly Asn Gly Gln Pro Val
            450                 455                 460

Gln Leu Gln Val Val Trp Gln Arg Ser Arg Asp Ile Cys Leu Lys Lys
465                 470                 475                 480

Phe Ile Lys Pro Ile Phe Thr Asp Glu Ser Tyr Leu Glu Leu Tyr Arg
            485                 490                 495

Lys Gln Lys Lys His Leu Asn Thr Gln Gln Leu Thr Ala Phe Gln Leu
            500                 505                 510

Leu Phe Ala Trp Arg Asp Lys Thr Ala Arg Arg Glu Asp Glu Ser Tyr
            515                 520                 525

Gly Tyr Val Leu Pro Asn His Met Met Leu Lys Ile Ala Glu Glu Leu
            530                 535                 540

Pro Lys Glu Pro Gln Gly Ile Ile Ala Cys Cys Asn Pro Val Pro Pro
545                 550                 555                 560

Leu Val Arg Gln Gln Ile Asn Glu Met His Leu Leu Ile Gln Gln Ala
```

```
                        565                 570                 575
Arg Glu Met Pro Leu Leu Lys Ser Glu Val Ala Ala Gly Val Lys Lys
                580                 585                 590

Ser Gly Pro Leu Pro Ser Ala Glu Arg Leu Glu Asn Val Leu Phe Gly
            595                 600                 605

Pro His Asp Cys Ser His Ala Pro Pro Asp Gly Tyr Pro Ile Ile Pro
        610                 615                 620

Thr Ser Gly Ser Val Pro Val Gln Lys Gln Ala Ser Leu Phe Pro Asp
625                 630                 635                 640

Glu Lys Glu Asp Asn Leu Leu Gly Thr Thr Cys Leu Ile Ala Thr Ala
                645                 650                 655

Val Ile Thr Leu Phe Asn Glu Pro Ser Ala Glu Asp Ser Lys Lys Gly
            660                 665                 670

Pro Leu Thr Val Ala Gln Lys Ala Gln Asn Ile Met Glu Ser Phe
        675                 680                 685

Glu Asn Pro Phe Arg Met Ile Ser Asn Arg Trp Lys Leu Ala Gln Val
        690                 695                 700

Gln Val Gln Lys Asp Ser Lys Glu Ala Val Lys Lys Ala Ala Glu
705                 710                 715                 720

Gln Thr Ala Ala Arg Glu Gln Ala Lys Glu Ala Cys Lys Ala Ala Ala
                725                 730                 735

Glu Gln Ala Ile Ser Val Arg Gln Gln Val Val Leu Glu Asn Ala Ala
            740                 745                 750

Lys Lys Arg Glu Arg Ala Thr Ser Asp Pro Arg Thr Thr Glu Gln Lys
        755                 760                 765

Gln Glu Lys Lys Arg Leu Lys Ile Ser Lys Lys Pro Lys Asp Pro Glu
770                 775                 780

Pro Pro Glu Lys Glu Phe Thr Pro Tyr Asp Tyr Ser Gln Ser Asp Phe
785                 790                 795                 800

Lys Ala Phe Ala Gly Asn Ser Lys Ser Lys Val Ser Ser Gln Phe Asp
                805                 810                 815

Pro Asn Lys Gln Thr Pro Ser Gly Lys Lys Cys Ile Ala Ala Lys Lys
            820                 825                 830

Ile Lys Gln Ser Val Gly Asn Lys Ser Met Ser Phe Pro Thr Gly Lys
        835                 840                 845

Ser Asp Arg Gly Phe Arg Tyr Asn Trp Pro Gln Arg
        850                 855                 860

<210> SEQ ID NO 43
<211> LENGTH: 328
<212> TYPE: PRT
<213> ORGANISM: Homo sapiens
<220> FEATURE:
<221> NAME/KEY: MISC_FEATURE
<222> LOCATION: (1)..(328)
<223> OTHER INFORMATION: MGC16943 (Human CRN-4 homolog)

<400> SEQUENCE: 43

Met Ala Thr Lys Arg Leu Ala Arg Gln Leu Gly Leu Ile Arg Arg Lys
1               5                   10                  15

Ser Ile Ala Pro Ala Asn Gly Asn Leu Gly Arg Ser Lys Ser Lys Gln
            20                  25                  30

Leu Phe Asp Tyr Leu Ile Val Ile Asp Phe Glu Ser Thr Cys Trp Asn
        35                  40                  45

Asp Gly Lys His His His Ser Gln Glu Ile Ile Glu Phe Pro Ala Val
    50                  55                  60
```

```
Leu Leu Asn Thr Ser Thr Gly Gln Ile Asp Ser Glu Phe Gln Ala Tyr
 65                  70                  75                  80

Val Gln Pro Gln Glu His Pro Ile Leu Ser Glu Phe Cys Met Glu Leu
                 85                  90                  95

Thr Gly Ile Lys Gln Ala Gln Val Asp Glu Gly Val Pro Leu Lys Ile
            100                 105                 110

Cys Leu Ser Gln Phe Cys Lys Trp Ile His Lys Ile Gln Gln Gln Lys
            115                 120                 125

Asn Ile Ile Phe Ala Thr Gly Ile Ser Glu Pro Ser Ala Ser Glu Val
130                 135                 140

Lys Leu Cys Ala Phe Val Thr Trp Ser Asp Trp Asp Leu Gly Val Cys
145                 150                 155                 160

Leu Glu Tyr Glu Cys Lys Arg Lys Gln Leu Leu Lys Pro Val Phe Leu
            165                 170                 175

Asn Ser Trp Ile Asp Leu Arg Ala Thr Tyr Lys Leu Phe Tyr Arg Arg
            180                 185                 190

Lys Pro Lys Gly Leu Ser Gly Ala Leu Gln Glu Val Gly Ile Glu Phe
            195                 200                 205

Ser Gly Arg Glu His Ser Gly Leu Asp Asp Ser Arg Asn Thr Ala Leu
210                 215                 220

Leu Ala Trp Lys Met Ile Arg Asp Gly Cys Val Met Lys Ile Thr Arg
225                 230                 235                 240

Ser Leu Asn Lys Gly Pro Phe Leu Leu Pro Ser Trp Thr Trp Asn Ser
            245                 250                 255

Asp Leu Ala Ser Gly Asp Gln His Ala Phe Leu Lys Gln Glu Phe Gly
            260                 265                 270

Cys Gly Thr Tyr Arg Thr Leu Leu Gln Lys Pro Asn Met Ser Lys Gln
            275                 280                 285

Glu Lys Gly Asn Ile Leu Trp Leu Thr Met Val Trp Leu Ser Leu Ala
            290                 295                 300

Cys Leu Gln Arg Lys Asn Tyr Asn Asp Cys Met Leu Asn Thr Ala Ser
305                 310                 315                 320

Gln Thr Val Thr Thr Glu Lys Phe
                325

<210> SEQ ID NO 44
<211> LENGTH: 235
<212> TYPE: PRT
<213> ORGANISM: Homo sapiens
<220> FEATURE:
<221> NAME/KEY: MISC_FEATURE
<222> LOCATION: (1)..(235)
<223> OTHER INFORMATION: RRP46 (Human CRN-5 homolog)

<400> SEQUENCE: 44

Met Glu Glu Thr His Thr Asp Ala Lys Ile Arg Ala Glu Asn Gly
  1               5                  10                  15

Thr Gly Ser Ser Pro Arg Gly Pro Gly Cys Ser Leu Arg His Phe Ala
             20                  25                  30

Cys Glu Gln Asn Leu Leu Ser Arg Pro Asp Gly Ser Ala Ser Phe Leu
         35                  40                  45

Gln Gly Asp Thr Ser Val Leu Ala Gly Val Tyr Gly Pro Ala Glu Val
     50                  55                  60

Lys Val Ser Lys Glu Ile Phe Asn Lys Ala Thr Leu Glu Val Ile Leu
 65                  70                  75                  80
```

```
Arg Pro Lys Ile Gly Leu Pro Gly Val Ala Glu Lys Ser Arg Glu Arg
                85                  90                  95

Leu Ile Arg Asn Thr Cys Glu Ala Val Val Leu Gly Thr Leu His Pro
            100                 105                 110

Arg Thr Ser Ile Thr Val Val Leu Gln Val Val Ser Asp Ala Gly Ser
        115                 120                 125

Leu Leu Ala Cys Cys Leu Asn Ala Ala Cys Met Ala Leu Val Asp Ala
    130                 135                 140

Gly Val Pro Met Arg Ala Leu Phe Cys Gly Val Ala Cys Ala Leu Asp
145                 150                 155                 160

Ser Asp Gly Thr Leu Val Leu Asp Pro Thr Ser Lys Gln Glu Lys Glu
                165                 170                 175

Ala Arg Ala Val Leu Thr Phe Ala Leu Asp Ser Val Glu Arg Lys Leu
            180                 185                 190

Leu Met Ser Ser Thr Lys Gly Leu Tyr Ser Asp Thr Glu Leu Gln Gln
        195                 200                 205

Cys Leu Ala Ala Ala Gln Ala Ala Ser Gln His Val Phe Arg Phe Tyr
    210                 215                 220

Arg Glu Ser Leu Gln Arg Arg Tyr Ser Lys Ser
225                 230                 235

<210> SEQ ID NO 45
<211> LENGTH: 360
<212> TYPE: PRT
<213> ORGANISM: Homo sapiens
<220> FEATURE:
<221> NAME/KEY: MISC_FEATURE
<222> LOCATION: (1)..(360)
<223> OTHER INFORMATION: DNaseII (Human CRN-6 homolog)

<400> SEQUENCE: 45

Met Ile Pro Leu Leu Ala Ala Leu Leu Cys Val Pro Ala Gly Ala
1               5                   10                  15

Leu Thr Cys Tyr Gly Asp Ser Gly Gln Pro Val Asp Trp Phe Val Val
            20                  25                  30

Tyr Lys Leu Pro Ala Leu Arg Gly Ser Gly Glu Ala Ala Gln Arg Gly
        35                  40                  45

Leu Gln Tyr Lys Tyr Leu Asp Glu Ser Ser Gly Gly Trp Arg Asp Gly
    50                  55                  60

Arg Ala Leu Ile Asn Ser Pro Glu Gly Ala Val Gly Arg Ser Leu Gln
65                  70                  75                  80

Pro Leu Tyr Arg Ser Asn Thr Ser Gln Leu Ala Phe Leu Leu Tyr Asn
                85                  90                  95

Asp Gln Pro Pro Gln Pro Ser Lys Ala Gln Asp Ser Ser Met Arg Gly
            100                 105                 110

His Thr Lys Gly Val Leu Leu Leu Asp His Asp Gly Gly Phe Trp Leu
        115                 120                 125

Val His Ser Val Pro Asn Phe Pro Pro Ala Ser Ser Ala Ala Tyr
    130                 135                 140

Ser Trp Pro His Ser Ala Cys Thr Tyr Gly Gln Thr Leu Leu Cys Val
145                 150                 155                 160

Ser Phe Pro Phe Ala Gln Phe Ser Lys Met Gly Lys Gln Leu Thr Tyr
                165                 170                 175

Thr Tyr Pro Trp Val Tyr Asn Tyr Gln Leu Glu Gly Ile Phe Ala Gln
            180                 185                 190

Glu Phe Pro Asp Leu Glu Asn Val Val Lys Gly His His Val Ser Gln
```

```
                195                 200                 205
Glu Pro Trp Asn Ser Ser Ile Thr Leu Thr Ser Gln Ala Gly Ala Val
    210                 215                 220

Phe Gln Ser Phe Ala Lys Phe Ser Lys Phe Gly Asp Asp Leu Tyr Ser
225                 230                 235                 240

Gly Trp Leu Ala Ala Ala Leu Gly Thr Asn Leu Gln Val Gln Phe Trp
                245                 250                 255

His Lys Thr Val Gly Ile Leu Pro Ser Asn Cys Ser Asp Ile Trp Gln
            260                 265                 270

Val Leu Asn Val Asn Gln Ile Ala Phe Pro Gly Pro Ala Gly Pro Ser
        275                 280                 285

Phe Asn Ser Thr Glu Asp His Ser Lys Trp Cys Val Ser Pro Lys Gly
290                 295                 300

Pro Trp Thr Cys Val Gly Asp Met Asn Arg Asn Gln Gly Glu Glu Gln
305                 310                 315                 320

Arg Gly Gly Gly Thr Leu Cys Ala Gln Leu Pro Ala Leu Trp Lys Ala
                325                 330                 335

Phe Gln Pro Leu Val Lys Asn Tyr Gln Pro Cys Asn Gly Met Ala Arg
                340                 345                 350

Lys Pro Ser Arg Ala Tyr Lys Ile
            355                 360

<210> SEQ ID NO 46
<211> LENGTH: 301
<212> TYPE: PRT
<213> ORGANISM: Homo sapiens
<220> FEATURE:
<221> NAME/KEY: MISC_FEATURE
<222> LOCATION: (1)..(301)
<223> OTHER INFORMATION: Cycliphylin E (Human CYP-13 homolog)

<400> SEQUENCE: 46

Met Ala Thr Thr Lys Arg Val Leu Tyr Val Gly Leu Ala Glu Glu
1               5                   10                  15

Val Asp Asp Lys Val Leu His Ala Ala Phe Ile Pro Phe Gly Asp Ile
                20                  25                  30

Thr Asp Ile Gln Ile Pro Leu Asp Tyr Glu Thr Glu Lys His Arg Gly
            35                  40                  45

Phe Ala Phe Val Glu Phe Glu Leu Ala Glu Asp Ala Ala Ala Ala Ile
    50                  55                  60

Asp Asn Met Asn Glu Ser Glu Leu Phe Gly Arg Thr Ile Arg Val Asn
65                  70                  75                  80

Leu Ala Lys Pro Met Arg Ile Lys Glu Gly Ser Ser Arg Pro Val Trp
                85                  90                  95

Ser Asp Asp Asp Trp Leu Lys Lys Phe Ser Gly Lys Thr Leu Glu Glu
                100                 105                 110

Asn Lys Glu Glu Glu Gly Ser Glu Pro Pro Lys Ala Glu Thr Gln Glu
            115                 120                 125

Gly Glu Pro Ile Ala Lys Lys Ala Arg Ser Asn Pro Gln Val Tyr Met
        130                 135                 140

Asp Ile Lys Ile Gly Asn Lys Pro Ala Gly Arg Ile Gln Met Leu Leu
145                 150                 155                 160

Arg Ser Asp Val Val Pro Met Thr Ala Glu Asn Phe Arg Cys Leu Cys
                165                 170                 175

Thr His Glu Lys Gly Phe Gly Phe Lys Gly Ser Ser Phe His Arg Ile
                180                 185                 190
```

```
Ile Pro Gln Phe Met Cys Gln Gly Gly Asp Phe Thr Asn His Asn Gly
        195                 200                 205

Thr Gly Gly Lys Ser Ile Tyr Gly Lys Lys Phe Asp Asp Glu Asn Phe
    210                 215                 220

Ile Leu Lys His Thr Gly Pro Gly Leu Leu Ser Met Ala Asn Ser Gly
225                 230                 235                 240

Pro Asn Thr Asn Gly Ser Gln Phe Phe Leu Thr Cys Asp Lys Thr Asp
                245                 250                 255

Trp Leu Asp Gly Lys His Val Val Phe Gly Glu Val Thr Glu Gly Leu
            260                 265                 270

Asp Val Leu Arg Gln Ile Glu Ala Gln Gly Ser Lys Asp Gly Lys Pro
        275                 280                 285

Lys Gln Lys Val Ile Ile Ala Asp Cys Gly Glu Tyr Val
    290                 295                 300

<210> SEQ ID NO 47
<211> LENGTH: 299
<212> TYPE: PRT
<213> ORGANISM: Arabidopsis thaliana
<220> FEATURE:
<221> NAME/KEY: MISC_FEATURE
<222> LOCATION: (1)..(299)
<223> OTHER INFORMATION: Arabadopsis CRN-2 homolog

<400> SEQUENCE: 47

Met Val Lys Met Asn Phe Gln Arg Ile Trp Lys Leu Lys Lys Leu Lys
1               5                   10                  15

Tyr Ile Ser Asn Ile Ile Ile Leu Lys Tyr Arg Leu Phe Thr Val Ile
            20                  25                  30

Ser Ile Val Thr Gly Gly Ser Leu Glu Glu Ser Arg Glu Ala Leu Ala
        35                  40                  45

Ile Ala Glu Thr Asp Gly Arg Leu Phe Cys Thr Val Gly Val His Pro
    50                  55                  60

Thr Arg Cys Asn Glu Phe Glu Glu Ser Gly Asp Pro Glu Lys His Tyr
65                  70                  75                  80

Gln Ala Leu Phe Ser Leu Ala Lys Glu Gly Met Gln Lys Gly Lys Val
                85                  90                  95

Val Ala Ile Gly Glu Cys Gly Leu Asp Tyr Asp Arg Leu Gln Phe Cys
            100                 105                 110

Ser Val Asp Ile Gln Lys Lys Tyr Phe Glu Lys Gln Phe Glu Leu Ala
        115                 120                 125

Tyr Ala Thr Lys Leu Pro Met Phe Leu His Met Arg Ala Ala Ala Glu
    130                 135                 140

Asp Phe Cys Glu Ile Val Glu Arg Asn Lys Asn Arg Phe Thr Gly Gly
145                 150                 155                 160

Val Ala His Ser Phe Thr Gly Ser Ala Ser Asp Arg Asp Lys Leu Leu
                165                 170                 175

Ser Phe Asp Lys Met Tyr Leu Gly Val Asn Gly Cys Ser Leu Lys Thr
            180                 185                 190

Ala Glu Asn Leu Glu Val Met Lys Gly Ile Pro Val Glu Arg Met Met
        195                 200                 205

Ile Glu Thr Asp Ser Pro Tyr Cys Asp Ile Lys Asn Thr His Ala Gly
    210                 215                 220

Ile Lys Phe Val Lys Ser Thr Trp Pro Ser Lys Lys Glu Lys Tyr
225                 230                 235                 240
```

-continued

```
Asp Gln Glu Ser Leu Val Lys Gly Arg Asn Glu Pro Cys Leu Val Arg
            245                 250                 255

Gln Val Leu Glu Val Val Ala Gly Tyr Lys Gly Leu Gly Asp Leu Asn
        260                 265                 270

Gln Val Ser Ser Thr Leu Tyr His Asn Thr Cys Arg His Val Phe Ser
    275                 280                 285

Phe Ser Val Ser His Asn Phe Met Thr Glu Ile
290                 295

<210> SEQ ID NO 48
<211> LENGTH: 642
<212> TYPE: PRT
<213> ORGANISM: Arabidopsis thaliana
<220> FEATURE:
<221> NAME/KEY: MISC_FEATURE
<222> LOCATION: (1)..(642)
<223> OTHER INFORMATION: Arabadopsis CRN-3 homolog

<400> SEQUENCE: 48

Met Arg Phe Asp Asp Pro Met Asp Glu Phe Lys Arg Asn Arg Lys Met
1               5                  10                  15

Glu Glu Asp Ser Lys Lys Val Ile Asp Val Lys Val Ala Glu Ser Asp
            20                  25                  30

Lys Gly Phe Ala Lys Phe Gly Lys Ala Glu Val Pro Phe His Ile Pro
        35                  40                  45

Thr Leu Thr Lys Pro Gln Glu Glu Tyr Lys Ile Leu Val Asp Asn Ala
    50                  55                  60

Asn Asn Pro Phe Glu His Val Leu Leu Glu Lys Ser Glu Asp Gly Leu
65                  70                  75                  80

Arg Phe Ile His Pro Leu Glu Glu Leu Ser Val Met Asp Phe Val Asp
                85                  90                  95

Arg Asn Leu Ser Glu Met Arg Pro Val Lys Pro Leu Pro Leu Glu Glu
            100                 105                 110

Thr Pro Phe Lys Leu Val Glu Glu Val Lys Asp Leu Glu Asp Leu Ala
        115                 120                 125

Ala Ala Leu Gln Ser Val Glu Glu Phe Ala Val Asp Leu Glu His Asn
    130                 135                 140

Gln Tyr Arg Thr Phe Gln Gly Leu Thr Cys Leu Met Gln Ile Ser Thr
145                 150                 155                 160

Arg Thr Glu Asp Tyr Ile Val Asp Ile Phe Lys Leu Trp Asp His Ile
                165                 170                 175

Gly Pro Tyr Leu Arg Glu Leu Phe Lys Asp Pro Lys Lys Lys Lys Val
            180                 185                 190

Ile His Gly Ala Asp Arg Asp Ile Ile Trp Leu Gln Arg Asp Phe Gly
        195                 200                 205

Ile Tyr Val Cys Asn Leu Phe Asp Thr Gly Gln Ala Ser Arg Val Leu
    210                 215                 220

Lys Leu Glu Arg Asn Ser Leu Glu Phe Leu Lys His Tyr Cys Gly
225                 230                 235                 240

Val Ala Ala Asn Lys Glu Tyr Gln Lys Ala Asp Trp Arg Ile Arg Pro
                245                 250                 255

Leu Pro Asp Val Met Lys Arg Tyr Ala Arg Glu Asp Thr His Tyr Leu
            260                 265                 270

Leu Tyr Ile Tyr Asp Val Met Arg Met Glu Leu His Thr Met Ala Lys
        275                 280                 285

Glu Asp Glu Gln Ser Asp Ser Pro Leu Val Glu Val Tyr Lys Arg Ser
```

```
            290                 295                 300
Tyr Asp Val Cys Met Gln Leu Tyr Glu Lys Glu Leu Trp Thr Arg Asp
305                 310                 315                 320

Ser Tyr Leu His Val Tyr Gly Val Gln Thr Gly Asn Leu Asn Ala Val
                325                 330                 335

Gln Leu Ser Ile Val Ala Leu Gln Gly Leu Cys Glu Trp Arg Asp Arg
            340                 345                 350

Ile Ala Arg Ala Asp Asp Glu Ser Thr Gly Tyr Val Leu Pro Asn Lys
        355                 360                 365

Thr Leu Phe Asp Ile Ala Lys Glu Met Pro Ile Val Ala Gln Leu
370                 375                 380

Arg Arg Leu Leu Lys Ser Lys Leu Pro Tyr Leu Glu Arg Asn Phe Asp
385                 390                 395                 400

Ala Val Ile Ser Val Ile Arg Arg Ser Met Gln Asn Ala Ala Ala Phe
                405                 410                 415

Glu Pro Val Val Gln Ser Leu Lys Asp Arg Arg Pro Glu Thr Val Val
            420                 425                 430

Glu Met Asn Ile Glu Pro Lys Ile Glu Lys Thr Asp Thr Gly Ala Ser
        435                 440                 445

Ala Ser Ser Leu Ser Leu Glu Lys Val Cys Val Asp Asp Ser Lys Lys
    450                 455                 460

Gln Ser Ser Gly Phe Gly Val Leu Pro Leu Lys Arg Lys Leu Glu Ser
465                 470                 475                 480

Asp Lys Thr Val Val Glu Lys Asn Ile Glu Pro Lys Ile Glu Lys Thr
                485                 490                 495

Gly Thr Glu Ala Ser Ala Ser Ser Leu Ser Ser Lys Lys Val Cys Val
            500                 505                 510

Asp Asp Ser Lys Lys Gln Ser Ser Gly Phe Gly Val Leu Leu Ser Lys
        515                 520                 525

Arg Lys Phe Glu Ser Asp Asn Lys Lys Leu Gln Val Lys Glu Glu Val
    530                 535                 540

Lys Val Ser Lys Ser Lys Pro Asp Lys Val Ile Ile Val Val Asp Asp
545                 550                 555                 560

Asp Asp Asp Asp Asp Asp Glu Ser Tyr Glu Gln Ser Thr Lys Ala
                565                 570                 575

Ala Asp Ala Leu Asp Arg Val Ser Glu Thr Pro Ser Lys Gly Ser Pro
            580                 585                 590

Ser Leu Thr Gln Lys Pro Lys Thr Cys Asn Thr Glu Val Ile Val Leu
        595                 600                 605

Asp Asp Asp Asp Asp Ser Glu Ser Arg Glu Asp Glu Asp Met Arg Arg
    610                 615                 620

Arg Ser Glu Lys His Arg Arg Phe Met Asn Met Lys Arg Gly Phe Leu
625                 630                 635                 640

Asn Ile

<210> SEQ ID NO 49
<211> LENGTH: 1161
<212> TYPE: PRT
<213> ORGANISM: Arabidopsis thaliana
<220> FEATURE:
<221> NAME/KEY: MISC_FEATURE
<222> LOCATION: (1)..(1161)
<223> OTHER INFORMATION: Arabidopsis CRN-4 homolog

<400> SEQUENCE: 49
```

-continued

```
Met Ala Ser Ala Phe Ser Ala Phe Arg Val Ser Leu Ser Arg Ile Ser
1               5                   10                  15

Pro Phe Arg Asp Thr Arg Phe Ser Tyr Pro Ala Thr Leu Ala Leu Ala
            20                  25                  30

His Thr Lys Arg Ile Met Cys Asn Ser Ser His Ser Val Ser Pro Ser
        35                  40                  45

Pro Ser Pro Ser Asp Phe Ser Ser Ser Ser Ser Ser Ser Ser Ser Ser
    50                  55                  60

Pro Ser Thr Phe Ser Leu Met Glu Thr Ser Glu Asn Ala Arg Trp Arg
65                  70                  75                  80

Pro Met Cys Leu Tyr Tyr Thr His Gly Lys Cys Thr Lys Met Asp Asp
                85                  90                  95

Pro Ala His Leu Glu Ile Phe Asn His Asp Cys Ser Lys Glu Leu Arg
            100                 105                 110

Val Ala Ala Ala Asp Leu Glu Arg Lys Lys Ser Gln Glu Phe Asn Phe
        115                 120                 125

Phe Leu Val Ile Asp Leu Glu Gly Lys Val Glu Ile Leu Glu Phe Pro
    130                 135                 140

Ile Leu Ile Val Asp Ala Lys Thr Met Glu Val Val Asp Leu Phe His
145                 150                 155                 160

Arg Phe Val Arg Pro Thr Lys Met Ser Glu Gln Ala Ile Asn Lys Tyr
                165                 170                 175

Ile Glu Gly Lys Tyr Gly Glu Leu Gly Val Asp Arg Val Trp His Asp
            180                 185                 190

Thr Ala Ile Pro Phe Lys Gln Val Val Glu Glu Phe Glu Val Trp Leu
        195                 200                 205

Ala Glu His Asp Leu Trp Asp Lys Asp Thr Asp Trp Gly Leu Asn Asp
    210                 215                 220

Ala Ala Phe Val Thr Cys Gly Asn Trp Asp Ile Lys Thr Lys Ile Pro
225                 230                 235                 240

Glu Gln Cys Val Val Ser Asn Ile Asn Leu Pro Pro Tyr Phe Met Glu
                245                 250                 255

Trp Ile Asn Leu Lys Asp Val Tyr Leu Asn Phe Tyr Gly Arg Glu Ala
            260                 265                 270

Arg Gly Met Val Ser Met Met Arg Gln Cys Gly Ile Lys Leu Met Gly
        275                 280                 285

Ser His His Leu Gly Ile Asp Asp Thr Lys Asn Ile Thr Arg Val Val
    290                 295                 300

Gln Arg Met Leu Ser Glu Gly Ala Val Leu Lys Leu Thr Ala Arg Arg
305                 310                 315                 320

Ser Lys Ser Asn Met Arg Asn Val Glu Phe Leu Phe Lys Asn Arg Ile
                325                 330                 335

Lys Leu Cys Ala Gly Ser Ser Glu Ser Gln Thr Ala Thr Ser Phe Ile
            340                 345                 350

Leu Ser Asp Ser Leu Thr Glu Glu Asp Ser Arg Val Leu Glu Phe Val
        355                 360                 365

Leu Leu Thr Asn Arg Asn Ser Ser Trp Ala Trp Val Cys Asn Ile Asp
    370                 375                 380

Lys Leu Ala Phe Tyr Ile Arg Val Ser Phe Gly Pro Asp Tyr Thr Asp
385                 390                 395                 400

Asp Pro Glu Ser Glu Thr Lys Pro Trp Leu Asn Leu Ile Thr Ser Asn
                405                 410                 415

Tyr Leu Ile Asp Met Tyr Cys Lys Cys Arg Glu Pro Leu Met Ala Tyr
```

-continued

```
                420                 425                 430
Lys Val Phe Asp Ser Met Pro Glu Arg Asn Val Ser Trp Ser Ala
            435                 440                 445

Leu Met Ser Gly His Val Leu Asn Gly Asp Leu Lys Gly Ser Leu Ser
450                 455                 460

Leu Phe Ser Glu Met Gly Arg Gln Gly Ile Tyr Pro Asn Glu Phe Thr
465             470                  475                 480

Phe Ser Thr Asn Leu Lys Ala Cys Gly Leu Asn Ala Leu Glu Lys
                485                 490                 495

Gly Leu Gln Ile His Gly Phe Cys Leu Lys Ile Gly Phe Glu Met Met
                500                 505                 510

Val Glu Val Gly Asn Ser Leu Val Asp Met Tyr Ser Lys Cys Gly Arg
            515                 520                 525

Ile Asn Glu Ala Glu Lys Val Phe Arg Arg Ile Val Asp Arg Ser Leu
530                 535                 540

Ile Ser Trp Asn Ala Met Ile Ala Gly Phe Val His Ala Gly Tyr Gly
545                 550                 555                 560

Ser Lys Ala Leu Asp Thr Phe Gly Met Met Gln Glu Ala Asn Ile Lys
                565                 570                 575

Glu Arg Pro Asp Glu Phe Thr Leu Thr Ser Leu Leu Lys Ala Cys Ser
            580                 585                 590

Ser Thr Gly Met Ile Tyr Ala Gly Lys Gln Ile His Gly Phe Leu Val
        595                 600                 605

Arg Ser Gly Phe His Cys Pro Ser Ser Ala Thr Ile Thr Gly Ser Leu
        610                 615                 620

Val Asp Leu Tyr Val Lys Cys Gly Tyr Leu Phe Ser Ala Arg Lys Ala
625                 630                 635                 640

Phe Asp Gln Ile Lys Glu Lys Thr Met Ile Ser Trp Ser Ser Leu Ile
                645                 650                 655

Leu Gly Tyr Ala Gln Glu Gly Glu Phe Val Glu Ala Met Gly Leu Phe
                660                 665                 670

Lys Arg Leu Gln Glu Leu Asn Ser Gln Ile Asp Ser Phe Ala Leu Ser
            675                 680                 685

Ser Ile Ile Gly Val Phe Ala Asp Phe Ala Leu Leu Arg Gln Gly Lys
        690                 695                 700

Gln Met Gln Ala Leu Ala Val Lys Leu Pro Ser Gly Leu Glu Thr Ser
705                 710                 715                 720

Val Leu Asn Ser Val Val Asp Met Tyr Leu Lys Cys Gly Leu Val Asp
                725                 730                 735

Glu Ala Glu Lys Cys Phe Ala Glu Met Gln Leu Lys Asp Val Ile Ser
                740                 745                 750

Trp Thr Val Val Ile Thr Gly Tyr Gly Lys His Gly Leu Gly Lys Lys
            755                 760                 765

Ser Val Arg Ile Phe Tyr Glu Met Leu Arg His Asn Ile Glu Pro Asp
        770                 775                 780

Glu Val Cys Tyr Leu Ala Val Leu Ser Ala Cys Ser His Ser Gly Met
785                 790                 795                 800

Ile Lys Glu Gly Glu Glu Leu Phe Ser Lys Leu Leu Glu Thr His Gly
                805                 810                 815

Ile Lys Pro Arg Val Glu His Tyr Ala Cys Val Val Asp Leu Leu Gly
            820                 825                 830

Arg Ala Gly Arg Leu Lys Glu Ala Lys His Leu Ile Asp Thr Met Pro
            835                 840                 845
```

```
Ile Lys Pro Asn Val Gly Ile Trp Gln Thr Leu Leu Ser Leu Cys Arg
    850                 855                 860

Val His Gly Asp Ile Glu Leu Gly Lys Glu Val Gly Lys Ile Leu Leu
865                 870                 875                 880

Arg Ile Asp Ala Lys Asn Pro Ala Asn Tyr Val Met Met Ser Asn Leu
                885                 890                 895

Tyr Gly Gln Ala Gly Tyr Trp Asn Glu Gln Gly Asn Ala Arg Glu Leu
            900                 905                 910

Gly Asn Ile Lys Gly Leu Lys Lys Glu Ala Gly Met Ser Trp Val Glu
        915                 920                 925

Ile Glu Arg Glu Val His Phe Phe Arg Ser Gly Glu Asp Ser His Pro
    930                 935                 940

Leu Thr Pro Val Ile Gln Glu Thr Leu Lys Glu Ala Glu Arg Arg Leu
945                 950                 955                 960

Arg Glu Glu Leu Gly Tyr Val Tyr Gly Leu Lys His Glu Leu His Asp
                965                 970                 975

Ile Asp Asp Glu Ser Lys Glu Glu Asn Leu Arg Ala His Ser Glu Lys
            980                 985                 990

Leu Ala Ile Gly Leu Ala Leu Ala Thr Gly Gly Leu Asn Gln Lys Gly
        995                 1000                1005

Lys Thr Ile Arg Val Phe Lys Asn Leu Arg Val Cys Val Asp Cys
    1010                1015                1020

His Glu Phe Ile Lys Gly Leu Ser Lys Ile Thr Lys Ile Ala Tyr
    1025                1030                1035

Val Val Arg Asp Ala Val Arg Phe His Ser Phe Glu Asp Gly Cys
    1040                1045                1050

Cys Ser Cys Gly Asp Tyr Cys Phe Phe Phe Asp Glu Gln Glu Lys
    1055                1060                1065

Val Ala Val Val Leu Asp Val Asp Glu His Leu His Thr Glu Thr
    1070                1075                1080

Ala Arg Tyr Arg Thr Thr Phe Ile Ile Gly Asp Gly Tyr Phe
    1085                1090                1095

Lys Ser Val Ser Leu Gly Glu Ala Leu Asn Val Tyr Val Gly Glu
    1100                1105                1110

Thr Gly Asn Phe Gly Tyr Thr Leu Arg Ile Tyr Cys Pro Pro Leu
    1115                1120                1125

Val Cys Ser Ser Cys Tyr Leu Leu Gln Ile Asn Gln Pro Arg Lys
    1130                1135                1140

Arg Lys Glu Arg Asp Asp Phe Asp Leu Leu Leu Ala Asn Leu Thr
    1145                1150                1155

Ala Cys Gln
    1160

<210> SEQ ID NO 50
<211> LENGTH: 239
<212> TYPE: PRT
<213> ORGANISM: Arabidopsis thaliana
<220> FEATURE:
<221> NAME/KEY: MISC_FEATURE
<222> LOCATION: (1)..(239)
<223> OTHER INFORMATION: Arabidopsis CRN-5 homolog

<400> SEQUENCE: 50

Met Glu Ile Asp Arg Glu Asp Gly Arg Thr Pro Asn Gln Leu Arg Pro
1               5                   10                  15
```

```
Leu Ala Cys Ser Arg Asn Ile Leu His Arg Pro His Gly Ser Ala Ser
            20                  25                  30

Trp Ser Gln Gly Asp Thr Lys Val Leu Ala Ala Val Tyr Gly Pro Lys
        35                  40                  45

Ala Gly Thr Lys Lys Asn Glu Asn Ala Glu Lys Ala Cys Phe Glu Val
    50                  55                  60

Ile Trp Lys Pro Lys Ser Gly Gln Ile Gly Lys Val Glu Lys Glu Tyr
65                  70                  75                  80

Glu Met Ile Leu Lys Arg Thr Ile Gln Ser Ile Cys Val Leu Thr Val
                85                  90                  95

Asn Pro Asn Thr Thr Thr Ser Val Ile Ile Gln Val Val His Asp Asp
            100                 105                 110

Gly Ser Leu Leu Pro Cys Ala Ile Asn Ala Ala Cys Ala Ala Leu Val
            115                 120                 125

Asp Ala Gly Ile Pro Met Lys His Leu Ala Val Ala Ile Cys Cys Cys
        130                 135                 140

Leu Ala Glu Asn Gly Tyr Leu Val Leu Asp Pro Asn Lys Leu Glu Glu
145                 150                 155                 160

Lys Lys Met Thr Ala Phe Ala Tyr Leu Val Phe Pro Asn Thr Thr Leu
                165                 170                 175

Ser Val Leu Pro Glu Gly Ser Val Ala Glu Gly Glu Pro Val Glu
            180                 185                 190

His Gly Ile Ile Thr Ser Ile Thr His Gly Val Met Ser Val Asp Asp
        195                 200                 205

Tyr Phe Leu Cys Val Glu Asn Gly Arg Ala Ala Thr Ala Ser Leu Ser
    210                 215                 220

Ala Phe Phe Arg Lys Asn Phe Gln Gln Ser Ser Ser Lys Ala Gly
225                 230                 235

<210> SEQ ID NO 51
<211> LENGTH: 380
<212> TYPE: PRT
<213> ORGANISM: Oryza sativa
<220> FEATURE:
<221> NAME/KEY: MISC_FEATURE
<222> LOCATION: (1)..(380)
<223> OTHER INFORMATION: Oryza sativa FEN-1 homolog

<400> SEQUENCE: 51

Met Gly Ile Lys Gly Leu Thr Lys Leu Leu Ala Asp Asn Ala Pro Lys
1               5                   10                  15

Ala Met Lys Glu Gln Lys Phe Glu Ser Tyr Phe Gly Arg Arg Ile Ala
            20                  25                  30

Val Asp Ala Ser Met Ser Ile Tyr Gln Phe Leu Ile Val Val Gly Arg
        35                  40                  45

Thr Gly Met Glu Thr Leu Thr Asn Glu Ala Gly Glu Val Thr Ser His
    50                  55                  60

Leu Gln Gly Met Phe Asn Arg Thr Ile Arg Leu Leu Glu Ala Gly Ile
65                  70                  75                  80

Lys Pro Val Tyr Val Phe Asp Gly Lys Pro Pro Asp Leu Lys Lys Gln
                85                  90                  95

Glu Leu Ala Lys Arg Tyr Ser Lys Arg Glu Asp Ala Thr Lys Glu Leu
            100                 105                 110

Thr Glu Ala Val Glu Glu Gly Asp Lys Asp Ala Ile Glu Lys Phe Ser
        115                 120                 125

Lys Arg Thr Val Lys Val Thr Lys Gln His Asn Glu Glu Cys Lys Arg
```

```
            130                 135                 140
Leu Leu Arg Leu Met Gly Val Pro Val Val Glu Ala Pro Cys Glu Ala
145                 150                 155                 160

Glu Ala Glu Cys Ala Ala Leu Cys Ile Asn Asp Met Val Tyr Ala Val
                165                 170                 175

Ala Ser Glu Asp Met Asp Ser Leu Thr Phe Gly Ala Pro Arg Phe Leu
            180                 185                 190

Arg His Leu Met Asp Pro Ser Ser Lys Lys Ile Pro Val Met Glu Phe
        195                 200                 205

Glu Val Ala Lys Val Leu Glu Glu Leu Glu Leu Thr Met Asp Gln Phe
210                 215                 220

Ile Asp Leu Cys Ile Leu Ser Gly Cys Asp Tyr Cys Asp Ser Ile Lys
225                 230                 235                 240

Gly Ile Gly Gly Gln Thr Ala Leu Lys Leu Ile Arg Gln His Gly Ser
                245                 250                 255

Ile Glu Ser Ile Leu Glu Asn Ile Asn Lys Asp Arg Tyr Gln Ile Pro
            260                 265                 270

Glu Asp Trp Pro Tyr Gln Glu Ala Arg Arg Leu Phe Lys Glu Pro Asn
        275                 280                 285

Val Thr Leu Asp Ile Pro Glu Leu Lys Trp Asn Ala Pro Asp Glu Glu
    290                 295                 300

Gly Leu Val Glu Phe Leu Val Lys Glu Asn Gly Phe Asn Gln Asp Arg
305                 310                 315                 320

Val Thr Lys Ala Ile Glu Lys Ile Lys Phe Ala Lys Asn Lys Ser Ser
                325                 330                 335

Gln Gly Arg Leu Glu Ser Phe Phe Lys Pro Val Val Ser Thr Ser Val
            340                 345                 350

Pro Leu Lys Arg Lys Asp Thr Ser Glu Lys Pro Thr Lys Ala Val Ala
        355                 360                 365

Asn Lys Lys Thr Lys Gly Ala Gly Gly Lys Lys Lys
        370                 375                 380

<210> SEQ ID NO 52
<211> LENGTH: 34
<212> TYPE: DNA
<213> ORGANISM: Synthetic DNA

<400> SEQUENCE: 52
gatgtcaagc agtcctaact ttgaggcaga gtcc                               34

<210> SEQ ID NO 53
<211> LENGTH: 30
<212> TYPE: DNA
<213> ORGANISM: Synthetic DNA

<400> SEQUENCE: 53
ggactctgcc tcaagacggt agtcaacgtg                                    30

<210> SEQ ID NO 54
<211> LENGTH: 16
<212> TYPE: DNA
<213> ORGANISM: Synthetic DNA

<400> SEQUENCE: 54
cacgttgact accgtc                                                   16

<210> SEQ ID NO 55
```

```
<211> LENGTH: 35
<212> TYPE: DNA
<213> ORGANISM: Synthetic DNA

<400> SEQUENCE: 55
ggactctgcc tcaagacggt agtcaacgtg gtgtg                           35

<210> SEQ ID NO 56
<211> LENGTH: 15
<212> TYPE: DNA
<213> ORGANISM: Synthetic DNA

<400> SEQUENCE: 56
cttgaggcag agtcc                                                15

<210> SEQ ID NO 57
<211> LENGTH: 19
<212> TYPE: DNA
<213> ORGANISM: Synthetic DNA

<400> SEQUENCE: 57
cacaccacgt tgactaccg                                            19

<210> SEQ ID NO 58
<211> LENGTH: 264
<212> TYPE: PRT
<213> ORGANISM: Escherichia coli
<220> FEATURE:
<221> NAME/KEY: MISC_FEATURE
<222> LOCATION: (1)..(264)
<223> OTHER INFORMATION: TatD

<400> SEQUENCE: 58
```

Met Glu Tyr Arg Met Phe Asp Ile Gly Val Asn Leu Thr Ser Ser Gln
1               5                   10                  15

Phe Ala Lys Asp Arg Asp Val Val Ala Arg Ala Phe Asp Ala Gly
            20                  25                  30

Val Asn Gly Leu Leu Ile Thr Gly Thr Asn Leu Arg Glu Ser Gln Gln
        35                  40                  45

Ala Gln Lys Leu Ala Arg Gln Tyr Ser Ser Cys Trp Ser Thr Ala Gly
    50                  55                  60

Val His Pro His Asp Ser Ser Gln Trp Gln Ala Ala Thr Glu Glu Ala
65                  70                  75                  80

Ile Ile Glu Leu Ala Ala Gln Pro Glu Val Val Ala Ile Gly Glu Cys
                85                  90                  95

Gly Leu Asp Phe Asn Arg Asn Phe Ser Thr Pro Glu Glu Gln Glu Arg
            100                 105                 110

Ala Phe Val Ala Gln Leu Arg Ile Ala Ala Asp Leu Asn Met Pro Val
        115                 120                 125

Phe Met His Cys Arg Asp Ala His Glu Arg Phe Met Thr Leu Leu Glu
    130                 135                 140

Pro Trp Leu Asp Lys Leu Pro Gly Ala Val Leu His Cys Phe Thr Gly
145                 150                 155                 160

Thr Arg Glu Glu Met Gln Ala Cys Val Ala His Gly Ile Tyr Ile Gly
                165                 170                 175

Ile Thr Gly Trp Val Cys Asp Glu Arg Arg Gly Leu Glu Leu Arg Glu
            180                 185                 190

Leu Leu Pro Leu Ile Pro Ala Glu Lys Leu Leu Ile Glu Thr Asp Ala
        195                 200                 205

```
Pro Tyr Leu Leu Pro Arg Asp Leu Thr Pro Lys Pro Ser Arg Arg
    210                 215                 220

Asn Glu Pro Ala His Leu Pro His Ile Leu Gln Arg Ile Ala His Trp
225                 230                 235                 240

Arg Gly Glu Asp Ala Ala Trp Leu Ala Ala Thr Thr Asp Ala Asn Val
                245                 250                 255

Lys Thr Leu Phe Gly Ile Ala Phe
                260
```

<210> SEQ ID NO 59
<211> LENGTH: 308
<212> TYPE: PRT
<213> ORGANISM: Caenorhabditis elegans
<220> FEATURE:
<221> NAME/KEY: MISC_FEATURE
<222> LOCATION: (1)..(308)
<223> OTHER INFORMATION: CPS-6

<400> SEQUENCE: 59

```
Met Ile Gly Lys Val Ala Gly Thr Ala Ala Ile Ala Gly Ile Ser Phe
1               5                   10                  15

Leu Ala Gly Lys Tyr Ser Asn Asp Asp Leu Pro Ile Phe Arg Asn Val
                20                  25                  30

Gln Ser Ala Thr Asn Val Pro Met Asn Gln Ile Gln Val Ser Glu Pro
            35                  40                  45

Met Thr Val Lys Pro Ala Ser Leu Asn Ala Asp Ala Met Gly Pro Ser
        50                  55                  60

Arg Ser Ala Glu Ile Met Lys His Gly Tyr Pro Gly Phe Thr Asn Val
65                  70                  75                  80

Arg Thr Tyr Glu Asp Phe Val Leu Ser Tyr Asp Tyr Lys Thr Arg Thr
                85                  90                  95

Ala His Trp Val Cys Glu His Leu Thr Pro Glu Arg Leu Lys His Ala
                100                 105                 110

Glu Gly Val Asp Arg Lys Leu Cys Glu Phe Lys Pro Asp Ile Thr Phe
            115                 120                 125

Pro Gln Lys Phe Leu Ser Gln Asn Thr Asp Tyr Lys Cys Ser Gly Phe
        130                 135                 140

Asp Arg Gly His Leu Ala Ala Ala Gly Asn His Arg Lys Ser Gln Leu
145                 150                 155                 160

Ala Val Asp Gln Thr Phe Tyr Leu Ser Asn Met Ser Pro Gln Val Gly
                165                 170                 175

Arg Gly Phe Asn Arg Asp Lys Trp Asn Asp Leu Glu Met His Cys Arg
                180                 185                 190

Arg Val Ala Lys Lys Met Ile Asn Ser Tyr Ile Ile Thr Gly Pro Leu
            195                 200                 205

Tyr Leu Pro Lys Leu Glu Gly Asp Gly Lys Lys Tyr Ile Lys Tyr Gln
        210                 215                 220

Val Ile Gly Asp Asn Asn Val Ala Val Pro Thr His Phe Phe Lys Val
225                 230                 235                 240

Ala Leu Phe Glu Val Thr Pro Gly Lys Phe Glu Leu Glu Ser Tyr Ile
                245                 250                 255

Leu Pro Asn Ala Val Ile Glu Asp Thr Val Glu Ile Ser Lys Phe His
                260                 265                 270

Val Pro Leu Asp Ala Val Glu Arg Ser Ala Gly Leu Glu Ile Phe Ala
            275                 280                 285

Arg Leu Asp Pro Lys Ser Ile Val Lys Glu Asn Gly Ala Lys Lys Gly
```

```
            290                 295                 300
Gly Leu Leu Trp
305

<210> SEQ ID NO 60
<211> LENGTH: 700
<212> TYPE: PRT
<213> ORGANISM: Caenorhabditis elegans
<220> FEATURE:
<221> NAME/KEY: MISC_FEATURE
<222> LOCATION: (1)..(700)
<223> OTHER INFORMATION: WAH-1

<400> SEQUENCE: 60

Met Leu Leu Arg Ala Val Gly Arg Gln Met Thr Ser Val Ile Phe Arg
1               5                   10                  15

Gln Gln Thr Ala Val Arg Ser Ile Ala Met Ser Arg Val Ala Leu Gly
            20                  25                  30

Gly Gly Gly His His His Glu Pro Thr Pro Val Tyr Ile Pro Lys Pro
        35                  40                  45

Gly Ser Leu Asp Trp Thr Phe Phe Ser Arg Ser His Thr Lys Ser Ala
    50                  55                  60

His Glu Phe Glu Pro Tyr Lys Pro Glu Ile Gly Ala Phe Ile Gly Ala
65                  70                  75                  80

Val Ala Phe Ile Gly Leu Thr Leu Ile Ala Val Val Ile Lys Thr Asp
                85                  90                  95

Val Phe Lys Lys Glu Asp Ser His Gly His Gly His Gly His Ala Lys
            100                 105                 110

His Ser Lys Lys His Glu Glu Lys His Glu Gln Lys His Glu Glu Lys
        115                 120                 125

Glu His Ala Glu Pro Glu Lys Lys Glu Glu Ala Lys Pro Glu Lys Pro
    130                 135                 140

Ala Glu Pro Lys Glu Pro Glu Pro Ala Gln Lys Gln Ala Glu Gln Pro
145                 150                 155                 160

Glu Gln Ala Glu Glu Lys Gln Glu Thr Lys Asp Ala Glu Pro Lys Glu
                165                 170                 175

Gln Val Asp Asp Arg Gln Thr Glu Glu Ala Val His Ala Arg Arg Ala
            180                 185                 190

Pro Ala Ala Glu Glu Pro Ala Pro Ser Thr Ser Lys Ala Asp Ala
        195                 200                 205

Val Glu Glu Lys Arg Ser Glu Gln Gln Ser Met Lys Pro Ser Glu Ser
    210                 215                 220

Thr Glu Glu Asn Thr Thr Thr Ser Ala Asp Gly Leu Leu His Cys
225                 230                 235                 240

Glu Tyr Val Ile Ile Gly Ser Gly Thr Ala Ala Tyr Tyr Ala Ser Leu
                245                 250                 255

Ser Ile Arg Ala Lys Gln Ala Glu Ala Lys Val Leu Met Ile Gly Glu
            260                 265                 270

Glu Pro Glu Leu Pro Tyr Asn Arg Pro Pro Leu Ser Lys Glu Leu Trp
        275                 280                 285

Trp Tyr Gly Asp Glu Thr Ser Ala Thr Lys Leu Ala Tyr Thr Pro Leu
    290                 295                 300

Ser Gly Lys Lys Arg Asp Ile Phe Tyr Glu Val Asp Gly Phe Phe Val
305                 310                 315                 320

Ser Pro Glu Asp Leu Pro Lys Ala Val His Gly Gly Val Ala Leu Leu
                325                 330                 335
```

```
Arg Gly Arg Lys Ala Val Lys Ile Cys Glu Glu Asp Lys Lys Val Ile
            340                 345                 350

Leu Glu Asp Gly Thr Thr Ile Gly Tyr Asp Lys Leu Leu Ile Ala Thr
            355                 360                 365

Gly Val Arg Pro Lys Lys Glu Gln Val Phe Glu Glu Ala Ser Glu Glu
            370                 375                 380

Ala Lys Gln Lys Ile Thr Tyr Phe His Tyr Pro Ala Asp Phe Lys Arg
385                 390                 395                 400

Val Glu Arg Gly Leu Ala Asp Lys Ser Val Gln Lys Val Thr Ile Ile
            405                 410                 415

Gly Asn Gly Leu Leu Ala Ser Glu Leu Ser Tyr Ser Ile Lys Arg Lys
            420                 425                 430

Tyr Gly Glu Asn Val Glu Val His Gln Val Phe Glu Glu Lys Tyr Pro
            435                 440                 445

Ala Glu Asp Ile Leu Pro Glu His Ile Ala Gln Lys Ser Ile Glu Ala
            450                 455                 460

Ile Arg Lys Gly Gly Val Asp Val Arg Ala Glu Gln Lys Val Glu Gly
465                 470                 475                 480

Val Arg Lys Cys Cys Lys Asn Val Val Leu Lys Leu Ser Asp Gly Ser
            485                 490                 495

Glu Leu Arg Thr Asp Leu Val Val Ala Thr Gly Glu Glu Pro Asn
            500                 505                 510

Ser Glu Ile Ile Glu Ala Ser Gly Leu Lys Ile Asp Glu Lys Leu Gly
            515                 520                 525

Gly Val Arg Ala Asp Lys Cys Leu Lys Val Gly Glu Asn Val Trp Ala
            530                 535                 540

Ala Gly Ala Ile Ala Thr Phe Glu Asp Gly Val Leu Gly Ala Arg Arg
545                 550                 555                 560

Val Ser Ser Trp Glu Asn Ala Gln Ile Ser Gly Arg Leu Ala Gly Glu
            565                 570                 575

Asn Met Ala Thr Ala Ala Ala Asp Gly Lys Ser Glu Gly Lys Ala Phe
            580                 585                 590

Trp Tyr Gln Pro Ser Phe Phe Thr Lys Phe Ala Pro His Leu His Ile
            595                 600                 605

Asn Ala Ile Gly Lys Cys Asp Ser Ser Leu Glu Thr Val Ser Val His
            610                 615                 620

Ala Glu Pro Asp Lys Asp Thr Pro Leu Glu Lys Ala Val Val Phe Tyr
625                 630                 635                 640

Lys Ser Lys Glu Asp Gly Ser Ile Val Gly Val Leu Leu Asn Val
            645                 650                 655

Phe Gly Pro Ser Leu Asp Val Ala Arg Arg Ile Ile Asp Asp Arg Lys
            660                 665                 670

Lys Val Asp Glu Tyr Lys Glu Ile Ala Lys Leu Phe Pro Leu Tyr Asp
            675                 680                 685

Pro Val Lys Ser Asp Glu Asp Ala Lys Ser Ala
690                 695                 700

<210> SEQ ID NO 61
<211> LENGTH: 375
<212> TYPE: PRT
<213> ORGANISM: Caenorhabditis elegans
<220> FEATURE:
<221> NAME/KEY: MISC_FEATURE
<222> LOCATION: (1)..(375)
<223> OTHER INFORMATION: NUC-1
```

<400> SEQUENCE: 61

| | | | | | | | | | | | | | | |
|---|---|---|---|---|---|---|---|---|---|---|---|---|---|---|
|Met|Gly|Leu|Ser|Pro|Ala|Ala|Val|Leu|Ile|Phe|Leu|Leu|Leu|Gly|Val|
|1| | | |5| | | |10| | | |15| | |

Ser Gln Thr Tyr Ala Ala Phe Ser Cys Lys Asp Gln Ser Gly Asn Asp
            20                  25                  30

Val Asp Trp Phe Ala Val Tyr Lys Met Pro Ile Glu Lys Asp Asp Gly
        35                  40                  45

Ser Val Thr Gly Leu Ala Gly Gly Val Ala Trp Tyr Tyr Val Asp Val
    50                  55                  60

Asn Lys Lys Gly Thr Leu Thr Pro Ser Ala Lys Thr Leu Asp Asp Asn
65                  70                  75                  80

Asp Gln Ala Ile Ala Tyr Thr Leu Gln Gln Tyr Tyr Asp Lys Gln Asn
                85                  90                  95

Asp Lys Thr Ile Phe His Val Met Tyr Asn Asp Glu Pro Trp Gly Ser
            100                 105                 110

Lys Ser Thr Ser Gly Ile Lys Leu Glu Glu Ile Leu Ser Asn Arg Val
            115                 120                 125

Tyr Ser Asn Tyr Thr His Glu Asp Asp Ser Thr Ser Thr Ala Phe Gly
    130                 135                 140

His Thr Lys Gly Thr Ile Phe Phe Asp Gly Thr Ser Gly Val Trp Leu
145                 150                 155                 160

Val His Ser Val Pro Leu Phe Pro Asn Pro Thr Lys Tyr Glu Tyr Pro
                165                 170                 175

Val Ser Gly His Asp Tyr Gly Gln Thr Met Leu Cys Met Thr Phe Lys
            180                 185                 190

Tyr Ala Gln Leu Lys Ser Ile Gly Thr Gln Leu Phe Phe Asn Arg Pro
        195                 200                 205

Asn Ile Tyr Ser Ser Asn Leu Pro Thr Asn Met Ala Ala Asp Asn Ala
    210                 215                 220

Asp Leu Ala Lys Ala Ile Ala Gly Gln Tyr Gln Lys Gly Gln Pro Phe
225                 230                 235                 240

Gln Ser Val Ile Glu Leu Glu Thr Met Ala Gly Tyr Ser Phe Thr Asn
                245                 250                 255

Phe Ala Lys Ser Lys Glu Phe Asn Ala Asp Leu Tyr Asp Thr Leu Val
            260                 265                 270

Ala Pro Thr Leu Lys Thr Asp Leu Val Val Glu Thr Trp Arg Arg Gly
        275                 280                 285

Ser Glu Ile Pro Leu Asp Cys Lys Leu Thr Tyr His Ala Asn Asp Ala
    290                 295                 300

Leu Ser Ile His Val Gly Ser Thr Ala Phe Ser Tyr Thr Lys Asp
305                 310                 315                 320

His Ser Lys Met Ala His Ser Ala Asp Met Thr Lys Pro Trp Val Cys
                325                 330                 335

Ile Gly Asp Ile Asn Arg Met Thr Ser Gln Tyr Val Arg Gly Gly Gly
            340                 345                 350

Thr Thr Cys Ile Ser Ser Ser Phe Leu Trp Lys Ala Tyr Ser Val Ile
        355                 360                 365

Ala Thr Gln Asn Asn Cys Ala
    370                 375

<210> SEQ ID NO 62
<211> LENGTH: 215
<212> TYPE: PRT

```
<213> ORGANISM: Escherichia coli
<220> FEATURE:
<221> NAME/KEY: MISC_FEATURE
<222> LOCATION: (1)..(215)
<223> OTHER INFORMATION:

<400> SEQUENCE: 62

Met Ser Asp Asn Ala Gln Leu Thr Gly Leu Cys Asp Arg Phe Arg Gly
1               5                   10                  15

Phe Tyr Pro Val Val Ile Asp Val Glu Thr Ala Gly Phe Asn Ala Lys
            20                  25                  30

Thr Asp Ala Leu Leu Glu Ile Ala Ala Ile Thr Leu Lys Met Asp Glu
        35                  40                  45

Gln Gly Trp Leu Met Pro Asp Thr Thr Leu His Phe His Val Glu Pro
    50                  55                  60

Phe Val Gly Ala Asn Leu Gln Pro Glu Ala Leu Ala Phe Asn Gly Ile
65                  70                  75                  80

Asp Pro Asn Asp Pro Asp Arg Gly Ala Val Ser Glu Tyr Glu Ala Leu
                85                  90                  95

His Glu Ile Phe Lys Val Val Arg Lys Gly Ile Lys Ala Ser Gly Cys
            100                 105                 110

Asn Arg Ala Ile Met Val Ala His Asn Ala Asn Phe Asp His Ser Phe
        115                 120                 125

Met Met Ala Ala Ala Glu Arg Ala Ser Leu Lys Arg Asn Pro Phe His
    130                 135                 140

Pro Phe Ala Thr Phe Asp Thr Ala Ala Leu Ala Gly Leu Ala Leu Gly
145                 150                 155                 160

Gln Thr Val Leu Ser Lys Ala Cys Gln Thr Ala Gly Met Asp Phe Asp
                165                 170                 175

Ser Thr Gln Ala His Ser Ala Leu Tyr Asp Thr Glu Arg Thr Ala Val
            180                 185                 190

Leu Phe Cys Glu Ile Val Asn Arg Trp Lys Arg Leu Gly Gly Trp Pro
        195                 200                 205

Leu Ser Ala Ala Glu Glu Val
    210                 215
```